(12) United States Patent
Klinger et al.

(10) Patent No.: US 11,866,748 B2
(45) Date of Patent: *Jan. 9, 2024

(54) COMPOSITIONS COMPRISING POLYPEPTIDES HAVING MANNANASE ACTIVITY

(71) Applicant: Novozymes A/S, Bagsvaerd (DK)

(72) Inventors: Markus Klinger, Vaerloese (DK); Tine Hoff, Holte (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/754,698

(22) PCT Filed: Oct. 23, 2018

(86) PCT No.: PCT/EP2018/079047
§ 371 (c)(1),
(2) Date: Apr. 8, 2020

(87) PCT Pub. No.: WO2019/081515
PCT Pub. Date: May 2, 2019

(65) Prior Publication Data
US 2020/0255774 A1    Aug. 13, 2020

(30) Foreign Application Priority Data
Oct. 24, 2017 (EP) .................................. 17197926

(51) Int. Cl.
| C12N 9/26 | (2006.01) |
| C11D 3/386 | (2006.01) |
| C12N 9/24 | (2006.01) |
| C11D 11/00 | (2006.01) |

(52) U.S. Cl.
CPC ........ *C12N 9/2488* (2013.01); *C11D 3/38636* (2013.01); *C11D 11/0017* (2013.01); *C11D 11/0023* (2013.01); *C07K 2319/21* (2013.01)

(58) Field of Classification Search
CPC .......................... C12N 9/2494; C11D 3/38636
See application file for complete search history.

(56) References Cited

FOREIGN PATENT DOCUMENTS

| NO | 2014/088934 A1 | 6/2014 |
| WO | 1999/64619 A2 | 12/1999 |
| WO | 2012/14933 A1 | 11/2012 |
| WO | 2012/149317 A1 | 11/2012 |
| WO | 2012/149325 A1 | 11/2012 |
| WO | 2013/109468 A2 | 7/2013 |
| WO | 2014/100018 A1 | 6/2014 |
| WO | 2015/040159 A2 | 3/2015 |
| WO | WO-2016007929 A2 * | 1/2016 ........... A23K 20/189 |
| WO | 2016/054176 A1 | 4/2016 |
| WO | 2016/079045 A1 | 5/2016 |
| WO | 2017/021514 A1 | 2/2017 |
| WO | 2017/021515 A1 | 2/2017 |
| WO | 2017/021516 A1 | 2/2017 |
| WO | 2017/021517 A1 | 2/2017 |
| WO | 2017/021518 A1 | 2/2017 |
| WO | 2017/079751 A1 | 5/2017 |
| WO | 2017/079756 A1 | 5/2017 |
| WO | 2018/085524 A2 | 5/2018 |
| WO | 2018/206300 A1 | 11/2018 |
| WO | 2018/206302 A1 | 11/2018 |

OTHER PUBLICATIONS

WP_095357935. NCBI Database. Aug. 2017.*
Cai et al., 2011, J Biosci Bioeng, vol. 112, No. 6, pp. 551-557.
Couturier et al., 2013, PLOS One, vol. 8, No. 11, page e79800.
Jorgensen et al., 2010, Appl Biochem Biotechnol, vol. 161. No. 1-8, pp. 318-332.
Lee et al., 2003, Poultry Science, vol. 82, pp. 1925-1931.
McCutchen et al., 1996, Biotechnol Bioeng, vol. 52, pp. 332-339.
Nunes et al., 2006, J Agric Food Chem, vol. 54, No. 9, pp. 3428-3439.
Suurnakki et al., 1997, Adv Biochem Eng Biotechnol, vol. 57, pp. 261-287.
Varnai et al., 2011, Bioresource Technology, vol. 102, No. 19, pp. 9096-9104.
Couturier et al., The J Of Biological Chem, 2013, 14624-14635, 288(20).
Freiesleben et al., Enzyme Microb Technol, 2015, 68-77, 83.

* cited by examiner

*Primary Examiner* — Yong D Pak
(74) *Attorney, Agent, or Firm* — Kelly K. Reynolds

(57) ABSTRACT

The present invention relates to compositions comprising at least two polypeptides having mannanase activity as well as methods of producing and using the compositions. The compositions comprise in particular a first mannanase which is a glycoside hydrolase family 5 (GH5) mannanase and a second mannanase which a glycoside hydrolase family 26 (GH26) mannanase.

19 Claims, No Drawings
Specification includes a Sequence Listing.

COMPOSITIONS COMPRISING POLYPEPTIDES HAVING MANNANASE ACTIVITY

CROSS-REFERENCE TO RELATED APPLICATIONS

This application is a 35 U.S.C. 371 national application of international application no. PCT/EP2018/079047 filed Oct. 23, 2018 which claims priority or the benefit under 35 U.S.C. 119 of European application no.17197926.3 filed Oct. 24, 2017, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to compositions comprising at least two polypeptides having mannanase activity as well as methods of producing and using the compositions.

Description of the Related Art

Mannans are polysaccharides with a backbone of β-1,4-linked D-mannopyranosyl residues, which can contain galactose or acetyl substitutions and may have glucose residues in the backbone. The main enzyme type participating in the degradation of mannans are endo-1,4-β-mannanases (EC 3.2.1.78), which hydrolyze the internal glycoside bonds in the mannan backbone. According to CAZy (www.cazy.org), endo-1,4-β-mannanases have been found in glycoside hydrolyase families 5, 26 and 113.

Mannans are a type of hemicellulose representing up to 25% of wood dry weight in softwoods, but are also found in other plant material, especially in a variety of seeds. Mannan-containing gums such as guar gum are used as a stabilizer in many food products.

Thus, it could be advantageous to use endomannanases in applications where mannan needs to be degraded. Examples of where mannanases could be used are in detergents to remove mannan containing stains, in the production of bioethanol from softwood (Varnai et al, (2011) "Synergistic action of xylanase and mannanase improves the total hydrolysis of softwood", *Bioresource tech.*, 102(19), pp. 9096-104) and palm kernel press cake (Jørgensen et al, (2010) "Production of ethanol and feed by high dry matter hydrolysis and fermentation of palm kernel press cake", *Applied Biochem. Biotech.*, 161(1-8), pp. 318-32), for the improvement of animal feed (Cai, et al, (2011), "Acidic β-mannanase from *Penicillium pinophilum* C1: Cloning, characterization and assessment of its potential for animal feed application", *J. Biosci. Bioeng.*, 112(6), pp. 551-557) and in the hydrolysis of coffee extract (Nunes et al, (2006), "Characterization of Galactomannan Derivatives in Roasted Coffee Beverages", *J. Agricultural Food Chem.*, 54(9), pp. 3428-3439).

The use of mannanases in the household care industry, e.g. in laundry detergents, has been described; see for example WO 1999/064619 and WO 2016/054176.

Beta-mannanases have also been used in commercial applications in, for example, industries such as the paper and pulp industry, foodstuff and feed industry, pharmaceutical industry and energy industry. Lee J. T., et al., (2003) Poult. Sci. 82: 1925-1931; McCutchen M. C., et al., (1996) Biotechnol. Bioeng. 52:332-339; Suurnakki A., et al., (1997) Adv. Biochem. Eng. Biotechnol, 57:261-287.

However, a need remains for improved solutions for e.g. removing mannan-based stains in the household care industry. The present invention provides compositions with advantageous properties containing at least first and second mannanases, wherein the first mannanase is of the glycoside hydrolase (GH) family 5 and the second mannanase is of the GH family 26.

SUMMARY OF THE INVENTION

The present invention relates to compositions comprising at least two mannanases, where a first mannanase is a glycoside hydrolase 5 (GH5) mannanase and the second mannanase is a glycoside hydrolase 26 (GH26) mannanase. Thus, the invention provides a composition comprising at least first and second mannanases, wherein:
(A) the first mannanase is a glycoside hydrolase family 5 mannanase or a variant or fragment thereof having mannanase activity; and
(B) the second mannanase is a glycoside hydrolase family 26 mannanase or a variant or fragment thereof having mannanase activity.

One aspect of the invention relates to compositions comprising at least first and second mannanases, wherein:
the first mannanase (A) is a variant of a parent mannanase comprising at least one modification at a position corresponding to a position selected from positions 1, 2, 3, 4, 5, 6, 8, 9, 10, 11, 13, 14, 15, 16, 17, 18, 19, 21, 23, 30, 32, 33, 34, 35, 37, 38, 39, 41, 44, 45, 47, 57, 59, 60, 62, 63, 65, 66, 67, 68, 70, 71, 74, 77, 78, 79, 80, 81, 82, 83, 93, 95, 96, 97, 98, 100, 104, 107, 108, 110, 111, 114, 115, 116, 118, 119, 131, 132, 133, 135, 136, 139, 142, 143, 146, 147, 150, 152, 154, 164, 167, 169, 172, 173, 174, 175, 176, 177, 180, 181, 183, 184, 185, 196, 199, 200, 201, 202, 203, 205, 206, 210, 212, 213, 214, 215, 226, 228, 229, 230, 234, 235, 241, 242, 243, 244, 245, 250, 254, 257, 258, 259, 260, 261, 262, 266, 267, 268, 270, 271, 272, 273, 276, 279, 280, 283, 285, 286, 288, 289, 290, 292, 293, 294, 295, 296, 298, 299, 300 and 301, wherein:
numbering is according to SEQ ID NO: 2,
each modification is independently a substitution or a deletion,
the variant has mannanase activity, and
the variant has at least 59%, e.g. at least 60%, at least 61%, at least 62%, at least 63%, at least 65%, at least 70%, at least 75%, at least 80%, at least 85%, at least 90%, at least 95%, at least 96%, at least 97%, at least 98%, or at least 99%, but less than 100% sequence identity to the mature polypeptide of SEQ ID NO: 2.

Another aspect of the invention relates to compositions comprising at least first and second mannanases, wherein the second mannanase (B) is selected from the group consisting of:
(a) a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16;

(b) a variant of the polypeptide in (a), wherein the variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28 or 29 positions compared to SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16;

(c) a polypeptide comprising the polypeptide of (a) or (b) and an N-terminal and/or C-terminal His-tag and/or HQ-tag;

(d) a polypeptide comprising the polypeptide of (a) or (b) and an N-terminal and/or C-terminal extension of up to 10 amino acids, e.g. 1, 2, 3, 4, 5, 6, 7, 8, 9 or 10 amino acids; and (e) a fragment of the polypeptide of (a) or (b) having mannanase activity and having at least 90% of the length of the mature polypeptide of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16.

A further aspect of the invention relates to compositions wherein the first mannanase (A) comprises a substitution in at least one of positions 3, 37, 47, 77, 82, 83, 93, 98, 116, 135, 136, 241, 257, 258, 260, 288, 294 and 295 compared to its parent mannanase. In this aspect, the first mannanase may e.g. comprise at least two substitutions compared to the parent and be selected from the group consisting of:

(a) a variant comprising a first substitution in at least one amino acid position selected from positions 260, 288, 294 and 295, and a second substitution in at least one other position in said variant; and (b) a variant comprising substitutions in any two or more positions selected from positions 3, 37, 47, 77, 82, 83, 93, 98, 116, 135, 136, 241, 257 and 258.

A further aspect of the invention relates to compositions wherein the first mannanase comprises or consists of a mannanase having at least 59%, e.g. at least 60%, at least 61%, at least 62%, at least 63%, at least 65%, at least 70%, at least 75%, at least 80%, at least 85%, at least 90%, at least 95%, at least 96%, at least 97%, at least 98%, at least 99%, or 100% sequence identity to the polypeptide of SEQ ID NO: 17, SEQ ID NO: 18, SEQ ID NO: 19, SEQ ID NO: 20, SEQ ID NO: 21, SEQ ID NO: 22, or SEQ ID NO: 23.

Further aspects of the invention and particular embodiments will be apparent from the detailed description below.

OVERVIEW OF SEQUENCE LISTING

SEQ ID NO: 1 is the amino acid sequence of a parent mannanase of a GH5 mannanase from *Bacillus bogoriensis*, including a signal peptide.

SEQ ID NO: 2 is the mature GH5 polypeptide of SEQ ID NO: 1 from *Bacillus bogoriensis*.

SEQ ID NO: 3 is the mature amino acid sequence of a GH26 mannanase from *Paenibacillus woosongensis*.

SEQ ID NO: 4 is the mature amino acid sequence of a GH26 mannanase from *Paenibacillus illinoisensis*.

SEQ ID NO: 5 is the mature amino acid sequence of a GH26 mannanase from *Neobulgaria* sp.

SEQ ID NO: 6 is the mature amino acid sequence of a GH26 mannanase from *Preussia aemulans*.

SEQ ID NO: 7 is the mature amino acid sequence of a GH26 mannanase from *Yunnania penicillata*.

SEQ ID NO: 8 is the mature amino acid sequence of a GH26 mannanase from *Myrothecium roridum*.

SEQ ID NO: 9 is the mature amino acid sequence of a GH26 mannanase from *Chaetomium brasiliense*.

SEQ ID NO: 10 is the mature amino acid sequence of a GH26 mannanase from *Ascobolus stictoideus*.

SEQ ID NO: 11 is the mature amino acid sequence of a GH26 mannanase from *Chaetomium virescens*.

SEQ ID NO: 12 is the mature amino acid sequence of a GH26 mannanase from *Paenibacillus ihumii*.

SEQ ID NO: 13 is the mature amino acid sequence of a GH26 mannanase from *Paenibacillus* sp.

SEQ ID NO: 14 is the mature amino acid sequence of a GH26 mannanase from *Salipaludibacillus agaradhaerens*.

SEQ ID NO: 15 is the mature amino acid sequence of a GH26 mannanase from *Geobacillus tepidamans*.

SEQ ID NO: 16 is the mature amino acid sequence of a GH26 mannanase from *Bacillus* sp. SWT81.

SEQ ID NO: 17 is residues 32-340 of the amino acid sequence of a GH5 mannanase from *Bacillus bogoriensis*, described in U.S. Pat. No. 6,566,114 as SEQ ID NO:2 therein.

SEQ ID NO: 18 is a variant GH5 mannanase from *Bacillus bogoriensis*.

SEQ ID NO: 19 is the mature amino acid sequence of a GH5 mannanase from *Bacillus lentus*.

SEQ ID NO: 20 is the mature amino acid sequence of a GH5 mannanase from *Paenibacillus* sp.

SEQ ID NO: 21 is a variant GH5 mannanase from *Paenibacillus* sp.

SEQ ID NO: 22 is a variant GH5 mannanase from *Paenibacillus* sp.

SEQ ID NO: 23 is a variant GH5 mannanase from *Paenibacillus* sp.

Definitions

In accordance with the detailed description, the following abbreviations and definitions apply. Note that the singular forms "a", "an", and "the" include plural referents unless the context clearly indicates otherwise. Thus, for example, reference to "an enzyme" includes a plurality of such enzymes, and reference to "the dosage" includes reference to one or more dosages and equivalents thereof known to those skilled in the art, and so forth.

Mannanase: The term "mannanase" means a polypeptide having mannan endo-1,4-beta-mannosidase activity (EC 3.2.1.78) that catalyses the hydrolysis of 1,4-β-D-mannosidic linkages in mannans, galactomannans and glucomannans. Alternative names for mannan endo-1,4-beta-mannosidase are 1,4-β-D-mannan mannanohydrolase; endo-1,4-β-mannanase; endo-P-1,4-mannase; β-mannanase B; β-1,4-mannan 4-mannanohydrolase; endo-β-mannanase; and 1-D-mannanase. It will be apparent that the invention described herein relates in particular to mannanases of the GH5 and GH26 families. For purposes of the present invention, mannanase activity may be determined using the Reducing End Assay in Example 1, and as described in WO 2017/021515. In one aspect, the GH5 polypeptides of the present invention have at least 50%, e.g., at least 60%, at least 70%, at least 80%, at least 90%, at least 95%, or at least 100% of the mannanase activity of the mature polypeptide of SEQ ID NO: 1 or 2, or SEQ ID NO: 17, SEQ ID NO: 18, SEQ ID NO: 19, SEQ ID NO: 20, SEQ ID NO: 21, SEQ ID NO: 22, or SEQ ID NO: 23. In another aspect, the GH26 polypeptides of the present invention have at least 50%, e.g., at least 60%, at least 70%, at least 80%, at least 90%, at least 95%, or at least 100% of the mannanase activity of the mature polypeptide of SEQ ID NO: 3, 4, 5, 6, 7, 8, 9, 10, 11, 12, 13, 14, 15, or 16.

Biofilm: The term "biofilm" means any group of microorganisms in which cells stick to each other on a surface, such as a textile, dishware or hard surface. These adherent cells are frequently embedded within a self-produced matrix of extracellular polymeric substance (EPS). Biofilm EPS is a polymeric conglomeration generally composed of extracellular DNA, proteins, and polysaccharides. Biofilms may form on living or non-living surfaces. The microbial cells growing in a biofilm are physiologically distinct from planktonic cells of the same organism, which, by contrast, are single-cells that may float or swim in a liquid medium.

Bacteria living in a biofilm usually have significantly different properties from free-floating bacteria of the same species, as the dense and protected environment of the film allows them to cooperate and interact in various ways. One effect of this environment is increased resistance to detergents and antibiotics, as the dense extracellular matrix and the outer layer of cells protect the interior of the community.

On laundry biofilm producing bacteria can be found among the following species: *Acinetobacter* sp., *Aeromicrobium* sp., *Brevundimonas* sp., *Microbacterium* sp., *Micrococcus luteus*, *Pseudomonas* sp., *Staphylococcus epidermidis*, and *Stenotrophomonas* sp.

Carbohydrate binding module: The term "carbohydrate binding module" means the region within a carbohydrate-active enzyme that provides carbohydrate-binding activity (Boraston et al., 2004, *Biochem. J.* 383: 769-781). A majority of known carbohydrate binding modules (CBMs) are contiguous amino acid sequences with a discrete fold. The carbohydrate binding module (CBM) is typically found either at the N-terminal or at the C-terminal extremity of an enzyme. Some CBMs are known to have specificity for cellulose. In one embodiment, the CBM is a family 35 CBM (Pfam PF16990) such as that disclosed in Tunnicliffe R B, Bolam D N, Pell G, Gilbert H J, Williamson M P; J Mol Biol. 2005; 347:287-296.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Detergent component: the term "detergent component" is defined herein to mean the types of chemicals which can be used in detergent compositions. Examples of detergent components are surfactants, hydrotropes, builders, co-builders, chelators or chelating agents, bleaching system or bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzyme inhibitors or stabilizers, enzyme activators, antioxidants, and solubilizers. The detergent composition may comprise of one or more of any type of detergent component.

Detergent composition: the term "detergent composition" refers to compositions that find use in the removal of undesired compounds from items to be cleaned, such as textiles, dishes, and hard surfaces. The detergent composition may be used to e.g. clean textiles, dishes and hard surfaces for both household cleaning and industrial cleaning. The terms encompass any materials/compounds selected for the particular type of cleaning composition desired and the form of the product (e.g., liquid, gel, powder, granulate, paste, or spray compositions) and includes, but is not limited to, detergent compositions (e.g., liquid and/or solid laundry detergents and fine fabric detergents; hard surface cleaning formulations, such as for glass, wood, ceramic and metal counter tops and windows; carpet cleaners; oven cleaners; fabric fresheners; fabric softeners; and textile and laundry pre-spotters, as well as dish wash detergents). In addition to comprising a first (GH5) mannanase and a second (GH26) mannanase of the invention, the detergent formulation may comprise one or more additional enzymes (such as amylases, proteases, proteases, peroxidases, cellulases, betaglucanases, xyloglucanases, hemicellulases, xanthanases, xanthan lyases, lipases, acyl transferases, phospholipases, esterases, laccases, catalases, aryl esterases, amylases, alpha-amylases, glucoamylases, cutinases, pectinases, pectate lyases, keratinases, reductases, oxidases, phenoloxidases, lipoxygenases, ligninases, carrageenases, pullulanases, tannases, arabinosidases, hyaluronidases, chondroitinases, xyloglucanases, xylanases, pectin acetyl esterases, polygalacturonases, rhamnogalacturonases, other endo-beta-mannanases, exo-beta-mannanases, pectin methylesterases, cellobiohydrolases, transglutaminases, and combinations thereof, or any mixture thereof), and/or components such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

Dish wash: The term "dish wash" refers to all forms of washing dishes, e.g., by hand or automatic dish wash (ADW). Washing dishes includes, but is not limited to, the cleaning of all forms of crockery such as plates, cups, glasses, bowls, all forms of cutlery such as spoons, knives, forks and serving utensils as well as ceramics, plastics, metals, china, glass and acrylics.

Dish washing composition: The term "dish washing composition" refers to all forms of compositions for cleaning hard surfaces. The present invention is not restricted to any particular type of dish wash composition or any particular detergent.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide or a catalytic or carbohydrate binding module having one or more amino acids absent from the amino and/or carboxyl terminus of a mature polypeptide or domain; wherein the fragment has mannanase or carbohydrate binding activity. In one aspect, the fragment comprises at least 90% of the length of the mature polypeptide, such as at least 92% of the length of the mature polypeptide, at least 94% of the length of the mature polypeptide, at least 96% of the length of the mature polypeptide, at least 98% of the length of the mature polypeptide, or at least 99% of the length of the mature polypeptide. The mature polypeptide may be any suitable GH5 or GH26 polypeptide having mannanase or carbohydrate binding activity, and may in particular be a GH5 polypeptide having SEQ ID NO: 1 or 2, or SEQ ID NO: 17, SEQ ID NO: 18, SEQ ID NO: 19, SEQ ID NO: 20, SEQ ID NO: 21, SEQ ID NO: 22, or SEQ ID NO: 23, or a GH26 polypeptide having SEQ ID NO: 3, 4, 5, 6, 7, 8, 9, 10, 11, 12, 13, 14, 15, or 16.

Glycoside hydrolase family: The terms "glycoside hydrolase 5", "glycoside hydrolase family 5" and "GH5" refer to the glycoside hydrolase family 5 as it is defined by the CAZy database (www.cazy.org) and in CAZypedia (www.cazypedia.org). Similarly, the terms "glycoside hydrolase 26", "glycoside hydrolase family 26" and "GH26" refer to the glycoside hydrolase family 26 as defined by CAZy and CAZypedia. The CAZy database, which is well-known to persons skilled in the art of carbohydrate-active enzymes, is a specialist database that describes families of structurally-related catalytic and carbohydrate-binding modules (or functional domains) of enzymes that degrade, modify or create glycosidic bonds. Glycoside hydrolases (GHs) are defined and classified in CAZy and CAZypedia based on their amino acid sequence and structural and folding similarities. Similar terms for other glycoside hydrolase families are to be understood in the same manner.

Hard surface cleaning: The term "hard surface cleaning" is defined herein as cleaning of hard surfaces wherein hard surfaces may include floors, tables, walls, roofs etc. as well as surfaces of hard objects such as cars (car wash) and dishes (dish wash). Dish washing includes but are not limited to cleaning of plates, cups, glasses, bowls, and cutlery such as spoons, knives, forks, serving utensils, ceramics, plastics, metals, china, glass and acrylics.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication, as well as a recombinant host cell, an isolated host cell (e.g., an isolated recombinant host cell), a heterologous host cell (e.g., a host cell that is not *Myrothecium roridum* host cell).

Improved property: The term "improved property" as used herein, refers to a characteristic associated with a variant that is improved compared to the parent. Such improved properties include, but are not limited to, catalytic efficiency, catalytic rate, in-detergent stability, chemical stability, oxidation stability, pH activity, pH stability, specific activity, stability under storage conditions, substrate binding, substrate cleavage, substrate specificity, substrate stability, surface properties, thermal activity, and thermostability.

In-detergent stability: The term "in-detergent stability" as used herein, refers to the stability of a mannanase enzyme, being both a wild-type, parent or variant, when it has been incubated in a detergent. For the purposes of the present invention, in-detergent stability may be determined as described in Example 7, wherein the wash performance of the enzyme is evaluated after incubation in a detergent comprising surfactants and other detergent ingredients.

Isolated: The term "isolated" means a substance in a form that does not occur in nature or in an environment in which the substance does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Laundering: The term "laundering" relates to both household laundering and industrial laundering and means the process of treating textiles with a solution containing a cleaning or detergent composition of the present invention. The laundering process can for example be carried out using e.g. a household or an industrial washing machine or can be carried out by hand.

Mature polypeptide: The term "mature polypeptide" means a polypeptide in its final form following translation and any post-translational modifications, such as N-terminal processing, C-terminal truncation, glycosylation, phosphorylation, etc.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having mannanase activity.

Malodour: The term "malodour" is meant an odour which is not desired on clean items. The cleaned item should smell fresh and clean without malodours adhered to the item. One example of malodour is compounds with an unpleasant smell, which may be produced by microorganisms. Another example is sweat or body odour adhering to an item which has been in contact with humans or animals. Another example of malodour can be the smell from spices, for example curry or other exotic spices adhering to an item such as a piece of textile. One way of measuring the ability of an item to adhere malodour is by using a sensory panel consisting of trained assessors.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent: The term "parent" as used herein refers to the starting polypeptide from which a variant polypeptide is made, i.e. variant mannanases of the present invention has been made from a starting mannanase. Such parent polypeptide may be a wild-type mannanase or it may by itself be a variant used as starting point to make further modified variants. In particular for the present invention, any mannanase having at least 59%, such as at least 60%, such as at least 65%, such as at least 70%, such as at least 75%, such as at least 80%, such as at least 85%, such as at least 90%, such as at least 95%, or such as 100% sequence identity to any one of SEQ ID Nos: 1, 2, 3, 4, 5, 6, 7, 8, 9, 10, 11, 12, 13, 14, 15, 16, 17, 18, 19, 20, 21, 22, or 23 may be the parent mannanase for a variant.

Sequence identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 6.6.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment)

Subsequence: The term "subsequence" means a polynucleotide having one or more nucleotides absent from the 5' and/or 3' end of a mature polypeptide coding sequence; wherein the subsequence encodes a fragment having mannanase activity.

Textile: The term "textile" means any textile material including yarns, yarn intermediates, fibers, non-woven materials, natural materials, synthetic materials, and any other textile material, fabrics made of these materials and products made from fabrics (e.g., garments and other articles). The textile or fabric may be in the form of knits, wovens, denims, non-wovens, felts, yarns, and towelling. The textile may be cellulose based such as natural cellulosics, including cotton, flax/linen, jute, ramie, sisal or coir or manmade cellulosics (e.g. originating from wood pulp) including viscose/rayon, ramie, cellulose acetate fibers (tricell), lyocell or blends thereof. The textile or fabric may also be non-cellulose based such as natural polyamides including wool, camel, cashmere, mohair, rabit and silk or synthetic polymer such as nylon, aramid, polyester, acrylic, polypropylen and spandex/elastane, or blends thereof as well as blend of cellulose based and non-cellulose based fibers. Examples of blends are blends of cotton and/or rayon/viscose with one or more companion material such as wool, synthetic fibers (e.g. polyamide fibers, acrylic fibers, polyester fibers, polyvinyl alcohol fibers, polyvinyl chloride fibers, polyurethane fibers, polyurea fibers, aramid fibers), and cellulose-containing fibers (e.g. rayon/viscose, ramie, flax/linen, jute, cellulose acetate fibers, lyocell). Fabric may be conventional washable laundry, for example stained household laundry. When the term fabric or garment is used, it is intended to include the broader term textiles as well.

Variant: The term "variant" means a polypeptide having mannanase activity comprising an alteration, i.e., a substitution, insertion, and/or deletion of one or more amino acid residues at one or more positions. A substitution means a replacement of an amino acid occupying a position with a different amino acid; a deletion means removal of an amino acid occupying a position; and an insertion means adding 1-3 amino acids adjacent to an amino acid occupying a position. The variants of the present invention typically have at least 50%, e.g., at least 60%, at least 70%, at least 80%, at least 90%, at least 95%, or at least 100% of the mannanase activity of the parent polypeptide.

In describing the variants of the present invention, the nomenclature described below is adapted for ease of reference. The accepted IUPAC single letter or three letter amino acid abbreviation is employed.

For an amino acid substitution, the following nomenclature is used: Original amino acid, position, substituted amino acid. Accordingly, the substitution of tyrosine at position 93 with glutamine may be designated as "Tyr93Gln" or more typically "Y93Q". Multiple mutations may be separated by a space, a comma or addition marks ("+"), for example "Y93Q+A136P" represents substitutions at position 93 of tyrosine (Y) with glutamine (Q) and at position 136 of alanine (A) with proline (P). An "X" preceding a position means that any original amino acid at that position may be substituted. For example, X93Q means that any amino acid residue at position 93 other than Q is substituted with Q. This allows for designation of substitution to a particular amino acid in different parent mannanases, where the original amino acid may vary among different parent polypeptides.

DETAILED DESCRIPTION OF THE INVENTION

Compositions Comprising Polypeptides Having Mannanase Activity

As indicated above, one aspect of the invention relates to compositions comprising at least first and second mannanases, wherein (A) the first mannanase is a glycoside hydrolase (GH) family 5 mannanase or a variant or fragment thereof having mannanase activity; and (B) the second mannanase is a glycoside hydrolase (GH) family 26 mannanase or a variant or fragment thereof having mannanase activity.

In another aspect, the composition comprising at least first and second mannanases, the first mannanase (A) is a variant of a parent mannanase comprising at least one modification at a position corresponding to a position selected from positions 1, 2, 3, 4, 5, 6, 8, 9, 10, 11, 13, 14, 15, 16, 17, 18, 19, 21, 23, 30, 32, 33, 34, 35, 37, 38, 39, 41, 44, 45, 47, 57, 59, 60, 62, 63, 65, 66, 67, 68, 70, 71, 74, 77, 78, 79, 80, 81, 82, 83, 93, 95, 96, 97, 98, 100, 104, 107, 108, 110, 111, 114, 115, 116, 118, 119, 131, 132, 133, 135, 136, 139, 142, 143, 146, 147, 150, 152, 154, 164, 167, 169, 172, 173, 174, 175, 176, 177, 180, 181, 183, 184, 185, 196, 199, 200, 201, 202, 203, 205, 206, 210, 212, 213, 214, 215, 226, 228, 229, 230, 234, 235, 241, 242, 243, 244, 245, 250, 254, 257, 258, 259, 260, 261, 262, 266, 267, 268, 270, 271, 272, 273, 276, 279, 280, 283, 285, 286, 288, 289, 290, 292, 293, 294, 295, 296, 298, 299, 300 and 301, wherein:

numbering is according to SEQ ID NO: 2, each modification is independently a substitution or a deletion, the variant has mannanase activity, and the variant has at least 59%, e.g. at least 60%, at least 61%, at least 62%, at least 63%, at least 65%, at least 70%, at least 75%, at least 80%, at least 85%, at least 90%, at least 95%, at least 96%, at least 97%, at least 98%, or at least 99%, but less than 100% sequence identity to the mature polypeptide of SEQ ID NO: 2.

In another aspect, the invention relates to compositions wherein the first mannanase is a polypeptide of an amino acid sequence having at least 59%, e.g. at least 60%, at least 61%, at least 62%, at least 63%, at least 65%, at least 70%, at least 75%, at least 80%, at least 85%, at least 90%, at least 95%, at least 96%, at least 97%, at least 98%, or at least 99% sequence identity to SEQ ID NO: 2, or first mannanase is a polypeptide consisting of SEQ ID NO: 2.

In an aspect, the invention relates to compositions wherein the first mannanase is a polypeptide of an amino acid sequence having at least 59%, e.g. at least 60%, at least 61%, at least 62%, at least 63%, at least 65%, at least 70%, at least 75%, at least 80%, at least 85%, at least 90%, at least 95%, at least 96%, at least 97%, at least 98%, or at least 99% sequence identity to SEQ ID NO: 2, or first mannanase is a polypeptide consisting of SEQ ID NO: 17, SEQ ID NO: 18, SEQ ID NO: 19, SEQ ID NO: 20, SEQ ID NO: 21, SEQ ID NO: 22, or SEQ ID NO: 23.

In another aspect, the invention relates to compositions comprising at least first and second mannanases, wherein the second mannanase (B) is selected from the group consisting of:

(a) a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16;

(b) a variant of the polypeptide in (a), wherein the variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28 or 29 positions compared to SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16;

(c) a polypeptide comprising the polypeptide of (a) or (b) and an N-terminal and/or C-terminal His-tag and/or HQ-tag;

(d) a polypeptide comprising the polypeptide of (a) or (b) and an N-terminal and/or C-terminal extension of up to 10 amino acids, e.g. 1, 2, 3, 4, 5, 6, 7, 8, 9 or 10 amino acids; and (e) a fragment of the polypeptide of (a) or (b) having mannanase activity and having at least 90% of the length of the mature polypeptide of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16.

In another aspect, the composition comprising at least first and second mannanases, the first mannanase (A) is a variant of a parent mannanase comprising at least one modification at a position corresponding to a position selected from positions 1, 2, 3, 4, 5, 6, 8, 9, 10, 11, 13, 14, 15, 16, 17, 18, 19, 21, 23, 30, 32, 33, 34, 35, 37, 38, 39, 41, 44, 45, 47, 57, 59, 60, 62, 63, 65, 66, 67, 68, 70, 71, 74, 77, 78, 79, 80, 81, 82, 83, 93, 95, 96, 97, 98, 100, 104, 107, 108, 110, 111, 114, 115, 116, 118, 119, 131, 132, 133, 135, 136, 139, 142, 143, 146, 147, 150, 152, 154, 164, 167, 169, 172, 173, 174, 175, 176, 177, 180, 181, 183, 184, 185, 196, 199, 200, 201, 202, 203, 205, 206, 210, 212, 213, 214, 215, 226, 228, 229, 230, 234, 235, 241, 242, 243, 244, 245, 250, 254, 257, 258, 259, 260, 261, 262, 266, 267, 268, 270, 271, 272, 273, 276, 279, 280, 283, 285, 286, 288, 289, 290, 292, 293, 294, 295, 296, 298, 299, 300 and 301, wherein numbering is according to SEQ ID NO: 2, and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16.

In another aspect, the composition comprises at least a first and second mannanase, the first mannanase is a polypeptide of an amino acid sequence having at least 59%, e.g. at least 60%, at least 61%, at least 62%, at least 63%, at least 65%, at least 70%, at least 75%, at least 80%, at least 85%, at least 90%, at least 95%, at least 96%, at least 97%, at least 98%, or at least 99% sequence identity to SEQ ID NO: 2, or first mannanase is a polypeptide consisting of SEQ ID NO: 17, SEQ ID NO: 18, SEQ ID NO: 19, SEQ ID NO: 20, SEQ ID NO: 21, SEQ ID NO: 22, or SEQ ID NO: 23, and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 3, SEQ ID NO: 4, SEQ ID NO: 5, SEQ ID NO: 6, SEQ ID NO: 7, SEQ ID NO:

8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16.

First Mannanase

As noted above, the first mannanase in compositions of the invention is a glycoside hydrolase family 5 (GH5) mannanase or a variant or fragment thereof having mannanase activity.

In a particular aspect, the composition of the invention comprises a first mannanase comprising a substitution in at least one of positions 3, 37, 47, 77, 82, 83, 93, 98, 116, 135, 136, 241, 257, 258, 260, 288, 294 and 295 compared to its parent mannanase.

In this aspect, the first mannanase may e.g. comprise at least two substitutions compared to the parent and be selected from the group consisting of:

(a) a variant comprising a first substitution in at least one amino acid position selected from positions 260, 288, 294 and 295, and a second substitution in at least one other position in said variant; and (b) a variant comprising substitutions in any two or more positions selected from positions 3, 37, 47, 77, 82, 83, 93, 98, 116, 135, 136, 241, 257 and 258.

It will be apparent that variants (a) and (b) are not mutually exclusive, and that a first mannanase of the invention may be a variant comprising the substitutions of both (a) and (b). Thus, the first mannanase may comprise a substitution in at least one amino acid position selected from positions 260, 288, 294 and 295 together with substitutions in any two or more positions selected from positions 3, 37, 47, 77, 82, 83, 93, 98, 116, 135, 136, 241, 257 and 258.

When the first mannanase is a variant (a) as defined above, the variant may comprise a second substitution in at least one position selected from positions 1, 2, 3, 4, 5, 6, 8, 11, 13, 14, 18, 30, 32, 33, 34, 35, 37, 41, 45, 47, 57, 59, 60, 63, 65, 70, 71, 74, 77, 78, 80, 82, 83, 93, 95, 97, 98, 100, 104, 108, 111, 114, 116, 118, 119, 131, 133, 135, 136, 139, 142, 143, 150, 169, 172, 174, 176, 177, 180, 183, 184, 185, 196, 200, 202, 203, 205, 210, 213, 228, 229, 234, 235, 241, 243, 244, 250, 254, 257, 262, 266, 268, 270, 272, 273, 276, 279, 280, 283, 286, 290, 296, and 298, wherein numbering is according to SEQ ID NO: 2.

It will be understood that when the first mannanase is a variant (a), the variant may have more than one "first substitution" and/or more than one "second substitution" compared to its parent. In other words, the word "first" in this context refers to a substitution in at least one position selected from positions 260, 288, 294 and 295 relative to SEQ ID NO: 2, while the word "second" in this context refers to a substitution in any one or more positions other than those of the first substitution.

In one embodiment, when the first mannanase is a variant (a), it comprises a second substitution in at least one position selected from positions 14, 37, 47, 77, 81, 82, 83, 93, 98, 116, 135, 136, 241, 242, 257 and 258 of the polypeptide of SEQ ID NO: 2.

In another embodiment, the first mannanase is a variant (a) comprising at least two substitutions in positions selected from the group of positions: 14+260, 14+288, 14+294, 14+295, 37+260, 37+288, 37+294, 37+295, 47+260, 47+288, 47+294, 47+295, 77+260, 77+288, 77+294, 77+295, 81+260, 81+288, 81+294, 81+295, 82+260, 82+288, 82+294, 82+295, 83+260, 83+288, 83+294, 83+295, 93+260, 93+288, 93+294, 93+295, 98+260, 98+288, 98+294, 98+295, 116+260, 116+288, 116+294, 116+295, 135+260, 135+288, 135+294, 135+295, 136+260, 136+288, 136+294, 136+295, 241+260, 241+288, 241+294, 241+295, 242+260, 242+288, 242+294, 242+295, 257+260, 257+288, 257+294, 257+295, 258+260, 258+288, 258+294, 258+295 and 260+288, wherein numbering is according to SEQ ID NO: 2.

In a further embodiment, the first mannanase may comprise at least two substitutions selected from A1G, A1V, N2E, S3P, G4D, F5H, Y6H, Y6M, Y6F, Y6W, Y6H, S8T, S8P, S8R, T11K, T11R, Y13F, D14S, D14K, N18V, N18R, A30T, Y32F, Y32W, K33Q, D34G, Q35L, T37P, E41V, E41N, N45G, G47S, G47A, D57N, G59Q, Q60R, K63R, K63Q, D65E, R70K, N71S, S74K, E77T, E77N, D78G, H80K, V82R, V82I, V82S, A83P, A83S, Y93Q, Y93A, S95D, A97R, S98P, S98D, N100Y, D104A, D104G, E108S, S111A, S111K, S111R, I114Q, I114M, I114W, K116R, D118K, T119R, S131T, E133R, E133Q, D135P, A136P, D139A, D139R, K142M, K142V, K142S, K142R, Q143R, N150T, N150R, N150S, Q169A, Q169R, Q169K, H172R, Y174R, Y174L, Y174W, Y174F, R176Q, E177S, E177Y, N180R, P183T, P183G, Q184E, Q184K, R185G, Y196W, Y196F, N200T, S202R, Q203T, R205K, R210L, R210G, R210M, N213V, N213D, T228S, N229D, E234F, E234Y, A235K, A235R, S241C, Q243K, Q243E, R244K, R244V, A250G, K254Y, G257W, G257E, G257A, G257G, W260F, Y262F, S266A, D268N, A270D, N272M, N272T, N273E, N273D, A276E, A276W, A276D, N279D, N279E, T280L, N283W, N283H, Y286W, Y286F, L288I, E290A, L294P, L294K, L294I, L294R, L294V, L294H, S295K, S295V, S295P, S295L, S295R, S295A, S295N, S295M, S295I, T296S and F298Y.

Accordingly, the at least two substitutions may be any combination of those listed above. Such at least two substitutions may be selected from the group consisting of: A1G+N2E, A1G+S3P, A1G+G4D, A1G+F5H, A1G+Y6H, A1G+Y6M, A1G+Y6F, A1G+Y6W, A1G+Y6H, A1G+S8T, A1G+S8P, A1G+S8R, A1G+T11K, A1G+T11R, A1G+Y13F, A1G+D14S, A1G+D14K, A1G+N18V, A1G+N18R, A1G+A30T, A1G+Y32F, A1G+Y32W, A1G+K33Q, A1G+D34G, A1G+Q35L, A1G+T37P, A1G+E41V, A1G+E41N, A1G+N45G, A1G+G47S, A1G+G47A, A1G+D57N, A1G+G59Q, A1G+Q60R, A1G+K63R, A1G+K63Q, A1G+D65E, A1G+R70K, A1G+N71S, A1G+S74K, A1G+E77T, A1G+E77N, A1G+D78G, A1G+H80K, A1G+V82R, A1G+V82I, A1G+V82S, A1G+A83P, A1G+A83S, A1G+Y93Q, A1G+Y93A, A1G+S95D, A1G+A97R, A1G+S98P, A1G+S98D, A1G+N100Y, A1G+D104A, A1G+D104G, A1G+E108S, A1G+S111A, A1G+S111K, A1G+S111R, A1G+I114Q, A1G+I114M, A1G+I114W, A1G+K116R, A1G+D118K, A1G+T119R, A1G+S131T, A1G+E133R, A1G+E133Q, A1G+D135P, A1G+A136P, A1G+D139A, A1G+D139R, A1G+K142M, A1G+K142V, A1G+K142S, A1G+K142R, A1G+Q143R, A1G+N150T, A1G+N150R, A1G+N150S, A1G+Q169A, A1G+Q169R, A1G+Q169K, A1G+H172R, A1G+Y174R, A1G+Y174L, A1G+Y174W, A1G+Y174F, A1G+R176Q, A1G+E177S, A1G+E177Y, A1G+N180R, A1G+P183T, A1G+P183G, A1G+Q184E, A1G+Q184K, A1G+R185G, A1G+Y196W, A1G+Y196F, A1G+N200T, A1G+S202R, A1G+Q203T, A1G+R205K, A1G+R210L, A1G+R210G, A1G+R210M, A1G+N213V, A1G+N213D, A1G+T228S, A1G+N229D, A1G+E234F, A1G+E234Y, A1G+A235K, A1G+A235R, A1G+S241C, A1G+Q243K, A1G+Q243E, A1G+R244K, A1G+R244V, A1G+A250G, A1G+K254Y, A1G+G257W, A1G+G257E, A1G+G257A, A1G+W260F, A1G+Y262F, A1G+S266A, A1G+D268N, A1G+A270D, A1G+N272M, A1G+N272T, A1G+N273E, A1G+N273D, A1G+A276E, A1G+A276W, A1G+A276D, A1G+N279D, A1G+N279E, A1G+T280L, A1G+N283W, A1G+N283H, A1G+Y286W, A1G+Y286F, A1G+L288I, A1G+E290A, A1G+L294P, A1G+L294K, A1G+L294I, A1G+L294R, A1G+L294V, A1G+L294H, A1G+S295K, A1G+S295V, A1G+S295P, A1G+S295L, A1G+S295R, A1G+S295A, A1G+S295N, A1G+S295M, A1G+S295I, A1G+T296S, A1G+F298Y, A1V+N2E, A1V+S3P, A1V+G4D, A1V+F5H, A1V+Y6H, A1V+Y6M, A1V+Y6F, A1V+Y6W, A1V+Y6H, A1V+S8T, A1V+S8P, A1V+S8R, A1V+T11K, A1V+T11R, A1V+Y13F, A1V+D14S, A1V+D14K, A1V+N18V, A1V+N18R, A1V+A30T, A1V+Y32F, A1V+Y32W, A1V+K33Q, A1V+D34G, A1V+Q35L, A1V+T37P, A1V+E41V, A1V+E41N, A1V+N45G, A1V+G47S, A1V+G47A, A1V+D57N, A1V+G59Q, A1V+Q60R, A1V+K63R, A1V+K63Q, A1V+D65E, A1V+R70K, A1V+N71S, A1V+S74K, A1V+E77T, A1V+E77N, A1V+D78G, A1V+H80K, A1V+V82R, A1V+V82I, A1V+V82S, A1V+A83P, A1V+A83S, A1V+Y93Q, A1V+Y93A, A1V+S95D, A1V+A97R, A1V+S98P, A1V+S98D, A1V+N100Y, A1V+D104A, A1V+D104G, A1V+E108S, A1V+S111A, A1V+S111K, A1V+S111R, A1V+I114Q, A1V+I114M, A1V+I114W, A1V+K116R, A1V+D118K, A1V+T119R, A1V+S131T, A1V+E133R, A1V+E133Q, A1V+D135P, A1V+A136P, A1V+D139A, A1V+D139R, A1V+K142M, A1V+K142V, A1V+K142S, A1V+K142R, A1V+Q143R, A1V+N150T, A1V+N150R, A1V+N150S, A1V+Q169A, A1V+Q169R, A1V+Q169K, A1V+H172R, A1V+Y174R, A1V+Y174L, A1V+Y174W, A1V+Y174F, A1V+R176Q, A1V+E177S, A1V+E177Y, A1V+N180R, A1V+P183T, A1V+P183G, A1V+Q184E, A1V+Q184K, A1V+R185G, A1V+Y196W, A1V+Y196F, A1V+N200T, A1V+S202R, A1V+Q203T, A1V+R205K, A1V+R210L, A1V+R210G, A1V+R210M, A1V+N213V, A1V+N213D, A1V+T228S, A1V+N229D, A1V+E234F, A1V+E234Y, A1V+A235K, A1V+A235R, A1V+S241C, A1V+Q243K, A1V+Q243E, A1V+R244K, A1V+R244V, A1V+A250G, A1V+K254Y, A1V+G257W, A1V+G257E, A1V+G257A, A1V+W260F, A1V+Y262F, A1V+S266A, A1V+D268N, A1V+A270D, A1V+N272M, A1V+N272T, A1V+N273E, A1V+N273D, A1V+A276E, A1V+A276W, A1V+A276D, A1V+N279D, A1V+N279E, A1V+T280L, A1V+N283W, A1V+N283H, A1V+Y286W, A1V+Y286F, A1V+L288I, A1V+E290A, A1V+L294P, A1V+L294K, A1V+L294I, A1V+L294R, A1V+L294V, A1V+L294H, A1V+S295K, A1V+S295V, A1V+S295P, A1V+S295L, A1V+S295R, A1V+S295A, A1V+S295N, A1V+S295M, A1V+S295I, A1V+T296S, A1V+F298Y, N2E+S3P, N2E+G4D, N2E+F5H, N2E+Y6H, N2E+Y6M, N2E+Y6F, N2E+Y6W, N2E+Y6H, N2E+S8T, N2E+S8P, N2E+S8R, N2E+T11K, N2E+T11R, N2E+Y13F, N2E+D14S, N2E+D14K, N2E+N18V, N2E+N18R, N2E+A30T, N2E+Y32F, N2E+Y32W, N2E+K33Q, N2E+D34G, N2E+Q35L, N2E+T37P, N2E+E41V, N2E+E41N, N2E+N45G, N2E+G47S, N2E+G47A, N2E+D57N, N2E+G59Q, N2E+Q60R, N2E+K63R, N2E+K63Q, N2E+D65E, N2E+R70K, N2E+N71S, N2E+S74K, N2E+E77T, N2E+E77N, N2E+D78G, N2E+H80K, N2E+V82R, N2E+V82I, N2E+V82S, N2E+A83P, N2E+A83S, N2E+Y93Q, N2E+Y93A, N2E+S95D, N2E+A97R, N2E+S98P, N2E+S98D, N2E+N100Y, N2E+D104A, N2E+D104G, N2E+E108S, N2E+S111A, N2E+S111K, N2E+S111R, N2E+I114Q, N2E+I114M, N2E+I114W, N2E+K116R, N2E+D118K, N2E+T119R, N2E+S131T, N2E+E133R, N2E+E133Q, N2E+D135P, N2E+A136P, N2E+D139A, N2E+D139R, N2E+K142M, N2E+K142V, N2E+K142S, N2E+K142R, N2E+Q143R, N2E+N150T, N2E+N150R, N2E+N150S, N2E+Q169A, N2E+Q169R, N2E+Q169K, N2E+H172R, N2E+Y174R, N2E+Y174L, N2E+Y174W, N2E+Y174F, N2E+R176Q, N2E+E177S, N2E+E177Y, N2E+N180R, N2E+P183T, N2E+P183G, N2E+Q184E, N2E+Q184K, N2E+R185G,

N2E+Y196W, N2E+Y196F, N2E+N200T, N2E+S202R, N2E+Q203T, N2E+R205K, N2E+R210L, N2E+R210G, N2E+R210M, N2E+N213V, N2E+N213D, N2E+T228S, N2E+N229D, N2E+E234F, N2E+E234Y, N2E+A235K, N2E+A235R, N2E+S241C, N2E+Q243K, N2E+Q243E, N2E+R244K, N2E+R244V, N2E+A250G, N2E+K254Y, N2E+G257W, N2E+G257E, N2E+G257A, N2E+W260F, N2E+Y262F, N2E+S266A, N2E+D268N, N2E+A270D, N2E+N272M, N2E+N272T, N2E+N273E, N2E+N273D, N2E+A276E, N2E+A276W, N2E+A276D, N2E+N279D, N2E+N279E, N2E+T280L, N2E+N283W, N2E+N283H, N2E+Y286W, N2E+Y286F, N2E+L288I, N2E+E290A, N2E+L294P, N2E+L294K, N2E+L294I, N2E+L294R, N2E+L294V, N2E+L294H, N2E+S295K, N2E+S295V, N2E+S295P, N2E+S295L, N2E+S295R, N2E+S295A, N2E+S295N, N2E+S295M, N2E+S295I, N2E+T296S, N2E+F298Y, S3P+G4D, S3P+F5H, S3P+Y6H, S3P+Y6M, S3P+Y6F, S3P+Y6W, S3P+Y6H, S3P+S8T, S3P+S8P, S3P+S8R, S3P+T11K, S3P+T11R, S3P+Y13F, S3P+D14S, S3P+D14K, S3P+N18V, S3P+N18R, S3P+A30T, S3P+Y32F, S3P+Y32W, S3P+K33Q, S3P+D34G, S3P+Q35L, S3P+T37P, S3P+E41V, S3P+E41N, S3P+N45G, S3P+G47S, S3P+G47A, S3P+D57N, S3P+G59Q, S3P+Q60R, S3P+K63R, S3P+K63Q, S3P+D65E, S3P+R70K, S3P+N71S, S3P+S74K, S3P+E77T, S3P+E77N, S3P+D78G, S3P+H80K, S3P+V82R, S3P+V82I, S3P+V82S, S3P+A83P, S3P+A83S, S3P+Y93Q, S3P+Y93A, S3P+S95D, S3P+A97R, S3P+S98P, S3P+S98D, S3P+N100Y, S3P+D104A, S3P+D104G, S3P+E108S, S3P+S111A, S3P+S111K, S3P+S111R, S3P+I114Q, S3P+I114M, S3P+I114W, S3P+K116R, S3P+D118K, S3P+T119R, S3P+S131T, S3P+E133R, S3P+E133Q, S3P+D135P, S3P+A136P, S3P+D139A, S3P+D139R, S3P+K142M, S3P+K142V, S3P+K142S, S3P+K142R, S3P+Q143R, S3P+N150T, S3P+N150R, S3P+N150S, S3P+Q169A, S3P+Q169R, S3P+Q169K, S3P+H172R, S3P+Y174R, S3P+Y174L, S3P+Y174W, S3P+Y174F, S3P+R176Q, S3P+E177S, S3P+E177Y, S3P+N180R, S3P+P183T, S3P+P183G, S3P+Q184E, S3P+Q184K, S3P+R185G, S3P+Y196W, S3P+Y196F, S3P+N200T, S3P+S202R, S3P+Q203T, S3P+R205K, S3P+R210L, S3P+R210G, S3P+R210M, S3P+N213V, S3P+N213D, S3P+T228S, S3P+N229D, S3P+E234F, S3P+E234Y, S3P+A235K, S3P+A235R, S3P+S241C, S3P+Q243K, S3P+Q243E, S3P+R244K, S3P+R244V, S3P+A250G, S3P+K254Y, S3P+G257W, S3P+G257E, S3P+G257A, S3P+W260F, S3P+Y262F, S3P+S266A, S3P+D268N, S3P+A270D, S3P+N272M, S3P+N272T, S3P+N273E, S3P+N273D, S3P+A276E, S3P+A276W, S3P+A276D, S3P+N279D, S3P+N279E, S3P+T280L, S3P+N283W, S3P+N283H, S3P+Y286W, S3P+Y286F, S3P+L288I, S3P+E290A, S3P+L294P, S3P+L294K, S3P+L294I, S3P+L294R, S3P+L294V, S3P+L294H, S3P+S295K, S3P+S295V, S3P+S295P, S3P+S295L, S3P+S295R, S3P+S295A, S3P+S295N, S3P+S295M, S3P+S295I, S3P+T296S, S3P+F298Y, G4D+F5H, G4D+Y6H, G4D+Y6M, G4D+Y6F, G4D+Y6W, G4D+Y6H, G4D+S8T, G4D+S8P, G4D+S8R, G4D+T11K, G4D+T11R, G4D+Y13F, G4D+D14S, G4D+D14K, G4D+N18V, G4D+N18R, G4D+A30T, G4D+Y32F, G4D+Y32W, G4D+K33Q, G4D+D34G, G4D+Q35L, G4D+T37P, G4D+E41V, G4D+E41N, G4D+N45G, G4D+G47S, G4D+G47A, G4D+D57N, G4D+G59Q, G4D+Q60R, G4D+K63R, G4D+K63Q, G4D+D65E, G4D+R70K, G4D+N71S, G4D+S74K, G4D+E77T, G4D+E77N, G4D+D78G, G4D+H80K, G4D+V82R, G4D+V82I, G4D+V82S, G4D+A83P, G4D+A83S, G4D+Y93Q, G4D+Y93A, G4D+S95D, G4D+A97R, G4D+S98P, G4D+S98D, G4D+N100Y, G4D+D104A, G4D+

D104G, G4D+E108S, G4D+S111A, G4D+S111K, G4D+ S111R, G4D+I114Q, G4D+I114M, G4D+I114W, G4D+ K116R, G4D+D118K, G4D+T119R, G4D+S131T, G4D+ E133R, G4D+E133Q, G4D+D135P, G4D+A136P, G4D+ D139A, G4D+D139R, G4D+K142M, G4D+K142V, G4D+ K142S, G4D+K142R, G4D+Q143R, G4D+N150T, G4D+ N150R, G4D+N150S, G4D+Q169A, G4D+Q169R, G4D+ Q169K, G4D+H172R, G4D+Y174R, G4D+Y174L, G4D+ Y174W, G4D+Y174F, G4D+R176Q, G4D+E177S, G4D+ E177Y, G4D+N180R, G4D+P183T, G4D+P183G, G4D+ Q184E, G4D+Q184K, G4D+R185G, G4D+Y196W, G4D+ Y196F, G4D+N200T, G4D+S202R, G4D+Q203T, G4D+ R205K, G4D+R210L, G4D+R210G, G4D+R210M, G4D+ N213V, G4D+N213D, G4D+T228S, G4D+N229D, G4D+ E234F, G4D+E234Y, G4D+A235K, G4D+A235R, G4D+ S241C, G4D+Q243K, G4D+Q243E, G4D+R244K, G4D+ R244V, G4D+A250G, G4D+K254Y, G4D+G257W, G4D+ G257E, G4D+G257A, G4D+W260F, G4D+Y262F, G4D+ S266A, G4D+D268N, G4D+A270D, G4D+N272M, G4D+ N272T, G4D+N273E, G4D+N273D, G4D+A276E, G4D+ A276W, G4D+A276D, G4D+N279D, G4D+N279E, G4D+ T280L, G4D+N283W, G4D+N283H, G4D+Y286W, G4D+ Y286F, G4D+L288I, G4D+E290A, G4D+L294P, G4D+ L294K, G4D+L294I, G4D+L294R, G4D+L294V, G4D+ L294H, G4D+S295K, G4D+S295V, G4D+S295P, G4D+ S295L, G4D+S295R, G4D+S295A, G4D+S295N, G4D+ S295M, G4D+S295I, G4D+T296S, G4D+F298Y, F5H+ Y6H, F5H+Y6M, F5H+Y6F, F5H+Y6W, F5H+Y6H, F5H+ S8T, F5H+S8P, F5H+S8R, F5H+T11K, F5H+T11R, F5H+ Y13F, F5H+D14S, F5H+D14K, F5H+N18V, F5H+N18R, F5H+A30T, F5H+Y32F, F5H+Y32W, F5H+K33Q, F5H+ D34G, F5H+Q35L, F5H+T37P, F5H+E41V, F5H+E41N, F5H+N45G, F5H+G47S, F5H+G47A, F5H+D57N, F5H+ G59Q, F5H+Q60R, F5H+K63R, F5H+K63Q, F5H+D65E, F5H+R70K, F5H+N71S, F5H+S74K, F5H+E77T, F5H+ E77N, F5H+D78G, F5H+H80K, F5H+V82R, F5H+V82I, F5H+V82S, F5H+A83P, F5H+A83S, F5H+Y93Q, F5H+ Y93A, F5H+S95D, F5H+A97R, F5H+S98P, F5H+S98D, F5H+N100Y, F5H+D104A, F5H+D104G, F5H+E108S, F5H+S111A, F5H+S111K, F5H+S111R, F5H+I114Q, F5H+I114M, F5H+I114W, F5H+K116R, F5H+D118K, F5H+T119R, F5H+S131T, F5H+E133R, F5H+E133Q, F5H+D135P, F5H+A136P, F5H+D139A, F5H+D139R, F5H+K142M, F5H+K142V, F5H+K142S, F5H+K142R, F5H+Q143R, F5H+N150T, F5H+N150R, F5H+N150S, F5H+Q169A, F5H+Q169R, F5H+Q169K, F5H+H172R, F5H+Y174R, F5H+Y174L, F5H+Y174W, F5H+Y174F, F5H+R176Q, F5H+E177S, F5H+E177Y, F5H+N180R, F5H+P183T, F5H+P183G, F5H+Q184E, F5H+Q184K, F5H+R185G, F5H+Y196W, F5H+Y196F, F5H+N200T, F5H+S202R, F5H+Q203T, F5H+R205K, F5H+R210L, F5H+R210G, F5H+R210M, F5H+N213V, F5H+N213D, F5H+T228S, F5H+N229D, F5H+E234F, F5H+E234Y, F5H+A235K, F5H+A235R, F5H+S241C, F5H+Q243K, F5H+Q243E, F5H+R244K, F5H+R244V, F5H+A250G, F5H+K254Y, F5H+G257W, F5H+G257E, F5H+G257A, F5H+W260F, F5H+Y262F, F5H+S266A, F5H+D268N, F5H+A270D, F5H+N272M, F5H+N272T, F5H+N273E, F5H+N273D, F5H+A276E, F5H+A276W, F5H+A276D, F5H+N279D, F5H+N279E, F5H+T280L, F5H+N283W, F5H+N283H, F5H+Y286W, F5H+Y286F, F5H+L288I, F5H+E290A, F5H+L294P, F5H+L294K, F5H+L294I, F5H+L294R, F5H+L294V, F5H+L294H, F5H+S295K, F5H+S295V, F5H+S295P, F5H+S295L, F5H+S295R, F5H+ S295A, F5H+S295N, F5H+S295M, F5H+S295I, F5H+ T296S, F5H+F298Y, Y6H+S8T, Y6H+S8P, Y6H+S8R, Y6H+T11K, Y6H+T11R, Y6H+Y13F, Y6H+D14S, Y6H+ D14K, Y6H+N18V, Y6H+N18R, Y6H+A30T, Y6H+Y32F, Y6H+Y32W, Y6H+K33Q, Y6H+D34G, Y6H+Q35L, Y6H+ T37P, Y6H+E41V, Y6H+E41N, Y6H+N45G, Y6H+G47S, Y6H+G47A, Y6H+D57N, Y6H+G59Q, Y6H+Q60R, Y6H+ K63R, Y6H+K63Q, Y6H+D65E, Y6H+R70K, Y6H+N71S, Y6H+S74K, Y6H+E77T, Y6H+E77N, Y6H+D78G, Y6H+ H80K, Y6H+V82R, Y6H+V82I, Y6H+V82S, Y6H+A83P, Y6H+A83S, Y6H+Y93Q, Y6H+Y93A, Y6H+S95D, Y6H+ A97R, Y6H+S98P, Y6H+S98D, Y6H+N100Y, Y6H+ D104A, Y6H+D104G, Y6H+E108S, Y6H+S111A, Y6H+ S111K, Y6H+S111R, Y6H+I114Q, Y6H+I114M, Y6H+ I114W, Y6H+K116R, Y6H+D118K, Y6H+T119R, Y6H+ S131T, Y6H+E133R, Y6H+E133Q, Y6H+D135P, Y6H+ A136P, Y6H+D139A, Y6H+D139R, Y6H+K142M, Y6H+ K142V, Y6H+K142S, Y6H+K142R, Y6H+Q143R, Y6H+ N150T, Y6H+N150R, Y6H+N150S, Y6H+Q169A, Y6H+ Q169R, Y6H+Q169K, Y6H+H172R, Y6H+Y174R, Y6H+ Y174L, Y6H+Y174W, Y6H+Y174F, Y6H+R176Q, Y6H+ E177S, Y6H+E177Y, Y6H+N180R, Y6H+P183T, Y6H+ P183G, Y6H+Q184E, Y6H+Q184K, Y6H+R185G, Y6H+ Y196W, Y6H+Y196F, Y6H+N200T, Y6H+S202R, Y6H+ Q203T, Y6H+R205K, Y6H+R210L, Y6H+R210G, Y6H+ R210M, Y6H+N213V, Y6H+N213D, Y6H+T228S, Y6H+ N229D, Y6H+E234F, Y6H+E234Y, Y6H+A235K, Y6H+ A235R, Y6H+S241C, Y6H+Q243K, Y6H+Q243E, Y6H+ R244K, Y6H+R244V, Y6H+A250G, Y6H+K254Y, Y6H+ G257W, Y6H+G257E, Y6H+G257A, Y6H+W260F, Y6H+ Y262F, Y6H+S266A, Y6H+D268N, Y6H+A270D, Y6H+ N272M, Y6H+N272T, Y6H+N273E, Y6H+N273D, Y6H+ A276E, Y6H+A276W, Y6H+A276D, Y6H+N279D, Y6H+ N279E, Y6H+T280L, Y6H+N283W, Y6H+N283H, Y6H+ Y286W, Y6H+Y286F, Y6H+L288I, Y6H+E290A, Y6H+ L294P, Y6H+L294K, Y6H+L294I, Y6H+L294R, Y6H+ L294V, Y6H+L294H, Y6H+S295K, Y6H+S295V, Y6H+ S295P, Y6H+S295L, Y6H+S295R, Y6H+S295A, Y6H+ S295N, Y6H+S295M, Y6H+S295I, Y6H+T296S, Y6H+ F298Y, Y6M+S8T, Y6M+S8P, Y6M+S8R, Y6M+T11K, Y6M+T11R, Y6M+Y13F, Y6M+D14S, Y6M+D14K, Y6M+N18V, Y6M+N18R, Y6M+A30T, Y6M+Y32F, Y6M+Y32W, Y6M+K33Q, Y6M+D34G, Y6M+Q35L, Y6M+T37P, Y6M+E41V, Y6M+E41N, Y6M+N45G, Y6M+ G47S, Y6M+G47A, Y6M+D57N, Y6M+G59Q, Y6M+ Q60R, Y6M+K63R, Y6M+K63Q, Y6M+D65E, Y6M+ R70K, Y6M+N71S, Y6M+S74K, Y6M+E77T, Y6M+E77N, Y6M+D78G, Y6M+H80K, Y6M+V82R, Y6M+V82I, Y6M+V82S, Y6M+A83P, Y6M+A83S, Y6M+Y93Q, Y6M+Y93A, Y6M+S95D, Y6M+A97R, Y6M+S98P, Y6M+S98D, Y6M+N100Y, Y6M+D104A, Y6M+D104G, Y6M+E108S, Y6M+S111A, Y6M+S111K, Y6M+S111R, Y6M+I114Q, Y6M+I114M, Y6M+I114W, Y6M+K116R, Y6M+D118K, Y6M+T119R, Y6M+S131T, Y6M+E133R, Y6M+E133Q, Y6M+D135P, Y6M+A136P, Y6M+D139A, Y6M+D139R, Y6M+K142M, Y6M+K142V, Y6M+K142S, Y6M+K142R, Y6M+Q143R, Y6M+N150T, Y6M+N150R, Y6M+N150S, Y6M+Q169A, Y6M+Q169R, Y6M+Q169K, Y6M+H172R, Y6M+Y174R, Y6M+Y174L, Y6M+Y174W, Y6M+Y174F, Y6M+R176Q, Y6M+E177S, Y6M+E177Y, Y6M+N180R, Y6M+P183T, Y6M+P183G, Y6M+Q184E, Y6M+Q184K, Y6M+R185G, Y6M+Y196W, Y6M+Y196F, Y6M+N200T, Y6M+S202R, Y6M+Q203T, Y6M+R205K, Y6M+R210L, Y6M+R210G, Y6M+R210M, Y6M+N213V, Y6M+N213D, Y6M+T228S, Y6M+N229D, Y6M+E234F, Y6M+E234Y, Y6M+A235K, Y6M+A235R, Y6M+S241C, Y6M+Q243K, Y6M+Q243E, Y6M+R244K, Y6M+R244V, Y6M+A250G, Y6M+K254Y, Y6M+G257W, Y6M+G257E, Y6M+G257A, Y6M+W260F, Y6M+Y262F, Y6M+S266A, Y6M+D268N, Y6M+A270D, Y6M+N272M, Y6M+N272T,

Y6M+N273E, Y6M+N273D, Y6M+A276E, Y6M+A276W, Y6M+A276D, Y6M+N279D, Y6M+N279E, Y6M+T280L, Y6M+N283W, Y6M+N283H, Y6M+Y286W, Y6M+Y286F, Y6M+L288I, Y6M+E290A, Y6M+L294P, Y6M+L294K, Y6M+L294I, Y6M+L294R, Y6M+L294V, Y6M+L294H, Y6M+S295K, Y6M+S295V, Y6M+S295P, Y6M+S295L, Y6M+S295R, Y6M+S295A, Y6M+S295N, Y6M+S295M, Y6M+S295I, Y6M+T296S, Y6M+F298Y, Y6F+S8T, Y6F+S8P, Y6F+S8R, Y6F+T11K, Y6F+T11R, Y6F+Y13F, Y6F+D14S, Y6F+D14K, Y6F+N18V, Y6F+N18R, Y6F+A30T, Y6F+Y32F, Y6F+Y32W, Y6F+K33Q, Y6F+D34G, Y6F+Q35L, Y6F+T37P, Y6F+E41V, Y6F+E41N, Y6F+N45G, Y6F+G47S, Y6F+G47A, Y6F+D57N, Y6F+G59Q, Y6F+Q60R, Y6F+K63R, Y6F+K63Q, Y6F+D65E, Y6F+R70K, Y6F+N71S, Y6F+S74K, Y6F+E77T, Y6F+E77N, Y6F+D78G, Y6F+H80K, Y6F+V82R, Y6F+V82I, Y6F+V82S, Y6F+A83P, Y6F+A83S, Y6F+Y93Q, Y6F+Y93A, Y6F+S95D, Y6F+A97R, Y6F+S98P, Y6F+S98D, Y6F+N100Y, Y6F+D104A, Y6F+D104G, Y6F+E108S, Y6F+S111A, Y6F+S111K, Y6F+S111R, Y6F+I114Q, Y6F+I114M, Y6F+I114W, Y6F+K116R, Y6F+D118K, Y6F+T119R, Y6F+S131T, Y6F+E133R, Y6F+E133Q, Y6F+D135P, Y6F+A136P, Y6F+D139A, Y6F+D139R, Y6F+K142M, Y6F+K142V, Y6F+K142S, Y6F+K142R, Y6F+Q143R, Y6F+N150T, Y6F+N150R, Y6F+N150S, Y6F+Q169A, Y6F+Q169R, Y6F+Q169K, Y6F+H172R, Y6F+Y174R, Y6F+Y174L, Y6F+Y174W, Y6F+Y174F, Y6F+R176Q, Y6F+E177S, Y6F+E177Y, Y6F+N180R, Y6F+P183T, Y6F+P183G, Y6F+Q184E, Y6F+Q184K, Y6F+R185G, Y6F+Y196W, Y6F+Y196F, Y6F+N200T, Y6F+S202R, Y6F+Q203T, Y6F+R205K, Y6F+R210L, Y6F+R210G, Y6F+R210M, Y6F+N213V, Y6F+N213D, Y6F+T228S, Y6F+N229D, Y6F+E234F, Y6F+E234Y, Y6F+A235K, Y6F+A235R, Y6F+S241C, Y6F+Q243K, Y6F+Q243E, Y6F+R244K, Y6F+R244V, Y6F+A250G, Y6F+K254Y, Y6F+G257W, Y6F+G257E, Y6F+G257A, Y6F+W260F, Y6F+Y262F, Y6F+S266A, Y6F+D268N, Y6F+A270D, Y6F+N272M, Y6F+N272T, Y6F+N273E, Y6F+N273D, Y6F+A276E, Y6F+A276W, Y6F+A276D, Y6F+N279D, Y6F+N279E, Y6F+T280L, Y6F+N283W, Y6F+N283H, Y6F+Y286W, Y6F+Y286F, Y6F+L288I, Y6F+E290A, Y6F+L294P, Y6F+L294K, Y6F+L294I, Y6F+L294R, Y6F+L294V, Y6F+L294H, Y6F+S295K, Y6F+S295V, Y6F+S295P, Y6F+S295L, Y6F+S295R, Y6F+S295A, Y6F+S295N, Y6F+S295M, Y6F+S295I, Y6F+T296S, Y6F+F298Y, Y6W+S8T, Y6W+S8P, Y6W+S8R, Y6W+T11K, Y6W+T11R, Y6W+Y13F, Y6W+D14S, Y6W+D14K, Y6W+N18V, Y6W+N18R, Y6W+A30T, Y6W+Y32F, Y6W+Y32W, Y6W+K33Q, Y6W+D34G, Y6W+Q35L, Y6W+T37P, Y6W+E41V, Y6W+E41N, Y6W+N45G, Y6W+G47S, Y6W+G47A, Y6W+D57N, Y6W+G59Q, Y6W+Q60R, Y6W+K63R, Y6W+K63Q, Y6W+D65E, Y6W+R70K, Y6W+N71S, Y6W+S74K, Y6W+E77T, Y6W+E77N, Y6W+D78G, Y6W+H80K, Y6W+V82R, Y6W+V82I, Y6W+V82S, Y6W+A83P, Y6W+A83S, Y6W+Y93Q, Y6W+Y93A, Y6W+S95D, Y6W+A97R, Y6W+S98P, Y6W+S98D, Y6W+N100Y, Y6W+D104A, Y6W+D104G, Y6W+E108S, Y6W+S111A, Y6W+S111K, Y6W+S111R, Y6W+I114Q, Y6W+I114M, Y6W+I114W, Y6W+K116R, Y6W+D118K, Y6W+T119R, Y6W+S131T, Y6W+E133R, Y6W+E133Q, Y6W+D135P, Y6W+A136P, Y6W+D139A, Y6W+D139R, Y6W+K142M, Y6W+K142V, Y6W+K142S, Y6W+K142R, Y6W+Q143R, Y6W+N150T, Y6W+N150R, Y6W+N150S, Y6W+Q169A, Y6W+Q169R, Y6W+Q169K, Y6W+H172R, Y6W+Y174R, Y6W+Y174L, Y6W+Y174W, Y6W+Y174F, Y6W+R176Q, Y6W+E177S, Y6W+E177Y, Y6W+N180R, Y6W+P183T, Y6W+P183G, Y6W+Q184E, Y6W+Q184K, Y6W+R185G, Y6W+Y196W, Y6W+Y196F, Y6W+N200T, Y6W+S202R, Y6W+Q203T, Y6W+R205K, Y6W+R210L, Y6W+R210G, Y6W+R210M, Y6W+N213V, Y6W+N213D, Y6W+T228S, Y6W+N229D, Y6W+E234F, Y6W+E234Y, Y6W+A235K, Y6W+A235R, Y6W+S241C, Y6W+Q243K, Y6W+Q243E, Y6W+R244K, Y6W+R244V, Y6W+A250G, Y6W+K254Y, Y6W+G257W, Y6W+G257E, Y6W+G257A, Y6W+W260F, Y6W+Y262F, Y6W+S266A, Y6W+D268N, Y6W+A270D, Y6W+N272M, Y6W+N272T, Y6W+N273E, Y6W+N273D, Y6W+A276E, Y6W+A276W, Y6W+A276D, Y6W+N279D, Y6W+N279E, Y6W+T280L, Y6W+N283W, Y6W+N283H, Y6W+Y286W, Y6W+Y286F, Y6W+L288I, Y6W+E290A, Y6W+L294P, Y6W+L294K, Y6W+L294I, Y6W+L294R, Y6W+L294V, Y6W+L294H, Y6W+S295K, Y6W+S295V, Y6W+S295P, Y6W+S295L, Y6W+S295R, Y6W+S295A, Y6W+S295N, Y6W+S295M, Y6W+S295I, Y6W+T296S, Y6W+F298Y, Y6H+S8T, Y6H+S8P, Y6H+S8R, Y6H+T11K, Y6H+T11R, Y6H+Y13F, Y6H+D14S, Y6H+D14K, Y6H+N18V, Y6H+N18R, Y6H+A30T, Y6H+Y32F, Y6H+Y32W, Y6H+K33Q, Y6H+D34G, Y6H+Q35L, Y6H+T37P, Y6H+E41V, Y6H+E41N, Y6H+N45G, Y6H+G47S, Y6H+G47A, Y6H+D57N, Y6H+G59Q, Y6H+Q60R, Y6H+K63R, Y6H+K63Q, Y6H+D65E, Y6H+R70K, Y6H+N71S, Y6H+S74K, Y6H+E77T, Y6H+E77N, Y6H+D78G, Y6H+H80K, Y6H+V82R, Y6H+V82I, Y6H+V82S, Y6H+A83P, Y6H+A83S, Y6H+Y93Q, Y6H+Y93A, Y6H+S95D, Y6H+A97R, Y6H+S98P, Y6H+S98D, Y6H+N100Y, Y6H+D104A, Y6H+D104G, Y6H+E108S, Y6H+S111A, Y6H+S111K, Y6H+S111R, Y6H+I114Q, Y6H+I114M, Y6H+I114W, Y6H+K116R, Y6H+D118K, Y6H+T119R, Y6H+S131T, Y6H+E133R, Y6H+E133Q, Y6H+D135P, Y6H+A136P, Y6H+D139A, Y6H+D139R, Y6H+K142M, Y6H+K142V, Y6H+K142S, Y6H+K142R, Y6H+Q143R, Y6H+N150T, Y6H+N150R, Y6H+N150S, Y6H+Q169A, Y6H+Q169R, Y6H+Q169K, Y6H+H172R, Y6H+Y174R, Y6H+Y174L, Y6H+Y174W, Y6H+Y174F, Y6H+R176Q, Y6H+E177S, Y6H+E177Y, Y6H+N180R, Y6H+P183T, Y6H+P183G, Y6H+Q184E, Y6H+Q184K, Y6H+R185G, Y6H+Y196W, Y6H+Y196F, Y6H+N200T, Y6H+S202R, Y6H+Q203T, Y6H+R205K, Y6H+R210L, Y6H+R210G, Y6H+R210M, Y6H+N213V, Y6H+N213D, Y6H+T228S, Y6H+N229D, Y6H+E234F, Y6H+E234Y, Y6H+A235K, Y6H+A235R, Y6H+S241C, Y6H+Q243K, Y6H+Q243E, Y6H+R244K, Y6H+R244V, Y6H+A250G, Y6H+K254Y, Y6H+G257W, Y6H+G257E, Y6H+G257A, Y6H+W260F, Y6H+Y262F, Y6H+S266A, Y6H+D268N, Y6H+A270D, Y6H+N272M, Y6H+N272T, Y6H+N273E, Y6H+N273D, Y6H+A276E, Y6H+A276W, Y6H+A276D, Y6H+N279D, Y6H+N279E, Y6H+T280L, Y6H+N283W, Y6H+N283H, Y6H+Y286W, Y6H+Y286F, Y6H+L288I, Y6H+E290A, Y6H+L294P, Y6H+L294K, Y6H+L294I, Y6H+L294R, Y6H+L294V, Y6H+L294H, Y6H+S295K, Y6H+S295V, Y6H+S295P, Y6H+S295L, Y6H+S295R, Y6H+S295A, Y6H+S295N, Y6H+S295M, Y6H+S295I, Y6H+T296S, Y6H+F298Y, S8T+T11K, S8T+T11R, S8T+Y13F, S8T+D14S, S8T+D14K, S8T+N18V, S8T+N18R, S8T+A30T, S8T+Y32F, S8T+Y32W, S8T+K33Q, S8T+D34G, S8T+Q35L, S8T+T37P, S8T+E41V, S8T+E41N, S8T+N45G, S8T+G47S, S8T+G47A, S8T+D57N, S8T+G59Q, S8T+Q60R, S8T+K63R, S8T+K63Q, S8T+D65E, S8T+R70K, S8T+N71S, S8T+S74K, S8T+E77T, S8T+E77N, S8T+D78G, S8T+H80K, S8T+V82R, S8T+V82I, S8T+V82S, S8T+A83P, S8T+A83S, S8T+Y93Q, S8T+Y93A, S8T+S95D, S8T+A97R, S8T+S98P, S8T+S98D, S8T+N100Y, S8T+D104A, S8T+D104G, S8T+E108S, S8T+S111A, S8T+S111K, S8T+S111R, S8T+I114Q, S8T+

I114M, S8T+I114W, S8T+K116R, S8T+D118K, S8T+ T119R, S8T+S131T, S8T+E133R, S8T+E133Q, S8T+ D135P, S8T+A136P, S8T+D139A, S8T+D139R, S8T+ K142M, S8T+K142V, S8T+K142S, S8T+K142R, S8T+ Q143R, S8T+N150T, S8T+N150R, S8T+N150S, S8T+ Q169A, S8T+Q169R, S8T+Q169K, S8T+H172R, S8T+ Y174R, S8T+Y174L, S8T+Y174W, S8T+Y174F, S8T+ R176Q, S8T+E177S, S8T+E177Y, S8T+N180R, S8T+ P183T, S8T+P183G, S8T+Q184E, S8T+Q184K, S8T+ R185G, S8T+Y196W, S8T+Y196F, S8T+N200T, S8T+ S202R, S8T+Q203T, S8T+R205K, S8T+R210L, S8T+ R210G, S8T+R210M, S8T+N213V, S8T+N213D, S8T+ T228S, S8T+N229D, S8T+E234F, S8T+E234Y, S8T+ A235K, S8T+A235R, S8T+S241C, S8T+Q243K, S8T+ Q243E, S8T+R244K, S8T+R244V, S8T+A250G, S8T+ K254Y, S8T+G257W, S8T+G257E, S8T+G257A, S8T+ W260F, S8T+Y262F, S8T+S266A, S8T+D268N, S8T+ A270D, S8T+N272M, S8T+N272T, S8T+N273E, S8T+ N273D, S8T+A276E, S8T+A276W, S8T+A276D, S8T+ N279D, S8T+N279E, S8T+T280L, S8T+N283W, S8T+ N283H, S8T+Y286W, S8T+Y286F, S8T+L288I, S8T+ E290A, S8T+L294P, S8T+L294K, S8T+L294I, S8T+ L294R, S8T+L294V, S8T+L294H, S8T+S295K, S8T+ S295V, S8T+S295P, S8T+S295L, S8T+S295R, S8T+ S295A, S8T+S295N, S8T+S295M, S8T+S295I, S8T+ T296S, S8T+F298Y, S8P+T11K, S8P+T11R, S8P+Y13F, S8P+D14S, S8P+D14K, S8P+N18V, S8P+N18R, S8P+ A30T, S8P+Y32F, S8P+Y32W, S8P+K33Q, S8P+D34G, S8P+Q35L, S8P+T37P, S8P+E41V, S8P+E41N, S8P+ N45G, S8P+G47S, S8P+G47A, S8P+D57N, S8P+G59Q, S8P+Q60R, S8P+K63R, S8P+K63Q, S8P+D65E, S8P+ R70K, S8P+N71S, S8P+S74K, S8P+E77T, S8P+E77N, S8P+D78G, S8P+H80K, S8P+V82R, S8P+V82I, S8P+ V82S, S8P+A83P, S8P+A83S, S8P+Y93Q, S8P+Y93A, S8P+S95D, S8P+A97R, S8P+S98P, S8P+S98D, S8P+ N100Y, S8P+D104A, S8P+D104G, S8P+E108S, S8P+ S111A, S8P+S111K, S8P+S111R, S8P+I114Q, S8P+I114M, S8P+I114W, S8P+K116R, S8P+D118K, S8P+T119R, S8P+ S131T, S8P+E133R, S8P+E133Q, S8P+D135P, S8P+ A136P, S8P+D139A, S8P+D139R, S8P+K142M, S8P+ K142V, S8P+K142S, S8P+K142R, S8P+Q143R, S8P+ N150T, S8P+N150R, S8P+N150S, S8P+Q169A, S8P+ Q169R, S8P+Q169K, S8P+H172R, S8P+Y174R, S8P+ Y174L, S8P+Y174W, S8P+Y174F, S8P+R176Q, S8P+ E177S, S8P+E177Y, S8P+N180R, S8P+P183T, S8P+ P183G, S8P+Q184E, S8P+Q184K, S8P+R185G, S8P+ Y196W, S8P+Y196F, S8P+N200T, S8P+S202R, S8P+ Q203T, S8P+R205K, S8P+R210L, S8P+R210G, S8P+ R210M, S8P+N213V, S8P+N213D, S8P+T228S, S8P+ N229D, S8P+E234F, S8P+E234Y, S8P+A235K, S8P+ A235R, S8P+S241C, S8P+Q243K, S8P+Q243E, S8P+ R244K, S8P+R244V, S8P+A250G, S8P+K254Y, S8P+ G257W, S8P+G257E, S8P+G257A, S8P+W260F, S8P+ Y262F, S8P+S266A, S8P+D268N, S8P+A270D, S8P+ N272M, S8P+N272T, S8P+N273E, S8P+N273D, S8P+ A276E, S8P+A276W, S8P+A276D, S8P+N279D, S8P+ N279E, S8P+T280L, S8P+N283W, S8P+N283H, S8P+ Y286W, S8P+Y286F, S8P+L288I, S8P+E290A, S8P+ L294P, S8P+L294K, S8P+L294I, S8P+L294R, S8P+ L294V, S8P+L294H, S8P+S295K, S8P+S295V, S8P+ S295P, S8P+S295L, S8P+S295R, S8P+S295A, S8P+ S295N, S8P+S295M, S8P+S295I, S8P+T296S, S8P+ F298Y, S8R+T11K, S8R+T11R, S8R+Y13F, S8R+D14S, S8R+D14K, S8R+N18V, S8R+N18R, S8R+A30T, S8R+ Y32F, S8R+Y32W, S8R+K33Q, S8R+D34G, S8R+Q35L, S8R+T37P, S8R+E41V, S8R+E41N, S8R+N45G, S8R+ G47S, S8R+G47A, S8R+D57N, S8R+G59Q, S8R+Q60R, S8R+K63R, S8R+K63Q, S8R+D65E, S8R+R70K, S8R+ N71S, S8R+S74K, S8R+E77T, S8R+E77N, S8R+D78G, S8R+H80K, S8R+V82R, S8R+V82I, S8R+V82S, S8R+ A83P, S8R+A83S, S8R+Y93Q, S8R+Y93A, S8R+S95D, S8R+A97R, S8R+S98P, S8R+S98D, S8R+N100Y, S8R+ D104A, S8R+D104G, S8R+E108S, S8R+S111A, S8R+ S111K, S8R+S111R, S8R+I114Q, S8R+I114M, S8R+ I114W, S8R+K116R, S8R+D118K, S8R+T119R, S8R+ S131T, S8R+E133R, S8R+E133Q, S8R+D135P, S8R+ A136P, S8R+D139A, S8R+D139R, S8R+K142M, S8R+ K142V, S8R+K142S, S8R+K142R, S8R+Q143R, S8R+ N150T, S8R+N150R, S8R+N150S, S8R+Q169A, S8R+ Q169R, S8R+Q169K, S8R+H172R, S8R+Y174R, S8R+ Y174L, S8R+Y174W, S8R+Y174F, S8R+R176Q, S8R+ E177S, S8R+E177Y, S8R+N180R, S8R+P183T, S8R+ P183G, S8R+Q184E, S8R+Q184K, S8R+R185G, S8R+ Y196W, S8R+Y196F, S8R+N200T, S8R+S202R, S8R+ Q203T, S8R+R205K, S8R+R210L, S8R+R210G, S8R+ R210M, S8R+N213V, S8R+N213D, S8R+T228S, S8R+ N229D, S8R+E234F, S8R+E234Y, S8R+A235K, S8R+ A235R, S8R+S241C, S8R+Q243K, S8R+Q243E, S8R+ R244K, S8R+R244V, S8R+A250G, S8R+K254Y, S8R+ G257W, S8R+G257E, S8R+G257A, S8R+W260F, S8R+ Y262F, S8R+S266A, S8R+D268N, S8R+A270D, S8R+ N272M, S8R+N272T, S8R+N273E, S8R+N273D, S8R+ A276E, S8R+A276W, S8R+A276D, S8R+N279D, S8R+ N279E, S8R+T280L, S8R+N283W, S8R+N283H, S8R+ Y286W, S8R+Y286F, S8R+L288I, S8R+E290A, S8R+ L294P, S8R+L294K, S8R+L294I, S8R+L294R, S8R+ L294V, S8R+L294H, S8R+S295K, S8R+S295V, S8R+ S295P, S8R+S295L, S8R+S295R, S8R+S295A, S8R+ S295N, S8R+S295M, S8R+S295I, S8R+T296S, S8R+ F298Y, T11K+Y13F, T11K+D14S, T11K+D14K, T11K+ N18V, T11K+N18R, T11K+A30T, T11K+Y32F, T11K+ Y32W, T11K+K33Q, T11K+D34G, T11K+Q35L, T11K+ T37P, T11K+E41V, T11K+E41N, T11K+N45G, T11K+ G47S, T11K+G47A, T11K+D57N, T11K+G59Q, T11K+ Q60R, T11K+K63R, T11K+K63Q, T11K+D65E, T11K+ R70K, T11K+N71S, T11K+S74K, T11K+E77T, T11K+ E77N, T11K+D78G, T11K+H80K, T11K+V82R, T11K+ V82I, T11K+V82S, T11K+A83P, T11K+A83S, T11K+ Y93Q, T11K+Y93A, T11K+S95D, T11K+A97R, T11K+ S98P, T11K+S98D, T11K+N100Y, T11K+D104A, T11K+ D104G, T11K+E108S, T11K+S111A, T11K+S111K, T11K+S111R, T11K+I114Q, T11K+I114M, T11K+114W, T11K+K116R, T11K+D118K, T11K+T119R, T11K+ S131T, T11K+E133R, T11K+E133Q, T11K+D135P, T11K+ A136P, T11K+D139A, T11K+D139R, T11K+K142M, T11K+K142V, T11K+K142S, T11K+K142R, T11K+ Q143R, T11K+N150T, T11K+N150R, T11K+N150S, T11K+Q169A, T11K+Q169R, T11K+Q169K, T11K+ H172R, T11K+Y174R, T11K+Y174L, T11K+Y174W, T11K+Y174F, T11K+R176Q, T11K+E177S, T11K+E177Y, T11K+N180R, T11K+P183T, T11K+P183G, T11K+ Q184E, T11K+Q184K, T11K+R185G, T11K+Y196W, T11K+Y196F, T11K+N200T, T11K+S202R, T11K+Q203T, T11K+R205K, T11K+R210L, T11K+R210G, T11K+ R210M, T11K+N213V, T11K+N213D, T11K+T228S, T11K+N229D, T11K+E234F, T11K+E234Y, T11K+ A235K, T11K+A235R, T11K+S241C, T11K+Q243K, T11K+Q243E, T11K+R244K, T11K+R244V, T11K+ A250G, T11K+K254Y, T11K+G257W, T11K+G257E, T11K+G257A, T11K+W260F, T11K+Y262F, T11K+ S266A, T11K+D268N, T11K+A270D, T11K+N272M, T11K+N272T, T11K+N273E, T11K+N273D, T11K+ A276E, T11K+A276W, T11K+A276D, T11K+N279D, T11K+N279E, T11K+T280L, T11K+N283W, T11K+

N283H, T11K+Y286W, T11K+Y286F, T11K+L288I, T11K+E290A, T11K+L294P, T11K+L294K, T11K+L294I, T11K+L294R, T11K+L294V, T11K+L294H, T11K+S295K, T11K+S295V, T11K+S295P, T11K+S295L, T11K+S295R, T11K+S295A, T11K+S295N, T11K+S295M, T11K+S295I, T11K+T296S, T11K+F298Y, T11R+Y13F, T11R+D14S, T11R+D14K, T11R+N18V, T11R+N18R, T11R+A30T, T11R+Y32F, T11R+Y32W, T11R+K33Q, T11R+D34G, T11R+Q35L, T11R+T37P, T11R+E41V, T11R+E41N, T11R+N45G, T11R+G47S, T11R+G47A, T11R+D57N, T11R+G59Q, T11R+Q60R, T11R+K63R, T11R+K63Q, T11R+D65E, T11R+R70K, T11R+N71S, T11R+S74K, T11R+E77T, T11R+E77N, T11R+D78G, T11R+H80K, T11R+V82R, T11R+V82I, T11R+V82S, T11R+A83P, T11R+A83S, T11R+Y93Q, T11R+Y93A, T11R+S95D, T11R+A97R, T11R+S98P, T11R+S98D, T11R+N100Y, T11R+D104A, T11R+D104G, T11R+E108S, T11R+S111A, T11R+S111K, T11R+S111R, T11R+I114Q, T11R+I114M, T11R+I114W, T11R+K116R, T11R+D118K, T11R+T119R, T11R+S131T, T11R+E133R, T11R+E133Q, T11R+D135P, T11R+A136P, T11R+D139A, T11R+D139R, T11R+K142M, T11R+K142V, T11R+K142S, T11R+K142R, T11R+Q143R, T11R+N150T, T11R+N150R, T11R+N150S, T11R+Q169A, T11R+Q169R, T11R+Q169K, T11R+H172R, T11R+Y174R, T11R+Y174L, T11R+Y174W, T11R+Y174F, T11R+R176Q, T11R+E177S, T11R+E177Y, T11R+N180R, T11R+P183T, T11R+P183G, T11R+Q184E, T11R+Q184K, T11R+R185G, T11R+Y196W, T11R+Y196F, T11R+N200T, T11R+S202R, T11R+Q203T, T11R+R205K, T11R+R210L, T11R+R210G, T11R+R210M, T11R+N213V, T11R+N213D, T11R+T228S, T11R+N229D, T11R+E234F, T11R+E234Y, T11R+A235K, T11R+A235R, T11R+S241C, T11R+Q243K, T11R+Q243E, T11R+R244K, T11R+R244V, T11R+A250G, T11R+K254Y, T11R+G257W, T11R+G257E, T11R+G257A, T11R+W260F, T11R+Y262F, T11R+S266A, T11R+D268N, T11R+A270D, T11R+N272M, T11R+N272T, T11R+N273E, T11R+N273D, T11R+A276E, T11R+A276W, T11R+A276D, T11R+N279D, T11R+N279E, T11R+T280L, T11R+N283W, T11R+N283H, T11R+Y286W, T11R+Y286F, T11R+L288I, T11R+E290A, T11R+L294P, T11R+L294K, T11R+L294I, T11R+L294R, T11R+L294V, T11R+L294H, T11R+S295K, T11R+S295V, T11R+S295P, T11R+S295L, T11R+S295R, T11R+S295A, T11R+S295N, T11R+S295M, T11R+S295I, T11R+T296S, T11R+F298Y, Y13F+D14S, Y13F+D14K, Y13F+N18V, Y13F+N18R, Y13F+A30T, Y13F+Y32F, Y13F+Y32W, Y13F+K33Q, Y13F+D34G, Y13F+Q35L, Y13F+T37P, Y13F+E41V, Y13F+E41N, Y13F+N45G, Y13F+G47S, Y13F+G47A, Y13F+D57N, Y13F+G59Q, Y13F+Q60R, Y13F+K63R, Y13F+K63Q, Y13F+D65E, Y13F+R70K, Y13F+N71S, Y13F+S74K, Y13F+E77T, Y13F+E77N, Y13F+D78G, Y13F+H80K, Y13F+V82R, Y13F+V82I, Y13F+V82S, Y13F+A83P, Y13F+A83S, Y13F+Y93Q, Y13F+Y93A, Y13F+S95D, Y13F+A97R, Y13F+S98P, Y13F+S98D, Y13F+N100Y, Y13F+D104A, Y13F+D104G, Y13F+E108S, Y13F+S111A, Y13F+S111K, Y13F+S111R, Y13F+I114Q, Y13F+I114M, Y13F+I114W, Y13F+K116R, Y13F+D118K, Y13F+T119R, Y13F+S131T, Y13F+E133R, Y13F+E133Q, Y13F+D135P, Y13F+A136P, Y13F+D139A, Y13F+D139R, Y13F+K142M, Y13F+K142V, Y13F+K142S, Y13F+K142R, Y13F+Q143R, Y13F+N150T, Y13F+N150R, Y13F+N150S, Y13F+Q169A, Y13F+Q169R, Y13F+Q169K, Y13F+H172R, Y13F+Y174R, Y13F+Y174L, Y13F+Y174W, Y13F+Y174F, Y13F+R176Q, Y13F+E177S, Y13F+E177Y, Y13F+N180R, Y13F+P183T, Y13F+P183G, Y13F+Q184E, Y13F+Q184K, Y13F+R185G, Y13F+Y196W, Y13F+Y196F, Y13F+N200T, Y13F+S202R, Y13F+Q203T, Y13F+R205K, Y13F+R210L, Y13F+R210G, Y13F+R210M, Y13F+N213V, Y13F+N213D, Y13F+T228S, Y13F+N229D, Y13F+E234F, Y13F+E234Y, Y13F+A235K, Y13F+A235R, Y13F+S241C, Y13F+Q243K, Y13F+Q243E, Y13F+R244K, Y13F+R244V, Y13F+A250G, Y13F+K254Y, Y13F+G257W, Y13F+G257E, Y13F+G257A, Y13F+W260F, Y13F+Y262F, Y13F+S266A, Y13F+D268N, Y13F+A270D, Y13F+N272M, Y13F+N272T, Y13F+N273E, Y13F+N273D, Y13F+A276E, Y13F+A276W, Y13F+A276D, Y13F+N279D, Y13F+N279E, Y13F+T280L, Y13F+N283W, Y13F+N283H, Y13F+Y286W, Y13F+Y286F, Y13F+L288I, Y13F+E290A, Y13F+L294P, Y13F+L294K, Y13F+L294I, Y13F+L294R, Y13F+L294V, Y13F+L294H, Y13F+S295K, Y13F+S295V, Y13F+S295P, Y13F+S295L, Y13F+S295R, Y13F+S295A, Y13F+S295N, Y13F+S295M, Y13F+S295I, Y13F+T296S, Y13F+F298Y, D14S+N18V, D14S+N18R, D14S+A30T, D14S+Y32F, D14S+Y32W, D14S+K33Q, D14S+D34G, D14S+Q35L, D14S+T37P, D14S+E41V, D14S+E41N, D14S+N45G, D14S+G47S, D14S+G47A, D14S+D57N, D14S+G59Q, D14S+Q60R, D14S+K63R, D14S+K63Q, D14S+D65E, D14S+R70K, D14S+N71S, D14S+S74K, D14S+E77T, D14S+E77N, D14S+D78G, D14S+H80K, D14S+V82R, D14S+V82I, D14S+V82S, D14S+A83P, D14S+A83S, D14S+Y93Q, D14S+Y93A, D14S+S95D, D14S+A97R, D14S+S98P, D14S+S98D, D14S+N100Y, D14S+D104A, D14S+D104G, D14S+E108S, D14S+S111A, D14S+S111K, D14S+S111R, D14S+I114Q, D14S+I114M, D14S+I114W, D14S+K116R, D14S+D118K, D14S+T119R, D14S+S131T, D14S+E133R, D14S+E133Q, D14S+D135P, D14S+A136P, D14S+D139A, D14S+D139R, D14S+K142M, D14S+K142V, D14S+K142S, D14S+K142R, D14S+Q143R, D14S+N150T, D14S+N150R, D14S+N150S, D14S+Q169A, D14S+Q169R, D14S+Q169K, D14S+H172R, D14S+Y174R, D14S+Y174L, D14S+Y174W, D14S+Y174F, D14S+R176Q, D14S+E177S, D14S+E177Y, D14S+N180R, D14S+P183T, D14S+P183G, D14S+Q184E, D14S+Q184K, D14S+R185G, D14S+Y196W, D14S+Y196F, D14S+N200T, D14S+S202R, D14S+Q203T, D14S+R205K, D14S+R210L, D14S+R210G, D14S+R210M, D14S+N213V, D14S+N213D, D14S+T228S, D14S+N229D, D14S+E234F, D14S+E234Y, D14S+A235K, D14S+A235R, D14S+S241C, D14S+Q243K, D14S+Q243E, D14S+R244K, D14S+R244V, D14S+A250G, D14S+K254Y, D14S+G257W, D14S+G257E, D14S+G257A, D14S+W260F, D14S+Y262F, D14S+S266A, D14S+D268N, D14S+A270D, D14S+N272M, D14S+N272T, D14S+N273E, D14S+N273D, D14S+A276E, D14S+A276W, D14S+A276D, D14S+N279D, D14S+N279E, D14S+T280L, D14S+N283W, D14S+N283H, D14S+Y286W, D14S+Y286F, D14S+L288I, D14S+E290A, D14S+L294P, D14S+L294K, D14S+L294I, D14S+L294R, D14S+L294V, D14S+L294H, D14S+S295K, D14S+S295V, D14S+S295P, D14S+S295L, D14S+S295R, D14S+S295A, D14S+S295N, D14S+S295M, D14S+S295I, D14S+T296S, D14S+F298Y, D14K+N18V, D14K+N18R, D14K+A30T, D14K+Y32F, D14K+Y32W, D14K+K33Q, D14K+D34G, D14K+Q35L, D14K+T37P, D14K+E41V, D14K+E41N, D14K+N45G, D14K+G47S, D14K+G47A, D14K+D57N, D14K+G59Q, D14K+Q60R, D14K+K63R, D14K+K63Q, D14K+D65E, D14K+R70K, D14K+N71S, D14K+S74K, D14K+E77T, D14K+E77N, D14K+D78G, D14K+H80K, D14K+V82R, D14K+V82I, D14K+V82S, D14K+A83P, D14K+A83S, D14K+Y93Q, D14K+Y93A,

D14K+S95D, D14K+A97R, D14K+S98P, D14K+S98D, D14K+N100Y, D14K+D104A, D14K+D104G, D14K+E108S, D14K+S111A, D14K+S111K, D14K+S111R, D14K+I114Q, D14K+I114M, D14K+I114W, D14K+K116R, D14K+D118K, D14K+T119R, D14K+S131T, D14K+E133R, D14K+E133Q, D14K+D135P, D14K+A136P, D14K+D139A, D14K+D139R, D14K+K142M, D14K+K142V, D14K+K142S, D14K+K142R, D14K+Q143R, D14K+N150T, D14K+N150R, D14K+N150S, D14K+Q169A, D14K+Q169R, D14K+Q169K, D14K+H172R, D14K+Y174R, D14K+Y174L, D14K+Y174W, D14K+Y174F, D14K+R176Q, D14K+E177S, D14K+E177Y, D14K+N180R, D14K+P183T, D14K+P183G, D14K+Q184E, D14K+Q184K, D14K+R185G, D14K+Y196W, D14K+Y196F, D14K+N200T, D14K+S202R, D14K+Q203T, D14K+R205K, D14K+R210L, D14K+R210G, D14K+R210M, D14K+N213V, D14K+N213D, D14K+T228S, D14K+N229D, D14K+E234F, D14K+E234Y, D14K+A235K, D14K+A235R, D14K+S241C, D14K+Q243K, D14K+Q243E, D14K+R244K, D14K+R244V, D14K+A250G, D14K+K254Y, D14K+G257W, D14K+G257E, D14K+G257A, D14K+W260F, D14K+Y262F, D14K+S266A, D14K+D268N, D14K+A270D, D14K+N272M, D14K+N272T, D14K+N273E, D14K+N273D, D14K+A276E, D14K+A276W, D14K+A276D, D14K+N279D, D14K+N279E, D14K+T280L, D14K+N283W, D14K+N283H, D14K+Y286W, D14K+Y286F, D14K+L288I, D14K+E290A, D14K+L294P, D14K+L294K, D14K+L294I, D14K+L294R, D14K+L294V, D14K+L294H, D14K+S295K, D14K+S295V, D14K+S295P, D14K+S295L, D14K+S295R, D14K+S295A, D14K+S295N, D14K+S295M, D14K+S295I, D14K+T296S, D14K+F298Y, N18V+A30T, N18V+Y32F, N18V+Y32W, N18V+K33Q, N18V+D34G, N18V+Q35L, N18V+T37P, N18V+E41V, N18V+E41N, N18V+N45G, N18V+G47S, N18V+G47A, N18V+D57N, N18V+G59Q, N18V+Q60R, N18V+K63R, N18V+K63Q, N18V+D65E, N18V+R70K, N18V+N71S, N18V+S74K, N18V+E77T, N18V+E77N, N18V+D78G, N18V+H80K, N18V+V82R, N18V+V82I, N18V+V82S, N18V+A83P, N18V+A83S, N18V+Y93Q, N18V+Y93A, N18V+S95D, N18V+A97R, N18V+S98P, N18V+S98D, N18V+N100Y, N18V+D104A, N18V+D104G, N18V+E108S, N18V+S111A, N18V+S111K, N18V+S111R, N18V+I114Q, N18V+I114M, N18V+I114W, N18V+K116R, N18V+D118K, N18V+T119R, N18V+S131T, N18V+E133R, N18V+E133Q, N18V+D135P, N18V+A136P, N18V+D139A, N18V+D139R, N18V+K142M, N18V+K142V, N18V+K142S, N18V+K142R, N18V+Q143R, N18V+N150T, N18V+N150R, N18V+N150S, N18V+Q169A, N18V+Q169R, N18V+Q169K, N18V+H172R, N18V+Y174R, N18V+Y174L, N18V+Y174W, N18V+Y174F, N18V+R176Q, N18V+E177S, N18V+E177Y, N18V+N180R, N18V+P183T, N18V+P183G, N18V+Q184E, N18V+Q184K, N18V+R185G, N18V+Y196W, N18V+Y196F, N18V+N200T, N18V+S202R, N18V+Q203T, N18V+R205K, N18V+R210L, N18V+R210G, N18V+R210M, N18V+N213V, N18V+N213D, N18V+T228S, N18V+N229D, N18V+E234F, N18V+E234Y, N18V+A235K, N18V+A235R, N18V+S241C, N18V+Q243K, N18V+Q243E, N18V+R244K, N18V+R244V, N18V+A250G, N18V+K254Y, N18V+G257W, N18V+G257E, N18V+G257A, N18V+W260F, N18V+Y262F, N18V+S266A, N18V+D268N, N18V+A270D, N18V+N272M, N18V+N272T, N18V+N273E, N18V+N273D, N18V+A276E, N18V+A276W, N18V+A276D, N18V+N279D, N18V+N279E, N18V+T280L, N18V+N283W, N18V+N283H, N18V+Y286W,

N18V+Y286F, N18V+L288I, N18V+E290A, N18V+L294P, N18V+L294K, N18V+L294I, N18V+L294R, N18V+L294V, N18V+L294H, N18V+S295K, N18V+S295V, N18V+S295P, N18V+S295L, N18V+S295R, N18V+S295A, N18V+S295N, N18V+S295M, N18V+S295I, N18V+T296S, N18V+F298Y, N18R+A30T, N18R+Y32F, N18R+Y32W, N18R+K33Q, N18R+D34G, N18R+Q35L, N18R+T37P, N18R+E41V, N18R+E41N, N18R+N45G, N18R+G47S, N18R+G47A, N18R+D57N, N18R+G59Q, N18R+Q60R, N18R+K63R, N18R+K63Q, N18R+D65E, N18R+R70K, N18R+N71S, N18R+S74K, N18R+E77T, N18R+E77N, N18R+D78G, N18R+H80K, N18R+V82R, N18R+V82I, N18R+V82S, N18R+A83P, N18R+A83S, N18R+Y93Q, N18R+Y93A, N18R+S95D, N18R+A97R, N18R+S98P, N18R+S98D, N18R+N100Y, N18R+D104A, N18R+D104G, N18R+E108S, N18R+S111A, N18R+S111K, N18R+S111R, N18R+I114Q, N18R+I114M, N18R+I114W, N18R+K116R, N18R+D118K, N18R+T119R, N18R+S131T, N18R+E133R, N18R+E133Q, N18R+D135P, N18R+A136P, N18R+D139A, N18R+D139R, N18R+K142M, N18R+K142V, N18R+K142S, N18R+K142R, N18R+Q143R, N18R+N150T, N18R+N150R, N18R+N150S, N18R+Q169A, N18R+Q169R, N18R+Q169K, N18R+H172R, N18R+Y174R, N18R+Y174L, N18R+Y174W, N18R+Y174F, N18R+R176Q, N18R+E177S, N18R+E177Y, N18R+N180R, N18R+P183T, N18R+P183G, N18R+Q184E, N18R+Q184K, N18R+R185G, N18R+Y196W, N18R+Y196F, N18R+N200T, N18R+S202R, N18R+Q203T, N18R+R205K, N18R+R210L, N18R+R210G, N18R+R210M, N18R+N213V, N18R+N213D, N18R+T228S, N18R+N229D, N18R+E234F, N18R+E234Y, N18R+A235K, N18R+A235R, N18R+S241C, N18R+Q243K, N18R+Q243E, N18R+R244K, N18R+R244V, N18R+A250G, N18R+K254Y, N18R+G257W, N18R+G257E, N18R+G257A, N18R+W260F, N18R+Y262F, N18R+S266A, N18R+D268N, N18R+A270D, N18R+N272M, N18R+N272T, N18R+N273E, N18R+N273D, N18R+A276E, N18R+A276W, N18R+A276D, N18R+N279D, N18R+N279E, N18R+T280L, N18R+N283W, N18R+N283H, N18R+Y286W, N18R+Y286F, N18R+L288I, N18R+E290A, N18R+L294P, N18R+L294K, N18R+L294I, N18R+L294R, N18R+L294V, N18R+L294H, N18R+S295K, N18R+S295V, N18R+S295P, N18R+S295L, N18R+S295R, N18R+S295A, N18R+S295N, N18R+S295M, N18R+S295I, N18R+T296S, N18R+F298Y, A30T+Y32F, A30T+Y32W, A30T+K33Q, A30T+D34G, A30T+Q35L, A30T+T37P, A30T+E41V, A30T+E41N, A30T+N45G, A30T+G47S, A30T+G47A, A30T+D57N, A30T+G59Q, A30T+Q60R, A30T+K63R, A30T+K63Q, A30T+D65E, A30T+R70K, A30T+N71S, A30T+S74K, A30T+E77T, A30T+E77N, A30T+D78G, A30T+H80K, A30T+V82R, A30T+V82I, A30T+V82S, A30T+A83P, A30T+A83S, A30T+Y93Q, A30T+Y93A, A30T+S95D, A30T+A97R, A30T+S98P, A30T+S98D, A30T+N100Y, A30T+D104A, A30T+D104G, A30T+E108S, A30T+S111A, A30T+S111K, A30T+S111R, A30T+I114Q, A30T+I114M, A30T+I114W, A30T+K116R, A30T+D118K, A30T+T119R, A30T+S131T, A30T+E133R, A30T+E133Q, A30T+D135P, A30T+A136P, A30T+D139A, A30T+D139R, A30T+K142M, A30T+K142V, A30T+K142S, A30T+K142R, A30T+Q143R, A30T+N150T, A30T+N150R, A30T+N150S, A30T+Q169A, A30T+Q169R, A30T+Q169K, A30T+H172R, A30T+Y174R, A30T+Y174L, A30T+Y174W, A30T+Y174F, A30T+R176Q, A30T+E177S, A30T+E177Y, A30T+N180R, A30T+P183T, A30T+P183G, A30T+Q184E, A30T+Q184K, A30T+R185G, A30T+Y196W,

A30T+Y196F, A30T+N200T, A30T+S202R, A30T+Q203T, A30T+R205K, A30T+R210L, A30T+R210G, A30T+R210M, A30T+N213V, A30T+N213D, A30T+T228S, A30T+N229D, A30T+E234F, A30T+E234Y, A30T+A235K, A30T+A235R, A30T+S241C, A30T+Q243K, A30T+Q243E, A30T+R244K, A30T+R244V, A30T+A250G, A30T+K254Y, A30T+G257W, A30T+G257E, A30T+G257A, A30T+W260F, A30T+Y262F, A30T+S266A, A30T+D268N, A30T+A270D, A30T+N272M, A30T+N272T, A30T+N273E, A30T+N273D, A30T+A276E, A30T+A276W, A30T+A276D, A30T+N279D, A30T+N279E, A30T+T280L, A30T+N283W, A30T+N283H, A30T+Y286W, A30T+Y286F, A30T+L288I, A30T+E290A, A30T+L294P, A30T+L294K, A30T+L294I, A30T+L294R, A30T+L294V, A30T+L294H, A30T+S295K, A30T+S295V, A30T+S295P, A30T+S295L, A30T+S295R, A30T+S295A, A30T+S295N, A30T+S295M, A30T+S295I, A30T+T296S, A30T+F298Y, Y32F+K33Q, Y32F+D34G, Y32F+Q35L, Y32F+T37P, Y32F+E41V, Y32F+E41N, Y32F+N45G, Y32F+G47S, Y32F+G47A, Y32F+D57N, Y32F+G59Q, Y32F+Q60R, Y32F+K63R, Y32F+K63Q, Y32F+D65E, Y32F+R70K, Y32F+N71S, Y32F+S74K, Y32F+E77T, Y32F+E77N, Y32F+D78G, Y32F+H80K, Y32F+V82R, Y32F+V82I, Y32F+V82S, Y32F+A83P, Y32F+A83S, Y32F+Y93Q, Y32F+Y93A, Y32F+S95D, Y32F+A97R, Y32F+S98P, Y32F+S98D, Y32F+N100Y, Y32F+D104A, Y32F+D104G, Y32F+E108S, Y32F+S111A, Y32F+S111K, Y32F+S111R, Y32F+I114Q, Y32F+I114M, Y32F+I114W, Y32F+K116R, Y32F+D118K, Y32F+T119R, Y32F+S131T, Y32F+E133R, Y32F+E133Q, Y32F+D135P, Y32F+A136P, Y32F+D139A, Y32F+D139R, Y32F+K142M, Y32F+K142V, Y32F+K142S, Y32F+K142R, Y32F+Q143R, Y32F+N150T, Y32F+N150R, Y32F+N150S, Y32F+Q169A, Y32F+Q169R, Y32F+Q169K, Y32F+H172R, Y32F+Y174R, Y32F+Y174L, Y32F+Y174W, Y32F+Y174F, Y32F+R176Q, Y32F+E177S, Y32F+E177Y, Y32F+N180R, Y32F+P183T, Y32F+P183G, Y32F+Q184E, Y32F+Q184K, Y32F+R185G, Y32F+Y196W, Y32F+Y196F, Y32F+N200T, Y32F+S202R, Y32F+Q203T, Y32F+R205K, Y32F+R210L, Y32F+R210G, Y32F+R210M, Y32F+N213V, Y32F+N213D, Y32F+T228S, Y32F+N229D, Y32F+E234F, Y32F+E234Y, Y32F+A235K, Y32F+A235R, Y32F+S241C, Y32F+Q243K, Y32F+Q243E, Y32F+R244K, Y32F+R244V, Y32F+A250G, Y32F+K254Y, Y32F+G257W, Y32F+G257E, Y32F+G257A, Y32F+W260F, Y32F+Y262F, Y32F+S266A, Y32F+D268N, Y32F+A270D, Y32F+N272M, Y32F+N272T, Y32F+N273E, Y32F+N273D, Y32F+A276E, Y32F+A276W, Y32F+A276D, Y32F+N279D, Y32F+N279E, Y32F+T280L, Y32F+N283W, Y32F+N283H, Y32F+Y286W, Y32F+Y286F, Y32F+L288I, Y32F+E290A, Y32F+L294P, Y32F+L294K, Y32F+L294I, Y32F+L294R, Y32F+L294V, Y32F+L294H, Y32F+S295K, Y32F+S295V, Y32F+S295P, Y32F+S295L, Y32F+S295R, Y32F+S295A, Y32F+S295N, Y32F+S295M, Y32F+S295I, Y32F+T296S, Y32F+F298Y, Y32W+K33Q, Y32W+D34G, Y32W+Q35L, Y32W+T37P, Y32W+E41V, Y32W+E41N, Y32W+N45G, Y32W+G47S, Y32W+G47A, Y32W+D57N, Y32W+G59Q, Y32W+Q60R, Y32W+K63R, Y32W+K63Q, Y32W+D65E, Y32W+R70K, Y32W+N71S, Y32W+S74K, Y32W+E77T, Y32W+E77N, Y32W+D78G, Y32W+H80K, Y32W+V82R, Y32W+V82I, Y32W+V82S, Y32W+A83P, Y32W+A83S, Y32W+Y93Q, Y32W+Y93A, Y32W+S95D, Y32W+A97R, Y32W+S98P, Y32W+S98D, Y32W+N100Y, Y32W+D104A, Y32W+D104G, Y32W+E108S, Y32W+S111A, Y32W+S111K, Y32W+S111R, Y32W+I114Q, Y32W+I114M, Y32W+I114W, Y32W+K116R, Y32W+D118K, Y32W+T119R, Y32W+S131T, Y32W+E133R, Y32W+E133Q, Y32W+D135P, Y32W+A136P, Y32W+D139A, Y32W+D139R, Y32W+K142M, Y32W+K142V, Y32W+K142S, Y32W+K142R, Y32W+Q143R, Y32W+N150T, Y32W+N150R, Y32W+N150S, Y32W+Q169A, Y32W+Q169R, Y32W+Q169K, Y32W+H172R, Y32W+Y174R, Y32W+Y174L, Y32W+Y174W, Y32W+Y174F, Y32W+R176Q, Y32W+E177S, Y32W+E177Y, Y32W+N180R, Y32W+P183T, Y32W+P183G, Y32W+Q184E, Y32W+Q184K, Y32W+R185G, Y32W+Y196W, Y32W+Y196F, Y32W+N200T, Y32W+S202R, Y32W+Q203T, Y32W+R205K, Y32W+R210L, Y32W+R210G, Y32W+R210M, Y32W+N213V, Y32W+N213D, Y32W+T228S, Y32W+N229D, Y32W+E234F, Y32W+E234Y, Y32W+A235K, Y32W+A235R, Y32W+S241C, Y32W+Q243K, Y32W+Q243E, Y32W+R244K, Y32W+R244V, Y32W+A250G, Y32W+K254Y, Y32W+G257W, Y32W+G257E, Y32W+G257A, Y32W+W260F, Y32W+Y262F, Y32W+S266A, Y32W+D268N, Y32W+A270D, Y32W+N272M, Y32W+N272T, Y32W+N273E, Y32W+N273D, Y32W+A276E, Y32W+A276W, Y32W+A276D, Y32W+N279D, Y32W+N279E, Y32W+T280L, Y32W+N283W, Y32W+N283H, Y32W+Y286W, Y32W+Y286F, Y32W+L288I, Y32W+E290A, Y32W+L294P, Y32W+L294K, Y32W+L294I, Y32W+L294R, Y32W+L294V, Y32W+L294H, Y32W+S295K, Y32W+S295V, Y32W+S295P, Y32W+S295L, Y32W+S295R, Y32W+S295A, Y32W+S295N, Y32W+S295M, Y32W+S295I, Y32W+T296S, Y32W+F298Y, K33Q+D34G, K33Q+Q35L, K33Q+T37P, K33Q+E41V, K33Q+E41N, K33Q+N45G, K33Q+G47S, K33Q+G47A, K33Q+D57N, K33Q+G59Q, K33Q+Q60R, K33Q+K63R, K33Q+K63Q, K33Q+D65E, K33Q+R70K, K33Q+N71S, K33Q+S74K, K33Q+E77T, K33Q+E77N, K33Q+D78G, K33Q+H80K, K33Q+V82R, K33Q+V82I, K33Q+V82S, K33Q+A83P, K33Q+A83S, K33Q+Y93Q, K33Q+Y93A, K33Q+S95D, K33Q+A97R, K33Q+S98P, K33Q+S98D, K33Q+N100Y, K33Q+D104A, K33Q+D104G, K33Q+E108S, K33Q+S111A, K33Q+S111K, K33Q+S111R, K33Q+I114Q, K33Q+I114M, K33Q+I114W, K33Q+K116R, K33Q+D118K, K33Q+T119R, K33Q+S131T, K33Q+E133R, K33Q+E133Q, K33Q+D135P, K33Q+A136P, K33Q+D139A, K33Q+D139R, K33Q+K142M, K33Q+K142V, K33Q+K142S, K33Q+K142R, K33Q+Q143R, K33Q+N150T, K33Q+N150R, K33Q+N150S, K33Q+Q169A, K33Q+Q169R, K33Q+Q169K, K33Q+H172R, K33Q+Y174R, K33Q+Y174L, K33Q+Y174W, K33Q+Y174F, K33Q+R176Q, K33Q+E177S, K33Q+E177Y, K33Q+N180R, K33Q+P183T, K33Q+P183G, K33Q+Q184E, K33Q+Q184K, K33Q+R185G, K33Q+Y196W, K33Q+Y196F, K33Q+N200T, K33Q+S202R, K33Q+Q203T, K33Q+R205K, K33Q+R210L, K33Q+R210G, K33Q+R210M, K33Q+N213V, K33Q+N213D, K33Q+T228S, K33Q+N229D, K33Q+E234F, K33Q+E234Y, K33Q+A235K, K33Q+A235R, K33Q+S241C, K33Q+Q243K, K33Q+Q243E, K33Q+R244K, K33Q+R244V, K33Q+A250G, K33Q+K254Y, K33Q+G257W, K33Q+G257E, K33Q+G257A, K33Q+W260F, K33Q+Y262F, K33Q+S266A, K33Q+D268N, K33Q+A270D, K33Q+N272M, K33Q+N272T, K33Q+N273E, K33Q+N273D, K33Q+A276E, K33Q+A276W, K33Q+A276D, K33Q+N279D, K33Q+N279E, K33Q+T280L, K33Q+N283W, K33Q+N283H, K33Q+Y286W, K33Q+Y286F, K33Q+L288I, K33Q+E290A, K33Q+L294P, K33Q+L294K, K33Q+L294I, K33Q+L294R, K33Q+L294V, K33Q+L294H, K33Q+S295K, K33Q+S295V, K33Q+S295P, K33Q+S295L, K33Q+S295R, K33Q+S295A,

K33Q+S295N, K33Q+S295M, K33Q+S295I, K33Q+T296S, K33Q+F298Y, D34G+Q35L, D34G+T37P, D34G+E41V, D34G+E41N, D34G+N45G, D34G+G47S, D34G+G47V, D34G+D57N, D34G+G59Q, D34G+Q60R, D34G+K63R, D34G+K63Q, D34G+D65E, D34G+R70K, D34G+N71S, D34G+S74K, D34G+E77T, D34G+E77N, D34G+D78G, D34G+H80K, D34G+V82R, D34G+V82I, D34G+V82S, D34G+A83P, D34G+A83S, D34G+Y93Q, D34G+Y93A, D34G+S95D, D34G+A97R, D34G+S98P, D34G+S98D, D34G+N100Y, D34G+D104A, D34G+D104G, D34G+E108S, D34G+S111A, D34G+S111K, D34G+S111R, D34G+I114Q, D34G+I114M, D34G+I114W, D34G+K116R, D34G+D118K, D34G+T119R, D34G+S131T, D34G+E133R, D34G+E133Q, D34G+D135P, D34G+A136P, D34G+D139A, D34G+D139R, D34G+K142M, D34G+K142V, D34G+K142S, D34G+K142R, D34G+Q143R, D34G+N150T, D34G+N150R, D34G+N150S, D34G+Q169A, D34G+Q169R, D34G+Q169K, D34G+H172R, D34G+Y174R, D34G+Y174L, D34G+Y174W, D34G+Y174F, D34G+R176Q, D34G+E177S, D34G+E177Y, D34G+N180R, D34G+P183T, D34G+P183G, D34G+Q184E, D34G+Q184K, D34G+R185G, D34G+Y196W, D34G+Y196F, D34G+N200T, D34G+S202R, D34G+Q203T, D34G+R205K, D34G+R210L, D34G+R210G, D34G+R210M, D34G+N213V, D34G+N213D, D34G+T228S, D34G+N229D, D34G+E234F, D34G+E234Y, D34G+A235K, D34G+A235R, D34G+S241C, D34G+Q243K, D34G+Q243E, D34G+R244K, D34G+R244V, D34G+A250G, D34G+K254Y, D34G+G257W, D34G+G257E, D34G+G257A, D34G+W260F, D34G+Y262F, D34G+S266A, D34G+D268N, D34G+A270D, D34G+N272M, D34G+N272T, D34G+N273E, D34G+N273D, D34G+A276E, D34G+A276W, D34G+A276D, D34G+N279D, D34G+N279E, D34G+T280L, D34G+N283W, D34G+N283H, D34G+Y286W, D34G+Y286F, D34G+L288I, D34G+E290A, D34G+L294P, D34G+L294K, D34G+L294I, D34G+L294R, D34G+L294V, D34G+L294H, D34G+S295K, D34G+S295V, D34G+S295P, D34G+S295L, D34G+S295R, D34G+S295A, D34G+S295N, D34G+S295M, D34G+S295I, D34G+T296S, D34G+F298Y, Q35L+T37P, Q35L+E41V, Q35L+E41N, Q35L+N45G, Q35L+G47S, Q35L+G47A, Q35L+D57N, Q35L+G59Q, Q35L+Q60R, Q35L+K63R, Q35L+K63Q, Q35L+D65E, Q35L+R70K, Q35L+N71S, Q35L+S74K, Q35L+E77T, Q35L+E77N, Q35L+D78G, Q35L+H80K, Q35L+V82R, Q35L+V82I, Q35L+V82S, Q35L+A83P, Q35L+A83S, Q35L+Y93Q, Q35L+Y93A, Q35L+S95D, Q35L+A97R, Q35L+S98P, Q35L+S98D, Q35L+N100Y, Q35L+D104A, Q35L+D104G, Q35L+E108S, Q35L+S111A, Q35L+S111K, Q35L+S111R, Q35L+I114Q, Q35L+I114M, Q35L+I114W, Q35L+K116R, Q35L+D118K, Q35L+T119R, Q35L+S131T, Q35L+E133R, Q35L+E133Q, Q35L+D135P, Q35L+A136P, Q35L+D139A, Q35L+D139R, Q35L+K142M, Q35L+K142V, Q35L+K142S, Q35L+K142R, Q35L+Q143R, Q35L+N150T, Q35L+N150R, Q35L+N150S, Q35L+Q169A, Q35L+Q169R, Q35L+Q169K, Q35L+H172R, Q35L+Y174R, Q35L+Y174L, Q35L+Y174W, Q35L+Y174F, Q35L+R176Q, Q35L+E177S, Q35L+E177Y, Q35L+N180R, Q35L+P183T, Q35L+P183G, Q35L+Q184E, Q35L+Q184K, Q35L+R185G, Q35L+Y196W, Q35L+Y196F, Q35L+N200T, Q35L+S202R, Q35L+Q203T, Q35L+R205K, Q35L+R210L, Q35L+R210G, Q35L+R210M, Q35L+N213V, Q35L+N213D, Q35L+T228S, Q35L+N229D, Q35L+E234F, Q35L+E234Y, Q35L+A235K, Q35L+A235R, Q35L+S241C, Q35L+Q243K, Q35L+Q243E, Q35L+R244K, Q35L+R244V, Q35L+A250G, Q35L+K254Y, Q35L+G257W, Q35L+G257E, Q35L+G257A, Q35L+W260F, Q35L+Y262F, Q35L+S266A, Q35L+D268N, Q35L+A270D, Q35L+N272M, Q35L+N272T, Q35L+N273E, Q35L+N273D, Q35L+A276E, Q35L+A276W, Q35L+A276D, Q35L+N279D, Q35L+N279E, Q35L+T280L, Q35L+N283W, Q35L+N283H, Q35L+Y286W, Q35L+Y286F, Q35L+L288I, Q35L+E290A, Q35L+L294P, Q35L+L294K, Q35L+L294I, Q35L+L294R, Q35L+L294V, Q35L+L294H, Q35L+S295K, Q35L+S295V, Q35L+S295P, Q35L+S295L, Q35L+S295R, Q35L+S295A, Q35L+S295N, Q35L+S295M, Q35L+S295I, Q35L+T296S, Q35L+F298Y, T37P+E41V, T37P+E41N, T37P+N45G, T37P+G47S, T37P+G47A, T37P+D57N, T37P+G59Q, T37P+Q60R, T37P+K63R, T37P+K63Q, T37P+D65E, T37P+R70K, T37P+N71S, T37P+S74K, T37P+E77T, T37P+E77N, T37P+D78G, T37P+H80K, T37P+V82R, T37P+V82I, T37P+V82S, T37P+A83P, T37P+A83S, T37P+Y93Q, T37P+Y93A, T37P+S95D, T37P+A97R, T37P+S98P, T37P+S98D, T37P+N100Y, T37P+D104A, T37P+D104G, T37P+E108S, T37P+S111A, T37P+S111K, T37P+S111R, T37P+I114Q, T37P+I114M, T37P+I114W, T37P+K116R, T37P+D118K, T37P+T119R, T37P+S131T, T37P+E133R, T37P+E133Q, T37P+D135P, T37P+A136P, T37P+D139A, T37P+D139R, T37P+K142M, T37P+K142V, T37P+K142S, T37P+K142R, T37P+Q143R, T37P+N150T, T37P+N150R, T37P+N150S, T37P+Q169A, T37P+Q169R, T37P+Q169K, T37P+H172R, T37P+Y174R, T37P+Y174L, T37P+Y174W, T37P+Y174F, T37P+R176Q, T37P+E177S, T37P+E177Y, T37P+N180R, T37P+P183T, T37P+P183G, T37P+Q184E, T37P+Q184K, T37P+R185G, T37P+Y196W, T37P+Y196F, T37P+N200T, T37P+S202R, T37P+Q203T, T37P+R205K, T37P+R210L, T37P+R210G, T37P+R210M, T37P+N213V, T37P+N213D, T37P+T228S, T37P+N229D, T37P+E234F, T37P+E234Y, T37P+A235K, T37P+A235R, T37P+S241C, T37P+Q243K, T37P+Q243E, T37P+R244K, T37P+R244V, T37P+A250G, T37P+K254Y, T37P+G257W, T37P+G257E, T37P+G257A, T37P+W260F, T37P+Y262F, T37P+S266A, T37P+D268N, T37P+A270D, T37P+N272M, T37P+N272T, T37P+N273E, T37P+N273D, T37P+A276E, T37P+A276W, T37P+A276D, T37P+N279D, T37P+N279E, T37P+T280L, T37P+N283W, T37P+N283H, T37P+Y286W, T37P+Y286F, T37P+L288I, T37P+E290A, T37P+L294P, T37P+L294K, T37P+L294I, T37P+L294R, T37P+L294V, T37P+L294H, T37P+S295K, T37P+S295V, T37P+S295P, T37P+S295L, T37P+S295R, T37P+S295A, T37P+S295N, T37P+S295M, T37P+S295I, T37P+T296S, T37P+F298Y, E41V+N45G, E41V+G47S, E41V+G47A, E41V+D57N, E41V+G59Q, E41V+Q60R, E41V+K63R, E41V+K63Q, E41V+D65E, E41V+R70K, E41V+N71S, E41V+S74K, E41V+E77T, E41V+E77N, E41V+D78G, E41V+H80K, E41V+V82R, E41V+V82I, E41V+V82S, E41V+A83P, E41V+A83S, E41V+Y93Q, E41V+Y93A, E41V+S95D, E41V+A97R, E41V+S98P, E41V+S98D, E41V+N100Y, E41V+D104A, E41V+D104G, E41V+E108S, E41V+S111A, E41V+S111K, E41V+S111R, E41V+I114Q, E41V+I114M, E41V+I114W, E41V+K116R, E41V+D118K, E41V+T119R, E41V+S131T, E41V+E133R, E41V+E133Q, E41V+D135P, E41V+A136P, E41V+D139A, E41V+D139R, E41V+K142M, E41V+K142V, E41V+K142S, E41V+K142R, E41V+Q143R, E41V+N150T, E41V+N150R, E41V+N150S, E41V+Q169A, E41V+Q169R, E41V+Q169K, E41V+H172R, E41V+Y174R, E41V+Y174L, E41V+Y174W, E41V+Y174F, E41V+R176Q, E41V+E177S, E41V+E177Y, E41V+N180R, E41V+P183T, E41V+P183G, E41V+Q184E, E41V+Q184K, E41V+

R185G, E41V+Y196W, E41V+Y196F, E41V+N200T, E41V+S202R, E41V+Q203T, E41V+R205K, E41V+R210L, E41V+R210G, E41V+R210M, E41V+N213V, E41V+N213D, E41V+T228S, E41V+N229D, E41V+E234F, E41V+E234Y, E41V+A235K, E41V+A235R, E41V+S241C, E41V+Q243K, E41V+Q243E, E41V+R244K, E41V+R244V, E41V+A250G, E41V+K254Y, E41V+G257W, E41V+G257E, E41V+G257A, E41V+W260F, E41V+Y262F, E41V+S266A, E41V+D268N, E41V+A270D, E41V+N272M, E41V+N272T, E41V+N273E, E41V+N273D, E41V+A276E, E41V+A276W, E41V+A276D, E41V+N279D, E41V+N279E, E41V+T280L, E41V+N283W, E41V+N283H, E41V+Y286W, E41V+Y286F, E41V+L288I, E41V+E290A, E41V+L294P, E41V+L294K, E41V+L294I, E41V+L294R, E41V+L294V, E41V+L294H, E41V+S295K, E41V+S295V, E41V+S295P, E41V+S295L, E41V+S295R, E41V+S295A, E41V+S295N, E41V+S295M, E41V+S295I, E41V+T296S, E41V+F298Y, E41N+N45G, E41N+G47S, E41N+G47A, E41N+D57N, E41N+G59Q, E41N+Q60R, E41N+K63R, E41N+K63Q, E41N+D65E, E41N+R70K, E41N+N71S, E41N+S74K, E41N+E77T, E41N+E77N, E41N+D78G, E41N+H80K, E41N+V82R, E41N+V82I, E41N+V82S, E41N+A83P, E41N+A83S, E41N+Y93Q, E41N+Y93A, E41N+S95D, E41N+A97R, E41N+S98P, E41N+S98D, E41N+N100Y, E41N+D104A, E41N+D104G, E41N+E108S, E41N+S111A, E41N+S111K, E41N+S111R, E41N+I114Q, E41N+I114M, E41N+I114W, E41N+K116R, E41N+D118K, E41N+T119R, E41N+S131T, E41N+E133R, E41N+E133Q, E41N+D135P, E41N+A136P, E41N+D139A, E41N+D139R, E41N+K142M, E41N+K142V, E41N+K142S, E41N+K142R, E41N+Q143R, E41N+N150T, E41N+N150R, E41N+N150S, E41N+Q169A, E41N+Q169R, E41N+Q169K, E41N+H172R, E41N+Y174R, E41N+Y174L, E41N+Y174W, E41N+Y174F, E41N+R176Q, E41N+E177S, E41N+E177Y, E41N+N180R, E41N+P183T, E41N+P183G, E41N+Q184E, E41N+Q184K, E41N+R185G, E41N+Y196W, E41N+Y196F, E41N+N200T, E41N+S202R, E41N+Q203T, E41N+R205K, E41N+R210L, E41N+R210G, E41N+R210M, E41N+N213V, E41N+N213D, E41N+T228S, E41N+N229D, E41N+E234F, E41N+E234Y, E41N+A235K, E41N+A235R, E41N+S241C, E41N+Q243K, E41N+Q243E, E41N+R244K, E41N+R244V, E41N+A250G, E41N+K254Y, E41N+G257W, E41N+G257E, E41N+G257A, E41N+W260F, E41N+Y262F, E41N+S266A, E41N+D268N, E41N+A270D, E41N+N272M, E41N+N272T, E41N+N273E, E41N+N273D, E41N+A276E, E41N+A276W, E41N+A276D, E41N+N279D, E41N+N279E, E41N+T280L, E41N+N283W, E41N+N283H, E41N+Y286W, E41N+Y286F, E41N+L288I, E41N+E290A, E41N+L294P, E41N+L294K, E41N+L294I, E41N+L294R, E41N+L294V, E41N+L294H, E41N+S295K, E41N+S295V, E41N+S295P, E41N+S295L, E41N+S295R, E41N+S295A, E41N+S295N, E41N+S295M, E41N+S295I, E41N+T296S, E41N+F298Y, N45G+G47S, N45G+G47A, N45G+D57N, N45G+G59Q, N45G+Q60R, N45G+K63R, N45G+K63Q, N45G+D65E, N45G+R70K, N45G+N71S, N45G+S74K, N45G+E77T, N45G+E77N, N45G+D78G, N45G+H80K, N45G+V82R, N45G+V82I, N45G+V82S, N45G+A83P, N45G+A83S, N45G+Y93Q, N45G+Y93A, N45G+S95D, N45G+A97R, N45G+S98P, N45G+S98D, N45G+N100Y, N45G+D104A, N45G+D104G, N45G+E108S, N45G+S111A, N45G+S111K, N45G+S111R, N45G+I114Q, N45G+I114M, N45G+I114W, N45G+K116R, N45G+D118K, N45G+T119R, N45G+S131T, N45G+E133R, N45G+E133Q, N45G+D135P, N45G+A136P, N45G+D139A, N45G+D139R, N45G+K142M, N45G+K142V, N45G+K142S, N45G+K142R, N45G+Q143R, N45G+N150T, N45G+N150R, N45G+N150S, N45G+Q169A, N45G+Q169R, N45G+Q169K, N45G+H172R, N45G+Y174R, N45G+Y174L, N45G+Y174W, N45G+Y174F, N45G+R176Q, N45G+E177S, N45G+E177Y, N45G+N180R, N45G+P183T, N45G+P183G, N45G+Q184E, N45G+Q184K, N45G+R185G, N45G+Y196W, N45G+Y196F, N45G+N200T, N45G+S202R, N45G+Q203T, N45G+R205K, N45G+R210L, N45G+R210G, N45G+R210M, N45G+N213V, N45G+N213D, N45G+T228S, N45G+N229D, N45G+E234F, N45G+E234Y, N45G+A235K, N45G+A235R, N45G+S241C, N45G+Q243K, N45G+Q243E, N45G+R244K, N45G+R244V, N45G+A250G, N45G+K254Y, N45G+G257W, N45G+G257E, N45G+G257A, N45G+W260F, N45G+Y262F, N45G+S266A, N45G+D268N, N45G+A270D, N45G+N272M, N45G+N272T, N45G+N273E, N45G+N273D, N45G+A276E, N45G+A276W, N45G+A276D, N45G+N279D, N45G+N279E, N45G+T280L, N45G+N283W, N45G+N283H, N45G+Y286W, N45G+Y286F, N45G+L288I, N45G+E290A, N45G+L294P, N45G+L294K, N45G+L294I, N45G+L294R, N45G+L294V, N45G+L294H, N45G+S295K, N45G+S295V, N45G+S295P, N45G+S295L, N45G+S295R, N45G+S295A, N45G+S295N, N45G+S295M, N45G+S295I, N45G+T296S, N45G+F298Y, G47S+D57N, G47S+G59Q, G47S+Q60R, G47S+K63R, G47S+K63Q, G47S+D65E, G47S+R70K, G47S+N71S, G47S+S74K, G47S+E77T, G47S+E77N, G47S+D78G, G47S+H80K, G47S+V82R, G47S+V82I, G47S+V82S, G47S+A83P, G47S+A83S, G47S+Y93Q, G47S+Y93A, G47S+S95D, G47S+A97R, G47S+S98P, G47S+S98D, G47S+N100Y, G47S+D104A, G47S+D104G, G47S+E108S, G47S+S111A, G47S+S111K, G47S+S111R, G47S+I114Q, G47S+I114M, G47S+I114W, G47S+K116R, G47S+D118K, G47S+T119R, G47S+S131T, G47S+E133R, G47S+E133Q, G47S+D135P, G47S+A136P, G47S+D139A, G47S+D139R, G47S+K142M, G47S+K142V, G47S+K142S, G47S+K142R, G47S+Q143R, G47S+N150T, G47S+N150R, G47S+N150S, G47S+Q169A, G47S+Q169R, G47S+Q169K, G47S+H172R, G47S+Y174R, G47S+Y174L, G47S+Y174W, G47S+Y174F, G47S+R176Q, G47S+E177S, G47S+E177Y, G47S+N180R, G47S+P183T, G47S+P183G, G47S+Q184E, G47S+Q184K, G47S+R185G, G47S+Y196W, G47S+Y196F, G47S+N200T, G47S+S202R, G47S+Q203T, G47S+R205K, G47S+R210L, G47S+R210G, G47S+R210M, G47S+N213V, G47S+N213D, G47S+T228S, G47S+N229D, G47S+E234F, G47S+E234Y, G47S+A235K, G47S+A235R, G47S+S241C, G47S+Q243K, G47S+Q243E, G47S+R244K, G47S+R244V, G47S+A250G, G47S+K254Y, G47S+G257W, G47S+G257E, G47S+G257A, G47S+W260F, G47S+Y262F, G47S+S266A, G47S+D268N, G47S+A270D, G47S+N272M, G47S+N272T, G47S+N273E, G47S+N273D, G47S+A276E, G47S+A276W, G47S+A276D, G47S+N279D, G47S+N279E, G47S+T280L, G47S+N283W, G47S+N283H, G47S+Y286W, G47S+Y286F, G47S+L288I, G47S+E290A, G47S+L294P, G47S+L294K, G47S+L294I, G47S+L294R, G47S+L294V, G47S+L294H, G47S+S295K, G47S+S295V, G47S+S295P, G47S+S295L, G47S+S295R, G47S+S295A, G47S+S295N, G47S+S295M, G47S+S295I, G47S+T296S, G47S+F298Y, G47A+D57N, G47A+G59Q, G47A+Q60R, G47A+K63R, G47A+K63Q, G47A+D6SE, G47A+R70K, G47A+N71S, G47A+S74K, G47A+E77T, G47A+E77N, G47A+D78G, G47A+H80K, G47A+V82R, G47A+V82I, G47A+V82S,

G47A+A83P, G47A+A83S, G47A+Y93Q, G47A+Y93A, G47A+S95D, G47A+A97R, G47A+S98P, G47A+S98D, G47A+N100Y, G47A+D104A, G47A+D104G, G47A+E108S, G47A+S111A, G47A+S111K, G47A+S111R, G47A+I114Q, G47A+I114M, G47A+I114W, G47A+K116R, G47A+D118K, G47A+T119R, G47A+S131T, G47A+E133R, G47A+E133Q, G47A+D135P, G47A+A136P, G47A+D139A, G47A+D139R, G47A+K142M, G47A+K142V, G47A+K142S, G47A+K142R, G47A+Q143R, G47A+N150T, G47A+N150R, G47A+N150S, G47A+Q169A, G47A+Q169R, G47A+Q169K, G47A+H172R, G47A+Y174R, G47A+Y174L, G47A+Y174W, G47A+Y174F, G47A+R176Q, G47A+E177S, G47A+E177Y, G47A+N180R, G47A+P183T, G47A+P183G, G47A+Q184E, G47A+Q184K, G47A+R185G, G47A+Y196W, G47A+Y196F, G47A+N200T, G47A+S202R, G47A+Q203T, G47A+R205K, G47A+R210L, G47A+R210G, G47A+R210M, G47A+N213V, G47A+N213D, G47A+T228S, G47A+N229D, G47A+E234F, G47A+E234Y, G47A+A235K, G47A+A235R, G47A+S241C, G47A+Q243K, G47A+Q243E, G47A+R244K, G47A+R244V, G47A+A250G, G47A+K254Y, G47A+G257W, G47A+G257E, G47A+G257A, G47A+W260F, G47A+Y262F, G47A+S266A, G47A+D268N, G47A+A270D, G47A+N272M, G47A+N272T, G47A+N273E, G47A+N273D, G47A+A276E, G47A+A276W, G47A+A276D, G47A+N279D, G47A+N279E, G47A+T280L, G47A+N283W, G47A+N283H, G47A+Y286W, G47A+Y286F, G47A+L288I, G47A+E290A, G47A+L294P, G47A+L294K, G47A+L294I, G47A+L294R, G47A+L294V, G47A+L294H, G47A+S295K, G47A+S295V, G47A+S295P, G47A+S295L, G47A+S295R, G47A+S295A, G47A+S295N, G47A+S295M, G47A+S295I, G47A+T296S, G47A+F298Y, D57N+G59Q, D57N+Q60R, D57N+K63R, D57N+K63Q, D57N+D65E, D57N+R70K, D57N+N71S, D57N+S74K, D57N+E77T, D57N+E77N, D57N+D78G, D57N+H80K, D57N+V82R, D57N+V82I, D57N+V82S, D57N+A83P, D57N+A83S, D57N+Y93Q, D57N+Y93A, D57N+S95D, D57N+A97R, D57N+S98P, D57N+S98D, D57N+N100Y, D57N+D104A, D57N+D104G, D57N+E108S, D57N+S111A, D57N+S111K, D57N+S111R, D57N+I114Q, D57N+I114M, D57N+I114W, D57N+K116R, D57N+D118K, D57N+T119R, D57N+S131T, D57N+E133R, D57N+E133Q, D57N+D135P, D57N+A136P, D57N+D139A, D57N+D139R, D57N+K142M, D57N+K142V, D57N+K142S, D57N+K142R, D57N+Q143R, D57N+N150T, D57N+N150R, D57N+N150S, D57N+Q169A, D57N+Q169R, D57N+Q169K, D57N+H172R, D57N+Y174R, D57N+Y174L, D57N+Y174W, D57N+Y174F, D57N+R176Q, D57N+E177S, D57N+E177Y, D57N+N180R, D57N+P183T, D57N+P183G, D57N+Q184E, D57N+Q184K, D57N+R185G, D57N+Y196W, D57N+Y196F, D57N+N200T, D57N+S202R, D57N+Q203T, D57N+R205K, D57N+R210L, D57N+R210G, D57N+R210M, D57N+N213V, D57N+N213D, D57N+T228S, D57N+N229D, D57N+E234F, D57N+E234Y, D57N+A235K, D57N+A235R, D57N+S241C, D57N+Q243K, D57N+Q243E, D57N+R244K, D57N+R244V, D57N+A250G, D57N+K254Y, D57N+G257W, D57N+G257E, D57N+G257A, D57N+W260F, D57N+Y262F, D57N+S266A, D57N+D268N, D57N+A270D, D57N+N272M, D57N+N272T, D57N+N273E, D57N+N273D, D57N+A276E, D57N+A276W, D57N+A276D, D57N+N279D, D57N+N279E, D57N+T280L, D57N+N283W, D57N+N283H, D57N+Y286W, D57N+Y286F, D57N+L288I, D57N+E290A, D57N+L294P, D57N+L294K, D57N+L294I, D57N+L294R, D57N+L294V, D57N+L294H, D57N+S295K, D57N+S295V, D57N+S295P, D57N+S295L, D57N+S295R, D57N+S295A, D57N+S295N, D57N+S295M, D57N+S295I, D57N+T296S, D57N+F298Y, G59Q+Q60R, G59Q+K63R, G59Q+K63Q, G59Q+D65E, G59Q+R70K, G59Q+N71S, G59Q+S74K, G59Q+E77T, G59Q+E77N, G59Q+D78G, G59Q+H80K, G59Q+V82R, G59Q+V82I, G59Q+V82S, G59Q+A83P, G59Q+A83S, G59Q+Y93Q, G59Q+Y93A, G59Q+S95D, G59Q+A97R, G59Q+S98P, G59Q+S98D, G59Q+N100Y, G59Q+D104A, G59Q+D104G, G59Q+E108S, G59Q+S111A, G59Q+S111K, G59Q+S111R, G59Q+I114Q, G59Q+I114M, G59Q+I114W, G59Q+K116R, G59Q+D118K, G59Q+T119R, G59Q+S131T, G59Q+E133R, G59Q+E133Q, G59Q+D135P, G59Q+A136P, G59Q+D139A, G59Q+D139R, G59Q+K142M, G59Q+K142V, G59Q+K142S, G59Q+K142R, G59Q+Q143R, G59Q+N150T, G59Q+N150R, G59Q+N150S, G59Q+Q169A, G59Q+Q169R, G59Q+Q169K, G59Q+H172R, G59Q+Y174R, G59Q+Y174L, G59Q+Y174W, G59Q+Y174F, G59Q+R176Q, G59Q+E177S, G59Q+E177Y, G59Q+N180R, G59Q+P183T, G59Q+P183G, G59Q+Q184E, G59Q+Q184K, G59Q+R185G, G59Q+Y196W, G59Q+Y196F, G59Q+N200T, G59Q+S202R, G59Q+Q203T, G59Q+R205K, G59Q+R210L, G59Q+R210G, G59Q+R210M, G59Q+N213V, G59Q+N213D, G59Q+T228S, G59Q+N229D, G59Q+E234F, G59Q+E234Y, G59Q+A235K, G59Q+A235R, G59Q+S241C, G59Q+Q243K, G59Q+Q243E, G59Q+R244K, G59Q+R244V, G59Q+A250G, G59Q+K254Y, G59Q+G257W, G59Q+G257E, G59Q+G257A, G59Q+W260F, G59Q+Y262F, G59Q+S266A, G59Q+D268N, G59Q+A270D, G59Q+N272M, G59Q+N272T, G59Q+N273E, G59Q+N273D, G59Q+A276E, G59Q+A276W, G59Q+A276D, G59Q+N279D, G59Q+N279E, G59Q+T280L, G59Q+N283W, G59Q+N283H, G59Q+Y286W, G59Q+Y286F, G59Q+L288I, G59Q+E290A, G59Q+L294P, G59Q+L294K, G59Q+L294I, G59Q+L294R, G59Q+L294V, G59Q+L294H, G59Q+S295K, G59Q+S295V, G59Q+S295P, G59Q+S295L, G59Q+S295R, G59Q+S295A, G59Q+S295N, G59Q+S295M, G59Q+S295I, G59Q+T296S, G59Q+F298Y, Q60R+K63R, Q60R+K63Q, Q60R+D6SE, Q60R+R70K, Q60R+N71S, Q60R+S74K, Q60R+E77T, Q60R+E77N, Q60R+D78G, Q60R+H80K, Q60R+V82R, Q60R+V82I, Q60R+V82S, Q60R+A83P, Q60R+A83S, Q60R+Y93Q, Q60R+Y93A, Q60R+S95D, Q60R+A97R, Q60R+S98P, Q60R+S98D, Q60R+N100Y, Q60R+D104A, Q60R+D104G, Q60R+E108S, Q60R+S111A, Q60R+S111K, Q60R+S111R, Q60R+I114Q, Q60R+I114M, Q60R+I114W, Q60R+K116R, Q60R+D118K, Q60R+T119R, Q60R+S131T, Q60R+E133R, Q60R+E133Q, Q60R+D135P, Q60R+A136P, Q60R+D139A, Q60R+D139R, Q60R+K142M, Q60R+K142V, Q60R+K142S, Q60R+K142R, Q60R+Q143R, Q60R+N150T, Q60R+N150R, Q60R+N150S, Q60R+Q169A, Q60R+Q169R, Q60R+Q169K, Q60R+H172R, Q60R+Y174R, Q60R+Y174L, Q60R+Y174W, Q60R+Y174F, Q60R+R176Q, Q60R+E177S, Q60R+E177Y, Q60R+N180R, Q60R+P183T, Q60R+P183G, Q60R+Q184E, Q60R+Q184K, Q60R+R185G, Q60R+Y196W, Q60R+Y196F, Q60R+N200T, Q60R+S202R, Q60R+Q203T, Q60R+R205K, Q60R+R210L, Q60R+R210G, Q60R+R210M, Q60R+N213V, Q60R+N213D, Q60R+T228S, Q60R+N229D, Q60R+E234F, Q60R+E234Y, Q60R+A235K, Q60R+A235R, Q60R+S241C, Q60R+Q243K, Q60R+Q243E, Q60R+R244K, Q60R+R244V, Q60R+A250G, Q60R+K254Y, Q60R+G257W, Q60R+G257E, Q60R+G257A, Q60R+W260F, Q60R+Y262F, Q60R+S266A, Q60R+

D268N, Q60R+A270D, Q60R+N272M, Q60R+N272T, Q60R+N273E, Q60R+N273D, Q60R+A276E, Q60R+A276W, Q60R+A276D, Q60R+N279D, Q60R+N279E, Q60R+T280L, Q60R+N283W, Q60R+N283H, Q60R+Y286W, Q60R+Y286F, Q60R+L288I, Q60R+E290A, Q60R+L294P, Q60R+L294K, Q60R+L294I, Q60R+L294R, Q60R+L294V, Q60R+L294H, Q60R+S295K, Q60R+S295V, Q60R+S295P, Q60R+S295L, Q60R+S295R, Q60R+S295A, Q60R+S295N, Q60R+S295M, Q60R+S295I, Q60R+T296S, Q60R+F298Y, K63R+D65E, K63R+R70K, K63R+N71S, K63R+S74K, K63R+E77T, K63R+E77N, K63R+D78G, K63R+H80K, K63R+V82R, K63R+V82I, K63R+V82S, K63R+A83P, K63R+A83S, K63R+Y93Q, K63R+Y93A, K63R+S95D, K63R+A97R, K63R+S98P, K63R+S98D, K63R+N100Y, K63R+D104A, K63R+D104G, K63R+E108S, K63R+S111A, K63R+S111K, K63R+S111R, K63R+I114Q, K63R+I114M, K63R+I114W, K63R+K116R, K63R+D118K, K63R+T119R, K63R+S131T, K63R+E133R, K63R+E133Q, K63R+D135P, K63R+A136P, K63R+D139A, K63R+D139R, K63R+K142M, K63R+K142V, K63R+K142S, K63R+K142R, K63R+Q143R, K63R+N150T, K63R+N150R, K63R+N150S, K63R+Q169A, K63R+Q169R, K63R+Q169K, K63R+H172R, K63R+Y174R, K63R+Y174L, K63R+Y174W, K63R+Y174F, K63R+R176Q, K63R+E177S, K63R+E177Y, K63R+N180R, K63R+P183T, K63R+P183G, K63R+Q184E, K63R+Q184K, K63R+R185G, K63R+Y196W, K63R+Y196F, K63R+N200T, K63R+S202R, K63R+Q203T, K63R+R205K, K63R+R210L, K63R+R210G, K63R+R210M, K63R+N213V, K63R+N213D, K63R+T228S, K63R+N229D, K63R+E234F, K63R+E234Y, K63R+A235K, K63R+A235R, K63R+S241C, K63R+Q243K, K63R+Q243E, K63R+R244K, K63R+R244V, K63R+A250G, K63R+K254Y, K63R+G257W, K63R+G257E, K63R+G257A, K63R+W260F, K63R+Y262F, K63R+S266A, K63R+D268N, K63R+A270D, K63R+N272M, K63R+N272T, K63R+N273E, K63R+N273D, K63R+A276E, K63R+A276W, K63R+A276D, K63R+N279D, K63R+N279E, K63R+T280L, K63R+N283W, K63R+N283H, K63R+Y286W, K63R+Y286F, K63R+L288I, K63R+E290A, K63R+L294P, K63R+L294K, K63R+L294I, K63R+L294R, K63R+L294V, K63R+L294H, K63R+S295K, K63R+S295V, K63R+S295P, K63R+S295L, K63R+S295R, K63R+S295A, K63R+S295N, K63R+S295M, K63R+S295I, K63R+T296S, K63R+F298Y, K63Q+D65E, K63Q+R70K, K63Q+N71S, K63Q+S74K, K63Q+E77T, K63Q+E77N, K63Q+D78G, K63Q+H80K, K63Q+V82R, K63Q+V82I, K63Q+V82S, K63Q+A83P, K63Q+A83S, K63Q+Y93Q, K63Q+Y93A, K63Q+S95D, K63Q+A97R, K63Q+S98P, K63Q+S98D, K63Q+N100Y, K63Q+D104A, K63Q+D104G, K63Q+E108S, K63Q+S111A, K63Q+S111K, K63Q+S111R, K63Q+I114Q, K63Q+I114M, K63Q+I114W, K63Q+K116R, K63Q+D118K, K63Q+T119R, K63Q+S131T, K63Q+E133R, K63Q+E133Q, K63Q+D135P, K63Q+A136P, K63Q+D139A, K63Q+D139R, K63Q+K142M, K63Q+K142V, K63Q+K142S, K63Q+K142R, K63Q+Q143R, K63Q+N150T, K63Q+N150R, K63Q+N150S, K63Q+Q169A, K63Q+Q169R, K63Q+Q169K, K63Q+H172R, K63Q+Y174R, K63Q+Y174L, K63Q+Y174W, K63Q+Y174F, K63Q+R176Q, K63Q+E177S, K63Q+E177Y, K63Q+N180R, K63Q+P183T, K63Q+P183G, K63Q+Q184E, K63Q+Q184K, K63Q+R185G, K63Q+Y196W, K63Q+Y196F, K63Q+N200T, K63Q+S202R, K63Q+Q203T, K63Q+R205K, K63Q+R210L, K63Q+R210G, K63Q+R210M, K63Q+N213V, K63Q+N213D, K63Q+T228S, K63Q+N229D, K63Q+E234F, K63Q+E234Y, K63Q+A235K, K63Q+A235R, K63Q+S241C, K63Q+Q243K, K63Q+Q243E, K63Q+R244K, K63Q+R244V, K63Q+A250G, K63Q+K254Y, K63Q+G257W, K63Q+G257E, K63Q+G257A, K63Q+W260F, K63Q+Y262F, K63Q+S266A, K63Q+D268N, K63Q+A270D, K63Q+N272M, K63Q+N272T, K63Q+N273E, K63Q+N273D, K63Q+A276E, K63Q+A276W, K63Q+A276D, K63Q+N279D, K63Q+N279E, K63Q+T280L, K63Q+N283W, K63Q+N283H, K63Q+Y286W, K63Q+Y286F, K63Q+L288I, K63Q+E290A, K63Q+L294P, K63Q+L294K, K63Q+L294I, K63Q+L294R, K63Q+L294V, K63Q+L294H, K63Q+S295K, K63Q+S295V, K63Q+S295P, K63Q+S295L, K63Q+S295R, K63Q+S295A, K63Q+S295N, K63Q+S295M, K63Q+S295I, K63Q+T296S, K63Q+F298Y, D65E+R70K, D65E+N71S, D65E+S74K, D65E+E77T, D65E+E77N, D65E+D78G, D65E+H80K, D65E+V82R, D65E+V82I, D65E+V82S, D65E+A83P, D65E+A83S, D65E+Y93Q, D65E+Y93A, D65E+S95D, D65E+A97R, D65E+S98P, D65E+S98D, D65E+N100Y, D65E+D104A, D65E+D104G, D65E+E108S, D65E+S111A, D65E+S111K, D65E+S111R, D65E+I114Q, D65E+I114M, D65E+I114W, D65E+K116R, D65E+D118K, D65E+T119R, D65E+S131T, D65E+E133R, D65E+E133Q, D65E+D135P, D65E+A136P, D65E+D139A, D65E+D139R, D65E+K142M, D65E+K142V, D65E+K142S, D65E+K142R, D65E+Q143R, D65E+N150T, D65E+N150R, D65E+N150S, D65E+Q169A, D65E+Q169R, D65E+Q169K, D65E+H172R, D65E+Y174R, D65E+Y174L, D65E+Y174W, D65E+Y174F, D65E+R176Q, D65E+E177S, D65E+E177Y, D65E+N180R, D65E+P183T, D65E+P183G, D65E+Q184E, D65E+Q184K, D65E+R185G, D65E+Y196W, D65E+Y196F, D65E+N200T, D65E+S202R, D65E+Q203T, D65E+R205K, D65E+R210L, D65E+R210G, D65E+R210M, D65E+N213V, D65E+N213D, D65E+T228S, D65E+N229D, D65E+E234F, D65E+E234Y, D65E+A235K, D65E+A235R, D65E+S241C, D65E+Q243K, D65E+Q243E, D65E+R244K, D65E+R244V, D65E+A250G, D65E+K254Y, D65E+G257W, D65E+G257E, D65E+G257A, D65E+W260F, D65E+Y262F, D65E+S266A, D65E+D268N, D65E+A270D, D65E+N272M, D65E+N272T, D65E+N273E, D65E+N273D, D65E+A276E, D65E+A276W, D65E+A276D, D65E+N279D, D65E+N279E, D65E+T280L, D65E+N283W, D65E+N283H, D65E+Y286W, D65E+Y286F, D65E+L288I, D65E+E290A, D65E+L294P, D65E+L294K, D65E+L294I, D65E+L294R, D65E+L294V, D65E+L294H, D65E+S295K, D65E+S295V, D65E+S295P, D65E+S295L, D65E+S295R, D65E+S295A, D65E+S295N, D65E+S295M, D65E+S295I, D65E+T296S, D65E+F298Y, R70K+N71S, R70K+S74K, R70K+E77T, R70K+E77N, R70K+D78G, R70K+H80K, R70K+V82R, R70K+V82I, R70K+V82S, R70K+A83P, R70K+A83S, R70K+Y93Q, R70K+Y93A, R70K+S95D, R70K+A97R, R70K+S98P, R70K+S98D, R70K+N100Y, R70K+D104A, R70K+D104G, R70K+E108S, R70K+S111A, R70K+S111K, R70K+S111R, R70K+I114Q, R70K+I114M, R70K+I114W, R70K+K116R, R70K+D118K, R70K+T119R, R70K+S131T, R70K+E133R, R70K+E133Q, R70K+D135P, R70K+A136P, R70K+D139A, R70K+D139R, R70K+K142M, R70K+K142V, R70K+K142S, R70K+K142R, R70K+Q143R, R70K+N150T, R70K+N150R, R70K+N150S, R70K+Q169A, R70K+Q169R, R70K+Q169K, R70K+H172R, R70K+Y174R, R70K+Y174L, R70K+Y174W, R70K+Y174F, R70K+R176Q, R70K+E177S, R70K+E177Y, R70K+N180R, R70K+P183T, R70K+P183G, R70K+Q184E, R70K+Q184K, R70K+R185G,

R70K+Y196W, R70K+Y196F, R70K+N200T, R70K+S202R, R70K+Q203T, R70K+R205K, R70K+R210L, R70K+R210G, R70K+R210M, R70K+N213V, R70K+N213D, R70K+T228S, R70K+N229D, R70K+E234F, R70K+E234Y, R70K+A235K, R70K+A235R, R70K+S241C, R70K+Q243K, R70K+Q243E, R70K+R244K, R70K+R244V, R70K+A250G, R70K+K254Y, R70K+G257W, R70K+G257E, R70K+G257A, R70K+W260F, R70K+Y262F, R70K+S266A, R70K+D268N, R70K+A270D, R70K+N272M, R70K+N272T, R70K+N273E, R70K+N273D, R70K+A276E, R70K+A276W, R70K+A276D, R70K+N279D, R70K+N279E, R70K+T280L, R70K+N283W, R70K+N283H, R70K+Y286W, R70K+Y286F, R70K+L288I, R70K+E290A, R70K+L294P, R70K+L294K, R70K+L294I, R70K+L294R, R70K+L294V, R70K+L294H, R70K+S295K, R70K+S295V, R70K+S295P, R70K+S295L, R70K+S295R, R70K+S295A, R70K+S295N, R70K+S295M, R70K+S295I, R70K+T296S, R70K+F298Y, N71S+S74K, N71S+E77T, N71S+E77N, N71S+D78G, N71S+H80K, N71S+V82R, N71S+V82I, N71S+V82S, N71S+A83P, N71S+A83S, N71S+Y93Q, N71S+Y93A, N71S+S95D, N71S+A97R, N71S+S98P, N71S+S98D, N71S+N100Y, N71S+D104A, N71S+D104G, N71S+E108S, N71S+S111A, N71S+S111K, N71S+S111R, N71S+I114Q, N71S+I114M, N71S+I114W, N71S+K116R, N71S+D118K, N71S+T119R, N71S+S131T, N71S+E133R, N71S+E133Q, N71S+D135P, N71S+A136P, N71S+D139A, N71S+D139R, N71S+K142M, N71S+K142V, N71S+K142S, N71S+K142R, N71S+Q143R, N71S+N150T, N71S+N150R, N71S+N150S, N71S+Q169A, N71S+Q169R, N71S+Q169K, N71S+H172R, N71S+Y174R, N71S+Y174L, N71S+Y174W, N71S+Y174F, N71S+R176Q, N71S+E177S, N71S+E177Y, N71S+N180R, N71S+P183T, N71S+P183G, N71S+Q184E, N71S+Q184K, N71S+R185G, N71S+Y196W, N71S+Y196F, N71S+N200T, N71S+S202R, N71S+Q203T, N71S+R205K, N71S+R210L, N71S+R210G, N71S+R210M, N71S+N213V, N71S+N213D, N71S+T228S, N71S+N229D, N71S+E234F, N71S+E234Y, N71S+A235K, N71S+A235R, N71S+S241C, N71S+Q243K, N71S+Q243E, N71S+R244K, N71S+R244V, N71S+A250G, N71S+K254Y, N71S+G257W, N71S+G257E, N71S+G257A, N71S+W260F, N71S+Y262F, N71S+S266A, N71S+D268N, N71S+A270D, N71S+N272M, N71S+N272T, N71S+N273E, N71S+N273D, N71S+A276E, N71S+A276W, N71S+A276D, N71S+N279D, N71S+N279E, N71S+T280L, N71S+N283W, N71S+N283H, N71S+Y286W, N71S+Y286F, N71S+L288I, N71S+E290A, N71S+L294P, N71S+L294K, N71S+L294I, N71S+L294R, N71S+L294V, N71S+L294H, N71S+S295K, N71S+S295V, N71S+S295P, N71S+S295L, N71S+S295R, N71S+S295A, N71S+S295N, N71S+S295M, N71S+S295I, N71S+T296S, N71S+F298Y, S74K+E77T, S74K+E77N, S74K+D78G, S74K+H80K, S74K+V82R, S74K+V82I, S74K+V82S, S74K+A83P, S74K+A83S, S74K+Y93Q, S74K+Y93A, S74K+S95D, S74K+A97R, S74K+S98P, S74K+S98D, S74K+N100Y, S74K+D104A, S74K+D104G, S74K+E108S, S74K+S111A, S74K+S111K, S74K+S111R, S74K+I114Q, S74K+I114M, S74K+I114W, S74K+K116R, S74K+D118K, S74K+T119R, S74K+S131T, S74K+E133R, S74K+E133Q, S74K+D135P, S74K+A136P, S74K+D139A, S74K+D139R, S74K+K142M, S74K+K142V, S74K+K142S, S74K+K142R, S74K+Q143R, S74K+N150T, S74K+N150R, S74K+N150S, S74K+Q169A, S74K+Q169R, S74K+Q169K, S74K+H172R, S74K+Y174R, S74K+Y174L, S74K+Y174W, S74K+Y174F, S74K+R176Q, S74K+E177S, S74K+E177Y, S74K+N180R, S74K+P183T, S74K+P183G, S74K+Q184E, S74K+Q184K, S74K+R185G, S74K+Y196W, S74K+Y196F, S74K+N200T, S74K+S202R, S74K+Q203T, S74K+R205K, S74K+R210L, S74K+R210G, S74K+R210M, S74K+N213V, S74K+N213D, S74K+T228S, S74K+N229D, S74K+E234F, S74K+E234Y, S74K+A235K, S74K+A235R, S74K+S241C, S74K+Q243K, S74K+Q243E, S74K+R244K, S74K+R244V, S74K+A250G, S74K+K254Y, S74K+G257W, S74K+G257E, S74K+G257A, S74K+W260F, S74K+Y262F, S74K+S266A, S74K+D268N, S74K+A270D, S74K+N272M, S74K+N272T, S74K+N273E, S74K+N273D, S74K+A276E, S74K+A276W, S74K+A276D, S74K+N279D, S74K+N279E, S74K+T280L, S74K+N283W, S74K+N283H, S74K+Y286W, S74K+Y286F, S74K+L288I, S74K+E290A, S74K+L294P, S74K+L294K, S74K+L294I, S74K+L294R, S74K+L294V, S74K+L294H, S74K+S295K, S74K+S295V, S74K+S295P, S74K+S295L, S74K+S295R, S74K+S295A, S74K+S295N, S74K+S295M, S74K+S295I, S74K+T296S, S74K+F298Y, E77T+D78G, E77T+H80K, E77T+V82R, E77T+V82I, E77T+V82S, E77T+A83P, E77T+A83S, E77T+Y93Q, E77T+Y93A, E77T+S95D, E77T+A97R, E77T+S98P, E77T+S98D, E77T+N100Y, E77T+D104A, E77T+D104G, E77T+E108S, E77T+S111A, E77T+S111K, E77T+S111R, E77T+I114Q, E77T+I114W, E77T+K116R, E77T+D118K, E77T+T119R, E77T+S131T, E77T+E133R, E77T+E133Q, E77T+D135P, E77T+A136P, E77T+D139A, E77T+D139R, E77T+K142M, E77T+K142V, E77T+K142S, E77T+K142R, E77T+Q143R, E77T+N150T, E77T+N150R, E77T+N150S, E77T+Q169A, E77T+Q169R, E77T+Q169K, E77T+H172R, E77T+Y174R, E77T+Y174L, E77T+Y174W, E77T+Y174F, E77T+R176Q, E77T+E177S, E77T+E177Y, E77T+N180R, E77T+P183T, E77T+P183G, E77T+Q184E, E77T+Q184K, E77T+R185G, E77T+Y196W, E77T+Y196F, E77T+N200T, E77T+S202R, E77T+Q203T, E77T+R205K, E77T+R210L, E77T+R210G, E77T+R210M, E77T+N213V, E77T+N213D, E77T+T228S, E77T+N229D, E77T+E234F, E77T+E234Y, E77T+A235K, E77T+A235R, E77T+S241C, E77T+Q243K, E77T+Q243E, E77T+R244K, E77T+R244V, E77T+A250G, E77T+K254Y, E77T+G257W, E77T+G257E, E77T+G257A, E77T+W260F, E77T+Y262F, E77T+S266A, E77T+D268N, E77T+A270D, E77T+N272M, E77T+N272T, E77T+N273E, E77T+N273D, E77T+A276E, E77T+A276W, E77T+A276D, E77T+N279D, E77T+N279E, E77T+T280L, E77T+N283W, E77T+N283H, E77T+Y286W, E77T+Y286F, E77T+L288I, E77T+E290A, E77T+L294P, E77T+L294K, E77T+L294I, E77T+L294R, E77T+L294V, E77T+L294H, E77T+S295K, E77T+S295V, E77T+S295P, E77T+S295L, E77T+S295R, E77T+S295A, E77T+S295N, E77T+S295M, E77T+S295I, E77T+T296S, E77T+F298Y, E77N+D78G, E77N+H80K, E77N+V82R, E77N+V82I, E77N+V82S, E77N+A83P, E77N+A83S, E77N+Y93Q, E77N+Y93A, E77N+S95D, E77N+A97R, E77N+S98P, E77N+S98D, E77N+N100Y, E77N+D104A, E77N+D104G, E77N+E108S, E77N+S111A, E77N+S111K, E77N+S111R, E77N+I114Q, E77N+I114M, E77N+I114W, E77N+K116R, E77N+D118K, E77N+T119R, E77N+S131T, E77N+E133R, E77N+E133Q, E77N+D135P, E77N+A136P, E77N+D139A, E77N+D139R, E77N+K142M, E77N+K142V, E77N+K142S, E77N+K142R, E77N+Q143R, E77N+N150T, E77N+N150R, E77N+N150S, E77N+Q169A, E77N+Q169R, E77N+Q169K, E77N+H172R, E77N+Y174R, E77N+Y174L, E77N+Y174W, E77N+Y174F, E77N+R176Q, E77N+E177S, E77N+E177Y, E77N+N180R, E77N+P183T, E77N+

P183G, E77N+Q184E, E77N+Q184K, E77N+R185G, E77N+Y196W, E77N+Y196F, E77N+N200T, E77N+ S202R, E77N+Q203T, E77N+R205K, E77N+R210L, E77N+R210M, E77N+R210G, E77N+N213V, E77N+ N213D, E77N+T228S, E77N+N229D, E77N+E234F, E77N+E234Y, E77N+A235K, E77N+A235R, E77N+ S241C, E77N+Q243K, E77N+Q243E, E77N+R244K, E77N+R244V, E77N+A250G, E77N+K254Y, E77N+ G257W, E77N+G257E, E77N+G257A, E77N+W260F, E77N+Y262F, E77N+S266A, E77N+D268N, E77N+ A270D, E77N+N272M, E77N+N272T, E77N+N273E, E77N+N273D, E77N+A276E, E77N+A276W, E77N+ A276D, E77N+N279D, E77N+N279E, E77N+T280L, E77N+N283W, E77N+N283H, E77N+Y286W, E77N+ Y286F, E77N+L288I, E77N+E290A, E77N+L294P, E77N+ L294K, E77N+L294I, E77N+L294R, E77N+L294V, E77N+L294H, E77N+S295K, E77N+S295V, E77N+S295P, E77N+S295L, E77N+S295R, E77N+S295A, E77N+ S295N, E77N+S295M, E77N+S295I, E77N+T296S, E77N+F298Y, D78G+H80K, D78G+V82R, D78G+V82I, D78G+V82S, D78G+A83P, D78G+A83S, D78G+Y93Q, D78G+Y93A, D78G+S95D, D78G+A97R, D78G+S98P, D78G+S98D, D78G+N100Y, D78G+D104A, D78G+ D104G, D78G+E108S, D78G+S111A, D78G+S111K, D78G+S111R, D78G+I114Q, D78G+I114M, D78G+ I114W, D78G+K116R, D78G+D118K, D78G+T119R, D78G+S131T, D78G+E133R, D78G+E133Q, D78G+ D135P, D78G+A136P, D78G+D139A, D78G+D139R, D78G+K142M, D78G+K142V, D78G+K142S, D78G+ K142R, D78G+Q143R, D78G+N150T, D78G+N150R, D78G+N150S, D78G+Q169A, D78G+Q169R, D78G+ Q169K, D78G+H172R, D78G+Y174R, D78G+Y174L, D78G+Y174W, D78G+Y174F, D78G+R176Q, D78G+ E177S, D78G+E177Y, D78G+N180R, D78G+P183T, D78G+P183G, D78G+Q184E, D78G+Q184K, D78G+ R185G, D78G+Y196W, D78G+Y196F, D78G+N200T, D78G+S202R, D78G+Q203T, D78G+R205K, D78G+ R210L, D78G+R210G, D78G+R210M, D78G+N213V, D78G+N213D, D78G+T228S, D78G+N229D, D78G+ E234F, D78G+E234Y, D78G+A235K, D78G+A235R, D78G+S241C, D78G+Q243K, D78G+Q243E, D78G+ R244K, D78G+R244V, D78G+A250G, D78G+K254Y, D78G+G257W, D78G+G257E, D78G+G257A, D78G+ W260F, D78G+Y262F, D78G+S266A, D78G+D268N, D78G+A270D, D78G+N272M, D78G+N272T, D78G+ N273E, D78G+N273D, D78G+A276E, D78G+A276W, D78G+A276D, D78G+N279D, D78G+N279E, D78G+ T280L, D78G+N283W, D78G+N283H, D78G+Y286W, D78G+Y286F, D78G+L288I, D78G+E290A, D78G+ L294P, D78G+L294K, D78G+L294I, D78G+L294R, D78G+L294V, D78G+L294H, D78G+S295K, D78G+ S295V, D78G+S295P, D78G+S295L, D78G+S295R, D78G+S295A, D78G+S295N, D78G+S295M, D78G+ S295I, D78G+T296S, D78G+F298Y, H80K+V82R, H80K+ V82I, H80K+V82S, H80K+A83P, H80K+A83S, H80K+ Y93Q, H80K+Y93A, H80K+S95D, H80K+A97R, H80K+ S98P, H80K+S98D, H80K+N100Y, H80K+D104A, H80K+ D104G, H80K+E108S, H80K+S111A, H80K+S111K, H80K+S111R, H80K+I114Q, H80K+I114M, H80K+ I114W, H80K+K116R, H80K+D118K, H80K+T119R, H80K+S131T, H80K+E133R, H80K+E133Q, H80K+ D135P, H80K+A136P, H80K+D139A, H80K+D139R, H80K+K142M, H80K+K142V, H80K+K142S, H80K+ K142R, H80K+Q143R, H80K+N150T, H80K+N150R, H80K+N150S, H80K+Q169A, H80K+Q169R, H80K+ Q169K, H80K+H172R, H80K+Y174R, H80K+Y174L, H80K+Y174W, H80K+Y174F, H80K+R176Q, H80K+ E177S, H80K+E177Y, H80K+N180R, H80K+P183T, H80K+P183G, H80K+Q184E, H80K+Q184K, H80K+ R185G, H80K+Y196W, H80K+Y196F, H80K+N200T, H80K+S202R, H80K+Q203T, H80K+R205K, H80K+ R210L, H80K+R210G, H80K+R210M, H80K+N213V, H80K+N213D, H80K+T228S, H80K+N229D, H80K+ E234F, H80K+E234Y, H80K+A235K, H80K+A235R, H80K+S241C, H80K+Q243K, H80K+Q243E, H80K+ R244K, H80K+R244V, H80K+A250G, H80K+K254Y, H80K+G257W, H80K+G257E, H80K+G257A, H80K+ W260F, H80K+Y262F, H80K+S266A, H80K+D268N, H80K+A270D, H80K+N272M, H80K+N272T, H80K+ N273E, H80K+N273D, H80K+A276E, H80K+A276W, H80K+A276D, H80K+N279D, H80K+N279E, H80K+ T280L, H80K+N283W, H80K+N283H, H80K+Y286W, H80K+Y286F, H80K+L288I, H80K+E290A, H80K+ L294P, H80K+L294K, H80K+L294I, H80K+L294R, H80K+L294V, H80K+L294H, H80K+S295K, H80K+ S295V, H80K+S295P, H80K+S295L, H80K+S295R, H80K+S295A, H80K+S295N, H80K+S295M, H80K+ S295I, H80K+T296S, H80K+F298Y, V82R+A83P, V82R+ A83S, V82R+Y93Q, V82R+Y93A, V82R+S95D, V82R+ A97R, V82R+S98P, V82R+S98D, V82R+N100Y, V82R+ D104A, V82R+D104G, V82R+E108S, V82R+S111A, V82R+S111K, V82R+S111R, V82R+I114Q, V82R+I114M, V82R+I114W, V82R+K116R, V82R+D118K, V82R+ T119R, V82R+S131T, V82R+E133R, V82R+E133Q, V82R+D135P, V82R+A136P, V82R+D139A, V82R+ D139R, V82R+K142M, V82R+K142V, V82R+K142S, V82R+K142R, V82R+Q143R, V82R+N150T, V82R+ N150R, V82R+N150S, V82R+Q169A, V82R+Q169R, V82R+Q169K, V82R+H172R, V82R+Y174R, V82R+ Y174L, V82R+Y174W, V82R+Y174F, V82R+R176Q, V82R+E177S, V82R+E177Y, V82R+N180R, V82R+ P183T, V82R+P183G, V82R+Q184E, V82R+Q184K, V82R+R185G, V82R+Y196W, V82R+Y196F, V82R+ N200T, V82R+S202R, V82R+Q203T, V82R+R205K, V82R+R210L, V82R+R210G, V82R+R210M, V82R+ N213V, V82R+N213D, V82R+T228S, V82R+N229D, V82R+E234F, V82R+E234Y, V82R+A235K, V82R+ A235R, V82R+S241C, V82R+Q243K, V82R+Q243E, V82R+R244K, V82R+R244V, V82R+A250G, V82R+ K254Y, V82R+G257W, V82R+G257E, V82R+G257A, V82R+W260F, V82R+Y262F, V82R+S266A, V82R+ D268N, V82R+A270D, V82R+N272M, V82R+N272T, V82R+N273E, V82R+N273D, V82R+A276E, V82R+ A276W, V82R+A276D, V82R+N279D, V82R+N279E, V82R+T280L, V82R+N283W, V82R+N283H, V82R+ Y286W, V82R+Y286F, V82R+L288I, V82R+E290A, V82R+L294P, V82R+L294K, V82R+L294I, V82R+L294R, V82R+L294V, V82R+L294H, V82R+S295K, V82R+ S295V, V82R+S295P, V82R+S295L, V82R+S295R, V82R+S295A, V82R+S295N, V82R+S295M, V82R+ S295I, V82R+T296S, V82R+F298Y, V82I+A83P, V82I+ A83S, V82I+Y93Q, V82I+Y93A, V82I+S95D, V82I+ A97R, V82I+S98P, V82I+S98D, V82I+N100Y, V82I+ D104A, V82I+D104G, V82I+E108S, V82I+S111A, V82I+ S111K, V82I+S111R, V82I+I114Q, V82I+I114M, V82I+ I114W, V82I+K116R, V82I+D118K, V82I+T119R, V82I+ S131T, V82I+E133R, V82I+E133Q, V82I+D135P, V82I+ A136P, V82I+D139A, V82I+D139R, V82I+K142M, V82I+ K142V, V82I+K142S, V82I+K142R, V82I+Q143R, V82I+ N150T, V82I+N150R, V82I+N150S, V82I+Q169A, V82I+ Q169R, V82I+Q169K, V82I+H172R, V82I+Y174R, V82I+ Y174L, V82I+Y174W, V82I+Y174F, V82I+R176Q, V82I+ E177S, V82I+E177Y, V82I+N180R, V82I+P183T, V82I+ P183G, V82I+Q184E, V82I+Q184K, V82I+R185G, V82I+

Y196W, V82I+Y196F, V82I+N200T, V82I+S202R, V82I+ Q203T, V82I+R205K, V82I+R210L, V82I+R210G, V82I+ R210M, V82I+N213V, V82I+N213D, V82I+T228S, V82I+ N229D, V82I+E234F, V82I+E234Y, V82I+A235K, V82I+ A235R, V82I+S241C, V82I+Q243K, V82I+Q243E, V82I+ R244K, V82I+R244V, V82I+A250G, V82I+K254Y, V82I+ G257W, V82I+G257E, V82I+G257A, V82I+W260F, V82I+ Y262F, V82I+S266A, V82I+D268N, V82I+A270D, V82I+ N272M, V82I+N272T, V82I+N273E, V82I+N273D, V82I+ A276E, V82I+A276W, V82I+A276D, V82I+N279D, V82I+ N279E, V82I+T280L, V82I+N283W, V82I+N283H, V82I+ Y286W, V82I+Y286F, V82I+L288I, V82I+E290A, V82I+ L294P, V82I+L294K, V82I+L294I, V82I+L294R, V82I+ L294V, V82I+L294H, V82I+S295K, V82I+S295V, V82I+ S295P, V82I+S295L, V82I+S295R, V82I+S295A, V82I+ S295N, V82I+S295M, V82I+S295I, V82I+T296S, V82I+ F298Y, V82S+A83P, V82S+A83S, V82S+Y93Q, V82S+ Y93A, V82S+S95D, V82S+A97R, V82S+S98P, V82S+ S98D, V82S+N100Y, V82S+D104A, V82S+D104G, V82S+E108S, V82S+S111A, V82S+S111K, V82S+S111R, V82S+I114Q, V82S+I114M, V82S+I114W, V82S+K116R, V82S+D118K, V82S+T119R, V82S+S131T, V82S+E133R, V82S+E133Q, V82S+D135P, V82S+A136P, V82S+D139A, V82S+D139R, V82S+K142M, V82S+K142V, V82S+ K142S, V82S+K142R, V82S+Q143R, V82S+N150T, V82S+N150R, V82S+N150S, V82S+Q169A, V82S+ Q169R, V82S+Q169K, V82S+H172R, V82S+Y174R, V82S+Y174L, V82S+Y174W, V82S+Y174F, V82S+ R176Q, V82S+E177S, V82S+E177Y, V82S+N180R, V82S+P183T, V82S+P183G, V82S+Q184E, V82S+Q184K, V82S+R185G, V82S+Y196W, V82S+Y196F, V82S+ N200T, V82S+S202R, V82S+Q203T, V82S+R205K, V82S+R210L, V82S+R210G, V82S+R210M, V82S+ N213V, V82S+N213D, V82S+T228S, V82S+N229D, V82S+E234F, V82S+E234Y, V82S+A235K, V82S+A235R, V82S+S241C, V82S+Q243K, V82S+Q243E, V82S+ R244K, V82S+R244V, V82S+A250G, V82S+K254Y, V82S+G257W, V82S+G257E, V82S+G257A, V82S+ W260F, V82S+Y262F, V82S+S266A, V82S+D268N, V82S+A270D, V82S+N272M, V82S+N272T, V82S+ N273E, V82S+N273D, V82S+A276E, V82S+A276W, V82S+A276D, V82S+N279D, V82S+N279E, V82S+ T280L, V82S+N283W, V82S+N283H, V82S+Y286W, V82S+Y286F, V82S+L288I, V82S+E290A, V82S+L294P, V82S+L294K, V82S+L294I, V82S+L294R, V82S+L294V, V82S+L294H, V82S+S295K, V82S+S295V, V82S+S295P, V82S+S295L, V82S+S295R, V82S+S295A, V82S+S295N, V82S+S295M, V82S+S295I, V82S+T296S, V82S+F298Y, A83P+Y93Q, A83P+Y93A, A83P+S95D, A83P+A97R, A83P+S98P, A83P+S98D, A83P+N100Y, A83P+D104A, A83P+D104G, A83P+E108S, A83P+S111A, A83P+S111K, A83P+S111R, A83P+I114Q, A83P+I114M, A83P+I114W, A83P+K116R, A83P+D118K, A83P+T119R, A83P+S131T, A83P+E133R, A83P+E133Q, A83P+D135P, A83P+A136P, A83P+D139A, A83P+D139R, A83P+K142M, A83P+ K142V, A83P+K142S, A83P+K142R, A83P+Q143R, A83P+N150T, A83P+N150R, A83P+N150S, A83P+ Q169A, A83P+Q169R, A83P+Q169K, A83P+H172R, A83P+Y174R, A83P+Y174L, A83P+Y174W, A83P+ Y174F, A83P+R176Q, A83P+E177S, A83P+E177Y, A83P+ N180R, A83P+P183T, A83P+P183G, A83P+Q184E, A83P+ Q184K, A83P+R185G, A83P+Y196W, A83P+Y196F, A83P+N200T, A83P+S202R, A83P+Q203T, A83P+R205K, A83P+R210L, A83P+R210G, A83P+R210M, A83P+ N213V, A83P+N213D, A83P+T228S, A83P+N229D, A83P+E234F, A83P+E234Y, A83P+A235K, A83P+A235R, A83P+S241C, A83P+Q243K, A83P+Q243E, A83P+ R244K, A83P+R244V, A83P+A250G, A83P+K254Y, A83P+G257W, A83P+G257E, A83P+G257A, A83P+ W260F, A83P+Y262F, A83P+S266A, A83P+D268N, A83P+A270D, A83P+N272M, A83P+N272T, A83P+ N273E, A83P+N273D, A83P+A276E, A83P+A276W, A83P+A276D, A83P+N279D, A83P+N279E, A83P+ T280L, A83P+N283W, A83P+N283H, A83P+Y286W, A83P+Y286F, A83P+L288I, A83P+E290A, A83P+L294P, A83P+L294K, A83P+L294I, A83P+L294R, A83P+L294V, A83P+L294H, A83P+S295K, A83P+S295V, A83P+S295P, A83P+S295L, A83P+S295R, A83P+S295A, A83P+S295N, A83P+S295M, A83P+S295I, A83P+T296S, A83P+F298Y, A83S+Y93Q, A83S+Y93A, A83S+S95D, A83S+A97R, A83S+S98P, A83S+S98D, A83S+N100Y, A83S+D104A, A83S+D104G, A83S+E108S, A83S+S111A, A83S+S111K, A83S+S111R, A83S+I114Q, A83S+I114M, A83S+I114W, A83S+K116R, A83S+D118K, A83S+T119R, A83S+S131T, A83S+E133R, A83S+E133Q, A83S+D135P, A83S+A136P, A83S+D139A, A83S+D139R, A83S+K142M, A83S+ K142V, A83S+K142S, A83S+K142R, A83S+Q143R, A83S+N150T, A83S+N150R, A83S+N150S, A83S+ Q169A, A83S+Q169R, A83S+Q169K, A83S+H172R, A83S+Y174R, A83S+Y174L, A83S+Y174W, A83S+ Y174F, A83S+R176Q, A83S+E177S, A83S+E177Y, A83S+ N180R, A83S+P183T, A83S+P183G, A83S+Q184E, A83S+ Q184K, A83S+R185G, A83S+Y196W, A83S+Y196F, A83S+N200T, A83S+S202R, A83S+Q203T, A83S+R205K, A83S+R210L, A83S+R210G, A83S+R210M, A83S+ N213V, A83S+N213D, A83S+T228S, A83S+N229D, A83S+E234F, A83S+E234Y, A83S+A235K, A83S+A235R, A83S+S241C, A83S+Q243K, A83S+Q243E, A83S+ R244K, A83S+R244V, A83S+A250G, A83S+K254Y, A83S+G257W, A83S+G257E, A83S+G257A, A83S+ W260F, A83S+Y262F, A83S+S266A, A83S+D268N, A83S+A270D, A83S+N272M, A83S+N272T, A83S+ N273E, A83S+N273D, A83S+A276E, A83S+A276W, A83S+A276D, A83S+N279D, A83S+N279E, A83S+ T280L, A83S+N283W, A83S+N283H, A83S+Y286W, A83S+Y286F, A83S+L288I, A83S+E290A, A83S+L294P, A83S+L294K, A83S+L294I, A83S+L294R, A83S+L294V, A83S+L294H, A83S+S295K, A83S+S295V, A83S+S295P, A83S+S295L, A83S+S295R, A83S+S295A, A83S+S295N, A83S+S295M, A83S+S295I, A83S+T296S, A83S+F298Y, Y93Q+S95D, Y93Q+A97R, Y93Q+S98P, Y93Q+S98D, Y93Q+N100Y, Y93Q+D104A, Y93Q+D104G, Y93Q+ E108S, Y93Q+S111A, Y93Q+S111K, Y93Q+S111R, Y93Q+I114Q, Y93Q+I114M, Y93Q+I114W, Y93Q+ K116R, Y93Q+D118K, Y93Q+T119R, Y93Q+S131T, Y93Q+E133R, Y93Q+E133Q, Y93Q+D135P, Y93Q+ A136P, Y93Q+D139A, Y93Q+D139R, Y93Q+K142M, Y93Q+K142V, Y93Q+K142S, Y93Q+K142R, Y93Q+ Q143R, Y93Q+N150T, Y93Q+N150R, Y93Q+N150S, Y93Q+Q169A, Y93Q+Q169R, Y93Q+Q169K, Y93Q+ H172R, Y93Q+Y174R, Y93Q+Y174L, Y93Q+Y174W, Y93Q+Y174F, Y93Q+R176Q, Y93Q+E177S, Y93Q+ E177Y, Y93Q+N180R, Y93Q+P183T, Y93Q+P183G, Y93Q+Q184E, Y93Q+Q184K, Y93Q+R185G, Y93Q+ Y196W, Y93Q+Y196F, Y93Q+N200T, Y93Q+S202R, Y93Q+Q203T, Y93Q+R205K, Y93Q+R210L, Y93Q+ R210G, Y93Q+R210M, Y93Q+N213V, Y93Q+N213D, Y93Q+T228S, Y93Q+N229D, Y93Q+E234F, Y93Q+ E234Y, Y93Q+A235K, Y93Q+A235R, Y93Q+S241C, Y93Q+Q243K, Y93Q+Q243E, Y93Q+R244K, Y93Q+ R244V, Y93Q+A250G, Y93Q+K254Y, Y93Q+G257W, Y93Q+G257E, Y93Q+G257A, Y93Q+W260F, Y93Q+ Y262F, Y93Q+S266A, Y93Q+D268N, Y93Q+A270D, Y93Q+N272M, Y93Q+N272T, Y93Q+N273E, Y93Q+

N273D, Y93Q+A276E, Y93Q+A276W, Y93Q+A276D, Y93Q+N279D, Y93Q+N279E, Y93Q+T280L, Y93Q+N283W, Y93Q+N283H, Y93Q+Y286W, Y93Q+Y286F, Y93Q+L288I, Y93Q+E290A, Y93Q+L294P, Y93Q+L294K, Y93Q+L294I, Y93Q+L294R, Y93Q+L294V, Y93Q+L294H, Y93Q+S295K, Y93Q+S295V, Y93Q+S295P, Y93Q+S295L, Y93Q+S295R, Y93Q+S295A, Y93Q+S295N, Y93Q+S295M, Y93Q+S295I, Y93Q+T296S, Y93Q+F298Y, Y93A+S95D, Y93A+A97R, Y93A+S98P, Y93A+S98D, Y93A+N100Y, Y93A+D104A, Y93A+D104G, Y93A+E108S, Y93A+S111A, Y93A+S111K, Y93A+S111R, Y93A+I114Q, Y93A+I114M, Y93A+I114W, Y93A+K116R, Y93A+D118K, Y93A+T119R, Y93A+S131T, Y93A+E133R, Y93A+E133Q, Y93A+D135P, Y93A+A136P, Y93A+D139A, Y93A+D139R, Y93A+K142M, Y93A+K142V, Y93A+K142S, Y93A+K142R, Y93A+Q143R, Y93A+N150T, Y93A+N150R, Y93A+N150S, Y93A+Q169A, Y93A+Q169R, Y93A+Q169K, Y93A+H172R, Y93A+Y174R, Y93A+Y174L, Y93A+Y174W, Y93A+Y174F, Y93A+R176Q, Y93A+E177S, Y93A+E177Y, Y93A+N180R, Y93A+P183T, Y93A+P183G, Y93A+Q184E, Y93A+Q184K, Y93A+R185G, Y93A+Y196W, Y93A+Y196F, Y93A+N200T, Y93A+S202R, Y93A+Q203T, Y93A+R205K, Y93A+R210L, Y93A+R210G, Y93A+R210M, Y93A+N213V, Y93A+N213D, Y93A+T228S, Y93A+N229D, Y93A+E234F, Y93A+E234Y, Y93A+A235K, Y93A+A235R, Y93A+S241C, Y93A+Q243K, Y93A+Q243E, Y93A+R244K, Y93A+R244V, Y93A+A250G, Y93A+K254Y, Y93A+G257W, Y93A+G257E, Y93A+G257A, Y93A+W260F, Y93A+Y262F, Y93A+S266A, Y93A+D268N, Y93A+A270D, Y93A+N272M, Y93A+N272T, Y93A+N273E, Y93A+N273D, Y93A+A276E, Y93A+A276W, Y93A+A276D, Y93A+N279D, Y93A+N279E, Y93A+T280L, Y93A+N283W, Y93A+N283H, Y93A+Y286W, Y93A+Y286F, Y93A+L288I, Y93A+E290A, Y93A+L294P, Y93A+L294K, Y93A+L294I, Y93A+L294R, Y93A+L294V, Y93A+L294H, Y93A+S295K, Y93A+S295V, Y93A+S295P, Y93A+S295L, Y93A+S295R, Y93A+S295A, Y93A+S295N, Y93A+S295M, Y93A+S295I, Y93A+T296S, Y93A+F298Y, S95D+A97R, S95D+S98P, S95D+S98D, S95D+N100Y, S95D+D104A, S95D+D104G, S95D+E108S, S95D+S111A, S95D+S111K, S95D+S111R, S95D+I114Q, S95D+I114M, S95D+I114W, S95D+K116R, S95D+D118K, S95D+T119R, S95D+S131T, S95D+E133R, S95D+E133Q, S95D+D135P, S95D+A136P, S95D+D139A, S95D+D139R, S95D+K142M, S95D+K142V, S95D+K142S, S95D+K142R, S95D+Q143R, S95D+N150T, S95D+N150R, S95D+N150S, S95D+Q169A, S95D+Q169R, S95D+Q169K, S95D+H172R, S95D+Y174R, S95D+Y174L, S95D+Y174W, S95D+Y174F, S95D+R176Q, S95D+E177S, S95D+E177Y, S95D+N180R, S95D+P183T, S95D+P183G, S95D+Q184E, S95D+Q184K, S95D+R185G, S95D+Y196W, S95D+Y196F, S95D+N200T, S95D+S202R, S95D+Q203T, S95D+R205K, S95D+R210L, S95D+R210G, S95D+R210M, S95D+N213V, S95D+N213D, S95D+T228S, S95D+N229D, S95D+E234F, S95D+E234Y, S95D+A235K, S95D+A235R, S95D+S241C, S95D+Q243K, S95D+Q243E, S95D+R244K, S95D+R244V, S95D+A250G, S95D+K254Y, S95D+G257W, S95D+G257E, S95D+G257A, S95D+W260F, S95D+Y262F, S95D+S266A, S95D+D268N, S95D+A270D, S95D+N272M, S95D+N272T, S95D+N273E, S95D+N273D, S95D+A276E, S95D+A276W, S95D+A276D, S95D+N279D, S95D+N279E, S95D+T280L, S95D+N283W, S95D+N283H, S95D+Y286W, S95D+Y286F, S95D+L288I, S95D+E290A, S95D+L294P, S95D+L294K, S95D+L294I, S95D+L294R, S95D+L294V, S95D+L294H, S95D+S295K, S95D+S295V, S95D+S295P, S95D+S295L, S95D+S295R, S95D+S295A, S95D+S295N, S95D+S295M, S95D+S295I, S95D+T296S, S95D+F298Y, A97R+S98P, A97R+S98D, A97R+N100Y, A97R+D104A, A97R+D104G, A97R+E108S, A97R+S111A, A97R+S111K, A97R+S111R, A97R+I114Q, A97R+I114M, A97R+I114W, A97R+K116R, A97R+D118K, A97R+T119R, A97R+S131T, A97R+E133R, A97R+E133Q, A97R+D135P, A97R+A136P, A97R+D139A, A97R+D139R, A97R+K142M, A97R+K142V, A97R+K142S, A97R+K142R, A97R+Q143R, A97R+N15OT, A97R+N150R, A97R+N150S, A97R+Q169A, A97R+Q169R, A97R+Q169K, A97R+H172R, A97R+Y174R, A97R+Y174L, A97R+Y174W, A97R+Y174F, A97R+R176Q, A97R+E177S, A97R+E177Y, A97R+N180R, A97R+P183T, A97R+P183G, A97R+Q184E, A97R+Q184K, A97R+R185G, A97R+Y196W, A97R+Y196F, A97R+N200T, A97R+S202R, A97R+Q203T, A97R+R205K, A97R+R210L, A97R+R210G, A97R+R210M, A97R+N213V, A97R+N213D, A97R+T228S, A97R+N229D, A97R+E234F, A97R+E234Y, A97R+A235K, A97R+A235R, A97R+S241C, A97R+Q243K, A97R+Q243E, A97R+R244K, A97R+R244V, A97R+A250G, A97R+K254Y, A97R+G257W, A97R+G257E, A97R+G257A, A97R+W260F, A97R+Y262F, A97R+S266A, A97R+D268N, A97R+A270D, A97R+N272M, A97R+N272T, A97R+N273E, A97R+N273D, A97R+A276E, A97R+A276W, A97R+A276D, A97R+N279D, A97R+N279E, A97R+T280L, A97R+N283W, A97R+N283H, A97R+Y286W, A97R+Y286F, A97R+L288I, A97R+E290A, A97R+L294P, A97R+L294K, A97R+L294 I, A97R+L294R, A97R+L294V, A97R+L294H, A97R+S295K, A97R+S295V, A97R+S295P, A97R+S295L, A97R+S295R, A97R+S295A, A97R+S295N, A97R+S295M, A97R+S295I, A97R+T296S, A97R+F298Y, S98P+N100Y, S98P+D104A, S98P+D104G, S98P+E108S, S98P+S111A, S98P+S111K, S98P+S111R, S98P+I114Q, S98P+I114M, S98P+I114W, S98P+K116R, S98P+D118K, S98P+T119R, S98P+S131T, S98P+E133R, S98P+E133Q, S98P+D135P, S98P+A136P, S98P+D139A, S98P+D139R, S98P+K142M, S98P+K142V, S98P+K142S, S98P+K142R, S98P+Q143R, S98P+N150T, S98P+N150R, S98P+N150S, S98P+Q169A, S98P+Q169R, S98P+Q169K, S98P+H172R, S98P+Y174R, S98P+Y174L, S98P+Y174W, S98P+Y174F, S98P+R176Q, S98P+E177S, S98P+E177Y, S98P+N180R, S98P+P183T, S98P+P183G, S98P+Q184E, S98P+Q184K, S98P+R185G, S98P+Y196W, S98P+Y196F, S98P+N200T, S98P+S202R, S98P+Q203T, S98P+R205K, S98P+R210L, S98P+R210G, S98P+R210M, S98P+N213V, S98P+N213D, S98P+T228S, S98P+N229D, S98P+E234F, S98P+E234Y, S98P+A235K, S98P+A235R, S98P+S241C, S98P+Q243K, S98P+Q243E, S98P+R244K, S98P+R244V, S98P+A250G, S98P+K254Y, S98P+G257W, S98P+G257E, S98P+G257A, S98P+W260F, S98P+Y262F, S98P+S266A, S98P+D268N, S98P+A270D, S98P+N272M, S98P+N272T, S98P+N273E, S98P+N273D, S98P+A276E, S98P+A276W, S98P+A276D, S98P+N279D, S98P+N279E, S98P+T280L, S98P+N283W, S98P+N283H, S98P+Y286W, S98P+Y286F, S98P+L288I, S98P+E290A, S98P+L294P, S98P+L294K, S98P+L294I, S98P+L294R, S98P+L294V, S98P+L294H, S98P+S295K, S98P+S295V, S98P+S295P, S98P+S295L, S98P+S295R, S98P+S295A, S98P+S295N, S98P+S295M, S98P+S295I, S98P+T296S, S98P+F298Y, S98D+N100Y, S98D+D104A, S98D+D104G, S98D+E108S, S98D+S111A, S98D+S111K, S98D+S111R, S98D+I114Q, S98D+I114M, S98D+I114W, S98D+K116R, S98D+D118K,

S98D+T119R, S98D+S131T, S98D+E133R, S98D+E133Q, S98D+D135P, S98D+A136P, S98D+D139A, S98D+D139R, S98D+K142M, S98D+K142V, S98D+K142S, S98D+K142R, S98D+Q143R, S98D+N150T, S98D+N150R, S98D+N150S, S98D+Q169A, S98D+Q169R, S98D+Q169K, S98D+H172R, S98D+Y174R, S98D+Y174L, S98D+Y174W, S98D+Y174F, S98D+R176Q, S98D+E177S, S98D+E177Y, S98D+N180R, S98D+P183T, S98D+P183G, S98D+Q184E, S98D+Q184K, S98D+R185G, S98D+Y196W, S98D+Y196F, S98D+N200T, S98D+S202R, S98D+Q203T, S98D+R205K, S98D+R210L, S98D+R210G, S98D+R210M, S98D+N213V, S98D+N213D, S98D+T228S, S98D+N229D, S98D+E234F, S98D+E234Y, S98D+A235K, S98D+A235R, S98D+S241C, S98D+Q243K, S98D+Q243E, S98D+R244K, S98D+R244V, S98D+A250G, S98D+K254Y, S98D+G257W, S98D+G257E, S98D+G257A, S98D+W260F, S98D+Y262F, S98D+S266A, S98D+D268N, S98D+A270D, S98D+N272M, S98D+N272T, S98D+N273E, S98D+N273D, S98D+A276E, S98D+A276W, S98D+A276D, S98D+N279D, S98D+N279E, S98D+T280L, S98D+N283W, S98D+N283H, S98D+Y286W, S98D+Y286F, S98D+L288I, S98D+E290A, S98D+L294P, S98D+L294K, S98D+L294I, S98D+L294R, S98D+L294V, S98D+L294H, S98D+S295K, S98D+S295V, S98D+S295P, S98D+S295L, S98D+S295R, S98D+S295A, S98D+S295N, S98D+S295M, S98D+S295I, S98D+T296S, S98D+F298Y, N100Y+D104A, N100Y+D104G, N100Y+E108S, N100Y+S111A, N100Y+S111K, N100Y+S111R, N100Y+I114Q, N100Y+I114M, N100Y+I114W, N100Y+K116R, N100Y+D118K, N100Y+T119R, N100Y+S131T, N100Y+E133R, N100Y+E133Q, N100Y+D135P, N100Y+A136P, N100Y+D139A, N100Y+D139R, N100Y+K142M, N100Y+K142V, N100Y+K142S, N100Y+K142R, N100Y+Q143R, N100Y+N150T, N100Y+N150R, N100Y+N150S, N100Y+Q169A, N100Y+Q169R, N100Y+Q169K, N100Y+H172R, N100Y+Y174R, N100Y+Y174L, N100Y+Y174W, N100Y+Y174F, N100Y+R176Q, N100Y+E177S, N100Y+E177Y, N100Y+N180R, N100Y+P183T, N100Y+P183G, N100Y+Q184E, N100Y+Q184K, N100Y+R185G, N100Y+Y196W, N100Y+Y196F, N100Y+N200T, N100Y+S202R, N100Y+Q203T, N100Y+R205K, N100Y+R210L, N100Y+R210G, N100Y+R210M, N100Y+N213V, N100Y+N213D, N100Y+T228S, N100Y+N229D, N100Y+E234F, N100Y+E234Y, N100Y+A235K, N100Y+A235R, N100Y+S241C, N100Y+Q243K, N100Y+Q243E, N100Y+R244K, N100Y+R244V, N100Y+A250G, N100Y+K254Y, N100Y+G257W, N100Y+G257E, N100Y+G257A, N100Y+W260F, N100Y+Y262F, N100Y+S266A, N100Y+D268N, N100Y+A270D, N100Y+N272M, N100Y+N272T, N100Y+N273E, N100Y+N273D, N100Y+A276E, N100Y+A276W, N100Y+A276D, N100Y+N279D, N100Y+N279E, N100Y+T280L, N100Y+N283W, N100Y+N283H, N100Y+Y286W, N100Y+Y286F, N100Y+L288I, N100Y+E290A, N100Y+L294P, N100Y+L294K, N100Y+L294I, N100Y+L294R, N100Y+L294V, N100Y+L294H, N100Y+S295K, N100Y+S295V, N100Y+S295P, N100Y+S295L, N100Y+S295R, N100Y+S295A, N100Y+S295N, N100Y+S295M, N100Y+S295I, N100Y+T296S, N100Y+F298Y, D104A+E108S, D104A+S111A, D104A+S111K, D104A+S111R, D104A+I114Q, D104A+I114M, D104A+I114W, D104A+K116R, D104A+D118K, D104A+T119R, D104A+S131T, D104A+E133R, D104A+E133Q, D104A+D135P, D104A+A136P, D104A+D139A, D104A+D139R, D104A+K142M, D104A+K142V, D104A+K142S, D104A+K142R, D104A+Q143R, D104A+N150T, D104A+N150R, D104A+N150S, D104A+Q169A, D104A+Q169R, D104A+Q169K, D104A+H172R, D104A+Y174R, D104A+Y174L, D104A+Y174W, D104A+Y174F, D104A+R176Q, D104A+E177S, D104A+E177Y, D104A+N180R, D104A+P183T, D104A+P183G, D104A+Q184E, D104A+Q184K, D104A+R185G, D104A+Y196W, D104A+Y196F, D104A+N200T, D104A+S202R, D104A+Q203T, D104A+R205K, D104A+R210L, D104A+R210G, D104A+R210M, D104A+N213V, D104A+N213D, D104A+T228S, D104A+N229D, D104A+E234F, D104A+E234Y, D104A+A235K, D104A+A235R, D104A+S241C, D104A+Q243K, D104A+Q243E, D104A+R244K, D104A+R244V, D104A+A250G, D104A+K254Y, D104A+G257W, D104A+G257E, D104A+G257A, D104A+W260F, D104A+Y262F, D104A+S266A, D104A+D268N, D104A+A270D, D104A+N272M, D104A+N272T, D104A+N273E, D104A+N273D, D104A+A276E, D104A+A276W, D104A+A276D, D104A+N279D, D104A+N279E, D104A+T280L, D104A+N283W, D104A+N283H, D104A+Y286W, D104A+Y286F, D104A+L288I, D104A+E290A, D104A+L294P, D104A+L294K, D104A+L294I, D104A+L294R, D104A+L294V, D104A+L294H, D104A+S295K, D104A+S295V, D104A+S295P, D104A+S295L, D104A+S295R, D104A+S295A, D104A+S295N, D104A+S295M, D104A+S295I, D104A+T296S, D104A+F298Y, D104G+E108S, D104G+S111A, D104G+S111K, D104G+S111R, D104G+I114Q, D104G+I114M, D104G+I114W, D104G+K116R, D104G+D118K, D104G+T119R, D104G+S131T, D104G+E133R, D104G+E133Q, D104G+D135P, D104G+A136P, D104G+D139A, D104G+D139R, D104G+K142M, D104G+K142V, D104G+K142S, D104G+K142R, D104G+Q143R, D104G+N150T, D104G+N150R, D104G+N150S, D104G+Q169A, D104G+Q169R, D104G+Q169K, D104G+H172R, D104G+Y174R, D104G+Y174L, D104G+Y174W, D104G+Y174F, D104G+R176Q, D104G+E177S, D104G+E177Y, D104G+N180R, D104G+P183T, D104G+P183G, D104G+Q184E, D104G+Q184K, D104G+R185G, D104G+Y196W, D104G+Y196F, D104G+N200T, D104G+S202R, D104G+Q203T, D104G+R205K, D104G+R210L, D104G+R210G, D104G+R210M, D104G+N213V, D104G+N213D, D104G+T228S, D104G+N229D, D104G+E234F, D104G+E234Y, D104G+A235K, D104G+A235R, D104G+S241C, D104G+Q243K, D104G+Q243E, D104G+R244K, D104G+R244V, D104G+A250G, D104G+K254Y, D104G+G257W, D104G+G257E, D104G+G257A, D104G+W260F, D104G+Y262F, D104G+S266A, D104G+D268N, D104G+A270D, D104G+N272M, D104G+N272T, D104G+N273E, D104G+N273D, D104G+A276E, D104G+A276W, D104G+A276D, D104G+N279D, D104G+N279E, D104G+T280L, D104G+N283W, D104G+N283H, D104G+Y286W, D104G+Y286F, D104G+L288I, D104G+E290A, D104G+L294P, D104G+L294K, D104G+L294I, D104G+L294R, D104G+L294V, D104G+L294H, D104G+S295K, D104G+S295V, D104G+S295P, D104G+S295L, D104G+S295R, D104G+S295A, D104G+S295N, D104G+S295M, D104G+S295I, D104G+T296S, D104G+F298Y, E108S+S111A, E108S+S111K, E108S+S111R, E108S+I114Q, E108S+I114M, E108S+I114W, E108S+K116R, E108S+D118K, E108S+T119R, E108S+S131T, E108S+E133R, E108S+E133Q, E108S+D135P, E108S+A136P, E108S+D139A, E108S+D139R, E108S+K142M, E108S+K142V, E108S+K142S, E108S+K142R, E108S+Q143R, E108S+N150T, E108S+N150R, E108S+N150S, E108S+Q169A, E108S+Q169R, E108S+Q169K, E108S+H172R, E108S+Y174R, E108S+Y174L, E108S+Y174W, E108S+Y174F, E108S+R176Q, E108S+E177S, E108S+E177Y, E108S+N180R, E108S+P183T, E108S+P183G, E108S+Q184E, E108S+Q184K, E108S+R185G, E108S+Y196W, E108S+Y196F, E108S+N200T, E108S+S202R, E108S+

Q203T, E108S+R205K, E108S+R210L, E108S+R210G, E108S+R210M, E108S+N213V, E108S+N213D, E108S+T228S, E108S+N229D, E108S+E234F, E108S+E234Y, E108S+A235K, E108S+A235R, E108S+S241C, E108S+Q243K, E108S+Q243E, E108S+R244K, E108S+R244V, E108S+A250G, E108S+K254Y, E108S+G257W, E108S+G257E, E108S+G257A, E108S+W260F, E108S+Y262F, E108S+S266A, E108S+D268N, E108S+A270D, E108S+N272M, E108S+N272T, E108S+N273E, E108S+N273D, E108S+A276E, E108S+A276W, E108S+A276D, E108S+N279D, E108S+N279E, E108S+T280L, E108S+N283W, E108S+N283H, E108S+Y286W, E108S+Y286F, E108S+L288I, E108S+E290A, E108S+L294P, E108S+L294K, E108S+L294I, E108S+L294R, E108S+L294V, E108S+L294H, E108S+S295K, E108S+S295V, E108S+S295P, E108S+S295L, E108S+S295R, E108S+S295A, E108S+S295N, E108S+S295M, E108S+S295I, E108S+T296S, E108S+F298Y, S111A+I114Q, S111A+I114M, S111A+I114W, S111A+K116R, S111A+D118K, S111A+T119R, S111A+S131T, S111A+E133R, S111A+E133Q, S111A+D135P, S111A+A136P, S111A+D139A, S111A+D139R, S111A+K142M, S111A+K142V, S111A+K142S, S111A+K142R, S111A+Q143R, S111A+N150T, S111A+N150R, S111A+N150S, S111A+Q169A, S111A+Q169R, S111A+Q169K, S111A+H172R, S111A+Y174R, S111A+Y174L, S111A+Y174W, S111A+Y174F, S111A+R176Q, S111A+E177S, S111A+E177Y, S111A+N180R, S111A+P183T, S111A+P183G, S111A+Q184E, S111A+Q184K, S111A+R185G, S111A+Y196W, S111A+Y196F, S111A+N200T, S111A+S202R, S111A+Q203T, S111A+R205K, S111A+R210L, S111A+R210G, S111A+R210M, S111A+N213V, S111A+N213D, S111A+T228S, S111A+N229D, S111A+E234F, S111A+E234Y, S111A+A235K, S111A+A235R, S111A+S241C, S111A+Q243K, S111A+Q243E, S111A+R244K, S111A+R244V, S111A+A250G, S111A+K254Y, S111A+G257W, S111A+G257E, S111A+G257A, S111A+W260F, S111A+Y262F, S111A+S266A, S111A+D268N, S111A+A270D, S111A+N272M, S111A+N272T, S111A+N273E, S111A+N273D, S111A+A276E, S111A+A276W, S111A+A276D, S111A+N279D, S111A+N279E, S111A+T280L, S111A+N283W, S111A+N283H, S111A+Y286W, S111A+Y286F, S111A+L288I, S111A+E290A, S111A+L294P, S111A+L294K, S111A+L294I, S111A+L294R, S111A+L294V, S111A+L294H, S111A+S295K, S111A+S295V, S111A+S295P, S111A+S295L, S111A+S295R, S111A+S295A, S111A+S295N, S111A+S295M, S111A+S295I, S111A+T296S, S111A+F298Y, S111K+I114Q, S111K+I114M, S111K+I114W, S111K+K116R, S111K+D118K, S111K+T119R, S111K+S131T, S111K+E133R, S111K+E133Q, S111K+D135P, S111K+A136P, S111K+D139A, S111K+D139R, S111K+K142M, S111K+K142V, S111K+K142S, S111K+K142R, S111K+Q143R, S111K+N150T, S111K+N150R, S111K+N150S, S111K+Q169A, S111K+Q169R, S111K+Q169K, S111K+H172R, S111K+Y174R, S111K+Y174L, S111K+Y174W, S111K+Y174F, S111K+R176Q, S111K+E177S, S111K+E177Y, S111K+N18R, S111K+P183T, S111K+P183G, S111K+Q184E, S111K+Q184K, S111K+R185G, S111K+Y196W, S111K+Y196F, S111K+N200T, S111K+S202R, S111K+Q203T, S111K+R205K, S111K+R210L, S111K+R210G, S111K+R210M, S111K+N213V, S111K+N213D, S111K+T228S, S111K+N229D, S111K+E234F, S111K+E234Y, S111K+A235K, S111K+A235R, S111K+S241C, S111K+Q243K, S111K+Q243E, S111K+R244K, S111K+R244V, S111K+A250G, S111K+K254Y, S111K+G257W, S111K+G257E, S111K+G257A, S111K+W260F, S111K+Y262F, S111K+S266A, S111K+D268N, S111K+A270D, S111K+N272M, S111K+N272T, S111K+N273E, S111K+N273D, S111K+A276E, S111K+A276W, S111K+A276D, S111K+N279D, S111K+N279E, S111K+T280L, S111K+N283W, S111K+N283H, S111K+Y286W, S111K+Y286F, S111K+L288I, S111K+E290A, S111K+L294P, S111K+L294K, S111K+L294I, S111K+L294R, S111K+L294V, S111K+L294H, S111K+S295K, S111K+S295V, S111K+S295P, S111K+S295L, S111K+S295R, S111K+S295A, S111K+S295N, S111K+S295M, S111K+S295I, S111K+T296S, S111K+F298Y, S111R+I114Q, S111R+I114M, S111R+I114W, S111R+K116R, S111R+D118K, S111R+T119R, S111R+S131T, S111R+E133R, S111R+E133Q, S111R+D135P, S111R+A136P, S111R+D139A, S111R+D139R, S111R+K142M, S111R+K142V, S111R+K142S, S111R+K142R, S111R+Q143R, S111R+N150T, S111R+N150R, S111R+N150S, S111R+Q169A, S111R+Q169R, S111R+Q169K, S111R+H172R, S111R+Y174R, S111R+Y174L, S111R+Y174W, S111R+Y174F, S111R+R176Q, S111R+E177S, S111R+E177Y, S111R+N180R, S111R+P183T, S111R+P183G, S111R+Q184E, S111R+Q184K, S111R+R185G, S111R+Y196W, S111R+Y196F, S111R+N200T, S111R+S202R, S111R+Q203T, S111R+R205K, S111R+R210L, S111R+R210G, S111R+R210M, S111R+N213V, S111R+N213D, S111R+T228S, S111R+N229D, S111R+E234F, S111R+E234Y, S111R+A235K, S111R+A235R, S111R+S241C, S111R+Q243K, S111R+Q243E, S111R+R244K, S111R+R244V, S111R+A250G, S111R+K254Y, S111R+G257W, S111R+G257E, S111R+G257A, S111R+W260F, S111R+Y262F, S111R+S266A, S111R+D268N, S111R+A270, S111R+N272M, S111R+N272T, S111R+N273E, S111R+N273D, S111R+A276E, S111R+A276W, S111R+A276D, S111R+N279D, S111R+N279E, S111R+T280L, S111R+N283W, S111R+N283H, S111R+Y286W, S111R+Y286F, S111R+L288I, S111R+E290A, S111R+L294P, S111R+L294K, S111R+L294I, S111R+L294R, S111R+L294V, S111R+L294H, S111R+S295K, S111R+S295V, S111R+S295P, S111R+S295L, S111R+S295R, S111R+S295A, S111R+S295N, S111R+S295M, S111R+S295I, S111R+T296S, S111R+F298Y, I114Q+K116R, I114Q+D118K, I114Q+T119R, I114Q+S131T, I114Q+E133R, I114Q+E133Q, I114Q+D135P, I114Q+A136P, I114Q+D139A, I114Q+D139R, I114Q+K142M, I114Q+K142V, I114Q+K142S, I114Q+K142R, I114Q+Q143R, I114Q+N150T, I114Q+N150R, I114Q+N150S, I114Q+Q169A, I114Q+Q169R, I114Q+Q169K, I114Q+H172R, I114Q+Y174R, I114Q+Y174L, I114Q+Y174W, I114Q+Y174F, I114Q+R176Q, I114Q+E177S, I114Q+E177Y, I114Q+N180R, I114Q+P183T, I114Q+P183G, I114Q+Q184E, I114Q+Q184K, I114Q+R185G, I114Q+Y196W, I114Q+Y196F, I114Q+N200T, I114Q+S202R, I114Q+Q203T, I114Q+R205K, I114Q+R210L, I114Q+R210G, I114Q+R210M, I114Q+N213V, I114Q+N213D, I114Q+T228S, I114Q+N229D, I114Q+E234F, I114Q+E234Y, I114Q+A235K, I114Q+A235R, I114Q+S241C, I114Q+Q243K, I114Q+Q243E, I114Q+R244K, I114Q+R244V, I114Q+A250G, I114Q+K254Y, I114Q+G257W, I114Q+G257E, I114Q+G257A, I114Q+W260F, I114Q+Y262F, I114Q+S266A, I114Q+D268N, I114Q+A270D, I114Q+N272M, I114Q+N272T, I114Q+N273E, I114Q+N273D, I114Q+A276E, I114Q+A276W, I114Q+A276D, I114Q+N279D, I114Q+N279E, I114Q+T280L, I114Q+N283W, I114Q+N283H, I114Q+Y286W, I114Q+Y286F, I114Q+L288I, I114Q+E290A, I114Q+L294P, I114Q+L294K, I114Q+L294I, I114Q+L294R, I114Q+L294V, I114Q+L294H, I114Q+S295K, I114Q+S295V, I114Q+S295P, I114Q+S295L, I114Q+S295R, I114Q+S295A, I114Q+S295N, I114Q+S295M, I114Q+S295I, I114Q+T296S, I114Q+

F298Y, I114M+K116R, I114M+D118K, I114M+T119R, I114M+S131T, I114M+E133R, I114M+E133Q, I114M+D135P, I114M+A136P, I114M+D139A, I114M+D139R, I114M+K142M, I114M+K142V, I114M+K142S, I114M+K142R, I114M+Q143R, I114M+N150T, I114M+N150R, I114M+N150S, I114M+Q169A, I114M+Q169R, I114M+Q169K, I114M+H172R, I114M+Y174R, I114M+Y174L, I114M+Y174W, I114M+Y174F, I114M+R176Q, I114M+E177S, I114M+E177Y, I114M+N180R, I114M+P183T, I114M+P183G, I114M+Q184E, I114M+Q184K, I114M+R185G, I114M+Y196W, I114M+Y196F, I114M+N200T, I114M+S202R, I114M+Q203T, I114M+R205K, I114M+R210L, I114M+R210G, I114M+R210M, I114M+N213V, I114M+N213D, I114M+T228S, I114M+N229D, I114M+E234F, I114M+E234Y, I114M+A235K, I114M+A235R, I114M+S241C, I114M+Q243K, I114M+Q243E, I114M+R244K, I114M+R244V, I114M+A250G, I114M+K254Y, I114M+G257W, I114M+G257E, I114M+G257A, I114M+W260F, I114M+Y262F, I114M+S266A, I114M+D268N, I114M+A270D, I114M+N272M, I114M+N272T, I114M+N273E, I114M+N273D, I114M+A276E, I114M+A276W, I114M+A276D, I114M+N279D, I114M+N279E, I114M+T280L, I114M+N283W, I114M+N283H, I114M+Y286W, I114M+Y286F, I114M+L288I, I114M+E290A, I114M+L294P, I114M+L294K, I114M+L294I, I114M+L294R, I114M+L294V, I114M+L294H, I114M+S295K, I114M+S295V, I114M+S295P, I114M+S295L, I114M+S295R, I114M+S295A, I114M+S295N, I114M+S295M, I114M+S295I, I114M+T296S, I114M+F298Y, I114W+K116R, I114W+D118K, I114W+T119R, I114W+S131T, I114W+E133R, I114W+E133Q, I114W+D135P, I114W+A136P, I114W+D139A, I114W+D139R, I114W+K142M, I114W+K142V, I114W+K142S, I114W+K142R, I114W+Q143R, I114W+N150T, I114W+N150R, I114W+N150S, I114W+Q169A, I114W+Q169R, I114W+Q169K, I114W+H172R, I114W+Y174R, I114W+Y174L, I114W+Y174W, I114W+Y174F, I114W+R176Q, I114W+E177S, I114W+E177Y, I114W+N180R, I114W+P183T, I114W+P183G, I114W+Q184E, I114W+Q184K, I114W+R185G, I114W+Y196W, I114W+Y196F, I114W+N200T, I114W+S202R, I114W+Q203T, I114W+R205K, I114W+R210L, I114W+R210G, I114W+R210M, I114W+N213V, I114W+N213D, I114W+T228S, I114W+N229D, I114W+E234F, I114W+E234Y, I114W+A235K, I114W+A235R, I114W+S241C, I114W+Q243K, I114W+Q243E, I114W+R244K, I114W+R244V, I114W+A250G, I114W+K254Y, I114W+G257W, I114W+G257E, I114W+G257A, I114W+W260F, I114W+Y262F, I114W+S266A, I114W+D268N, I114W+A270D, I114W+N272M, I114W+N272T, I114W+N273E, I114W+N273D, I114W+A276E, I114W+A276W, I114W+A276D, I114W+N279D, I114W+N279E, I114W+T280L, I114W+N283W, I114W+N283H, I114W+Y286W, I114W+Y286F, I114W+L288I, I114W+E290A, I114W+L294P, I114W+L294K, I114W+L294I, I114W+L294R, I114W+L294V, I114W+L294H, I114W+S295K, I114W+S295V, I114W+S295P, I114W+S295L, I114W+S295R, I114W+S295A, I114W+S295N, I114W+S295M, I114W+S295I, I114W+T296S, I114W+F298Y, K116R+D118K, K116R+T119R, K116R+S131T, K116R+E133R, K116R+E133Q, K116R+D135P, K116R+A136P, K116R+D139A, K116R+D139R, K116R+K142M, K116R+K142V, K116R+K142S, K116R+K142R, K116R+Q143R, K116R+N150T, K116R+N150R, K116R+N150S, K116R+Q169A, K116R+Q169R, K116R+Q169K, K116R+H172R, K116R+Y174R, K116R+Y174L, K116R+Y174W, K116R+Y174F, K116R+R176Q, K116R+E177S, K116R+E177Y, K116R+N180R, K116R+P183T, K116R+P183G, K116R+Q184E, K116R+Q184K, K116R+R185G, K116R+Y196W, K116R+Y196F, K116R+N200T, K116R+S202R, K116R+Q203T, K116R+R205K, K116R+R210L, K116R+R210G, K116R+R210M, K116R+N213V, K116R+N213D, K116R+T228S, K116R+N229D, K116R+E234F, K116R+E234Y, K116R+A235K, K116R+A235R, K116R+S241C, K116R+Q243K, K116R+Q243E, K116R+R244K, K116R+R244V, K116R+A250G, K116R+K254Y, K116R+G257W, K116R+G257E, K116R+G257A, K116R+W260F, K116R+Y262F, K116R+S266A, K116R+D268N, K116R+A270D, K116R+N272M, K116R+N272T, K116R+N273E, K116R+N273D, K116R+A276E, K116R+A276W, K116R+A276D, K116R+N279D, K116R+N279E, K116R+T280L, K116R+N283W, K116R+N283H, K116R+Y286W, K116R+Y286F, K116R+L288I, K116R+E290A, K116R+L294P, K116R+L294K, K116R+L294I, K116R+L294R, K116R+L294V, K116R+L294H, K116R+S295K, K116R+S295V, K116R+S295P, K116R+S295L, K116R+S295R, K116R+S295A, K116R+S295N, K116R+S295M, K116R+S295I, K116R+T296S, K116R+F298Y, D118K+T119R, D118K+S131T, D118K+E133R, D118K+E133Q, D118K+D135P, D118K+A136P, D118K+D139A, D118K+D139R, D118K+K142M, D118K+K142V, D118K+K142S, D118K+K142R, D118K+Q143R, D118K+N150T, D118K+N150R, D118K+N150S, D118K+Q169A, D118K+Q169R, D118K+Q169K, D118K+H172R, D118K+Y174R, D118K+Y174L, D118K+Y174W, D118K+Y174F, D118K+R176Q, D118K+E177S, D118K+E177Y, D118K+N180R, D118K+P183T, D118K+P183G, D118K+Q184E, D118K+Q184K, D118K+R185G, D118K+Y196W, D118K+Y196F, D118K+N200T, D118K+S202R, D118K+Q203T, D118K+R205K, D118K+R210L, D118K+R210G, D118K+R210M, D118K+N213V, D118K+N213D, D118K+T228S, D118K+N229D, D118K+E234F, D118K+E234Y, D118K+A235K, D118K+A235R, D118K+S241C, D118K+Q243K, D118K+Q243E, D118K+R244K, D118K+R244V, D118K+A250G, D118K+K254Y, D118K+G257W, D118K+G257E, D118K+G257A, D118K+W260F, D118K+Y262F, D118K+S266A, D118K+D268N, D118K+A270D, D118K+N272M, D118K+N272T, D118K+N273E, D118K+N273D, D118K+A276E, D118K+A276W, D118K+A276D, D118K+N279D, D118K+N279E, D118K+T280L, D118K+N283W, D118K+N283H, D118K+Y286W, D118K+Y286F, D118K+L288I, D118K+E290A, D118K+L294P, D118K+L294K, D118K+L294I, D118K+L294R, D118K+L294V, D118K+L294H, D118K+S295K, D118K+S295V, D118K+S295P, D118K+S295L, D118K+S295R, D118K+S295A, D118K+S295N, D118K+S295M, D118K+S295I, D118K+T296S, D118K+F298Y, T119R+S131T, T119R+E133R, T119R+E133Q, T119R+D135P, T119R+A136P, T119R+D139A, T119R+D139R, T119R+K142M, T119R+K142V, T119R+K142S, T119R+K142R, T119R+Q143R, T119R+N150T, T119R+N150R, T119R+N150S, T119R+Q169A, T119R+Q169R, T119R+Q169K, T119R+H172R, T119R+Y174R, T119R+Y174L, T119R+Y174W, T119R+Y174F, T119R+R176Q, T119R+E177S, T119R+E177Y, T119R+N180R, T119R+P183T, T119R+P183G, T119R+Q184E, T119R+Q184K, T119R+R185G, T119R+Y196W, T119R+Y196F, T119R+N200T, T119R+S202R, T119R+Q203T, T119R+R205K, T119R+R210L, T119R+R210G, T119R+R210M, T119R+N213V, T119R+N213D, T119R+T228S, T119R+N229D, T119R+E234F, T119R+E234Y, T119R+A235K, T119R+A235R, T119R+S241C, T119R+Q243K, T119R+Q243E, T119R+R244K, T119R+R244V, T119R+A250G, T119R+K254Y, T119R+G257W, T119R+G257E, T119R+G257A, T119R+W260F, T119R+Y262F, T119R+S266A, T119R+D268N, T119R+A270D, T119R+N272M, T119R+N272T, T119R+N273E, T119R+N273D, T119R+A276E, T119R+A276W, T119R+

A276D, T119R+N279D, T119R+N279E, T119R+T280L, T119R+N283W, T119R+N283H, T119R+Y286W, T119R+Y286F, T119R+L288I, T119R+E290A, T119R+L294P, T119R+L294K, T119R+L294I, T119R+L294R, T119R+L294V, T119R+L294H, T119R+S295K, T119R+S295V, T119R+S295P, T119R+S295L, T119R+S295R, T119R+S295A, T119R+S295N, T119R+S295M, T119R+S295I, T119R+T296S, T119R+F298Y, S131T+E133R, S131T+E133Q, S131T+D135P, S131T+A136P, S131T+D39A, S131T+D139R, S131T+K142M, S131T+K142V, S131T+K142S, S131T+K142R, S131T+Q143R, S131T+N150T, S131T+N150R, S131T+N150S, S131T+Q169A, S131T+Q169R, S131T+Q169K, S131T+H172R, S131T+Y174R, S131T+Y174L, S131T+Y174W, S131T+Y174F, S131T+R176Q, S131T+E177S, S131T+E177Y, S131T+N180R, S131T+P183T, S131T+P183G, S131T+Q184E, S131T+Q184K, S131T+R185G, S131T+Y196W, S131T+Y196F, S131T+N200T, S131T+S202R, S131T+Q203T, S131T+R205K, S131T+R210L, S131T+R210G, S131T+R210M, S131T+N213V, S131T+N213D, S131T+T228S, S131T+N229D, S131T+E234F, S131T+E234Y, S131T+A235K, S131T+A235R, S131T+S241C, S131T+Q243K, S131T+Q243E, S131T+R244K, S131T+R244V, S131T+A250G, S131T+K254Y, S131T+G257W, S131T+G257E, S131T+G257A, S131T+W260F, S131T+Y262F, S131T+S266A, S131T+D268N, S131T+A270D, S131T+N272M, S131T+N272T, S131T+N273E, S131T+N273D, S131T+A276E, S131T+A276W, S131T+A276D, S131T+N279D, S131T+N279E, S131T+T280L, S131T+N283W, S131T+N283H, S131T+Y286W, S131T+Y286F, S131T+L288I, S131T+E290A, S131T+L294P, S131T+L294K, S131T+L294I, S131T+L294R, S131T+L294V, S131T+L294H, S131T+S295K, S131T+S295V, S131T+S295P, S131T+S295L, S131T+S295R, S131T+S295A, S131T+S295N, S131T+S295M, S131T+S295I, S131T+T296S, S131T+F298Y, E133R+D135P, E133R+A136P, E133R+D139A, E133R+D139R, E133R+K142M, E133R+K142V, E133R+K142S, E133R+K142R, E133R+Q143R, E133R+N150T, E133R+N150R, E133R+N150S, E133R+Q169A, E133R+Q169R, E133R+Q169K, E133R+H172R, E133R+Y174R, E133R+Y174L, E133R+Y174W, E133R+Y174F, E133R+R176Q, E133R+E177S, E133R+E177Y, E133R+N180R, E133R+P183T, E133R+P183G, E133R+Q184E, E133R+Q184K, E133R+R185G, E133R+Y196W, E133R+Y196F, E133R+N200T, E133R+S202R, E133R+Q203T, E133R+R205K, E133R+R210L, E133R+R210G, E133R+R210M, E133R+N213V, E133R+N213D, E133R+T228S, E133R+N229D, E133R+E234F, E133R+E234Y, E133R+A235K, E133R+A235R, E133R+S241C, E133R+Q243K, E133R+Q243E, E133R+R244K, E133R+R244V, E133R+A250G, E133R+K254Y, E133R+G257W, E133R+G257E, E133R+G257A, E133R+W260F, E133R+Y262F, E133R+S266A, E133R+D268N, E133R+A270D, E133R+N272M, E133R+N272T, E133R+N273E, E133R+N273D, E133R+A276E, E133R+A276W, E133R+A276D, E133R+N279D, E133R+N279E, E133R+T280L, E133R+N283W, E133R+N283H, E133R+Y286W, E133R+Y286F, E133R+L288I, E133R+E290A, E133R+L294P, E133R+L294K, E133R+L294I, E133R+L294R, E133R+L294V, E133R+L294H, E133R+S295K, E133R+S295V, E133R+S295P, E133R+S295L, E133R+S295R, E133R+S295A, E133R+S295N, E133R+S295M, E133R+S295I, E133R+T296S, E133R+F298Y, E133Q+D135P, E133Q+A136P, E133Q+D139A, E133Q+D139R, E133Q+K142M, E133Q+K142V, E133Q+K142S, E133Q+K142R, E133Q+Q143R, E133Q+N150T, E133Q+N150R, E133Q+N150S, E133Q+Q169A, E133Q+Q169R, E133Q+Q169K, E133Q+H172R, E133Q+Y174R, E133Q+Y174L, E133Q+Y174W, E133Q+Y174F, E133Q+R176Q, E133Q+E177S, E133Q+E177Y, E133Q+N180R, E133Q+P183T, E133Q+P183G, E133Q+Q184E, E133Q+Q184K, E133Q+R185G, E133Q+Y196W, E133Q+Y196F, E133Q+N200T, E133Q+S202R, E133Q+Q203T, E133Q+R205K, E133Q+R210L, E133Q+R210G, E133Q+R210M, E133Q+N213V, E133Q+N213D, E133Q+T228S, E133Q+N229D, E133Q+E234F, E133Q+E234Y, E133Q+A235K, E133Q+A235R, E133Q+S241C, E133Q+Q243K, E133Q+Q243E, E133Q+R244K, E133Q+R244V, E133Q+A250G, E133Q+K254Y, E133Q+G257W, E133Q+G257E, E133Q+G257A, E133Q+W260F, E133Q+Y262F, E133Q+S266A, E133Q+D268N, E133Q+A270D, E133Q+N272M, E133Q+N272T, E133Q+N273E, E133Q+N273D, E133Q+A276E, E133Q+A276W, E133Q+A276D, E133Q+N279D, E133Q+N279E, E133Q+T280L, E133Q+N283W, E133Q+N283H, E133Q+Y286W, E133Q+Y286F, E133Q+L288I, E133Q+E290A, E133Q+L294P, E133Q+L294K, E133Q+L294I, E133Q+L294R, E133Q+L294V, E133Q+L294H, E133Q+S295K, E133Q+S295V, E133Q+S295P, E133Q+S295L, E133Q+S295R, E133Q+S295A, E133Q+S295N, E133Q+S295M, E133Q+S295I, E133Q+T296S, E133Q+F298Y, D135P+A136P, D135P+D139A, D135P+D139R, D135P+K142M, D135P+K142V, D135P+K142S, D135P+K142R, D135P+Q143R, D135P+N150T, D135P+N150R, D135P+N150S, D135P+Q169A, D135P+Q169R, D135P+Q169K, D135P+H172R, D135P+Y174R, D135P+Y174L, D135P+Y174W, D135P+Y174F, D135P+R176Q, D135P+E177S, D135P+E177Y, D135P+N180R, D135P+P183T, D135P+P183G, D135P+Q184E, D135P+Q184K, D135P+R185G, D135P+Y196W, D135P+Y196F, D135P+N200T, D135P+S202R, D135P+Q203T, D135P+R205K, D135P+R210L, D135P+R210G, D135P+R210M, D135P+N213V, D135P+N213D, D135P+T228S, D135P+N229D, D135P+E234F, D135P+E234Y, D135P+A235K, D135P+A235R, D135P+S241C, D135P+Q243K, D135P+Q243E, D135P+R244K, D135P+R244V, D135P+A250G, D135P+K254Y, D135P+G257W, D135P+G257E, D135P+G257A, D135P+W260F, D135P+Y262F, D135P+S266A, D135P+D268N, D135P+A270D, D135P+N272M, D135P+N272T, D135P+N273E, D135P+N273D, D135P+A276E, D135P+A276W, D135P+A276D, D135P+N279D, D135P+N279E, D135P+T280L, D135P+N283W, D135P+N283H, D135P+Y286W, D135P+Y286F, D135P+L288I, D135P+E290A, D135P+L294P, D135P+L294K, D135P+L294I, D135P+L294R, D135P+L294V, D135P+L294H, D135P+S295K, D135P+S295V, D135P+S295P, D135P+S295L, D135P+S295R, D135P+S295A, D135P+S295N, D135P+S295M, D135P+S295I, D135P+T296S, D135P+F298Y, A136P+D139A, A136P+D139R, A136P+K142M, A136P+K142V, A136P+K142S, A136P+K142R, A136P+Q143R, A136P+N150T, A136P+N150R, A136P+N150S, A136P+Q169A, A136P+Q169R, A136P+Q169K, A136P+H172R, A136P+Y174R, A136P+Y174L, A136P+Y174W, A136P+Y174F, A136P+R176Q, A136P+E177S, A136P+E177Y, A136P+N180R, A136P+P183T, A136P+P183G, A136P+Q184E, A136P+Q184K, A136P+R185G, A136P+Y196W, A136P+Y196F, A136P+N200T, A136P+S202R, A136P+Q203T, A136P+R205K, A136P+R210L, A136P+R210G, A136P+R210M, A136P+N213V, A136P+N213D, A136P+T228S, A136P+N229D, A136P+E234F, A136P+E234Y, A136P+A235K, A136P+A235R, A136P+S241C, A136P+Q243K, A136P+Q243E, A136P+R244K, A136P+R244V, A136P+A250G, A136P+K254Y, A136P+G257W, A136P+G257E, A136P+G257A, A136P+W260F, A136P+Y262F, A136P+S266A, A136P+D268N, A136P+A270D, A136P+N272M, A136P+N272T, A136P+N273E, A136P+N273D, A136P+A276E, A136P+A276W, A136P+

A276D, A136P+N279D, A136P+N279E, A136P+T280L, A136P+N283W, A136P+N283H, A136P+Y286W, A136P+Y286F, A136P+L288I, A136P+E290A, A136P+L294P, A136P+L294K, A136P+L294I, A136P+L294R, A136P+L294V, A136P+L294H, A136P+S295K, A136P+S295V, A136P+S295P, A136P+S295L, A136P+S295R, A136P+S295A, A136P+S295N, A136P+S295M, A136P+S295I, A136P+T296S, A136P+F298Y, D139A+K142M, D139A+K142V, D139A+K142S, D139A+K142R, D139A+Q143R, D139A+N150T, D139A+N150R, D139A+N150S, D139A+Q169A, D139A+Q169R, D139A+Q169K, D139A+H172R, D139A+Y174R, D139A+Y174L, D139A+Y174W, D139A+Y174F, D139A+R176Q, D139A+E177S, D139A+E177Y, D139A+N180R, D139A+P183T, D139A+P183G, D139A+Q184E, D139A+Q184K, D139A+R185G, D139A+Y196W, D139A+Y196F, D139A+N200T, D139A+S202R, D139A+Q203T, D139A+R205K, D139A+R210L, D139A+R210G, D139A+R210M, D139A+N213V, D139A+N213D, D139A+T228S, D139A+N229D, D139A+E234F, D139A+E234Y, D139A+A235K, D139A+A235R, D139A+S241C, D139A+Q243K, D139A+Q243E, D139A+R244K, D139A+R244V, D139A+A250G, D139A+K254Y, D139A+G257W, D139A+G257E, D139A+G257A, D139A+W260F, D139A+Y262F, D139A+S266A, D139A+D268N, D139A+A270D, D139A+N272M, D139A+N272T, D139A+N273E, D139A+N273D, D139A+A276E, D139A+A276W, D139A+A276D, D139A+N279D, D139A+N279E, D139A+T280L, D139A+N283W, D139A+N283H, D139A+Y286W, D139A+Y286F, D139A+L288I, D139A+E290A, D139A+L294P, D139A+L294K, D139A+L294I, D139A+L294R, D139A+L294V, D139A+L294H, D139A+S295K, D139A+S295V, D139A+S295P, D139A+S295L, D139A+S295R, D139A+S295A, D139A+S295N, D139A+S295M, D139A+S295I, D139A+T296S, D139A+F298Y, D139R+K142M, D139R+K142V, D139R+K142S, D139R+K142R, D139R+Q143R, D139R+N150T, D139R+N150R, D139R+N150S, D139R+Q169A, D139R+Q169R, D139R+Q169K, D139R+H172R, D139R+Y174R, D139R+Y174L, D139R+Y174W, D139R+Y174F, D139R+R176Q, D139R+E177S, D139R+E177Y, D139R+N180R, D139R+P183T, D139R+P183G, D139R+Q184E, D139R+Q184K, D139R+R185G, D139R+Y196W, D139R+Y196F, D139R+N200T, D139R+S202R, D139R+Q203T, D139R+R205K, D139R+R210L, D139R+R210G, D139R+R210M, D139R+N213V, D139R+N213D, D139R+T228S, D139R+N229D, D139R+E234F, D139R+E234Y, D139R+A235K, D139R+A235R, D139R+S241C, D139R+Q243K, D139R+Q243E, D139R+R244K, D139R+R244V, D139R+A250G, D139R+K254Y, D139R+G257W, D139R+G257E, D139R+G257A, D139R+W260F, D139R+Y262F, D139R+S266A, D139R+D268N, D139R+A270D, D139R+N272M, D139R+N272T, D139R+N273E, D139R+N273D, D139R+A276E, D139R+A276W, D139R+A276D, D139R+N279D, D139R+N279E, D139R+T280L, D139R+N283W, D139R+N283H, D139R+Y286W, D139R+Y286F, D139R+L288I, D139R+E290A, D139R+L294P, D139R+L294K, D139R+L294I, D139R+L294R, D139R+L294V, D139R+L294H, D139R+S295K, D139R+S295V, D139R+S295P, D139R+S295L, D139R+S295R, D139R+S295A, D139R+S295N, D139R+S295M, D139R+S295I, D139R+T296S, D139R+F298Y, K142M+Q143R, K142M+N150T, K142M+N150R, K142M+N150S, K142M+Q169A, K142M+Q169R, K142M+Q169K, K142M+H172R, K142M+Y174R, K142M+Y174L, K142M+Y174W, K142M+Y174F, K142M+R176Q, K142M+E177S, K142M+E177Y, K142M+N180R, K142M+P183T, K142M+P183G, K142M+Q184E, K142M+Q184K, K142M+R185G, K142M+Y196W, K142M+Y196F, K142M+N200T, K142M+S202R, K142M+Q203T, K142M+R205K, K142M+R210L, K142M+R210G, K142M+R210M, K142M+N213V, K142M+N213D, K142M+T228S, K142M+N229D, K142M+E234F, K142M+E234Y, K142M+A235R, K142M+A235R, K142M+S241C, K142M+Q243K, K142M+Q243E, K142M+R244K, K142M+R244V, K142M+A250G, K142M+K254Y, K142M+G257W, K142M+G257E, K142M+G257A, K142M+W260F, K142M+Y262F, K142M+S266A, K142M+D268N, K142M+A270D, K142M+N272M, K142M+N272T, K142M+N273E, K142M+N273D, K142M+A276E, K142M+A276W, K142M+A276D, K142M+N279D, K142M+N279E, K142M+T280L, K142M+N283W, K142M+N283H, K142M+Y286W, K142M+Y286F, K142M+L288I, K142M+E290A, K142M+L294P, K142M+L294K, K142M+L294I, K142M+L294R, K142M+L294V, K142M+L294H, K142M+S295K, K142M+S295V, K142M+S295P, K142M+S295L, K142M+S295R, K142M+S295A, K142M+S295N, K142M+S295M, K142M+S295I, K142M+T296S, K142M+F298Y, K142V+Q143R, K142V+N150T, K142V+N150R, K142V+N150S, K142V+Q169A, K142V+Q169R, K142V+Q169K, K142V+H172R, K142V+Y174R, K142V+Y174L, K142V+Y174W, K142V+Y174F, K142V+R176Q, K142V+E177S, K142V+E177Y, K142V+N180R, K142V+P183T, K142V+P183G, K142V+Q184E, K142V+Q184K, K142V+R185G, K142V+Y196W, K142V+Y196F, K142V+N200T, K142V+S202R, K142V+Q203T, K142V+R205K, K142V+R210L, K142V+R210G, K142V+R210M, K142V+N213V, K142V+N213D, K142V+T228S, K142V+N229D, K142V+E234F, K142V+E234Y, K142V+A235K, K142V+A235R, K142V+S241C, K142V+Q243K, K142V+Q243E, K142V+R244K, K142V+R244V, K142V+A250G, K142V+K254Y, K142V+G257W, K142V+G257E, K142V+G257A, K142V+W260F, K142V+Y262F, K142V+S266A, K142V+D268N, K142V+A270D, K142V+N272M, K142V+N272T, K142V+N273E, K142V+N273D, K142V+A276E, K142V+A276W, K142V+A276D, K142V+N279D, K142V+N279E, K142V+T280L, K142V+N283W, K142V+N283H, K142V+Y286W, K142V+Y286F, K142V+L288I, K142V+E290A, K142V+L294P, K142V+L294K, K142V+L294I, K142V+L294R, K142V+L294V, K142V+L294H, K142V+S295K, K142V+S295V, K142V+S295P, K142V+S295L, K142V+S295R, K142V+S295A, K142V+S295N, K142V+S295M, K142V+S295I, K142V+T296S, K142V+F298Y, K142S+Q143R, K142S+N150T, K142S+N150R, K142S+N150S, K142S+Q169A, K142S+Q169R, K142S+Q169K, K142S+H172R, K142S+Y174R, K142S+Y174L, K142S+Y174W, K142S+Y174F, K142S+R176Q, K142S+E177S, K142S+E177Y, K142S+N180R, K142S+P183T, K142S+P183G, K142S+Q184E, K142S+Q184K, K142S+R185G, K142S+Y196W, K142S+Y196F, K142S+N200T, K142S+S202R, K142S+Q203T, K142S+R205K, K142S+R210L, K142S+R210G, K142S+R210M, K142S+N213V, K142S+N213D, K142S+T228S, K142S+N229D, K142S+E234F, K142S+E234Y, K142S+A235K, K142S+A235R, K142S+S241C, K142S+Q243K, K142S+Q243E, K142S+R244K, K142S+R244V, K142S+A250G, K142S+K254Y, K142S+G257W, K142S+G257E, K142S+G257A, K142S+W260F, K142S+Y262F, K142S+S266A, K142S+D268N, K142S+A270D, K142S+N272M, K142S+N272T, K142S+N273E, K142S+N273D, K142S+A276E, K142S+A276W, K142S+A276D, K142S+N279D, K142S+N279E, K142S+T280L, K142S+N283W, K142S+N283H, K142S+Y286W, K142S+Y286F, K142S+L288I, K142S+E290A, K142S+L294P, K142S+L294K, K142S+L294I, K142S+L294R, K142S+

L294V, K142S+L294H, K142S+S295K, K142S+S295V, K142S+S295P, K142S+S295L, K142S+S295R, K142S+S295A, K142S+S295N, K142S+S295M, K142S+S295I, K142S+T296S, K142S+F298Y, K142R+Q143R, K142R+N150T, K142R+N150R, K142R+N150S, K142R+Q169A, K142R+Q169R, K142R+Q169K, K142R+H172R, K142R+Y174R, K142R+Y174L, K142R+Y174W, K142R+Y174F, K142R+R176Q, K142R+E177S, K142R+E177Y, K142R+N180R, K142R+P183T, K142R+P183G, K142R+Q184E, K142R+Q184K, K142R+R185G, K142R+Y196W, K142R+Y196F, K142R+N200T, K142R+S202R, K142R+Q203T, K142R+R205K, K142R+R210L, K142R+R210G, K142R+R210M, K142R+N213V, K142R+N213D, K142R+T228S, K142R+N229D, K142R+E234F, K142R+E234Y, K142R+A235K, K142R+A235R, K142R+S241C, K142R+Q243K, K142R+Q243E, K142R+R244K, K142R+R244V, K142R+A250G, K142R+K254Y, K142R+G257W, K142R+G257E, K142R+G257A, K142R+W260F, K142R+Y262F, K142R+S266A, K142R+D268N, K142R+A270D, K142R+N272M, K142R+N272T, K142R+N273E, K142R+N273D, K142R+A276E, K142R+A276W, K142R+A276D, K142R+N279D, K142R+N279E, K142R+T280L, K142R+N283W, K142R+N283H, K142R+Y286W, K142R+Y286F, K142R+L288I, K142R+E290A, K142R+L294P, K142R+L294K, K142R+L294I, K142R+L294R, K142R+L294V, K142R+L294H, K142R+S295K, K142R+S295V, K142R+S295P, K142R+S295L, K142R+S295R, K142R+S295A, K142R+S295N, K142R+S295M, K142R+S295I, K142R+T296S, K142R+F298Y, Q143R+N150T, Q143R+N150R, Q143R+N150S, Q143R+Q169A, Q143R+Q169R, Q143R+Q169K, Q143R+H172R, Q143R+Y174R, Q143R+Y174L, Q143R+Y174W, Q143R+Y174F, Q143R+R176Q, Q143R+E177S, Q143R+E177Y, Q143R+N180R, Q143R+P183T, Q143R+P183G, Q143R+Q184E, Q143R+Q184K, Q143R+R185G, Q143R+Y196W, Q143R+Y196F, Q143R+N200T, Q143R+S202R, Q143R+Q203T, Q143R+R205K, Q143R+R210L, Q143R+R210G, Q143R+R210M, Q143R+N213V, Q143R+N213D, Q143R+T228S, Q143R+N229D, Q143R+E234F, Q143R+E234Y, Q143R+A235K, Q143R+A235R, Q143R+S241C, Q143R+Q243K, Q143R+Q243E, Q143R+R244K, Q143R+R244V, Q143R+A250G, Q143R+K254Y, Q143R+G257W, Q143R+G257E, Q143R+G257A, Q143R+W260F, Q143R+Y262F, Q143R+S266A, Q143R+D268N, Q143R+A270D, Q143R+N272M, Q143R+N272T, Q143R+N273E, Q143R+N273D, Q143R+A276E, Q143R+A276W, Q143R+A276D, Q143R+N279D, Q143R+N279E, Q143R+T280L, Q143R+N283W, Q143R+N283H, Q143R+Y286W, Q143R+Y286F, Q143R+L288I, Q143R+E290A, Q143R+L294P, Q143R+L294K, Q143R+L294I, Q143R+L294R, Q143R+L294V, Q143R+L294H, Q143R+S295K, Q143R+S295V, Q143R+S295P, Q143R+S295L, Q143R+S295R, Q143R+S295A, Q143R+S295N, Q143R+S295M, Q143R+S295I, Q143R+T296S, Q143R+F298Y, N150T+Q169A, N150T+Q169R, N150T+Q169K, N150T+H172R, N150T+Y174R, N150T+Y174L, N150T+Y174W, N150T+Y174F, N150T+R176Q, N150T+E177S, N150T+E177Y, N150T+N180R, N150T+P183T, N150T+P183G, N150T+Q184E, N150T+Q184K, N150T+R185G, N150T+Y196W, N150T+Y196F, N150T+N200T, N150T+S202R, N150T+Q203T, N150T+R205K, N150T+R210L, N150T+R210G, N150T+R210M, N150T+N213V, N150T+N213D, N150T+T228S, N150T+N229D, N150T+E234F, N150T+E234Y, N150T+A235K, N150T+A235R, N150T+S241C, N150T+Q243K, N150T+Q243E, N150T+R244K, N150T+R244V, N150T+A250G, N150T+K254Y, N150T+G257W, N150T+G257E, N150T+G257A, N150T+W260F, N150T+Y262F, N150T+S266A, N150T+D268N, N150T+A270D, N150T+N272M, N150T+N272T, N150T+N273E, N150T+N273D, N150T+A276E, N150T+A276W, N150T+A276D, N150T+N279D, N150T+N279E, N150T+T280L, N150T+N283W, N150T+N283H, N150T+Y286W, N150T+Y286F, N150T+L288I, N150T+E290A, N150T+L294P, N150T+L294K, N150T+L294I, N150T+L294R, N150T+L294V, N150T+L294H, N150T+S295K, N150T+S295V, N150T+S295P, N150T+S295L, N150T+S295R, N150T+S295A, N150T+S295N, N150T+S295M, N150T+S295I, N150T+T296S, N150T+F298Y, N150R+Q169A, N150R+Q169R, N150R+Q169K, N150R+H172R, N150R+Y174R, N150R+Y174L, N150R+Y174W, N150R+Y174F, N150R+R176Q, N150R+E177S, N150R+E177Y, N150R+N180R, N150R+P183T, N150R+P183G, N150R+Q184E, N150R+Q184K, N150R+R185G, N150R+Y196W, N150R+Y196F, N150R+N200T, N150R+S202R, N150R+Q203T, N150R+R205K, N150R+R210L, N150R+R210G, N150R+R210M, N150R+N213V, N150R+N213D, N150R+T228S, N150R+N229D, N150R+E234F, N150R+E234Y, N150R+A235K, N150R+A235R, N150R+S241C, N150R+Q243K, N150R+Q243E, N150R+R244K, N150R+R244V, N150R+A250G, N150R+K254Y, N150R+G257W, N150R+G257E, N150R+G257A, N150R+W260F, N150R+Y262F, N150R+S266A, N150R+D268N, N150R+A270D, N150R+N272M, N150R+N272T, N150R+N273E, N150R+N273D, N150R+A276E, N150R+A276W, N150R+A276D, N150R+N279D, N150R+N279E, N150R+T280L, N150R+N283W, N150R+N283H, N150R+Y286W, N150R+Y286F, N150R+L288I, N150R+E290A, N150R+L294P, N150R+L294K, N150R+L294I, N150R+L294R, N150R+L294V, N150R+L294H, N150R+S295K, N150R+S295V, N150R+S295P, N150R+S295L, N150R+S295R, N150R+S295A, N150R+S295N, N150R+S295M, N150R+S295I, N150R+T296S, N150R+F298Y, N150S+Q169A, N150S+Q169R, N150S+Q169K, N150S+H172R, N150S+Y174R, N150S+Y174L, N150S+Y174W, N150S+Y174F, N150S+R176Q, N150S+E177S, N150S+E177Y, N150S+N180R, N150S+P183T, N150S+P183G, N150S+Q184E, N150S+Q184K, N150S+R185G, N150S+Y196W, N150S+Y196F, N150S+N200T, N150S+S202R, N150S+Q203T, N150S+R205K, N150S+R210L, N150S+R210G, N150S+R210M, N150S+N213V, N150S+N213D, N150S+T228S, N150S+N229D, N150S+E234F, N150S+E234Y, N150S+A235K, N150S+A235R, N150S+S241C, N150S+Q243K, N150S+Q243E, N150S+R244K, N150S+R244V, N150S+A250G, N150S+K254Y, N150S+G257W, N150S+G257E, N150S+G257A, N150S+W260F, N150S+Y262F, N150S+S266A, N150S+D268N, N150S+A270D, N150S+N272M, N150S+N272T, N150S+N273E, N150S+N273D, N150S+A276E, N150S+A276W, N150S+A276D, N150S+N279D, N150S+N279E, N150S+T280L, N150S+N283W, N150S+N283H, N150S+Y286W, N150S+Y286F, N150S+L288I, N150S+E290A, N150S+L294P, N150S+L294K, N150S+L294I, N150S+L294R, N150S+L294V, N150S+L294H, N150S+S295K, N150S+S295V, N150S+S295P, N150S+S295L, N150S+S295R, N150S+S295A, N150S+S295N, N150S+S295M, N150S+S295I, N150S+T296S, N150S+F298Y, Q169A+H172R, Q169A+Y174R, Q169A+Y174L, Q169A+Y174W, Q169A+Y174F, Q169A+R176Q, Q169A+E177S, Q169A+E177Y, Q169A+N180R, Q169A+P183T, Q169A+P183G, Q169A+Q184E, Q169A+Q184K, Q169A+R185G, Q169A+Y196W, Q169A+Y196F, Q169A+N200T, Q169A+S202R, Q169A+Q203T, Q169A+R205K, Q169A+R210L, Q169A+R210G, Q169A+R210M, Q169A+N213V, Q169A+N213D, Q169A+T228S, Q169A+N229D, Q169A+E234F, Q169A+E234Y, Q169A+A235K, Q169A+A235R, Q169A+S241C, Q169A+Q243K, Q169A+Q243E, Q169A+R244K, Q169A+R244V, Q169A+A250G, Q169A+K254Y,

Q169A+G257W, Q169A+G257E, Q169A+G257A, Q169A+W260F, Q169A+Y262F, Q169A+S266A, Q169A+D268N, Q169A+A270D, Q169A+N272M, Q169A+N272T, Q169A+N273E, Q169A+N273D, Q169A+A276E, Q169A+A276W, Q169A+A276D, Q169A+N279D, Q169A+N279E, Q169A+T280L, Q169A+N283W, Q169A+N283H, Q169A+Y286W, Q169A+Y286F, Q169A+L288I, Q169A+E290A, Q169A+L294P, Q169A+L294K, Q169A+L294I, Q169A+L294R, Q169A+L294V, Q169A+L294H, Q169A+S295K, Q169A+S295V, Q169A+S295P, Q169A+S295L, Q169A+S295R, Q169A+S295A, Q169A+S295N, Q169A+S295M, Q169A+S295I, Q169A+T296S, Q169A+F298Y, Q169R+H172R, Q169R+Y174R, Q169R+Y174L, Q169R+Y174W, Q169R+Y174F, Q169R+R176Q, Q169R+E177S, Q169R+E177Y, Q169R+N180R, Q169R+P183T, Q169R+P183G, Q169R+Q184E, Q169R+Q184K, Q169R+R185G, Q169R+Y196W, Q169R+Y196F, Q169R+N200T, Q169R+S202R, Q169R+Q203T, Q169R+R205K, Q169R+R210L, Q169R+R210G, Q169R+R210M, Q169R+N213V, Q169R+N213D, Q169R+T228S, Q169R+N229D, Q169R+E234F, Q169R+E234Y, Q169R+A235K, Q169R+A235R, Q169R+S241C, Q169R+Q243K, Q169R+Q243E, Q169R+R244K, Q169R+R244V, Q169R+A250G, Q169R+K254Y, Q169R+G257W, Q169R+G257E, Q169R+G257A, Q169R+W260F, Q169R+Y262F, Q169R+S266A, Q169R+D268N, Q169R+A270D, Q169R+N272M, Q169R+N272T, Q169R+N273E, Q169R+N273D, Q169R+A276E, Q169R+A276W, Q169R+A276D, Q169R+N279D, Q169R+N279E, Q169R+T280L, Q169R+N283W, Q169R+N283H, Q169R+Y286W, Q169R+Y286F, Q169R+L288I, Q169R+E290A, Q169R+L294P, Q169R+L294K, Q169R+L294I, Q169R+L294R, Q169R+L294V, Q169R+L294H, Q169R+S295K, Q169R+S295V, Q169R+S295P, Q169R+S295L, Q169R+S295R, Q169R+S295A, Q169R+S295N, Q169R+S295M, Q169R+S295I, Q169R+T296S, Q169R+F298Y, Q169K+H172R, Q169K+Y174R, Q169K+Y174L, Q169K+Y174W, Q169K+Y174F, Q169K+R176Q, Q169K+E177S, Q169K+E177Y, Q169K+N180R, Q169K+P183T, Q169K+P183G, Q169K+Q184E, Q169K+Q184K, Q169K+R185G, Q169K+Y196W, Q169K+Y196F, Q169K+N200T, Q169K+S202R, Q169K+Q203T, Q169K+R205K, Q169K+R210L, Q169K+R210G, Q169K+R210M, Q169K+N213V, Q169K+N213D, Q169K+T228S, Q169K+N229D, Q169K+E234F, Q169K+E234Y, Q169K+A235K, Q169K+A235R, Q169K+S241C, Q169K+Q243K, Q169K+Q243E, Q169K+R244K, Q169K+R244V, Q169K+A250G, Q169K+K254Y, Q169K+G257W, Q169K+G257E, Q169K+G257A, Q169K+W260F, Q169K+Y262F, Q169K+S266A, Q169K+D268N, Q169K+A270D, Q169K+N272M, Q169K+N272T, Q169K+N273E, Q169K+N273D, Q169K+A276E, Q169K+A276W, Q169K+A276D, Q169K+N279D, Q169K+N279E, Q169K+T280L, Q169K+N283W, Q169K+N283H, Q169K+Y286W, Q169K+Y286F, Q169K+L288I, Q169K+E290A, Q169K+L294P, Q169K+L294K, Q169K+L294I, Q169K+L294R, Q169K+L294V, Q169K+L294H, Q169K+S295K, Q169K+S295V, Q169K+S295P, Q169K+S295L, Q169K+S295R, Q169K+S295A, Q169K+S295N, Q169K+S295M, Q169K+S295I, Q169K+T296S, Q169K+F298Y, H172R+Y174R, H172R+Y174L, H172R+Y174W, H172R+Y174F, H172R+R176Q, H172R+E177S, H172R+E177Y, H172R+N180R, H172R+P183T, H172R+P183G, H172R+Q184E, H172R+Q184K, H172R+R185G, H172R+Y196W, H172R+Y196F, H172R+N200T, H172R+S202R, H172R+Q203T, H172R+R205K, H172R+R210L, H172R+R210G, H172R+R210M, H172R+N213V, H172R+N213D, H172R+T228S, H172R+N229D, H172R+E234F, H172R+E234Y, H172R+A235K, H172R+A235R, H172R+S241C, H172R+Q243K, H172R+Q243E, H172R+R244K, H172R+R244V, H172R+A250G, H172R+K254Y, H172R+G257W, H172R+G257E, H172R+G257A, H172R+W260F, H172R+Y262F, H172R+S266A, H172R+D268N, H172R+A270D, H172R+N272M, H172R+N272T, H172R+N273E, H172R+N273D, H172R+A276E, H172R+A276W, H172R+A276D, H172R+N279D, H172R+N279E, H172R+T280L, H172R+N283W, H172R+N283H, H172R+Y286W, H172R+Y286F, H172R+L288I, H172R+E290A, H172R+L294P, H172R+L294K, H172R+L294I, H172R+L294R, H172R+L294V, H172R+L294H, H172R+S295K, H172R+S295V, H172R+S295P, H172R+S295L, H172R+S295R, H172R+S295A, H172R+S295N, H172R+S295M, H172R+S295I, H172R+T296S, H172R+F298Y, Y174R+R176Q, Y174R+E177S, Y174R+E177Y, Y174R+N180R, Y174R+P183T, Y174R+P183G, Y174R+Q184E, Y174R+Q184K, Y174R+R185G, Y174R+Y196W, Y174R+Y196F, Y174R+N200T, Y174R+S202R, Y174R+Q203T, Y174R+R205K, Y174R+R210L, Y174R+R210G, Y174R+R210M, Y174R+N213V, Y174R+N213D, Y174R+T228S, Y174R+N229D, Y174R+E234F, Y174R+E234Y, Y174R+A235K, Y174R+A235R, Y174R+S241C, Y174R+Q243K, Y174R+Q243E, Y174R+R244K, Y174R+R244V, Y174R+A250G, Y174R+K254Y, Y174R+G257W, Y174R+G257E, Y174R+G257A, Y174R+W260F, Y174R+Y262F, Y174R+S266A, Y174R+D268N, Y174R+A270D, Y174R+N272M, Y174R+N272T, Y174R+N273E, Y174R+N273D, Y174R+A276E, Y174R+A276W, Y174R+A276D, Y174R+N279D, Y174R+N279E, Y174R+T280L, Y174R+N283W, Y174R+N283H, Y174R+Y286W, Y174R+Y286F, Y174R+L288I, Y174R+E290A, Y174R+L294P, Y174R+L294K, Y174R+L294I, Y174R+L294R, Y174R+L294V, Y174R+L294H, Y174R+S295K, Y174R+S295V, Y174R+S295P, Y174R+S295L, Y174R+S295R, Y174R+S295A, Y174R+S295N, Y174R+S295M, Y174R+S295I, Y174R+T296S, Y174R+F298Y, Y174L+R176Q, Y174L+E177S, Y174L+E177Y, Y174L+N180R, Y174L+P183T, Y174L+P183G, Y174L+Q184E, Y174L+Q184K, Y174L+R185G, Y174L+Y196W, Y174L+Y196F, Y174L+N200T, Y174L+S202R, Y174L+Q203T, Y174L+R205K, Y174L+R210L, Y174L+R210G, Y174L+R210M, Y174L+N213V, Y174L+N213D, Y174L+T228S, Y174L+N229D, Y174L+E234F, Y174L+E234Y, Y174L+A235K, Y174L+A235R, Y174L+S241C, Y174L+Q243K, Y174L+Q243E, Y174L+R244K, Y174L+R244V, Y174L+A250G, Y174L+K254Y, Y174L+G257W, Y174L+G257E, Y174L+G257A, Y174L+W260F, Y174L+Y262F, Y174L+S266A, Y174L+D268N, Y174L+A270D, Y174L+N272M, Y174L+N272T, Y174L+N273E, Y174L+N273D, Y174L+A276E, Y174L+A276W, Y174L+A276D, Y174L+N279D, Y174L+N279E, Y174L+T280L, Y174L+N283W, Y174L+N283H, Y174L+Y286W, Y174L+Y286F, Y174L+L288I, Y174L+E290A, Y174L+L294P, Y174L+L294K, Y174L+L294I, Y174L+L294R, Y174L+L294V, Y174L+L294H, Y174L+S295K, Y174L+S295V, Y174L+S295P, Y174L+S295L, Y174L+S295R, Y174L+S295A, Y174L+S295N, Y174L+S295M, Y174L+S295I, Y174L+T296S, Y174L+F298Y, Y174W+R176Q, Y174W+E177S, Y174W+E177Y, Y174W+N180R, Y174W+P183T, Y174W+P183G, Y174W+Q184E, Y174W+Q184K, Y174W+R185G, Y174W+Y196W, Y174W+Y196F, Y174W+N200T, Y174W+S202R, Y174W+Q203T, Y174W+R205K, Y174W+R210L, Y174W+R210G, Y174W+R210M, Y174W+N213V, Y174W+N213D, Y174W+T228S, Y174W+N229D, Y174W+E234F, Y174W+E234Y, Y174W+A235K, Y174W+S241C, Y174W+Q243K, Y174W+Q243E, Y174W+R244K, Y174W+R244V, Y174W+A250G, Y174W+K254Y, Y174W+G257W, Y174W+G257E,

Y174W+G257A, Y174W+W260F, Y174W+Y262F, Y174W+S266A, Y174W+D268N, Y174W+A270D, Y174W+N272M, Y174W+N272T, Y174W+N273E, Y174W+N273D, Y174W+A276E, Y174W+A276W, Y174W+A276D, Y174W+N279D, Y174W+N279E, Y174W+T280L, Y174W+N283W, Y174W+N283H, Y174W+Y286W, Y174W+Y286F, Y174W+L288I, Y174W+E290A, Y174W+L294P, Y174W+L294K, Y174W+L294I, Y174W+L294R, Y174W+L294V, Y174W+L294H, Y174W+S295K, Y174W+S295V, Y174W+S295P, Y174W+S295L, Y174W+S295R, Y174W+S295A, Y174W+S295N, Y174W+S295M, Y174W+S295I, Y174W+T296S, Y174W+F298Y, Y174F+R176Q, Y174F+E177S, Y174F+E177Y, Y174F+N180R, Y174F+P183T, Y174F+P183G, Y174F+Q184E, Y174F+Q184K, Y174F+R185G, Y174F+Y196W, Y174F+Y196F, Y174F+N200T, Y174F+S202R, Y174F+Q203T, Y174F+R205K, Y174F+R210L, Y174F+R210G, Y174F+R210M, Y174F+N213V, Y174F+N213D, Y174F+T228S, Y174F+N229D, Y174F+E234F, Y174F+E234Y, Y174F+A235K, Y174F+A235R, Y174F+S241C, Y174F+Q243K, Y174F+Q243E, Y174F+R244K, Y174F+R244V, Y174F+A250G, Y174F+K254Y, Y174F+G257W, Y174F+G257E, Y174F+G257A, Y174F+W260F, Y174F+Y262F, Y174F+S266A, Y174F+D268N, Y174F+A270D, Y174F+N272M, Y174F+N272T, Y174F+N273E, Y174F+N273D, Y174F+A276E, Y174F+A276W, Y174F+A276D, Y174F+N279D, Y174F+N279E, Y174F+T280L, Y174F+N283W, Y174F+N283H, Y174F+Y286W, Y174F+Y286F, Y174F+L288I, Y174F+E290A, Y174F+L294P, Y174F+L294K, Y174F+L294I, Y174F+L294R, Y174F+L294V, Y174F+L294H, Y174F+S295K, Y174F+S295V, Y174F+S295P, Y174F+S295L, Y174F+S295R, Y174F+S295A, Y174F+S295N, Y174F+S295M, Y174F+S295I, Y174F+T296S, Y174F+F298Y, R176Q+E177S, R176Q+E177Y, R176Q+N180R, R176Q+P183T, R176Q+P183G, R176Q+Q184E, R176Q+Q184K, R176Q+R185G, R176Q+Y196W, R176Q+Y196F, R176Q+N200T, R176Q+S202R, R176Q+Q203T, R176Q+R205K, R176Q+R210L, R176Q+R210G, R176Q+R210M, R176Q+N213V, R176Q+N213D, R176Q+T228S, R176Q+N229D, R176Q+E234F, R176Q+E234Y, R176Q+A235K, R176Q+A235R, R176Q+S241C, R176Q+Q243K, R176Q+Q243E, R176Q+R244K, R176Q+R244V, R176Q+A250G, R176Q+K254Y, R176Q+G257W, R176Q+G257E, R176Q+G257A, R176Q+W260F, R176Q+Y262F, R176Q+S266A, R176Q+D268N, R176Q+A270D, R176Q+N272M, R176Q+N272T, R176Q+N273E, R176Q+N273D, R176Q+A276E, R176Q+A276W, R176Q+A276D, R176Q+N279D, R176Q+N279E, R176Q+T280L, R176Q+N283W, R176Q+N283H, R176Q+Y286W, R176Q+Y286F, R176Q+L288I, R176Q+E290A, R176Q+L294P, R176Q+L294K, R176Q+L294I, R176Q+L294R, R176Q+L294V, R176Q+L294H, R176Q+S295K, R176Q+S295V, R176Q+S295P, R176Q+S295L, R176Q+S295R, R176Q+S295A, R176Q+S295N, R176Q+S295M, R176Q+S295I, R176Q+T296S, R176Q+F298Y, E177S+N180R, E177S+P183T, E177S+P183G, E177S+Q184E, E177S+Q184K, E177S+R185G, E177S+Y196W, E177S+Y196F, E177S+N200T, E177S+S202R, E177S+Q203T, E177S+R205K, E177S+R210L, E177S+R210G, E177S+R210M, E177S+N213V, E177S+N213D, E177S+T228S, E177S+N229D, E177S+E234F, E177S+E234Y, E177S+A235K, E177S+A235R, E177S+S241C, E177S+Q243K, E177S+Q243E, E177S+R244K, E177S+R244V, E177S+A250G, E177S+K254Y, E177S+G257W, E177S+G257E, E177S+G257A, E177S+W260F, E177S+Y262F, E177S+S266A, E177S+D268N, E177S+A270D, E177S+N272M, E177S+N272T, E177S+N273E, E177S+N273D, E177S+A276E, E177S+A276W, E177S+A276D, E177S+N279D, E177S+N279E, E177S+T280L, E177S+N283W, E177S+N283H, E177S+Y286W, E177S+Y286F, E177S+L288I, E177S+E290A, E177S+L294P, E177S+L294K, E177S+L294I, E177S+L294R, E177S+L294V, E177S+L294H, E177S+S295K, E177S+S295V, E177S+S295P, E177S+S295L, E177S+S295R, E177S+S295A, E177S+S295N, E177S+S295M, E177S+S295I, E177S+T296S, E177S+F298Y, E177Y+N180R, E177Y+P183T, E177Y+P183G, E177Y+Q184E, E177Y+Q184K, E177Y+R185G, E177Y+Y196W, E177Y+Y196F, E177Y+N200T, E177Y+S202R, E177Y+Q203T, E177Y+R205K, E177Y+R210L, E177Y+R210G, E177Y+R210M, E177Y+N213V, E177Y+N213D, E177Y+T228S, E177Y+N229D, E177Y+E234F, E177Y+E234Y, E177Y+A235K, E177Y+A235R, E177Y+S241C, E177Y+Q243K, E177Y+Q243E, E177Y+R244K, E177Y+R244V, E177Y+A250G, E177Y+K254Y, E177Y+G257W, E177Y+G257E, E177Y+G257A, E177Y+W260F, E177Y+Y262F, E177Y+S266A, E177Y+D268N, E177Y+A270D, E177Y+N272M, E177Y+N272T, E177Y+N273E, E177Y+N273D, E177Y+A276E, E177Y+A276W, E177Y+A276D, E177Y+N279D, E177Y+N279E, E177Y+T280L, E177Y+N283W, E177Y+N283H, E177Y+Y286W, E177Y+Y286F, E177Y+L288I, E177Y+E290A, E177Y+L294P, E177Y+L294K, E177Y+L294I, E177Y+L294R, E177Y+L294V, E177Y+L294H, E177Y+S295K, E177Y+S295V, E177Y+S295P, E177Y+S295L, E177Y+S295R, E177Y+S295A, E177Y+S295N, E177Y+S295M, E177Y+S295I, E177Y+T296S, E177Y+F298Y, N180R+P183T, N180R+P183G, N180R+Q184E, N180R+Q184K, N180R+R185G, N180R+Y196W, N180R+Y196F, N180R+N200T, N180R+S202R, N180R+Q203T, N180R+R205K, N180R+R210L, N180R+R210G, N180R+R210M, N180R+N213V, N180R+N213D, N180R+T228S, N180R+N229D, N180R+E234F, N180R+E234Y, N180R+A235K, N180R+A235R, N180R+S241C, N180R+Q243K, N180R+Q243E, N180R+R244K, N180R+R244V, N180R+A250G, N180R+K254Y, N180R+G257W, N180R+G257E, N180R+G257A, N180R+W260F, N180R+Y262F, N180R+S266A, N180R+D268N, N180R+A270D, N180R+N272M, N180R+N272T, N180R+N273E, N180R+N273D, N180R+A276E, N180R+A276W, N180R+A276D, N180R+N279D, N180R+N279E, N180R+T280L, N180R+N283W, N180R+N283H, N180R+Y286W, N180R+Y286F, N180R+L288I, N180R+E290A, N180R+L294P, N180R+L294K, N180R+L294I, N180R+L294R, N180R+L294V, N180R+L294H, N180R+S295K, N180R+S295V, N180R+S295P, N180R+S295L, N180R+S295R, N180R+S295A, N180R+S295N, N180R+S295M, N180R+S295I, N180R+T296S, N180R+F298Y, P183T+Q184E, P183T+Q184K, P183T+R185G, P183T+Y196W, P183T+Y196F, P183T+N200T, P183T+S202R, P183T+Q203T, P183T+R205K, P183T+R210L, P183T+R210G, P183T+R210M, P183T+N213V, P183T+N213D, P183T+T228S, P183T+N229D, P183T+E234F, P183T+E234Y, P183T+A235K, P183T+A235R, P183T+S241C, P183T+Q243K, P183T+Q243E, P183T+R244K, P183T+R244V, P183T+A250G, P183T+K254Y, P183T+G257W, P183T+G257E, P183T+G257A, P183T+W260F, P183T+Y262F, P183T+S266A, P183T+D268N, P183T+A270D, P183T+N272M, P183T+N272T, P183T+N273E, P183T+N273D, P183T+A276E, P183T+A276W, P183T+A276D, P183T+N279D, P183T+N279E, P183T+T280L, P183T+N283W, P183T+N283H, P183T+Y286W, P183T+Y286F, P183T+L288I, P183T+E290A, P183T+L294P, P183T+L294K, P183T+L294I, P183T+L294R, P183T+L294V, P183T+L294H, P183T+S295K, P183T+S295V, P183T+S295P, P183T+S295L, P183T+S295R, P183T+S295A, P183T+S295N, P183T+S295M, P183T+

S295I, P183T+T296S, P183T+F298Y, P183G+Q184E, P183G+Q184K, P183G+R185G, P183G+Y196W, P183G+Y196F, P183G+N200T, P183G+S202R, P183G+Q203T, P183G+R205K, P183G+R210L, P183G+R210G, P183G+R210M, P183G+N213V, P183G+N213D, P183G+T228S, P183G+N229D, P183G+E234F, P183G+E234Y, P183G+A235K, P183G+A235R, P183G+S241C, P183G+Q243K, P183G+Q243E, P183G+R244K, P183G+R244V, P183G+A250G, P183G+K254Y, P183G+G257W, P183G+G257E, P183G+G257A, P183G+W260F, P183G+Y262F, P183G+S266A, P183G+D268N, P183G+A270D, P183G+N272M, P183G+N272T, P183G+N273E, P183G+N273D, P183G+A276E, P183G+A276W, P183G+A276D, P183G+N279D, P183G+N279E, P183G+T280L, P183G+N283W, P183G+N283H, P183G+Y286W, P183G+Y286F, P183G+L288I, P183G+E290A, P183G+L294P, P183G+L294K, P183G+L294I, P183G+L294R, P183G+L294V, P183G+L294H, P183G+S295K, P183G+S295V, P183G+S295P, P183G+S295L, P183G+S295R, P183G+S295A, P183G+S295N, P183G+S295M, P183G+S295I, P183G+T296S, P183G+F298Y, Q184E+R185G, Q184E+Y196W, Q184E+Y196F, Q184E+N200T, Q184E+S202R, Q184E+Q203T, Q184E+R205K, Q184E+R210L, Q184E+R210G, Q184E+R210M, Q184E+N213V, Q184E+N213D, Q184E+T228S, Q184E+N229D, Q184E+E234F, Q184E+E234Y, Q184E+A235K, Q184E+A235R, Q184E+S241C, Q184E+Q243K, Q184E+Q243E, Q184E+R244K, Q184E+R244V, Q184E+A250G, Q184E+K254Y, Q184E+G257W, Q184E+G257E, Q184E+G257A, Q184E+W260F, Q184E+Y262F, Q184E+S266A, Q184E+D268N, Q184E+A270D, Q184E+N272M, Q184E+N272T, Q184E+N273E, Q184E+N273D, Q184E+A276E, Q184E+A276W, Q184E+A276D, Q184E+N279D, Q184E+N279E, Q184E+T280L, Q184E+N283W, Q184E+N283H, Q184E+Y286W, Q184E+Y286F, Q184E+L288I, Q184E+E290A, Q184E+L294P, Q184E+L294K, Q184E+L294I, Q184E+L294R, Q184E+L294V, Q184E+L294H, Q184E+S295K, Q184E+S295V, Q184E+S295P, Q184E+S295L, Q184E+S295R, Q184E+S295A, Q184E+S295N, Q184E+S295M, Q184E+S295I, Q184E+T296S, Q184E+F298Y, Q184K+R185G, Q184K+Y196W, Q184K+Y196F, Q184K+N200T, Q184K+S202R, Q184K+Q203T, Q184K+R205K, Q184K+R210L, Q184K+R210G, Q184K+R210M, Q184K+N213V, Q184K+N213D, Q184K+T228S, Q184K+N229D, Q184K+E234F, Q184K+E234Y, Q184K+A235K, Q184K+A235R, Q184K+S241C, Q184K+Q243K, Q184K+Q243E, Q184K+R244K, Q184K+R244V, Q184K+A250G, Q184K+K254Y, Q184K+G257W, Q184K+G257E, Q184K+G257A, Q184K+W260F, Q184K+Y262F, Q184K+S266A, Q184K+D268N, Q184K+A270D, Q184K+N272M, Q184K+N272T, Q184K+N273E, Q184K+N273D, Q184K+A276E, Q184K+A276W, Q184K+A276D, Q184K+N279D, Q184K+N279E, Q184K+T280L, Q184K+N283W, Q184K+N283H, Q184K+Y286W, Q184K+Y286F, Q184K+L288I, Q184K+E290A, Q184K+L294P, Q184K+L294K, Q184K+L294I, Q184K+L294R, Q184K+L294V, Q184K+L294H, Q184K+S295K, Q184K+S295V, Q184K+S295P, Q184K+S295L, Q184K+S295R, Q184K+S295A, Q184K+S295N, Q184K+S295M, Q184K+S295I, Q184K+T296S, Q184K+F298Y, R185G+Y196W, R185G+Y196F, R185G+N200T, R185G+S202R, R185G+Q203T, R185G+R205K, R185G+R210L, R185G+R210G, R185G+R210M, R185G+N213V, R185G+N213D, R185G+T228S, R185G+N229D, R185G+E234F, R185G+E234Y, R185G+A235K, R185G+A235R, R185G+S241C, R185G+Q243K, R185G+Q243E, R185G+R244K, R185G+R244V, R185G+A250G, R185G+K254Y, R185G+G257W, R185G+G257E, R185G+G257A, R185G+W260F, R185G+Y262F, R185G+S266A, R185G+D268N, R185G+A270D, R185G+N272M, R185G+N272T, R185G+N273E, R185G+N273D, R185G+A276E, R185G+A276W, R185G+A276D, R185G+N279D, R185G+N279E, R185G+T280L, R185G+N283W, R185G+N283H, R185G+Y286W, R185G+Y286F, R185G+L288I, R185G+E290A, R185G+L294P, R185G+L294K, R185G+L294I, R185G+L294R, R185G+L294V, R185G+L294H, R185G+S295K, R185G+S295V, R185G+S295P, R185G+S295L, R185G+S295R, R185G+S295A, R185G+S295N, R185G+S295M, R185G+S295I, R185G+T296S, R185G+F298Y, Y196W+N200T, Y196W+S202R, Y196W+Q203T, Y196W+R205K, Y196W+R210L, Y196W+R210G, Y196W+R210M, Y196W+N213V, Y196W+N213D, Y196W+T228S, Y196W+N229D, Y196W+E234F, Y196W+E234Y, Y196W+A235K, Y196W+A235R, Y196W+S241C, Y196W+Q243K, Y196W+Q243E, Y196W+R244K, Y196W+R244V, Y196W+A250G, Y196W+K254Y, Y196W+G257W, Y196W+G257E, Y196W+G257A, Y196W+W260F, Y196W+Y262F, Y196W+S266A, Y196W+D268N, Y196W+A270D, Y196W+N272M, Y196W+N272T, Y196W+N273E, Y196W+N273D, Y196W+A276E, Y196W+A276W, Y196W+A276D, Y196W+N279D, Y196W+N279E, Y196W+T280L, Y196W+N283W, Y196W+N283H, Y196W+Y286W, Y196W+Y286F, Y196W+L288I, Y196W+E290A, Y196W+L294P, Y196W+L294K, Y196W+L294I, Y196W+L294R, Y196W+L294V, Y196W+L294H, Y196W+S295K, Y196W+S295V, Y196W+S295P, Y196W+S295L, Y196W+S295R, Y196W+S295A, Y196W+S295N, Y196W+S295M, Y196W+S295I, Y196W+T296S, Y196W+F298Y, Y196F+N200T, Y196F+S202R, Y196F+Q203T, Y196F+R205K, Y196F+R210L, Y196F+R210G, Y196F+R210M, Y196F+N213V, Y196F+N213D, Y196F+T228S, Y196F+N229D, Y196F+E234F, Y196F+E234Y, Y196F+A235K, Y196F+A235R, Y196F+S241C, Y196F+Q243K, Y196F+Q243E, Y196F+R244K, Y196F+R244V, Y196F+A250G, Y196F+K254Y, Y196F+G257W, Y196F+G257E, Y196F+G257A, Y196F+W260F, Y196F+Y262F, Y196F+S266A, Y196F+D268N, Y196F+A270D, Y196F+N272M, Y196F+N272T, Y196F+N273E, Y196F+N273D, Y196F+A276E, Y196F+A276W, Y196F+A276D, Y196F+N279D, Y196F+N279E, Y196F+T280L, Y196F+N283W, Y196F+N283H, Y196F+Y286W, Y196F+Y286F, Y196F+L288I, Y196F+E290A, Y196F+L294P, Y196F+L294K, Y196F+L294I, Y196F+L294R, Y196F+L294V, Y196F+L294H, Y196F+S295K, Y196F+S295V, Y196F+S295P, Y196F+S295L, Y196F+S295R, Y196F+S295A, Y196F+S295N, Y196F+S295M, Y196F+S295I, Y196F+T296S, Y196F+F298Y, N200T+S202R, N200T+Q203T, N200T+R205K, N200T+R210L, N200T+R210G, N200T+R210M, N200T+N213V, N200T+N213D, N200T+T228S, N200T+N229D, N200T+E234F, N200T+E234Y, N200T+A235K, N200T+A235R, N200T+S241C, N200T+Q243K, N200T+Q243E, N200T+R244K, N200T+R244V, N200T+A250G, N200T+K254Y, N200T+G257W, N200T+G257E, N200T+G257A, N200T+W260F, N200T+Y262F, N200T+S266A, N200T+D268N, N200T+A270D, N200T+N272M, N200T+N272T, N200T+N273E, N200T+N273D, N200T+A276E, N200T+A276W, N200T+A276D, N200T+N279D, N200T+N279E, N200T+T280L, N200T+N283W, N200T+N283H, N200T+Y286W, N200T+Y286F, N200T+L288I, N200T+E290A, N200T+L294P, N200T+L294K, N200T+L294I, N200T+L294R, N200T+L294V, N200T+L294H, N200T+S295K, N200T+S295V, N200T+S295P, N200T+S295L, N200T+S295R, N200T+S295A, N200T+S295N, N200T+S295M, N200T+S295I, N200T+T296S, N200T+F298Y, S202R+Q203T, S202R+R205K, S202R+R210L, S202R+R210G, S202R+R210M,

S202R+N213V, S202R+N213D, S202R+T228S, S202R+ N229D, S202R+E234F, S202R+E234Y, S202R+A235K, S202R+A235R, S202R+S241C, S202R+Q243K, S202R+ Q243E, S202R+R244K, S202R+R244V, S202R+A250G, S202R+K254Y, S202R+G257W, S202R+G257E, S202R+ G257A, S202R+W260F, S202R+Y262F, S202R+S266A, S202R+D268N, S202R+A270D, S202R+N272M, S202R+ N272T, S202R+N273E, S202R+N273D, S202R+A276E, S202R+A276W, S202R+A276D, S202R+N279D, S202R+ N279E, S202R+T280L, S202R+N283W, S202R+N283H, S202R+Y286W, S202R+Y286F, S202R+L288 I, S202R+ E290A, S202R+L294P, S202R+L294K, S202R+L294I, S202R+L294R, S202R+L294V, S202R+L294H, S202R+ S295K, S202R+S295V, S202R+S295P, S202R+S295L, S202R+S295R, S202R+S295A, S202R+S295N, S202R+ S295M, S202R+S295I, S202R+T296S, S202R+F298Y, Q203T+R205K, Q203T+R210L, Q203T+R210G, Q203T+ R210M, Q203T+N213V, Q203T+N213D, Q203T+T228S, Q203T+N229D, Q203T+E234F, Q203T+E234Y, Q203T+ A235K, Q203T+A235R, Q203T+S241C, Q203T+Q243K, Q203T+Q243E, Q203T+R244K, Q203T+R244V, Q203T+ A250G, Q203T+K254Y, Q203T+G257W, Q203T+G257E, Q203T+G257A, Q203T+W260F, Q203T+Y262F, Q203T+ S266A, Q203T+D268N, Q203T+A270D, Q203T+N272M, Q203T+N272T, Q203T+N273E, Q203T+N273D, Q203T+ A276E, Q203T+A276W, Q203T+A276D, Q203T+N279D, Q203T+N279E, Q203T+T280L, Q203T+N283W, Q203T+ N283H, Q203T+Y286W, Q203T+Y286F, Q203T+L288 I, Q203T+E290A, Q203T+L294P, Q203T+L294K, Q203T+ L294 I, Q203T+L294R, Q203T+L294V, Q203T+L294H, Q203T+S295K, Q203T+S295V, Q203T+S295P, Q203T+ S295L, Q203T+S295R, Q203T+S295A, Q203T+S295N, Q203T+S295M, Q203T+S295I, Q203T+T296S, Q203T+ F298Y, R205K+R210L, R205K+R210G, R205K+R210M, R205K+N213V, R205K+N213D, R205K+T228S, R205K+ N229D, R205K+E234F, R205K+E234Y, R205K+A235K, R205K+A235R, R205K+S241C, R205K+Q243K, R205K+ Q243E, R205K+R244K, R205K+R244V, R205K+A250G, R205K+K254Y, R205K+G257W, R205K+G257E, R205K+ G257A, R205K+W260F, R205K+Y262F, R205K+S266A, R205K+D268N, R205K+A270D, R205K+N272M, R205K+N272T, R205K+N273E, R205K+N273D, R205K+ A276E, R205K+A276W, R205K+A276D, R205K+N279D, R205K+N279E, R205K+T280L, R205K+N283W, R205K+ N283H, R205K+Y286W, R205K+Y286F, R205K+L288I, R205K+E290A, R205K+L294P, R205K+L294K, R205K+ L294I, R205K+L294R, R205K+L294V, R205K+L294H, R205K+S295K, R205K+S295V, R205K+S295P, R205K+ S295L, R205K+S295R, R205K+S295A, R205K+S295N, R205K+S295M, R205K+S295I, R205K+T296S, R205K+ F298Y, R210L+N213V, R210L+N213D, R210L+T228S, R210L+N229D, R210L+E234F, R210L+E234Y, R210L+ A235K, R210L+A235R, R210L+S241C, R210L+Q243K, R210L+Q243E, R210L+R244K, R210L+R244V, R210L+ A250G, R210L+K254Y, R210L+G257W, R210L+G257E, R210L+G257A, R210L+W260F, R210L+Y262F, R210L+ S266A, R210L+D268N, R210L+A270D, R210L+N272M, R210L+N272T, R210L+N273E, R210L+N273D, R210L+ A276E, R210L+A276W, R210L+A276D, R210L+N279D, R210L+N279E, R210L+T280L, R210L+N283W, R210L+ N283H, R210L+Y286W, R210L+Y286F, R210L+L288I, R210L+E290A, R210L+L294P, R210L+L294K, R210L+ L294I, R210L+L294R, R210L+L294V, R210L+L294H, R210L+S295K, R210L+S295V, R210L+S295P, R210L+ S295L, R210L+S295R, R210L+S295A, R210L+S295N, R210L+S295M, R210L+S295I, R210L+T296S, R210L+ F298Y, R210G+N213V, R210G+N213D, R210G+T228S, R210G+N229D, R210G+E234F, R210G+E234Y, R210G+ A235K, R210G+A235R, R210G+S241C, R210G+Q243K, R210G+Q243E, R210G+R244K, R210G+R244V, R210G+ A250G, R210G+K254Y, R210G+G257W, R210G+G257E, R210G+G257A, R210G+W260F, R210G+Y262F, R210G+ S266A, R210G+D268N, R210G+A270D, R210G+N272M, R210G+N272T, R210G+N273E, R210G+N273D, R210G+ A276E, R210G+A276W, R210G+A276D, R210G+N279D, R210G+N279E, R210G+T280L, R210G+N283W, R210G+ N283H, R210G+Y286W, R210G+Y286F, R210G+L288I, R210G+E290A, R210G+L294P, R210G+L294K, R210G+ L294I, R210G+L294R, R210G+L294V, R210G+L294H, R210G+S295K, R210G+S295V, R210G+S295P, R210G+ S295L, R210G+S295R, R210G+S295A, R210G+S295N, R210G+S295M, R210G+S295I, R210G+T296S, R210G+ F298Y, R210M+N213V, R210M+N213D, R210M+T228S, R210M+N229D, R210M+E234F, R210M+E234Y, R210M+A235K, R210M+A235R, R210M+S241C, R210M+Q243K, R210M+Q243E, R210M+R244K, R210M+R244V, R210M+A250G, R210M+K254Y, R210M+G257W, R210M+G257E, R210M+G257A, R210M+W260F, R210M+Y262F, R210M+S266A, R210M+D268N, R210M+A270D, R210M+N272M, R210M+N272T, R210M+N273E, R210M+N273D, R210M+A276E, R210M+A276W, R210M+A276D, R210M+N279D, R210M+N279E, R210M+T280L, R210M+N283W, R210M+N283H, R210M+Y286W, R210M+Y286F, R210M+L288I, R210M+E290A, R210M+ L294P, R210M+L294K, R210M+L294I, R210M+L294R, R210M+L294V, R210M+L294H, R210M+S295K, R210M+S295V, R210M+S295P, R210M+S295L, R210M+ S295R, R210M+S295A, R210M+S295N, R210M+S295M, R210M+S295I, R210M+T296S, R210M+F298Y, N213V+ T228S, N213V+N229D, N213V+E234F, N213V+E234Y, N213V+A235K, N213V+A235R, N213V+S241C, N213V+ Q243K, N213V+Q243E, N213V+R244K, N213V+R244V, N213V+A250G, N213V+K254Y, N213V+G257W, N213V+G257E, N213V+G257A, N213V+W260F, N213V+Y262F, N213V+S266A, N213V+D268N, N213V+ A270D, N213V+N272M, N213V+N272T, N213V+N273E, N213V+N273D, N213V+A276E, N213V+A276W, N213V+A276D, N213V+N279D, N213V+N279E, N213V+T280L, N213V+N283W, N213V+N283H, N213V+Y286W, N213V+Y286F, N213V+L288I, N213V+ E290A, N213V+L294P, N213V+L294K, N213V+L294I, N213V+L294R, N213V+L294V, N213V+L294H, N213V+ S295K, N213V+S295V, N213V+S295P, N213V+S295L, N213V+S295R, N213V+S295A, N213V+S295N, N213V+ S295M, N213V+S295I, N213V+T296S, N213V+F298Y, N213D+T228S, N213D+N229D, N213D+E234F, N213D+ E234Y, N213D+A235K, N213D+A235R, N213D+S241C, N213D+Q243K, N213D+Q243E, N213D+R244K, N213D+ R244V, N213D+A250G, N213D+K254Y, N213D+G257W, N213D+G257E, N213D+G257A, N213D+W260F, N213D+Y262F, N213D+S266A, N213D+D268N, N213D+ A270D, N213D+N272M, N213D+N272T, N213D+N273E, N213D+N273D, N213D+A276E, N213D+A276W, N213D+A276D, N213D+N279D, N213D+N279E, N213D+T280L, N213D+N283W, N213D+N283H, N213D+Y286W, N213D+Y286F, N213D+L288I, N213D+ E290A, N213D+L294P, N213D+L294K, N213D+L294I, N213D+L294R, N213D+L294V, N213D+L294H, N213D+ S295K, N213D+S295V, N213D+S295P, N213D+S295L, N213D+S295R, N213D+S295A, N213D+S295N, N213D+ S295M, N213D+S295I, N213D+T296S, N213D+F298Y, T228S+N229D, T228S+E234F, T228S+E234Y, T228S+ A235K, T228S+A235R, T228S+S241C, T228S+Q243K,

T228S+Q243E, T228S+R244K, T228S+R244V, T228S+ A250G, T228S+K254Y, T228S+G257W, T228S+G257E, T228S+G257A, T228S+W260F, T228S+Y262F, T228S+ S266A, T228S+D268N, T228S+A270D, T228S+N272M, T228S+N272T, T228S+N273E, T228S+N273D, T228S+ A276E, T228S+A276W, T228S+A276D, T228S+N279D, T228S+N279E, T228S+T280L, T228S+N283W, T228S+ N283H, T228S+Y286W, T228S+Y286F, T228S+L288I, T228S+E290A, T228S+L294P, T228S+L294K, T228S+ L294I, T228S+L294R, T228S+L294V, T228S+L294H, T228S+S295K, T228S+S295V, T228S+S295P, T228S+ S295L, T228S+S295R, T228S+S295A, T228S+S295N, T228S+S295M, T228S+S295I, T228S+T296S, T228S+ F298Y, N229D+E234F, N229D+E234Y, N229D+A235K, N229D+A235R, N229D+S241C, N229D+Q243K, N229D+ Q243E, N229D+R244K, N229D+R244V, N229D+A250G, N229D+K254Y, N229D+G257W, N229D+G257E, N229D+G257A, N229D+W260F, N229D+Y262F, N229D+ S266A, N229D+D268N, N229D+A270D, N229D+N272M, N229D+N272T, N229D+N273E, N229D+N273D, N229D+ A276E, N229D+A276W, N229D+A276D, N229D+N279D, N229D+N279E, N229D+T280L, N229D+N283W, N229D+ N283H, N229D+Y286W, N229D+Y286F, N229D+L288I, N229D+E290A, N229D+L294P, N229D+L294K, N229D+ L294I, N229D+L294R, N229D+L294V, N229D+L294H, N229D+S295K, N229D+S295V, N229D+S295P, N229D+ S295L, N229D+S295R, N229D+S295A, N229D+S295N, N229D+S295M, N229D+S295I, N229D+T296S, N229D+ F298Y, E234F+A235K, E234F+A235R, E234F+S241C, E234F+Q243K, E234F+Q243E, E234F+R244K, E234F+ R244V, E234F+A250G, E234F+K254Y, E234F+G257W, E234F+G257E, E234F+G257A, E234F+W260F, E234F+ Y262F, E234F+S266A, E234F+D268N, E234F+A270D, E234F+N272M, E234F+N272T, E234F+N273E, E234F+ N273D, E234F+A276E, E234F+A276W, E234F+A276D, E234F+N279D, E234F+N279E, E234F+T280L, E234F+ N283W, E234F+N283H, E234F+Y286W, E234F+Y286F, E234F+L288I, E234F+E290A, E234F+L294P, E234F+ L294K, E234F+L294I, E234F+L294R, E234F+L294V, E234F+L294H, E234F+S295K, E234F+S295V, E234F+ S295P, E234F+S295L, E234F+S295R, E234F+S295A, E234F+S295N, E234F+S295M, E234F+S295I, E234F+ T296S, E234F+F298Y, E234Y+A235K, E234Y+A235R, E234Y+S241C, E234Y+Q243K, E234Y+Q243E, E234Y+ R244K, E234Y+R244V, E234Y+A250G, E234Y+K254Y, E234Y+G257W, E234Y+G257E, E234Y+G257A, E234Y+ W260F, E234Y+Y262F, E234Y+S266A, E234Y+D268N, E234Y+A270D, E234Y+N272M, E234Y+N272T, E234Y+ N273E, E234Y+N273D, E234Y+A276E, E234Y+A276W, E234Y+A276D, E234Y+N279D, E234Y+N279E, E234Y+ T280L, E234Y+N283W, E234Y+N283H, E234Y+Y286W, E234Y+Y286F, E234Y+L288I, E234Y+E290A, E234Y+ L294P, E234Y+L294K, E234Y+L294I, E234Y+L294R, E234Y+L294V, E234Y+L294H, E234Y+S295K, E234Y+ S295V, E234Y+S295P, E234Y+S295L, E234Y+S295R, E234Y+S295A, E234Y+S295N, E234Y+S295M, E234Y+ S295I, E234Y+T296S, E234Y+F298Y, A235K+S241C, A235K+Q243K, A235K+Q243E, A235K+R244K, A235K+ R244V, A235K+A250G, A235K+K254Y, A235K+G257W, A235K+G257E, A235K+G257A, A235K+W260F, A235K+ Y262F, A235K+S266A, A235K+D268N, A235K+A270D, A235K+N272M, A235K+N272T, A235K+N273E, A235K+ N273D, A235K+A276E, A235K+A276W, A235K+A276D, A235K+N279D, A235K+N279E, A235K+T280L, A235K+ N283W, A235K+N283H, A235K+Y286W, A235K+Y286F, A235K+L288I, A235K+E290A, A235K+L294P, A235K+ L294K, A235K+L294I, A235K+L294R, A235K+L294V, A235K+L294H, A235K+S295K, A235K+S295V, A235K+ S295P, A235K+S295L, A235K+S295R, A235K+S295A, A235K+S295N, A235K+S295M, A235K+S295I, A235K+ T296S, A235K+F298Y, A235K+S241C, A235R+Q243K, A235R+Q243E, A235R+R244K, A235R+R244V, A235R+ A250G, A235R+K254Y, A235R+G257W, A235R+G257E, A235R+G257A, A235R+W260F, A235R+Y262F, A235R+ S266A, A235R+D268N, A235R+A270D, A235R+N272M, A235R+N272T, A235R+N273E, A235R+N273D, A235R+ A276E, A235R+A276W, A235R+A276D, A235R+N279D, A235R+N279E, A235R+T280L, A235R+N283W, A235R+ N283H, A235R+Y286W, A235R+Y286F, A235R+L288I, A235R+E290A, A235R+L294P, A235R+L294K, A235R+ L294I, A235R+L294R, A235R+L294V, A235R+L294H, A235R+S295K, A235R+S295V, A235R+S295P, A235R+ S295L, A235R+S295R, A235R+S295A, A235R+S295N, A235R+S295M, A235R+S295I, A235R+T296S, A235R+ F298Y, S241C+Q243K, S241C+Q243E, S241C+R244K, S241C+R244V, S241C+A250G, S241C+K254Y, S241C+ G257W, S241C+G257E, S241C+G257A, S241C+W260F, S241C+Y262F, S241C+S266A, S241C+D268N, S241C+ A270D, S241C+N272M, S241C+N272T, S241C+N273E, S241C+N273D, S241C+A276E, S241C+A276W, S241C+ A276D, S241C+N279D, S241C+N279E, S241C+T280L, S241C+N283W, S241C+N283H, S241C+Y286W, S241C+ Y286F, S241C+L288I, S241C+E290A, S241C+L294P, S241C+L294K, S241C+L294I, S241C+L294R, S241C+ L294V, S241C+L294H, S241C+S295K, S241C+S295V, S241C+S295P, S241C+S295L, S241C+S295R, S241C+ S295A, S241C+S295N, S241C+S295M, S241C+S295I, S241C+T296S, S241C+F298Y, Q243K+R244K, Q243K+ R244V, Q243K+A250G, Q243K+K254Y, Q243K+G257W, Q243K+G257E, Q243K+G257A, Q243K+W260F, Q243K+Y262F, Q243K+S266A, Q243K+D268N, Q243K+ A270D, Q243K+N272M, Q243K+N272T, Q243K+N273E, Q243K+N273D, Q243K+A276E, Q243K+A276W, Q243K+A276D, Q243K+N279D, Q243K+N279E, Q243K+T280L, Q243K+N283W, Q243K+N283H, Q243K+Y286W, Q243K+Y286F, Q243K+L288I, Q243K+ E290A, Q243K+L294P, Q243K+L294K, Q243K+L294I, Q243K+L294R, Q243K+L294V, Q243K+L294H, Q243K+ S295K, Q243K+S295V, Q243K+S295P, Q243K+S295L, Q243K+S295R, Q243K+S295A, Q243K+S295N, Q243K+ S295M, Q243K+S295I, Q243K+T296S, Q243K+F298Y, Q243E+R244K, Q243E+R244V, Q243E+A250G, Q243E+ K254Y, Q243E+G257W, Q243E+G257E, Q243E+G257A, Q243E+W260F, Q243E+Y262F, Q243E+S266A, Q243E+ D268N, Q243E+A270D, Q243E+N272M, Q243E+N272T, Q243E+N273E, Q243E+N273D, Q243E+A276E, Q243E+ A276W, Q243E+A276D, Q243E+N279D, Q243E+N279E, Q243E+T280L, Q243E+N283W, Q243E+N283H, Q243E+ Y286W, Q243E+Y286F, Q243E+L288I, Q243E+E290A, Q243E+L294P, Q243E+L294K, Q243E+L294I, Q243E+ L294R, Q243E+L294V, Q243E+L294H, Q243E+S295K, Q243E+S295V, Q243E+S295P, Q243E+S295L, Q243E+ S295R, Q243E+S295A, Q243E+S295N, Q243E+S295M, Q243E+S295I, Q243E+T296S, Q243E+F298Y, R244K+ A250G, R244K+K254Y, R244K+G257W, R244K+G257E, R244K+G257A, R244K+W260F, R244K+Y262F, R244K+ S266A, R244K+D268N, R244K+A270D, R244K+N272M, R244K+N272T, R244K+N273E, R244K+N273D, R244K+ A276E, R244K+A276W, R244K+A276D, R244K+N279D, R244K+N279E, R244K+T280L, R244K+N283W, R244K+ N283H, R244K+Y286W, R244K+Y286F, R244K+L288I, R244K+E290A, R244K+L294P, R244K+L294K, R244K+ L294I, R244K+L294R, R244K+L294V, R244K+L294H, R244K+S295K, R244K+S295V, R244K+S295P, R244K+

S295L, R244K+S295R, R244K+S295A, R244K+S295N, R244K+S295M, R244K+S295I, R244K+T296S, R244K+F298Y, R244V+A250G, R244V+K254Y, R244V+G257W, R244V+G257E, R244V+G257A, R244V+W260F, R244V+Y262F, R244V+S266A, R244V+D268N, R244V+A270D, R244V+N272M, R244V+N272T, R244V+N273E, R244V+N273D, R244V+A276E, R244V+A276W, R244V+A276D, R244V+N279D, R244V+N279E, R244V+T280L, R244V+N283W, R244V+N283H, R244V+Y286W, R244V+Y286F, R244V+L288I, R244V+E290A, R244V+L294P, R244V+L294K, R244V+L294I, R244V+L294R, R244V+L294V, R244V+L294H, R244V+S295K, R244V+S295V, R244V+S295P, R244V+S295L, R244V+S295R, R244V+S295A, R244V+S295N, R244V+S295M, R244V+S295I, R244V+T296S, R244V+F298Y, A250G+K254Y, A250G+G257W, A250G+G257E, A250G+G257A, A250G+W260F, A250G+Y262F, A250G+S266A, A250G+D268N, A250G+A270D, A250G+N272M, A250G+N272T, A250G+N273E, A250G+N273D, A250G+A276E, A250G+A276W, A250G+A276D, A250G+N279D, A250G+N279E, A250G+T280L, A250G+N283W, A250G+N283H, A250G+Y286W, A250G+Y286F, A250G+L288I, A250G+E290A, A250G+L294P, A250G+L294K, A250G+L294I, A250G+L294R, A250G+L294V, A250G+L294H, A250G+S295K, A250G+S295V, A250G+S295P, A250G+S295L, A250G+S295R, A250G+S295A, A250G+S295N, A250G+S295M, A250G+S295I, A250G+T296S, A250G+F298Y, K254Y+G257W, K254Y+G257E, K254Y+G257A, K254Y+W260F, K254Y+Y262F, K254Y+S266A, K254Y+D268N, K254Y+A270D, K254Y+N272M, K254Y+N272T, K254Y+N273E, K254Y+N273D, K254Y+A276E, K254Y+A276W, K254Y+A276D, K254Y+N279D, K254Y+N279E, K254Y+T280L, K254Y+N283W, K254Y+N283H, K254Y+Y286W, K254Y+Y286F, K254Y+L288I, K254Y+E290A, K254Y+L294P, K254Y+L294K, K254Y+L294I, K254Y+L294R, K254Y+L294V, K254Y+L294H, K254Y+S295K, K254Y+S295V, K254Y+S295P, K254Y+S295L, K254Y+S295R, K254Y+S295A, K254Y+S295N, K254Y+S295M, K254Y+S295I, K254Y+T296S, K254Y+F298Y, G257W+W260F, G257W+Y262F, G257W+S266A, G257W+D268N, G257W+A270D, G257W+N272M, G257W+N272T, G257W+N273E, G257W+N273D, G257W+A276E, G257W+A276W, G257W+A276D, G257W+N279D, G257W+N279E, G257W+T280L, G257W+N283W, G257W+N283H, G257W+Y286W, G257W+Y286F, G257W+L288I, G257W+E290A, G257W+L294P, G257W+L294K, G257W+L294I, G257W+L294R, G257W+L294V, G257W+L294H, G257W+S295K, G257W+S295V, G257W+S295P, G257W+S295L, G257W+S295R, G257W+S295A, G257W+S295N, G257W+S295M, G257W+S295I, G257W+T296S, G257W+F298Y, G257E+W260F, G257E+Y262F, G257E+S266A, G257E+D268N, G257E+A270D, G257E+N272M, G257E+N272T, G257E+N273E, G257E+N273D, G257E+A276E, G257E+A276W, G257E+A276D, G257E+N279D, G257E+N279E, G257E+T280L, G257E+N283W, G257E+N283H, G257E+Y286W, G257E+Y286F, G257E+L288I, G257E+E290A, G257E+L294P, G257E+L294K, G257E+L294I, G257E+L294R, G257E+L294V, G257E+L294H, G257E+S295K, G257E+S295V, G257E+S295P, G257E+S295L, G257E+S295R, G257E+S295A, G257E+S295N, G257E+S295M, G257E+S295I, G257E+T296S, G257E+F298Y, G257A+W260F, G257A+Y262F, G257A+S266A, G257A+D268N, G257A+A270D, G257A+N272M, G257A+N272T, G257A+N273E, G257A+N273D, G257A+A276E, G257A+A276W, G257A+A276D, G257A+N279D, G257A+N279E, G257A+T280L, G257A+N283W, G257A+N283H, G257A+Y286W, G257A+Y286F, G257A+L288I, G257A+E290A, G257A+L294P, G257A+L294K, G257A+L294I, G257A+L294R, G257A+L294V, G257A+L294H, G257A+S295K, G257A+S295V, G257A+S295P, G257A+S295L, G257A+S295R, G257A+S295A, G257A+S295N, G257A+S295M, G257A+S295I, G257A+T296S, G257A+F298Y, W260F+Y262F, W260F+S266A, W260F+D268N, W260F+A270D, W260F+N272M, W260F+N272T, W260F+N273E, W260F+N273D, W260F+A276E, W260F+A276W, W260F+A276D, W260F+N279D, W260F+N279E, W260F+T280L, W260F+N283W, W260F+N283H, W260F+Y286W, W260F+Y286F, W260F+L288I, W260F+E290A, W260F+L294P, W260F+L294K, W260F+L294I, W260F+L294R, W260F+L294V, W260F+L294H, W260F+S295K, W260F+S295V, W260F+S295P, W260F+S295L, W260F+S295R, W260F+S295A, W260F+S295N, W260F+S295M, W260F+S295I, W260F+T296S, W260F+F298Y, Y262F+S266A, Y262F+D268N, Y262F+A270D, Y262F+N272M, Y262F+N272T, Y262F+N273E, Y262F+N273D, Y262F+A276E, Y262F+A276W, Y262F+A276D, Y262F+N279D, Y262F+N279E, Y262F+T280L, Y262F+N283W, Y262F+N283H, Y262F+Y286W, Y262F+Y286F, Y262F+L288I, Y262F+E290A, Y262F+L294P, Y262F+L294K, Y262F+L294I, Y262F+L294R, Y262F+L294V, Y262F+L294H, Y262F+S295K, Y262F+S295V, Y262F+S295P, Y262F+S295L, Y262F+S295R, Y262F+S295A, Y262F+S295N, Y262F+S295M, Y262F+S295I, Y262F+T296S, Y262F+F298Y, S266A+D268N, S266A+A270D, S266A+N272M, S266A+N272T, S266A+N273E, S266A+N273D, S266A+A276E, S266A+A276W, S266A+A276D, S266A+N279D, S266A+N279E, S266A+T280L, S266A+N283W, S266A+N283H, S266A+Y286W, S266A+Y286F, S266A+L288I, S266A+E290A, S266A+L294P, S266A+L294K, S266A+L294I, S266A+L294R, S266A+L294V, S266A+L294H, S266A+S295K, S266A+S295V, S266A+S295P, S266A+S295L, S266A+S295R, S266A+S295A, S266A+S295N, S266A+S295M, S266A+S295I, S266A+T296S, S266A+F298Y, D268N+A270D, D268N+N272M, D268N+N272T, D268N+N273E, D268N+N273D, D268N+A276E, D268N+A276W, D268N+A276D, D268N+N279D, D268N+N279E, D268N+T280L, D268N+N283W, D268N+N283H, D268N+Y286W, D268N+Y286F, D268N+L288I, D268N+E290A, D268N+L294P, D268N+L294K, D268N+L294I, D268N+L294R, D268N+L294V, D268N+L294H, D268N+S295K, D268N+S295V, D268N+S295P, D268N+S295L, D268N+S295R, D268N+S295A, D268N+S295N, D268N+S295M, D268N+S295I, D268N+T296S, D268N+F298Y, A270D+N272M, A270D+N272T, A270D+N273E, A270D+N273D, A270D+A276E, A270D+A276W, A270D+A276D, A270D+N279D, A270D+N279E, A270D+T280L, A270D+N283W, A270D+N283H, A270D+Y286W, A270D+Y286F, A270D+L288I, A270D+E290A, A270D+L294P, A270D+L294K, A270D+L294I, A270D+L294R, A270D+L294V, A270D+L294H, A270D+S295K, A270D+S295V, A270D+S295P, A270D+S295L, A270D+S295R, A270D+S295A, A270D+S295N, A270D+S295M, A270D+S295I, A270D+T296S, A270D+F298Y, N272M+N273E, N272M+N273D, N272M+A276E, N272M+A276W, N272M+A276D, N272M+N279D, N272M+N279E, N272M+T280L, N272M+N283W, N272M+N283H, N272M+Y286W, N272M+Y286F, N272M+L288I, N272M+E290A, N272M+L294P, N272M+L294K, N272M+L294I, N272M+L294R, N272M+L294V, N272M+L294H, N272M+S295K, N272M+S295V, N272M+S295P, N272M+S295L, N272M+S295R, N272M+S295A, N272M+S295N, N272M+S295M, N272M+S295I, N272M+T296S, N272M+F298Y, N272T+N273E, N272T+N273D, N272T+A276E, N272T+A276W,

N272T+A276D, N272T+N279D, N272T+N279E, N272T+ T280L, N272T+N283W, N272T+N283H, N272T+Y286W, N272T+Y286F, N272T+L288I, N272T+E290A, N272T+ L294P, N272T+L294K, N272T+L294I, N272T+L294R, N272T+L294V, N272T+L294H, N272T+S295K, N272T+ S295V, N272T+S295P, N272T+S295L, N272T+S295R, N272T+S295A, N272T+S295N, N272T+S295M, N272T+ S295I, N272T+T296S, N272T+F298Y, N273E+A276E, N273E+A276W, N273E+A276D, N273E+N279D, N273E+ N279E, N273E+T280L, N273E+N283W, N273E+N283H, N273E+Y286W, N273E+Y286F, N273E+L288I, N273E+ E290A, N273E+L294P, N273E+L294K, N273E+L294I, N273E+L294R, N273E+L294V, N273E+L294H, N273E+ S295K, N273E+S295V, N273E+S295P, N273E+S295L, N273E+S295R, N273E+S295A, N273E+S295N, N273E+ S295M, N273E+S295I, N273E+T296S, N273E+F298Y, N273D+A276E, N273D+A276W, N273D+A276D, N273D+N279D, N273D+N279E, N273D+T280L, N273D+ N283W, N273D+N283H, N273D+Y286W, N273D+Y286F, N273D+L288I, N273D+E290A, N273D+L294P, N273D+ L294K, N273D+L294I, N273D+L294R, N273D+L294V, N273D+L294H, N273D+S295K, N273D+S295V, N273D+ S295P, N273D+S295L, N273D+S295R, N273D+S295A, N273D+S295N, N273D+S295M, N273D+S295I, N273D+ T296S, N273D+F298Y, A276E+N279D, A276E+N279E, A276E+T280L, A276E+N283W, A276E+N283H, A276E+ Y286W, A276E+Y286F, A276E+L288I, A276E+E290A, A276E+L294P, A276E+L294K, A276E+L294I, A276E+ L294R, A276E+L294V, A276E+L294H, A276E+S295K, A276E+S295V, A276E+S295P, A276E+S295L, A276E+ S295R, A276E+S295A, A276E+S295N, A276E+S295M, A276E+S295I, A276E+T296S, A276E+F298Y, A276W+ N279D, A276W+N279E, A276W+T280L, A276W+ N283W, A276W+N283H, A276W+Y286W, A276W+ Y286F, A276W+L288I, A276W+E290A, A276W+L294P, A276W+L294K, A276W+L294I, A276W+L294R, A276W+L294V, A276W+L294H, A276W+S295K, A276W+S295V, A276W+S295P, A276W+S295L, A276W+ S295R, A276W+S295A, A276W+S295N, A276W+S295M, A276W+S295I, A276W+T296S, A276W+F298Y, A276D+ N279D, A276D+N279E, A276D+T280L, A276D+N283W, A276D+N283H, A276D+Y286W, A276D+Y286F, A276D+ L288I, A276D+E290A, A276D+L294P, A276D+L294K, A276D+L294I, A276D+L294R, A276D+L294V, A276D+ L294H, A276D+S295K, A276D+S295V, A276D+S295P, A276D+S295L, A276D+S295R, A276D+S295A, A276D+ S295N, A276D+S295M, A276D+S295I, A276D+T296S, A276D+F298Y, N279D+T280L, N279D+N283W, N279D+ N283H, N279D+Y286W, N279D+Y286F, N279D+L288I, N279D+E290A, N279D+L294P, N279D+L294K, N279D+ L294I, N279D+L294R, N279D+L294V, N279D+L294H, N279D+S295K, N279D+S295V, N279D+S295P, N279D+ S295L, N279D+S295R, N279D+S295A, N279D+S295N, N279D+S295M, N279D+S295I, N279D+T296S, N279D+ F298Y, N279E+T280L, N279E+N283W, N279E+N283H, N279E+Y286W, N279E+Y286F, N279E+L288I, N279E+ E290A, N279E+L294P, N279E+L294K, N279E+L294I, N279E+L294R, N279E+L294V, N279E+L294H, N279E+ S295K, N279E+S295V, N279E+S295P, N279E+S295L, N279E+S295R, N279E+S295A, N279E+S295N, N279E+ S295M, N279E+S295I, N279E+T296S, N279E+F298Y, T280L+N283W, T280L+N283H, T280L+Y286W, T280L+ Y286F, T280L+L288I, T280L+E290A, T280L+L294P, T280L+L294K, T280L+L294I, T280L+L294R, T280L+ L294V, T280L+L294H, T280L+S295K, T280L+S295V, T280L+S295P, T280L+S295L, T280L+S295R, T280L+ S295A, T280L+S295N, T280L+S295M, T280L+S295I, T280L+T296S, T280L+F298Y, N283W+Y286W, N283W+ Y286F, N283W+L288I, N283W+E290A, N283W+L294P, N283W+L294K, N283W+L294I, N283W+L294R, N283W+L294V, N283W+L294H, N283W+S295K, N283W+S295V, N283W+S295P, N283W+S295L, N283W+S295R, N283W+S295A, N283W+S295N, N283W+S295M, N283W+S295I, N283W+T296S, N283W+F298Y, N283H+Y286W, N283H+Y286F, N283H+ L288I, N283H+E290A, N283H+L294P, N283H+L294K, N283H+L294I, N283H+L294R, N283H+L294V, N283H+ L294H, N283H+S295K, N283H+S295V, N283H+S295P, N283H+S295L, N283H+S295R, N283H+S295A, N283H+ S295N, N283H+S295M, N283H+S295I, N283H+T296S, Y286W+L288I, Y286W+E290A, Y286W+L294P, Y286W+ L294K, Y286W+L294I, Y286W+L294R, Y286W+L294V, Y286W+L294H, Y286W+S295K, Y286W+S295V, Y286W+S295P, Y286W+S295L, Y286W+S295R, Y286W+ S295A, Y286W+S295N, Y286W+S295M, Y286W+S295I, Y286W+T296S, Y286W+F298Y, Y286F+L288I, Y286F+ E290A, Y286F+L294P, Y286F+L294K, Y286F+L294I, Y286F+L294R, Y286F+L294V, Y286F+L294H, Y286F+ S295K, Y286F+S295V, Y286F+S295P, Y286F+S295L, Y286F+S295R, Y286F+S295A, Y286F+S295N, Y286F+ S295M, Y286F+S295I, Y286F+T296S, Y286F+F298Y, L288I+E290A, L288I+L294P, L288I+L294K, L288I+ L294I, L288I+L294R, L288I+L294V, L288I+L294H, L288I+S295K, L288I+S295V, L288I+S295P, L288I+ S295L, L288I+S295R, L288I+S295A, L288I+S295N, L288I+S295M, L288I+S295I, L288I+T296S, L288I+ F298Y, E290A+L294P, E290A+L294K, E290A+L294I, E290A+L294R, E290A+L294V, E290A+L294H, E290A+ S295K, E290A+S295V, E290A+S295P, E290A+S295L, E290A+S295R, E290A+S295A, E290A+S295N, E290A+ S295M, E290A+S295I, E290A+T296S, E290A+F298Y, L294P+S295K, L294P+S295V, L294P+S295P, L294P+ S295L, L294P+S295R, L294P+S295A, L294P+S295N, L294P+S295M, L294P+S295I, L294P+T296S, L294P+ F298Y, L294K+S295K, L294K+S295V, L294K+S295P, L294K+S295L, L294K+S295R, L294K+S295A, L294K+ S295N, L294K+S295M, L294K+S295I, L294K+T296S, L294K+F298Y, L294I+S295K, L294I+S295V, L294I+ S295P, L294I+S295L, L294I+S295R, L294I+S295A, L294I+S295N, L294I+S295M, L294I+S295I, L294I+ T296S, L294I+F298Y, L294R+S295K, L294R+S295V, L294R+S295P, L294R+S295L, L294R+S295R, L294R+ S295A, L294R+S295N, L294R+S295M, L294R+S295I, L294R+T296S, L294R+F298Y, L294V+S295K, L294V+ S295V, L294V+S295P, L294V+S295L, L294V+S295R, L294V+S295A, L294V+S295N, L294V+S295M, L294V+ S295I, L294V+T296S, L294V+F298Y, L294H+S295K, L294H+S295V, L294H+S295P, L294H+S295L, L294H+ S295R, L294H+S295A, L294H+S295N, L294H+S295M, L294H+S295I, L294H+T296S, L294H+F298Y, S295K+ T296S, S295K+F298Y, S295V+T296S, S295V+F298Y, S295P+T296S, S295P+F298Y, S295L+T296S, S295L+ F298Y, S295R+T296S, S295R+F298Y, S295A+T296S, S295A+F298Y, S295N+T296S, S295N+F298Y, S295M+ T296S, S295M+F298Y, S295I+T296S, S295I+F298Y, and T296S+F298Y.

In one specific embodiment, the first mannanase is a variant (b) as defined above comprising at least two substitutions selected from the group consisting of: S3P, T37P, G47A, G47S, E77T, V82I, V82R, A83P, Y93Q, Y93C, Y93A, Y93F, Y93I, Y93R, S98P, K116R, D135P, A136P, S241C, G257W, G257E, G257L, G257A, G257S, G257Y, G257F and P258Q.

In one embodiment, when the first mannanase is a variant (a) it comprises a substitution in the position corresponding to position 260 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is W260F.

In another embodiment, when the first mannanase is a variant (a) it comprises a substitution in the position corresponding to position 288 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is L288I.

In another embodiment, when the first mannanase is a variant (a) it comprises a substitution in the position corresponding to position 294 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of L294P, L294K, L294I, L294R, L294V, and L294H.

In another embodiment, when the first mannanase is a variant (a) it comprises a substitution in the position corresponding to position 295 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of S295K, S295V, S295P, S295L, S295R, S295A, S295N, S295M, and S295I.

In one embodiment, when the first mannanase is a variant (a) the second substitution is in the position corresponding to position 1 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of A1G and A1V.

In another embodiment, when the first mannanase is a variant (a) the second substitution is in the position corresponding to position 2 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is N2E.

In another embodiment, when the first mannanase is a variant (a) the second substitution is in the position corresponding to position 3 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is S3P.

In another embodiment, when the first mannanase is a variant (a) the second substitution is in the position corresponding to position 4 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is G4D.

In another embodiment, when the first mannanase is a variant (a) the second substitution is in the position corresponding to position 5 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is F5H.

In another embodiment, when the first mannanase is a variant (a) the second substitution is in the position corresponding to position 6 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of Y6H, Y6M, Y6F, Y6W, and Y6H.

In another embodiment, when the first mannanase is a variant (a) the second substitution is in the position corresponding to position 8 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of S8T, S8P, and S8R.

In another embodiment, when the first mannanase is a variant (a) the second substitution is in the position corresponding to position 11 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of T11K, and T11R.

In another embodiment, when the first mannanase is a variant (a) the second substitution is in the position corresponding to position 13 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is Y13F.

In another embodiment, when the first mannanase is a variant (a) the second substitution is in the position corresponding to position 14 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of D14S and D14K.

In another embodiment, when the first mannanase is a variant (a) the second substitution is in the position corresponding to position 18 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of N18V and N18R.

In another embodiment, when the first mannanase is a variant (a) the second substitution is in the position corresponding to position 30 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is A30T.

In another embodiment, when the first mannanase is a variant (a) the second substitution is in the position corresponding to position 32 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of Y32F and Y32W.

In another embodiment, when the first mannanase is a variant (a) the second substitution is in the position corresponding to position 33 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is K33Q.

In another embodiment, when the first mannanase is a variant (a) the second substitution is in the position corresponding to position 34 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is D34G.

In another embodiment, when the first mannanase is a variant (a) the second substitution is in the position corresponding to position 35 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is Q35L.

In another embodiment, when the first mannanase is a variant (a) the second substitution is in the position corresponding to position 37 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is T37P.

In another embodiment, when the first mannanase is a variant (a) the second substitution is in the position corresponding to position 41 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of E41V and E41N.

In another embodiment, when the first mannanase is a variant (a) the second substitution is in the position corresponding to position 45 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is N45G.

In another embodiment, when the first mannanase is a variant (a) the second substitution is in the position corresponding to position 47 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of G47S and G47A.

In another embodiment, when the first mannanase is a variant (a) the second substitution is in the position corresponding to position 57 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is D57N.

In another embodiment, when the first mannanase is a variant (a) the second substitution is in the position corresponding to position 59 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is G59Q.

In another embodiment, when the first mannanase is a variant (a) the second substitution is in the position corresponding to position 60 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is Q60R.

In another embodiment, when the first mannanase is a variant (a) the second substitution is in the position corresponding to position 63 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of K63R and K63Q.

In another embodiment, when the first mannanase is a variant (a) the second substitution is in the position corresponding to position 65 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is D65E.

In another embodiment, when the first mannanase is a variant (a) the second substitution is in the position corresponding to position 70 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is R70K.

In another embodiment, when the first mannanase is a variant (a) the second substitution is in the position corresponding to position 71 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is N71S.

In another embodiment, when the first mannanase is a variant (a) the second substitution is in the position corresponding to position 74 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is S74K.

In another embodiment, when the first mannanase is a variant (a) the second substitution is in the position corresponding to position 77 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of E77T and E77N.

In another embodiment, when the first mannanase is a variant (a) the second substitution is in the position corresponding to position 78 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is D78G.

In another embodiment, when the first mannanase is a variant (a) the second substitution is in the position corresponding to position 80 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is H80K.

In another embodiment, when the first mannanase is a variant (a) the second substitution is in the position corresponding to position 82 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of V82R, V82I and V82S.

In another embodiment, when the first mannanase is a variant (a) the second substitution is in the position corresponding to position 83 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of A83P and A83S.

In another embodiment, when the first mannanase is a variant (a) the second substitution is in the position corresponding to position 93 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of Y93Q and Y93A.

In another embodiment, when the first mannanase is a variant (a) the second substitution is in the position corresponding to position 95 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is S95D.

In another embodiment, when the first mannanase is a variant (a) the second substitution is in the position corresponding to position 97 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is A97R.

In another embodiment, when the first mannanase is a variant (a) the second substitution is in the position corresponding to position 98 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is S98D.

In another embodiment, when the first mannanase is a variant (a) the second substitution is in the position corresponding to position 100 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is N100Y.

In another embodiment, when the first mannanase is a variant (a) the second substitution is in the position corresponding to position 104 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of D104A and D104G.

In another embodiment, when the first mannanase is a variant (a) the second substitution is in the position corresponding to position 108 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is E108S.

In another embodiment, when the first mannanase is a variant (a) the second substitution is in the position corresponding to position 111 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of S111A, S111K, and S111R.

In another embodiment, when the first mannanase is a variant (a) the second substitution is in the position corresponding to position 114 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of I114Q, I114M, and I114W.

In another embodiment, when the first mannanase is a variant (a) the second substitution is in the position corresponding to position 116 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is K116R.

In another embodiment, when the first mannanase is a variant (a) the second substitution is in the position corresponding to position 118 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is D118K.

In another embodiment, when the first mannanase is a variant (a) the second substitution is in the position corresponding to position 119 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is T119R.

In another embodiment, when the first mannanase is a variant (a) the second substitution is in the position corresponding to position 131 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is S131T.

In another embodiment, when the first mannanase is a variant (a) the second substitution is in the position corresponding to position 133 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of E133R and E133Q.

In another embodiment, when the first mannanase is a variant (a) the second substitution is in the position corresponding to position 135 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is D135P.

In another embodiment, when the first mannanase is a variant (a) the second substitution is in the position corresponding to position 136 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is A136P.

In another embodiment, when the first mannanase is a variant (a) the second substitution is in the position corresponding to position 139 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of D139R and D139A.

In another embodiment, when the first mannanase is a variant (a) the second substitution is in the position corresponding to position 142 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of K142R, K142M, K142S, and K142V.

In another embodiment, when the first mannanase is a variant (a) the second substitution is in the position corresponding to position 143 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is Q143R.

In another embodiment, when the first mannanase is a variant (a) the second substitution is in the position corresponding to position 150 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of N150R, N150T, and N150S.

In another embodiment, when the first mannanase is a variant (a) the second substitution is in the position corresponding to position 169 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of Q169A, Q169R, and Q169K.

In another embodiment, when the first mannanase is a variant (a) the second substitution is in the position corresponding to position 172 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is H172R.

In another embodiment, when the first mannanase is a variant (a) the second substitution is in the position corresponding to position 174 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of Y174R, Y174L, Y174W, and Y174F.

In another embodiment, when the first mannanase is a variant (a) the second substitution is in the position corresponding to position 176 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is R176Q.

In another embodiment, when the first mannanase is a variant (a) the second substitution is in the position corresponding to position 177 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of E177S and E177Y.

In another embodiment, when the first mannanase is a variant (a) the second substitution is in the position corresponding to position 180 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is N180R.

In another embodiment, when the first mannanase is a variant (a) the second substitution is in the position corresponding to position 183 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of P183T and P183G.

In another embodiment, when the first mannanase is a variant (a) the second substitution is in the position corresponding to position 184 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of Q184E and Q184K.

In another embodiment, when the first mannanase is a variant (a) the second substitution is in the position corresponding to position 185 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is R185G.

In another embodiment, when the first mannanase is a variant (a) the second substitution is in the position corresponding to position 196 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of Y196W or Y196F.

In another embodiment, when the first mannanase is a variant (a) the second substitution is in the position corresponding to position 200 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is N200T.

In another embodiment, when the first mannanase is a variant (a) the second substitution is in the position corresponding to position 202 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is S202R.

In another embodiment, when the first mannanase is a variant (a) the second substitution is in the position corresponding to position 203 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is Q203T.

In another embodiment, when the first mannanase is a variant (a) the second substitution is in the position corresponding to position 205 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is R205K.

In another embodiment, when the first mannanase is a variant (a) the second substitution is in the position corresponding to position 210 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of R210M, R210G, and R210L.

In another embodiment, when the first mannanase is a variant (a) the second substitution is in the position corresponding to position 213 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of N213V and N213D.

In another embodiment, when the first mannanase is a variant (a) the second substitution is in the position corresponding to position 228 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is T228S.

In another embodiment, when the first mannanase is a variant (a) the second substitution is in the position corresponding to position 229 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is N229D.

In another embodiment, when the first mannanase is a variant (a) the second substitution is in the position corresponding to position 234 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of E234F and E234Y.

In another embodiment, when the first mannanase is a variant (a) the second substitution is in the position corresponding to position 235 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of A235R and A235K.

In another embodiment, when the first mannanase is a variant (a) the second substitution is in the position corresponding to position 241 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is S241C.

In another embodiment, when the first mannanase is a variant (a) the second substitution is in the position corresponding to position 243 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of Q243E and Q243K.

In another embodiment, when the first mannanase is a variant (a) the second substitution is in the position corresponding to position 244 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of R244K and R244V.

In another embodiment, when the first mannanase is a variant (a) the second substitution is in the position corresponding to position 250 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is A250G.

In another embodiment, when the first mannanase is a variant (a) the second substitution is in the position corresponding to position 254 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is K254Y.

In another embodiment, when the first mannanase is a variant (a) the second substitution is in the position corresponding to position 257 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of G257W, G257E, G257A, and G257G.

In another embodiment, when the first mannanase is a variant (a) the second substitution is in the position corresponding to position 260 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is W260F.

In another embodiment, when the first mannanase is a variant (a) the second substitution is in the position corresponding to position 262 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is Y262F.

In another embodiment, when the first mannanase is a variant (a) the second substitution is in the position corresponding to position 266 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is S266A.

In another embodiment, when the first mannanase is a variant (a) the second substitution is in the position corresponding to position 268 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is D268N.

In another embodiment, when the first mannanase is a variant (a) the second substitution is in the position corresponding to position 270 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is A270D.

In another embodiment, when the first mannanase is a variant (a) the second substitution is in the position corresponding to position 272 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of N272M and N272T.

In another embodiment, when the first mannanase is a variant (a) the second substitution is in the position corresponding to position 273 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of N273E and N273D.

In another embodiment, when the first mannanase is a variant (a) the second substitution is in the position corresponding to position 276 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of A276E, A276D, and A276W.

In another embodiment, when the first mannanase is a variant (a) the second substitution is in the position corresponding to position 279 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of N279D and N279E.

In another embodiment, when the first mannanase is a variant (a) the second substitution is in the position corresponding to position 280 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is T280L.

In another embodiment, when the first mannanase is a variant (a) the second substitution is in the position corresponding to position 283 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of N283H and N283W.

In another embodiment, when the first mannanase is a variant (a) the second substitution is in the position corresponding to position 286 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of Y286W and Y286F.

In another embodiment, when the first mannanase is a variant (a) the second substitution is in the position corresponding to position 288 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is L288I.

In another embodiment, when the first mannanase is a variant (a) the second substitution is in the position corresponding to position 290 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is E290A.

In another embodiment, when the first mannanase is a variant (a) the second substitution is in the position corresponding to position 294 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of L294R, L294V, L294P, L294H, L294K, and L294I.

In another embodiment, when the first mannanase is a variant (a) the second substitution is in the position corresponding to position 295 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is selected from the group of S295I, S295K, S295A, S295M, S295N, S295V, S295P, S295L, and S295R.

In another embodiment, when the first mannanase is a variant (a) the second substitution is in the position corresponding to position 296 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is T296S.

In another embodiment, when the first mannanase is a variant (a) the second substitution is in the position corresponding to position 298 of the polypeptide of SEQ ID NO: 2, or of a polypeptide having at least 59%, at least 60%, at least 61%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2 which has mannanase activity, wherein the variant has improved stability compared to the mannanase of SEQ ID NO: 2. In one embodiment, the substitution is F298Y.

In one aspect, the first mannanase is a variant (a) comprising substitutions in two or more positions selected from positions 260, 288, 294 and 295 compared to SEQ ID NO: 2, for example in three or all four of these positions.

Thus, in one embodiment, the first mannanase is a variant (a) comprising substitutions in positions 260 and 288. In another embodiment, the first mannanase is a variant (a) comprising substitutions in positions 260 and 294. In another embodiment, the first mannanase is a variant (a) comprising substitutions in positions 260 and 295. In another embodiment, the first mannanase is a variant (a) comprising substitutions in positions 288 and 294. In another embodiment, the first mannanase is a variant (a) comprising substitutions in positions 288 and 295. In another embodiment, the first mannanase is a variant (a) comprising substitutions in positions 294 and 295. In another embodiment, the first mannanase is a variant (a) comprising substitutions in positions 260, 288 and 294. In another embodiment, the first mannanase is a variant (a) comprising substitutions in positions 260, 288 and 295. In another embodiment, the first mannanase is a variant (a) comprising substitutions in positions 260, 294 and 295. In another embodiment, the first mannanase is a variant (a) comprising substitutions in positions 288, 294 and 295. In another embodiment, the first mannanase is a variant (a) comprising substitutions in each of positions 260, 288, 294 and 295.

When the variant includes a substitution in position 260, one preferred substitution is W260F.

When the variant includes a substitution in position 288, one preferred substitution is L288I.

When the variant includes a substitution in position 294, one preferred substitution is L294P.

When the variant includes a substitution in position 295, one preferred substitution is S295V.

In one embodiment, the first mannanase is a variant comprising a second substitution in one or both of positions 93 and 136 of the polypeptide of SEQ ID NO: 2. For example, the variant may comprise a second substitution in one or both of positions 93 and 136 and a first substitution in two or more of positions 260, 288, 294 and 295, for example in three or all four of positions 260, 288 294 and 295.

When the variant includes a substitution in position 93, one preferred substitution is Y93Q.

When the variant includes a substitution in position 136, one preferred substitution is A136P.

In a particular embodiment, the first mannanase is a variant comprising the substitutions A30T, Y93Q, S95D, D118K, A136P, D139R, N200T, S202R, R210G, W260F, N283H, L288I, L294P and S295V, e.g. wherein the parent is the polypeptide of SEQ ID NO: 2. In a further embodiment, the variant and/or the parent has at least 59% sequence identity to SEQ ID NO: 2.

In another particular embodiment, the first mannanase is a variant comprising the substitutions A30T, Y93Q, S95D, D118K, A136P, D139R, S202R, R210G, W260F, A276E, L288I, L294P and S295V, e.g. wherein the parent is the polypeptide of SEQ ID NO: 2. In a further embodiment, the variant and/or the parent has at least 59% sequence identity to SEQ ID NO: 2.

In a further particular embodiment, the first mannanase is a variant comprising the substitutions A30T, Y93Q, S95D, D118K, A136P, D139R, S202R, R210G, W260F, A276D, L288I, L294P and S295V, e.g. wherein the parent is the polypeptide of SEQ ID NO: 2. In a further embodiment, the variant and/or the parent has at least 59% sequence identity to SEQ ID NO: 2.

In a still further particular embodiment, the first mannanase is a variant comprising the substitutions S8T, A30T, Y93Q, S95D, D118K, A136P, D139R, N150T, S202R, R210G, Q243K, W260F, A276D, L288I, L294P and S295V, e.g. wherein the parent is the polypeptide of SEQ ID NO: 2. In a further embodiment, the variant and/or the parent has at least 59% sequence identity to SEQ ID NO: 2.

In a particular embodiment, the first mannanase is a variant comprising the substitutions A30T, Y93Q, S95D, D118K, D139R, N200T, S202R, R210G, W260F, N283H, L288I, L294P and S295V, e.g. wherein the parent is the polypeptide of SEQ ID NO: 2. In a further embodiment, the variant and/or the parent has at least 59% sequence identity to SEQ ID NO: 2.

In another particular embodiment, the first mannanase is a variant comprising the substitutions A30T, Y93Q, S95D, D118K, D139R, S202R, R210G, W260F, A276E, L288I, L294P and S295V, e.g. wherein the parent is the polypeptide of SEQ ID NO: 2. In a further embodiment, the variant and/or the parent has at least 59% sequence identity to SEQ ID NO: 2.

In a further particular embodiment, the first mannanase is a variant comprising the substitutions A30T, Y93Q, S95D, D118K, D139R, S202R, R210G, W260F, A276D, L288I, L294P and S295V, e.g. wherein the parent is the polypeptide of SEQ ID NO: 2. In a further embodiment, the variant and/or the parent has at least 59% sequence identity to SEQ ID NO: 2.

In a still further particular embodiment, the first mannanase is a variant comprising the substitutions S8T, A30T, Y93Q, S95D, D118K, D139R, N150T, S202R, R210G, Q243K, W260F, A276D, L288I, L294P and S295V, e.g. wherein the parent is the polypeptide of SEQ ID NO: 2. In a further embodiment, the variant and/or the parent has at least 59% sequence identity to SEQ ID NO: 2.

A first mannanase which is a variant preferably has improved stability compared to its parent, for example improved in-detergent stability, chemical stability, oxidation stability, pH stability, stability under storage conditions, substrate stability and/or thermostability. The improved stability may in particular be improved in-detergent stability, thermostability and/or storage stability.

The stability, such as the in-detergent stability or thermostability, may be evaluated by AMSA, i.e. as wash performance after storage in a detergent, or after storage under elevated temperature such as 50° C., as described in Example 7. The stability may, for example, be determined at a pH in the range of from about 9.0 to about 11.0. Thus, in one embodiment, the first mannanase of the present invention has an improved stability compared to its parent when measured at pH 9.0, 10.5 and/or 10.8.

Stability may alternatively be measured at either more alkaline or more acidic pH. The pH that stability is measured at may vary depending on the detergent composition in which the first mannanase is to be used.

Parent Mannanase of the First Mannanase

When the first mannanase of the invention is a variant of a parent mannanase, the parent mannanase may be any glycoside hydrolase family 5 (GH5) mannanase.

In one aspect, the parent mannanase of the first mannanase is a mannanase having at least 59%, e.g. at least 60%, at least 61%, at least 62%, at least 63%, at least 65%, at least 70%, at least 75%, at least 80%, at least 85%, at least 90%, at least 95%, at least 96%, at least 97%, at least 98%, at least 99%, or 100% sequence identity to the polypeptide of SEQ ID NO: 1 or SEQ ID NO: 2.

In one embodiment, the parent mannanase is a polypeptide having a sequence identity to the polypeptide of SEQ ID NO: 1 of at least 59%, e.g. at least 60%, at least 61%, at least 62%, at least 63%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and which has mannanase activity. The amino acid sequence of the parent mannanase may for example differ by up to 20 amino acids, e.g., 1, 2, 3, 4, 5, 6, 7, 8, 9, 10, 11, 12, 13, 14, 15, 16, 17, 18, 19, or 20 amino acids, from the polypeptide of SEQ ID NO: 1.

In another embodiment, the parent mannanase is a polypeptide having a sequence identity to the polypeptide of SEQ ID NO: 2 of at least 59%, e.g. at least 60%, at least 61%, at least 62%, at least 63%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and which has mannanase activity. The amino acid sequence of the parent mannanase may for example differ by up to 20 amino acids, e.g., 1, 2, 3, 4, 5, 6, 7, 8, 9, 10, 11, 12, 13, 14, 15, 16, 17, 18, 19, or 20 from the polypeptide of SEQ ID NO: 2.

In another embodiment, the parent comprises or consists of the amino acid sequence of SEQ ID NO: 2. In another embodiment, the parent comprises or consists of the mature polypeptide of SEQ ID NO: 1.

In another embodiment, the parent is a fragment of the polypeptide of SEQ ID NO: 2 containing at least 250 amino acid residues, e.g., at least 270 and at least 290 amino acid residues.

In one aspect, the parent mannanase of the first mannanase is a mannanase having at least 59%, e.g. at least 60%, at least 61%, at least 62%, at least 63%, at least 65%, at least 70%, at least 75%, at least 80%, at least 85%, at least 90%, at least 95%, at least 96%, at least 97%, at least 98%, at least 99%, or 100% sequence identity to the polypeptide of SEQ ID NO: 19.

In one embodiment, the parent mannanase is a polypeptide having a sequence identity to the polypeptide of SEQ ID NO: 19 of at least 59%, e.g. at least 60%, at least 61%, at least 62%, at least 63%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and which has mannanase activity. The amino acid sequence of the parent mannanase may for example differ by up to 20 amino acids, e.g., 1, 2, 3, 4, 5, 6, 7, 8, 9, 10, 11, 12, 13, 14, 15, 16, 17, 18, 19, or 20 amino acids, from the polypeptide of SEQ ID NO: 19.

In another embodiment, the parent mannanase is a polypeptide having a sequence identity to the polypeptide of SEQ ID NO: 19 of at least 59%, e.g. at least 60%, at least 61%, at least 62%, at least 63%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and which has mannanase activity. The amino acid sequence of the parent mannanase may for example differ by up to 20 amino acids, e.g., 1, 2, 3, 4, 5, 6, 7, 8, 9, 10, 11, 12, 13, 14, 15, 16, 17, 18, 19, or 20 from the polypeptide of SEQ ID NO: 19.

In another embodiment, the parent comprises or consists of the amino acid sequence of SEQ ID NO: 19.

In another embodiment, the parent is a fragment of the polypeptide of SEQ ID NO: 19 containing at least 250 amino acid residues, e.g., at least 270 and at least 290 amino acid residues.

In one aspect, the parent mannanase of the first mannanase is a mannanase having at least 59%, e.g. at least 60%, at least 61%, at least 62%, at least 63%, at least 65%, at least 70%, at least 75%, at least 80%, at least 85%, at least 90%, at least 95%, at least 96%, at least 97%, at least 98%, at least 99%, or 100% sequence identity to the polypeptide of SEQ ID NO: 20.

In one embodiment, the parent mannanase is a polypeptide having a sequence identity to the polypeptide of SEQ ID NO: 20 of at least 59%, e.g. at least 60%, at least 61%, at least 62%, at least 63%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and which has mannanase activity. The amino acid sequence of the parent mannanase may for example differ by up to 20 amino acids, e.g., 1, 2, 3, 4, 5, 6, 7, 8, 9, 10, 11, 12, 13, 14, 15, 16, 17, 18, 19, or 20 amino acids, from the polypeptide of SEQ ID NO: 20.

In another embodiment, the parent mannanase is a polypeptide having a sequence identity to the polypeptide of SEQ ID NO: 20 of at least 59%, e.g. at least 60%, at least 61%, at least 62%, at least 63%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and which has mannanase activity. The amino acid sequence of the parent mannanase may for example differ by up to 20 amino acids, e.g., 1, 2, 3, 4, 5, 6, 7, 8, 9, 10, 11, 12, 13, 14, 15, 16, 17, 18, 19, or 20 from the polypeptide of SEQ ID NO: 20.

In another embodiment, the parent comprises or consists of the amino acid sequence of SEQ ID NO: 20.

In another embodiment, the parent is a fragment of the polypeptide of SEQ ID NO: 20 containing at least 250 amino acid residues, e.g., at least 270 and at least 290 amino acid residues.

The parent mannanase may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. The parent may be secreted extracellularly.

The parent mannanase may be a bacterial mannanase. For example, the parent may be a Gram-positive bacterial polypeptide such as a *Bacillus, Clostridium, Enterococcus, Geobacillus, Lactobacillus, Lactococcus, Oceanobacillus, Staphylococcus, Streptococcus*, or *Streptomyces* mannanase, or a Gram-negative bacterial polypeptide such as a *Campy-* lobacter, *E. coli*, *Flavobacterium*, *Fusobacterium*, *Helicobacter*, *Ilyobacter*, *Neisseria*, *Pseudomonas*, *Salmonella*, or *Ureaplasma* mannanase.

In one aspect, the parent is a *Bacillus alkalophilus*, *Bacillus amyloliquefaciens*, *Bacillus bogoriensis*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, or *Bacillus thuringiensis* mannanase.

In another aspect, the parent is a *Streptococcus equisimilis*, *Streptococcus pyogenes*, *Streptococcus uberis*, or *Streptococcus equi* subsp. *Zooepidemicus* mannanase.

In another aspect, the parent is a *Streptomyces achromogenes*, *Streptomyces avermitilis*, *Streptomyces coelicolor*, *Streptomyces griseus*, or *Streptomyces lividans* mannanase.

In another aspect, the parent is a *Bacillus bogoriensis* mannanase.

In another aspect, the parent is a *Paenibacillus* sp. mannanase.

Second Mannanase

As noted above, the second mannanase in compositions of the present invention is a glycoside hydrolase family 26 (GH26) mannanase or a variant or fragment thereof having mannanase activity.

In one aspect, the second mannanase is selected from the group consisting of:

(a) a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 3;

(b) a variant of the polypeptide in (a), wherein the variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28 or 29 positions compared to SEQ ID NO: 3;

(c) a polypeptide comprising the polypeptide of (a) or (b) and an N-terminal and/or C-terminal His-tag and/or HQ-tag;

(d) a polypeptide comprising the polypeptide of (a) or (b) and an N-terminal and/or C-terminal extension of up to 10 amino acids, e.g. 1, 2, 3, 4, 5, 6, 7, 8, 9 or 10 amino acids; and (e) a fragment of the polypeptide of (a) or (b) having mannanase activity and having at least 90% of the length of the mature polypeptide of SEQ ID NO: 3.

In another aspect, the second mannanase is selected from the group consisting of:

(a) a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 4;

(b) a variant of the polypeptide in (a), wherein the variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28 or 29 positions compared to SEQ ID NO: 4;

(c) a polypeptide comprising the polypeptide of (a) or (b) and an N-terminal and/or C-terminal His-tag and/or HQ-tag;

(d) a polypeptide comprising the polypeptide of (a) or (b) and an N-terminal and/or C-terminal extension of up to 10 amino acids, e.g. 1, 2, 3, 4, 5, 6, 7, 8, 9 or 10 amino acids; and (e) a fragment of the polypeptide of (a) or (b) having mannanase activity and having at least 90% of the length of the mature polypeptide of SEQ ID NO: 4.

In a further aspect, the second mannanase is selected from the group consisting of:

(a) a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 5;

(b) a variant of the polypeptide in (a), wherein the variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28 or 29 positions compared to SEQ ID NO: 5;

(c) a polypeptide comprising the polypeptide of (a) or (b) and an N-terminal and/or C-terminal His-tag and/or HQ-tag;

(d) a polypeptide comprising the polypeptide of (a) or (b) and an N-terminal and/or C-terminal extension of up to 10 amino acids, e.g. 1, 2, 3, 4, 5, 6, 7, 8, 9 or 10 amino acids; and (e) a fragment of the polypeptide of (a) or (b) having mannanase activity and having at least 90% of the length of the mature polypeptide of SEQ ID NO: 5.

In a further aspect, the second mannanase is selected from the group consisting of:

(a) a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 6;

(b) a variant of the polypeptide in (a), wherein the variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28 or 29 positions compared to SEQ ID NO: 6;

(c) a polypeptide comprising the polypeptide of (a) or (b) and an N-terminal and/or C-terminal His-tag and/or HQ-tag;

(d) a polypeptide comprising the polypeptide of (a) or (b) and an N-terminal and/or C-terminal extension of up to 10 amino acids, e.g. 1, 2, 3, 4, 5, 6, 7, 8, 9 or 10 amino acids; and (e) a fragment of the polypeptide of (a) or (b) having mannanase activity and having at least 90% of the length of the mature polypeptide of SEQ ID NO: 6.

In a further aspect, the second mannanase is selected from the group consisting of:

(a) a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 7;

(b) a variant of the polypeptide in (a), wherein the variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28 or 29 positions compared to SEQ ID NO: 7;

(c) a polypeptide comprising the polypeptide of (a) or (b) and an N-terminal and/or C-terminal His-tag and/or HQ-tag;

(d) a polypeptide comprising the polypeptide of (a) or (b) and an N-terminal and/or C-terminal extension of up to 10 amino acids, e.g. 1, 2, 3, 4, 5, 6, 7, 8, 9 or 10 amino acids; and (e) a fragment of the polypeptide of (a) or (b) having mannanase activity and having at least 90% of the length of the mature polypeptide of SEQ ID NO: 7.

In a further aspect, the second mannanase is selected from the group consisting of:

(a) a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 8;

(b) a variant of the polypeptide in (a), wherein the variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28 or 29 positions compared to SEQ ID NO: 8;

(c) a polypeptide comprising the polypeptide of (a) or (b) and an N-terminal and/or C-terminal His-tag and/or HQ-tag;

(d) a polypeptide comprising the polypeptide of (a) or (b) and an N-terminal and/or C-terminal extension of up to 10 amino acids, e.g. 1, 2, 3, 4, 5, 6, 7, 8, 9 or 10 amino acids; and (e) a fragment of the polypeptide of (a) or (b) having mannanase activity and having at least 90% of the length of the mature polypeptide of SEQ ID NO: 8.

In a further aspect, the second mannanase is selected from the group consisting of:

(a) a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 9;

(b) a variant of the polypeptide in (a), wherein the variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28 or 29 positions compared to SEQ ID NO: 9;

(c) a polypeptide comprising the polypeptide of (a) or (b) and an N-terminal and/or C-terminal His-tag and/or HQ-tag;

(d) a polypeptide comprising the polypeptide of (a) or (b) and an N-terminal and/or C-terminal extension of up to 10 amino acids, e.g. 1, 2, 3, 4, 5, 6, 7, 8, 9 or 10 amino acids; and (e) a fragment of the polypeptide of (a) or (b) having mannanase activity and having at least 90% of the length of the mature polypeptide of SEQ ID NO: 9.

In a further aspect, the second mannanase is selected from the group consisting of:

(a) a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 10;

(b) a variant of the polypeptide in (a), wherein the variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28 or 29 positions compared to SEQ ID NO: 10;

(c) a polypeptide comprising the polypeptide of (a) or (b) and an N-terminal and/or C-terminal His-tag and/or HQ-tag;

(d) a polypeptide comprising the polypeptide of (a) or (b) and an N-terminal and/or C-terminal extension of up to 10 amino acids, e.g. 1, 2, 3, 4, 5, 6, 7, 8, 9 or 10 amino acids; and (e) a fragment of the polypeptide of (a) or (b) having mannanase activity and having at least 90% of the length of the mature polypeptide of SEQ ID NO: 10.

In a further aspect, the second mannanase is selected from the group consisting of:

(a) a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 11;

(b) a variant of the polypeptide in (a), wherein the variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28 or 29 positions compared to SEQ ID NO: 11;

(c) a polypeptide comprising the polypeptide of (a) or (b) and an N-terminal and/or C-terminal His-tag and/or HQ-tag;

(d) a polypeptide comprising the polypeptide of (a) or (b) and an N-terminal and/or C-terminal extension of up to 10 amino acids, e.g. 1, 2, 3, 4, 5, 6, 7, 8, 9 or 10 amino acids; and (e) a fragment of the polypeptide of (a) or (b) having mannanase activity and having at least 90% of the length of the mature polypeptide of SEQ ID NO: 11.

In a further aspect, the second mannanase is selected from the group consisting of:

(a) a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 12;

(b) a variant of the polypeptide in (a), wherein the variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28 or 29 positions compared to SEQ ID NO: 12;

(c) a polypeptide comprising the polypeptide of (a) or (b) and an N-terminal and/or C-terminal His-tag and/or HQ-tag;

(d) a polypeptide comprising the polypeptide of (a) or (b) and an N-terminal and/or C-terminal extension of up to 10 amino acids, e.g. 1, 2, 3, 4, 5, 6, 7, 8, 9 or 10 amino acids; and (e) a fragment of the polypeptide of (a) or (b) having mannanase activity and having at least 90% of the length of the mature polypeptide of SEQ ID NO: 12.

In a further aspect, the second mannanase is selected from the group consisting of:

(a) a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 13;

(b) a variant of the polypeptide in (a), wherein the variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28 or 29 positions compared to SEQ ID NO: 13;

(c) a polypeptide comprising the polypeptide of (a) or (b) and an N-terminal and/or C-terminal His-tag and/or HQ-tag;

(d) a polypeptide comprising the polypeptide of (a) or (b) and an N-terminal and/or C-terminal extension of up to 10 amino acids, e.g. 1, 2, 3, 4, 5, 6, 7, 8, 9 or 10 amino acids; and (e) a fragment of the polypeptide of (a) or (b) having mannanase activity and having at least 90% of the length of the mature polypeptide of SEQ ID NO: 13.

In a further aspect, the second mannanase is selected from the group consisting of:

(a) a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 14;

(b) a variant of the polypeptide in (a), wherein the variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28 or 29 positions compared to SEQ ID NO: 14;

(c) a polypeptide comprising the polypeptide of (a) or (b) and an N-terminal and/or C-terminal His-tag and/or HQ-tag;

(d) a polypeptide comprising the polypeptide of (a) or (b) and an N-terminal and/or C-terminal extension of up to 10 amino acids, e.g. 1, 2, 3, 4, 5, 6, 7, 8, 9 or 10 amino acids; and (e) a fragment of the polypeptide of (a) or (b) having mannanase activity and having at least 90% of the length of the mature polypeptide of SEQ ID NO: 14.

In a further aspect, the second mannanase is selected from the group consisting of:

(a) a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 15;

(b) a variant of the polypeptide in (a), wherein the variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28 or 29 positions compared to SEQ ID NO: 15;

(c) a polypeptide comprising the polypeptide of (a) or (b) and an N-terminal and/or C-terminal His-tag and/or HQ-tag;

(d) a polypeptide comprising the polypeptide of (a) or (b) and an N-terminal and/or C-terminal extension of up to 10 amino acids, e.g. 1, 2, 3, 4, 5, 6, 7, 8, 9 or 10 amino acids; and (e) a fragment of the polypeptide of (a) or (b) having mannanase activity and having at least 90% of the length of the mature polypeptide of SEQ ID NO: 15.

In a further aspect, the second mannanase is selected from the group consisting of:

(a) a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 16;

(b) a variant of the polypeptide in (a), wherein the variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28 or 29 positions compared to SEQ ID NO: 16;

(c) a polypeptide comprising the polypeptide of (a) or (b) and an N-terminal and/or C-terminal His-tag and/or HQ-tag;

(d) a polypeptide comprising the polypeptide of (a) or (b) and an N-terminal and/or C-terminal extension of up to 10 amino acids, e.g. 1, 2, 3, 4, 5, 6, 7, 8, 9 or 10 amino acids; and (e) a fragment of the polypeptide of (a) or (b) having mannanase activity and having at least 90% of the length of the mature polypeptide of SEQ ID NO: 16.

Combinations

In one aspect of the present invention, the composition of a first and a second mannanase comprises a first mannanase having at least 59% sequence identity to SEQ ID NO: 2; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 3, optionally the second mannanase is a variant of SEQ ID NO: 3.

In one aspect of the present invention, the composition of a first and a second mannanase comprises a first mannanase having at least 59% sequence identity to SEQ ID NO: 2; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 4, optionally the second mannanase is a variant of SEQ ID NO: 4.

In one aspect of the present invention, the composition of a first and a second mannanase comprises a first mannanase having at least 59% sequence identity to SEQ ID NO: 2; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 5, optionally the second mannanase is a variant of SEQ ID NO: 5.

In one aspect of the present invention, the composition of a first and a second mannanase comprises a first mannanase having at least 59% sequence identity to SEQ ID NO: 2; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 6, optionally the second mannanase is a variant of SEQ ID NO: 6.

In one aspect of the present invention, the composition of a first and a second mannanase comprises a first mannanase having at least 59% sequence identity to SEQ ID NO: 2; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 7, optionally the second mannanase is a variant of SEQ ID NO: 7.

In one aspect of the present invention, the composition of a first and a second mannanase comprises a first mannanase having at least 59% sequence identity to SEQ ID NO: 2; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 8, optionally the second mannanase is a variant of SEQ ID NO: 8.

In one aspect of the present invention, the composition of a first and a second mannanase comprises a first mannanase having at least 59% sequence identity to SEQ ID NO: 2; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 9, optionally the second mannanase is a variant of SEQ ID NO: 9.

In one aspect of the present invention, the composition of a first and a second mannanase comprises a first mannanase having at least 59% sequence identity to SEQ ID NO: 2; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 10, optionally the second mannanase is a variant of SEQ ID NO: 10.

In one aspect of the present invention, the composition of a first and a second mannanase comprises a first mannanase having at least 59% sequence identity to SEQ ID NO: 2; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 11, optionally the second mannanase is a variant of SEQ ID NO: 11.

In one aspect of the present invention, the composition of a first and a second mannanase comprises a first mannanase having at least 59% sequence identity to SEQ ID NO: 2; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 12, optionally the second mannanase is a variant of SEQ ID NO: 12.

In one aspect of the present invention, the composition of a first and a second mannanase comprises a first mannanase having at least 59% sequence identity to SEQ ID NO: 2; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 13, optionally the second mannanase is a variant of SEQ ID NO: 13.

In one aspect of the present invention, the composition of a first and a second mannanase comprises a first mannanase having at least 59% sequence identity to SEQ ID NO: 2; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 14, optionally the second mannanase is a variant of SEQ ID NO: 14.

In one aspect of the present invention, the composition of a first and a second mannanase comprises a first mannanase having at least 59% sequence identity to SEQ ID NO: 2; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 15, optionally the second mannanase is a variant of SEQ ID NO: 15.

In one aspect of the present invention, the composition of a first and a second mannanase comprises a first mannanase having at least 59% sequence identity to SEQ ID NO: 2; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 16, optionally the second mannanase is a variant of SEQ ID NO: 16.

In one aspect of the present invention, the composition of a first and a second mannanase comprises a first mannanase which is a variant of a parent mannanase having at least 59% sequence identity to SEQ ID NO: 2 comprising one or more substitutions in the positions corresponding to positions 260, 288, 294, and 295 of SEQ ID NO: 2; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 3, optionally the second mannanase is a variant of SEQ ID NO: 3.

In one aspect of the present invention, the composition of a first and a second mannanase comprises a first mannanase which is a variant of a parent mannanase having at least 59% sequence identity to SEQ ID NO: 2 comprising one or more substitutions in the positions corresponding to positions 260, 288, 294, and 295 of SEQ ID NO: 2; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 4, optionally the second mannanase is a variant of SEQ ID NO: 4.

In one aspect of the present invention, the composition of a first and a second mannanase comprises a first mannanase which is a variant of a parent mannanase having at least 59% sequence identity to SEQ ID NO: 2 comprising one or more substitutions in the positions corresponding to positions 260, 288, 294, and 295 of SEQ ID NO: 2; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 5, optionally the second mannanase is a variant of SEQ ID NO: 5.

In one aspect of the present invention, the composition of a first and a second mannanase comprises a first mannanase which is a variant of a parent mannanase having at least 59% sequence identity to SEQ ID NO: 2 comprising one or more substitutions in the positions corresponding to positions 260, 288, 294, and 295 of SEQ ID NO: 2; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 6, optionally the second mannanase is a variant of SEQ ID NO: 6.

In one aspect of the present invention, the composition of a first and a second mannanase comprises a first mannanase which is a variant of a parent mannanase having at least 59% sequence identity to SEQ ID NO: 2 comprising one or more substitutions in the positions corresponding to positions 260, 288, 294, and 295 of SEQ ID NO: 2; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 7, optionally the second mannanase is a variant of SEQ ID NO: 7.

In one aspect of the present invention, the composition of a first and a second mannanase comprises a first mannanase which is a variant of a parent mannanase having at least 59% sequence identity to SEQ ID NO: 2 comprising one or more substitutions in the positions corresponding to positions 260, 288, 294, and 295 of SEQ ID NO: 2; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 8, optionally the second mannanase is a variant of SEQ ID NO: 8.

In one aspect of the present invention, the composition of a first and a second mannanase comprises a first mannanase which is a variant of a parent mannanase having at least 59% sequence identity to SEQ ID NO: 2 comprising one or more substitutions in the positions corresponding to positions 260, 288, 294, and 295 of SEQ ID NO: 2; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 9, optionally the second mannanase is a variant of SEQ ID NO: 9.

In one aspect of the present invention, the composition of a first and a second mannanase comprises a first mannanase which is a variant of a parent mannanase having at least 59% sequence identity to SEQ ID NO: 2 comprising one or more substitutions in the positions corresponding to positions 260, 288, 294, and 295 of SEQ ID NO: 2; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 10, optionally the second mannanase is a variant of SEQ ID NO: 10.

In one aspect of the present invention, the composition of a first and a second mannanase comprises a first mannanase which is a variant of a parent mannanase having at least 59% sequence identity to SEQ ID NO: 2 comprising one or more substitutions in the positions corresponding to positions 260, 288, 294, and 295 of SEQ ID NO: 2; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 11, optionally the second mannanase is a variant of SEQ ID NO: 11.

In one aspect of the present invention, the composition of a first and a second mannanase comprises a first mannanase which is a variant of a parent mannanase having at least 59% sequence identity to SEQ ID NO: 2 comprising one or more substitutions in the positions corresponding to positions 260, 288, 294, and 295 of SEQ ID NO: 2; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 12, optionally the second mannanase is a variant of SEQ ID NO: 12.

In one aspect of the present invention, the composition of a first and a second mannanase comprises a first mannanase which is a variant of a parent mannanase having at least 59% sequence identity to SEQ ID NO: 2 comprising one or more substitutions in the positions corresponding to positions 260, 288, 294, and 295 of SEQ ID NO: 2; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 13, optionally the second mannanase is a variant of SEQ ID NO: 13.

In one aspect of the present invention, the composition of a first and a second mannanase comprises a first mannanase which is a variant of a parent mannanase having at least 59% sequence identity to SEQ ID NO: 2 comprising one or more substitutions in the positions corresponding to positions 260, 288, 294, and 295 of SEQ ID NO: 2; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 14, optionally the second mannanase is a variant of SEQ ID NO: 14.

In one aspect of the present invention, the composition of a first and a second mannanase comprises a first mannanase which is a variant of a parent mannanase having at least 59% sequence identity to SEQ ID NO: 2 comprising one or more substitutions in the positions corresponding to positions 260, 288, 294, and 295 of SEQ ID NO: 2; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 15, optionally the second mannanase is a variant of SEQ ID NO: 15.

In one aspect of the present invention, the composition of a first and a second mannanase comprises a first mannanase which is a variant of a parent mannanase having at least 59% sequence identity to SEQ ID NO: 2 comprising one or more substitutions in the positions corresponding to positions 260, 288, 294, and 295 of SEQ ID NO: 2; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 16, optionally the second mannanase is a variant of SEQ ID NO: 16.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, N200T, S202R, R210G, W260F, N283H, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 3, optionally the second mannanase is a variant of SEQ ID NO: 3.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, N200T, S202R, R210G, W260F, N283H, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 4, optionally the second mannanase is a variant of SEQ ID NO: 4.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, N200T, S202R, R210G, W260F, N283H, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 5, optionally the second mannanase is a variant of SEQ ID NO: 5.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, N200T, S202R, R210G, W260F, N283H, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 6, optionally the second mannanase is a variant of SEQ ID NO: 6.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, N200T, S202R, R210G, W260F, N283H, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 7, optionally the second mannanase is a variant of SEQ ID NO: 7.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, N200T, S202R, R210G, W260F, N283H, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 8, optionally the second mannanase is a variant of SEQ ID NO: 8.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, N200T, S202R, R210G, W260F, N283H, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 9, optionally the second mannanase is a variant of SEQ ID NO: 9.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, N200T, S202R, R210G, W260F, N283H, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 10, optionally the second mannanase is a variant of SEQ ID NO: 10.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, N200T, S202R, R210G, W260F, N283H, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 11, optionally the second mannanase is a variant of SEQ ID NO: 11.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, N200T, S202R, R210G, W260F, N283H, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 12, optionally the second mannanase is a variant of SEQ ID NO: 12.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, N200T, S202R, R210G, W260F, N283H, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 13, optionally the second mannanase is a variant of SEQ ID NO: 13.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, N200T, S202R, R210G, W260F, N283H, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 14, optionally the second mannanase is a variant of SEQ ID NO: 14.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, N200T, S202R, R210G, W260F, N283H, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 15, optionally the second mannanase is a variant of SEQ ID NO: 15.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, N200T, S202R, R210G, W260F, N283H, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 16, optionally the second mannanase is a variant of SEQ ID NO: 16.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, S202R, R210G, W260F, A276E, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 3, optionally the second mannanase is a variant of SEQ ID NO: 3.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, S202R, R210G, W260F, A276E, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 4, optionally the second mannanase is a variant of SEQ ID NO: 4.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, S202R, R210G, W260F, A276E, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 5, optionally the second mannanase is a variant of SEQ ID NO: 5.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, S202R, R210G, W260F, A276E, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 6, optionally the second mannanase is a variant of SEQ ID NO: 6.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, S202R, R210G, W260F, A276E, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 7, optionally the second mannanase is a variant of SEQ ID NO: 7.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, S202R, R210G, W260F, A276E, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 8, optionally the second mannanase is a variant of SEQ ID NO: 8.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, S202R, R210G, W260F, A276E, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 9, optionally the second mannanase is a variant of SEQ ID NO: 9.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, S202R, R210G, W260F, A276E, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 10, optionally the second mannanase is a variant of SEQ ID NO: 10.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, S202R, R210G, W260F, A276E, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 11, optionally the second mannanase is a variant of SEQ ID NO: 11.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, S202R, R210G, W260F, A276E, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 12, optionally the second mannanase is a variant of SEQ ID NO: 12.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, S202R, R210G, W260F, A276E, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 13, optionally the second mannanase is a variant of SEQ ID NO: 13.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, S202R, R210G, W260F, A276E, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 14, optionally the second mannanase is a variant of SEQ ID NO: 14.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, S202R, R210G, W260F, A276E, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 15, optionally the second mannanase is a variant of SEQ ID NO: 15.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, S202R, R210G, W260F, A276E, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 16, optionally the second mannanase is a variant of SEQ ID NO: 16.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, S202R, R210G, W260F, A276D, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 3, optionally the second mannanase is a variant of SEQ ID NO: 3.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, S202R, R210G, W260F, A276D, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 4, optionally the second mannanase is a variant of SEQ ID NO: 4.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, S202R, R210G, W260F, A276D, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 5, optionally the second mannanase is a variant of SEQ ID NO: 5.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, S202R, R210G, W260F, A276D, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 6, optionally the second mannanase is a variant of SEQ ID NO: 6.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, S202R, R210G, W260F, A276D, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 7, optionally the second mannanase is a variant of SEQ ID NO: 7.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, S202R, R210G, W260F, A276D, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 8, optionally the second mannanase is a variant of SEQ ID NO: 8.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, S202R, R210G, W260F, A276D, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 9, optionally the second mannanase is a variant of SEQ ID NO: 9.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, S202R, R210G, W260F, A276D, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 10, optionally the second mannanase is a variant of SEQ ID NO: 10.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, S202R, R210G, W260F, A276D, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 11, optionally the second mannanase is a variant of SEQ ID NO: 11.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, S202R, R210G, W260F, A276D, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 12, optionally the second mannanase is a variant of SEQ ID NO: 12.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, S202R, R210G, W260F, A276D, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 13, optionally the second mannanase is a variant of SEQ ID NO: 13.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, S202R, R210G, W260F, A276D, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 14, optionally the second mannanase is a variant of SEQ ID NO: 14.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, S202R, R210G, W260F, A276D, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 15, optionally the second mannanase is a variant of SEQ ID NO: 15.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, S202R, R210G, W260F, A276D, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 16, optionally the second mannanase is a variant of SEQ ID NO: 16.

In one aspect of the present invention, the composition of a first and a second mannanase comprises a first mannanase which is a variant of a parent mannanase having at least 59% sequence identity to SEQ ID NO: 2 comprising the substitutions A30T, Y93Q, S95D, D118K, A136P, D139R, S202R, R210G, W260F, A276D, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 3, optionally the second mannanase is a variant of SEQ ID NO: 3.

In one aspect of the present invention, the composition of a first and a second mannanase comprises a first mannanase which is a variant of a parent mannanase having at least 59% sequence identity to SEQ ID NO: 2 comprising the substitutions S8T, A30T, Y93Q, S95D, D118K, A136P, D139R, N150T, S202R, R210G, Q243K, W260F, A276D, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 4, optionally the second mannanase is a variant of SEQ ID NO: 4.

In one aspect of the present invention, the composition of a first and a second mannanase comprises a first mannanase which is a variant of a parent mannanase having at least 59% sequence identity to SEQ ID NO: 2 comprising the substitutions S8T, A30T, Y93Q, S95D, D118K, A136P, D139R, N150T, S202R, R210G, Q243K, W260F, A276D, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 5, optionally the second mannanase is a variant of SEQ ID NO: 5.

In one aspect of the present invention, the composition of a first and a second mannanase comprises a first mannanase which is a variant of a parent mannanase having at least 59% sequence identity to SEQ ID NO: 2 comprising the substitutions S8T, A30T, Y93Q, S95D, D118K, A136P, D139R, N150T, S202R, R210G, Q243K, W260F, A276D, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 6, optionally the second mannanase is a variant of SEQ ID NO: 6.

In one aspect of the present invention, the composition of a first and a second mannanase comprises a first mannanase which is a variant of a parent mannanase having at least 59% sequence identity to SEQ ID NO: 2 comprising the substitutions S8T, A30T, Y93Q, S95D, D118K, A136P, D139R, N150T, S202R, R210G, Q243K, W260F, A276D, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 7, optionally the second mannanase is a variant of SEQ ID NO: 7.

In one aspect of the present invention, the composition of a first and a second mannanase comprises a first mannanase which is a variant of a parent mannanase having at least 59% sequence identity to SEQ ID NO: 2 comprising the substitutions S8T, A30T, Y93Q, S95D, D118K, A136P, D139R, N150T, S202R, R210G, Q243K, W260F, A276D, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 8, optionally the second mannanase is a variant of SEQ ID NO: 8.

In one aspect of the present invention, the composition of a first and a second mannanase comprises a first mannanase which is a variant of a parent mannanase having at least 59% sequence identity to SEQ ID NO: 2 comprising the substitutions S8T, A30T, Y93Q, S95D, D118K, A136P, D139R, N150T, S202R, R210G, Q243K, W260F, A276D, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 9, optionally the second mannanase is a variant of SEQ ID NO: 9.

In one aspect of the present invention, the composition of a first and a second mannanase comprises a first mannanase which is a variant of a parent mannanase having at least 59% sequence identity to SEQ ID NO: 2 comprising the substitutions S8T, A30T, Y93Q, S95D, D118K, A136P, D139R, N150T, S202R, R210G, Q243K, W260F, A276D, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 10, optionally the second mannanase is a variant of SEQ ID NO: 10.

In one aspect of the present invention, the composition of a first and a second mannanase comprises a first mannanase which is a variant of a parent mannanase having at least 59% sequence identity to SEQ ID NO: 2 comprising the substitutions S8T, A30T, Y93Q, S95D, D118K, A136P, D139R, N150T, S202R, R210G, Q243K, W260F, A276D, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 11, optionally the second mannanase is a variant of SEQ ID NO: 11.

In one aspect of the present invention, the composition of a first and a second mannanase comprises a first mannanase which is a variant of a parent mannanase having at least 59% sequence identity to SEQ ID NO: 2 comprising the substitutions S8T, A30T, Y93Q, S95D, D118K, A136P, D139R, N150T, S202R, R210G, Q243K, W260F, A276D, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 12, optionally the second mannanase is a variant of SEQ ID NO: 12.

In one aspect of the present invention, the composition of a first and a second mannanase comprises a first mannanase which is a variant of a parent mannanase having at least 59% sequence identity to SEQ ID NO: 2 comprising the substitutions S8T, A30T, Y93Q, S95D, D118K, A136P, D139R, N150T, S202R, R210G, Q243K, W260F, A276D, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 13, optionally the second mannanase is a variant of SEQ ID NO: 13.

In one aspect of the present invention, the composition of a first and a second mannanase comprises a first mannanase which is a variant of a parent mannanase having at least 59% sequence identity to SEQ ID NO: 2 comprising the substitutions S8T, A30T, Y93Q, S95D, D118K, A136P, D139R, N150T, S202R, R210G, Q243K, W260F, A276D, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 14, optionally the second mannanase is a variant of SEQ ID NO: 14.

In one aspect of the present invention, the composition of a first and a second mannanase comprises a first mannanase which is a variant of a parent mannanase having at least 59% sequence identity to SEQ ID NO: 2 comprising the substitutions S8T, A30T, Y93Q, S95D, D118K, A136P, D139R, N150T, S202R, R210G, Q243K, W260F, A276D, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 15, optionally the second mannanase is a variant of SEQ ID NO: 15.

In one aspect of the present invention, the composition of a first and a second mannanase comprises a first mannanase which is a variant of a parent mannanase having at least 59% sequence identity to SEQ ID NO: 2 comprising the substitutions S8T, A30T, Y93Q, S95D, D118K, A136P, D139R, N150T, S202R, R210G, Q243K, W260F, A276D, L288I, L294P and S295V; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 16, optionally the second mannanase is a variant of SEQ ID NO: 16.

In one aspect of the present invention, the composition of a first and a second mannanase comprises a first mannanase having at least 59% sequence identity to SEQ ID NO: 17; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 3, optionally the second mannanase is a variant of SEQ ID NO: 3.

In one aspect of the present invention, the composition of a first and a second mannanase comprises a first mannanase having at least 59% sequence identity to SEQ ID NO: 17; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 4, optionally the second mannanase is a variant of SEQ ID NO: 4.

In one aspect of the present invention, the composition of a first and a second mannanase comprises a first mannanase having at least 59% sequence identity to SEQ ID NO: 17; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 5, optionally the second mannanase is a variant of SEQ ID NO: 5.

In one aspect of the present invention, the composition of a first and a second mannanase comprises a first mannanase having at least 59% sequence identity to SEQ ID NO: 17; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 6, optionally the second mannanase is a variant of SEQ ID NO: 6.

In one aspect of the present invention, the composition of a first and a second mannanase comprises a first mannanase having at least 59% sequence identity to SEQ ID NO: 17; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 7, optionally the second mannanase is a variant of SEQ ID NO: 7.

In one aspect of the present invention, the composition of a first and a second mannanase comprises a first mannanase having at least 59% sequence identity to SEQ ID NO: 17; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 8, optionally the second mannanase is a variant of SEQ ID NO: 8.

In one aspect of the present invention, the composition of a first and a second mannanase comprises a first mannanase having at least 59% sequence identity to SEQ ID NO: 17; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 9, optionally the second mannanase is a variant of SEQ ID NO: 9.

In one aspect of the present invention, the composition of a first and a second mannanase comprises a first mannanase having at least 59% sequence identity to SEQ ID NO: 17; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 10, optionally the second mannanase is a variant of SEQ ID NO: 10.

In one aspect of the present invention, the composition of a first and a second mannanase comprises a first mannanase having at least 59% sequence identity to SEQ ID NO: 17; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 11, optionally the second mannanase is a variant of SEQ ID NO: 11.

In one aspect of the present invention, the composition of a first and a second mannanase comprises a first mannanase having at least 59% sequence identity to SEQ ID NO: 17; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 12, optionally the second mannanase is a variant of SEQ ID NO: 12.

In one aspect of the present invention, the composition of a first and a second mannanase comprises a first mannanase having at least 59% sequence identity to SEQ ID NO: 17; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 13, optionally the second mannanase is a variant of SEQ ID NO: 13.

In one aspect of the present invention, the composition of a first and a second mannanase comprises a first mannanase having at least 59% sequence identity to SEQ ID NO: 17; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 14, optionally the second mannanase is a variant of SEQ ID NO: 14.

In one aspect of the present invention, the composition of a first and a second mannanase comprises a first mannanase having at least 59% sequence identity to SEQ ID NO: 17; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 15, optionally the second mannanase is a variant of SEQ ID NO: 15.

In one aspect of the present invention, the composition of a first and a second mannanase comprises a first mannanase having at least 59% sequence identity to SEQ ID NO: 17; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 16, optionally the second mannanase is a variant of SEQ ID NO: 16.

In one aspect of the present invention, the composition of a first and a second mannanase comprises a first mannanase having at least 59% sequence identity to SEQ ID NO: 18; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 3, optionally the second mannanase is a variant of SEQ ID NO: 3.

In one aspect of the present invention, the composition of a first and a second mannanase comprises a first mannanase having at least 59% sequence identity to SEQ ID NO: 18; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 4, optionally the second mannanase is a variant of SEQ ID NO: 4.

In one aspect of the present invention, the composition of a first and a second mannanase comprises a first mannanase having at least 59% sequence identity to SEQ ID NO: 18; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 5, optionally the second mannanase is a variant of SEQ ID NO: 5.

In one aspect of the present invention, the composition of a first and a second mannanase comprises a first mannanase having at least 59% sequence identity to SEQ ID NO: 18; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 6, optionally the second mannanase is a variant of SEQ ID NO: 6.

In one aspect of the present invention, the composition of a first and a second mannanase comprises a first mannanase having at least 59% sequence identity to SEQ ID NO: 18; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 7, optionally the second mannanase is a variant of SEQ ID NO: 7.

In one aspect of the present invention, the composition of a first and a second mannanase comprises a first mannanase having at least 59% sequence identity to SEQ ID NO: 18; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 8, optionally the second mannanase is a variant of SEQ ID NO: 8.

In one aspect of the present invention, the composition of a first and a second mannanase comprises a first mannanase having at least 59% sequence identity to SEQ ID NO: 18; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 9, optionally the second mannanase is a variant of SEQ ID NO: 9.

In one aspect of the present invention, the composition of a first and a second mannanase comprises a first mannanase having at least 59% sequence identity to SEQ ID NO: 18; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 10, optionally the second mannanase is a variant of SEQ ID NO: 10.

In one aspect of the present invention, the composition of a first and a second mannanase comprises a first mannanase having at least 59% sequence identity to SEQ ID NO: 18; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 11, optionally the second mannanase is a variant of SEQ ID NO: 11.

In one aspect of the present invention, the composition of a first and a second mannanase comprises a first mannanase having at least 59% sequence identity to SEQ ID NO: 18; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 12, optionally the second mannanase is a variant of SEQ ID NO: 12.

In one aspect of the present invention, the composition of a first and a second mannanase comprises a first mannanase having at least 59% sequence identity to SEQ ID NO: 18; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 13, optionally the second mannanase is a variant of SEQ ID NO: 13.

In one aspect of the present invention, the composition of a first and a second mannanase comprises a first mannanase having at least 59% sequence identity to SEQ ID NO: 18; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 14, optionally the second mannanase is a variant of SEQ ID NO: 14.

In one aspect of the present invention, the composition of a first and a second mannanase comprises a first mannanase having at least 59% sequence identity to SEQ ID NO: 18; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 15, optionally the second mannanase is a variant of SEQ ID NO: 15.

In one aspect of the present invention, the composition of a first and a second mannanase comprises a first mannanase having at least 59% sequence identity to SEQ ID NO: 18; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 16, optionally the second mannanase is a variant of SEQ ID NO: 16.

In one aspect of the present invention, the composition of a first and a second mannanase comprises a first mannanase having at least 59% sequence identity to SEQ ID NO: 19; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 3, optionally the second mannanase is a variant of SEQ ID NO: 3.

In one aspect of the present invention, the composition of a first and a second mannanase comprises a first mannanase having at least 59% sequence identity to SEQ ID NO: 19; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 4, optionally the second mannanase is a variant of SEQ ID NO: 4.

In one aspect of the present invention, the composition of a first and a second mannanase comprises a first mannanase having at least 59% sequence identity to SEQ ID NO: 19; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 5, optionally the second mannanase is a variant of SEQ ID NO: 5.

In one aspect of the present invention, the composition of a first and a second mannanase comprises a first mannanase having at least 59% sequence identity to SEQ ID NO: 19; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 6, optionally the second mannanase is a variant of SEQ ID NO: 6.

In one aspect of the present invention, the composition of a first and a second mannanase comprises a first mannanase having at least 59% sequence identity to SEQ ID NO: 19; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 7, optionally the second mannanase is a variant of SEQ ID NO: 7.

In one aspect of the present invention, the composition of a first and a second mannanase comprises a first mannanase having at least 59% sequence identity to SEQ ID NO: 19; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 8, optionally the second mannanase is a variant of SEQ ID NO: 8.

In one aspect of the present invention, the composition of a first and a second mannanase comprises a first mannanase having at least 59% sequence identity to SEQ ID NO: 19; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 9, optionally the second mannanase is a variant of SEQ ID NO: 9.

In one aspect of the present invention, the composition of a first and a second mannanase comprises a first mannanase having at least 59% sequence identity to SEQ ID NO: 19; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 10, optionally the second mannanase is a variant of SEQ ID NO: 10.

In one aspect of the present invention, the composition of a first and a second mannanase comprises a first mannanase having at least 59% sequence identity to SEQ ID NO: 19; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 11, optionally the second mannanase is a variant of SEQ ID NO: 11.

In one aspect of the present invention, the composition of a first and a second mannanase comprises a first mannanase having at least 59% sequence identity to SEQ ID NO: 19; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 12, optionally the second mannanase is a variant of SEQ ID NO: 12.

In one aspect of the present invention, the composition of a first and a second mannanase comprises a first mannanase having at least 59% sequence identity to SEQ ID NO: 19; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 13, optionally the second mannanase is a variant of SEQ ID NO: 13.

In one aspect of the present invention, the composition of a first and a second mannanase comprises a first mannanase having at least 59% sequence identity to SEQ ID NO: 19; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 14, optionally the second mannanase is a variant of SEQ ID NO: 14.

In one aspect of the present invention, the composition of a first and a second mannanase comprises a first mannanase having at least 59% sequence identity to SEQ ID NO: 19; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 15, optionally the second mannanase is a variant of SEQ ID NO: 15.

In one aspect of the present invention, the composition of a first and a second mannanase comprises a first mannanase having at least 59% sequence identity to SEQ ID NO: 19; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 16, optionally the second mannanase is a variant of SEQ ID NO: 16.

In one aspect of the present invention, the composition of a first and a second mannanase comprises a first mannanase having at least 59% sequence identity to SEQ ID NO: 20; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 3, optionally the second mannanase is a variant of SEQ ID NO: 3.

In one aspect of the present invention, the composition of a first and a second mannanase comprises a first mannanase having at least 59% sequence identity to SEQ ID NO: 20; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 4, optionally the second mannanase is a variant of SEQ ID NO: 4.

In one aspect of the present invention, the composition of a first and a second mannanase comprises a first mannanase having at least 59% sequence identity to SEQ ID NO: 20; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 5, optionally the second mannanase is a variant of SEQ ID NO: 5.

In one aspect of the present invention, the composition of a first and a second mannanase comprises a first mannanase having at least 59% sequence identity to SEQ ID NO: 20; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 6, optionally the second mannanase is a variant of SEQ ID NO: 6.

In one aspect of the present invention, the composition of a first and a second mannanase comprises a first mannanase having at least 59% sequence identity to SEQ ID NO: 20; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 7, optionally the second mannanase is a variant of SEQ ID NO: 7.

In one aspect of the present invention, the composition of a first and a second mannanase comprises a first mannanase having at least 59% sequence identity to SEQ ID NO: 20; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 8, optionally the second mannanase is a variant of SEQ ID NO: 8.

In one aspect of the present invention, the composition of a first and a second mannanase comprises a first mannanase having at least 59% sequence identity to SEQ ID NO: 20; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 9, optionally the second mannanase is a variant of SEQ ID NO: 9.

In one aspect of the present invention, the composition of a first and a second mannanase comprises a first mannanase having at least 59% sequence identity to SEQ ID NO: 20; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 10, optionally the second mannanase is a variant of SEQ ID NO: 10.

In one aspect of the present invention, the composition of a first and a second mannanase comprises a first mannanase having at least 59% sequence identity to SEQ ID NO: 20; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 11, optionally the second mannanase is a variant of SEQ ID NO: 11.

In one aspect of the present invention, the composition of a first and a second mannanase comprises a first mannanase having at least 59% sequence identity to SEQ ID NO: 20; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 12, optionally the second mannanase is a variant of SEQ ID NO: 12.

In one aspect of the present invention, the composition of a first and a second mannanase comprises a first mannanase having at least 59% sequence identity to SEQ ID NO: 20; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 13, optionally the second mannanase is a variant of SEQ ID NO: 13.

In one aspect of the present invention, the composition of a first and a second mannanase comprises a first mannanase having at least 59% sequence identity to SEQ ID NO: 20; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 14, optionally the second mannanase is a variant of SEQ ID NO: 14.

In one aspect of the present invention, the composition of a first and a second mannanase comprises a first mannanase having at least 59% sequence identity to SEQ ID NO: 20; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 15, optionally the second mannanase is a variant of SEQ ID NO: 15.

In one aspect of the present invention, the composition of a first and a second mannanase comprises a first mannanase having at least 59% sequence identity to SEQ ID NO: 20; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 16, optionally the second mannanase is a variant of SEQ ID NO: 16.

In one aspect of the present invention, the composition of a first and a second mannanase comprises a first mannanase having at least 59% sequence identity to SEQ ID NO: 21; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 3, optionally the second mannanase is a variant of SEQ ID NO: 3.

In one aspect of the present invention, the composition of a first and a second mannanase comprises a first mannanase having at least 59% sequence identity to SEQ ID NO: 21; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 4, optionally the second mannanase is a variant of SEQ ID NO: 4.

In one aspect of the present invention, the composition of a first and a second mannanase comprises a first mannanase having at least 59% sequence identity to SEQ ID NO: 21; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 5, optionally the second mannanase is a variant of SEQ ID NO: 5.

In one aspect of the present invention, the composition of a first and a second mannanase comprises a first mannanase having at least 59% sequence identity to SEQ ID NO: 21; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 6, optionally the second mannanase is a variant of SEQ ID NO: 6.

In one aspect of the present invention, the composition of a first and a second mannanase comprises a first mannanase having at least 59% sequence identity to SEQ ID NO: 21; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 7, optionally the second mannanase is a variant of SEQ ID NO: 7.

In one aspect of the present invention, the composition of a first and a second mannanase comprises a first mannanase having at least 59% sequence identity to SEQ ID NO: 21; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 8, optionally the second mannanase is a variant of SEQ ID NO: 8.

In one aspect of the present invention, the composition of a first and a second mannanase comprises a first mannanase having at least 59% sequence identity to SEQ ID NO: 21; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 9, optionally the second mannanase is a variant of SEQ ID NO: 9.

In one aspect of the present invention, the composition of a first and a second mannanase comprises a first mannanase having at least 59% sequence identity to SEQ ID NO: 21; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 10, optionally the second mannanase is a variant of SEQ ID NO: 10.

In one aspect of the present invention, the composition of a first and a second mannanase comprises a first mannanase having at least 59% sequence identity to SEQ ID NO: 21; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 11, optionally the second mannanase is a variant of SEQ ID NO: 11.

In one aspect of the present invention, the composition of a first and a second mannanase comprises a first mannanase having at least 59% sequence identity to SEQ ID NO: 21; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 12, optionally the second mannanase is a variant of SEQ ID NO: 12.

In one aspect of the present invention, the composition of a first and a second mannanase comprises a first mannanase having at least 59% sequence identity to SEQ ID NO: 21; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 13, optionally the second mannanase is a variant of SEQ ID NO: 13.

In one aspect of the present invention, the composition of a first and a second mannanase comprises a first mannanase having at least 59% sequence identity to SEQ ID NO: 21; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 14, optionally the second mannanase is a variant of SEQ ID NO: 14.

In one aspect of the present invention, the composition of a first and a second mannanase comprises a first mannanase having at least 59% sequence identity to SEQ ID NO: 21; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 15, optionally the second mannanase is a variant of SEQ ID NO: 15.

In one aspect of the present invention, the composition of a first and a second mannanase comprises a first mannanase having at least 59% sequence identity to SEQ ID NO: 21; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 16, optionally the second mannanase is a variant of SEQ ID NO: 16.

In one aspect of the present invention, the composition of a first and a second mannanase comprises a first mannanase having at least 59% sequence identity to SEQ ID NO: 22; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 3, optionally the second mannanase is a variant of SEQ ID NO: 3.

In one aspect of the present invention, the composition of a first and a second mannanase comprises a first mannanase having at least 59% sequence identity to SEQ ID NO: 22; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 4, optionally the second mannanase is a variant of SEQ ID NO: 4.

In one aspect of the present invention, the composition of a first and a second mannanase comprises a first mannanase having at least 59% sequence identity to SEQ ID NO: 22; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 5, optionally the second mannanase is a variant of SEQ ID NO: 5.

In one aspect of the present invention, the composition of a first and a second mannanase comprises a first mannanase having at least 59% sequence identity to SEQ ID NO: 22; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 6, optionally the second mannanase is a variant of SEQ ID NO: 6.

In one aspect of the present invention, the composition of a first and a second mannanase comprises a first mannanase having at least 59% sequence identity to SEQ ID NO: 22; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 7, optionally the second mannanase is a variant of SEQ ID NO: 7.

In one aspect of the present invention, the composition of a first and a second mannanase comprises a first mannanase having at least 59% sequence identity to SEQ ID NO: 22; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 8, optionally the second mannanase is a variant of SEQ ID NO: 8.

In one aspect of the present invention, the composition of a first and a second mannanase comprises a first mannanase having at least 59% sequence identity to SEQ ID NO: 22; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 9, optionally the second mannanase is a variant of SEQ ID NO: 9.

In one aspect of the present invention, the composition of a first and a second mannanase comprises a first mannanase having at least 59% sequence identity to SEQ ID NO: 22; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 10, optionally the second mannanase is a variant of SEQ ID NO: 10.

In one aspect of the present invention, the composition of a first and a second mannanase comprises a first mannanase having at least 59% sequence identity to SEQ ID NO: 22; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 11, optionally the second mannanase is a variant of SEQ ID NO: 11.

In one aspect of the present invention, the composition of a first and a second mannanase comprises a first mannanase having at least 59% sequence identity to SEQ ID NO: 22; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 12, optionally the second mannanase is a variant of SEQ ID NO: 12.

In one aspect of the present invention, the composition of a first and a second mannanase comprises a first mannanase having at least 59% sequence identity to SEQ ID NO: 22; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 13, optionally the second mannanase is a variant of SEQ ID NO: 13.

In one aspect of the present invention, the composition of a first and a second mannanase comprises a first mannanase having at least 59% sequence identity to SEQ ID NO: 22; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 14, optionally the second mannanase is a variant of SEQ ID NO: 14.

In one aspect of the present invention, the composition of a first and a second mannanase comprises a first mannanase having at least 59% sequence identity to SEQ ID NO: 22; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 15, optionally the second mannanase is a variant of SEQ ID NO: 15.

In one aspect of the present invention, the composition of a first and a second mannanase comprises a first mannanase having at least 59% sequence identity to SEQ ID NO: 22; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 16, optionally the second mannanase is a variant of SEQ ID NO: 16.

In one aspect of the present invention, the composition of a first and a second mannanase comprises a first mannanase having at least 59% sequence identity to SEQ ID NO: 23; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 3, optionally the second mannanase is a variant of SEQ ID NO: 3.

In one aspect of the present invention, the composition of a first and a second mannanase comprises a first mannanase having at least 59% sequence identity to SEQ ID NO: 23; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 4, optionally the second mannanase is a variant of SEQ ID NO: 4.

In one aspect of the present invention, the composition of a first and a second mannanase comprises a first mannanase having at least 59% sequence identity to SEQ ID NO: 23; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 5, optionally the second mannanase is a variant of SEQ ID NO: 5.

In one aspect of the present invention, the composition of a first and a second mannanase comprises a first mannanase having at least 59% sequence identity to SEQ ID NO: 23; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 6, optionally the second mannanase is a variant of SEQ ID NO: 6.

In one aspect of the present invention, the composition of a first and a second mannanase comprises a first mannanase having at least 59% sequence identity to SEQ ID NO: 23; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 7, optionally the second mannanase is a variant of SEQ ID NO: 7.

In one aspect of the present invention, the composition of a first and a second mannanase comprises a first mannanase having at least 59% sequence identity to SEQ ID NO: 23; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 8, optionally the second mannanase is a variant of SEQ ID NO: 8.

In one aspect of the present invention, the composition of a first and a second mannanase comprises a first mannanase having at least 59% sequence identity to SEQ ID NO: 23; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 9, optionally the second mannanase is a variant of SEQ ID NO: 9.

In one aspect of the present invention, the composition of a first and a second mannanase comprises a first mannanase having at least 59% sequence identity to SEQ ID NO: 23; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 10, optionally the second mannanase is a variant of SEQ ID NO: 10.

In one aspect of the present invention, the composition of a first and a second mannanase comprises a first mannanase having at least 59% sequence identity to SEQ ID NO: 23; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 11, optionally the second mannanase is a variant of SEQ ID NO: 11.

In one aspect of the present invention, the composition of a first and a second mannanase comprises a first mannanase having at least 59% sequence identity to SEQ ID NO: 23; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 12, optionally the second mannanase is a variant of SEQ ID NO: 12.

In one aspect of the present invention, the composition of a first and a second mannanase comprises a first mannanase having at least 59% sequence identity to SEQ ID NO: 23; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 13, optionally the second mannanase is a variant of SEQ ID NO: 13.

In one aspect of the present invention, the composition of a first and a second mannanase comprises a first mannanase having at least 59% sequence identity to SEQ ID NO: 23; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 14, optionally the second mannanase is a variant of SEQ ID NO: 14.

In one aspect of the present invention, the composition of a first and a second mannanase comprises a first mannanase having at least 59% sequence identity to SEQ ID NO: 23; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 15, optionally the second mannanase is a variant of SEQ ID NO: 15.

In one aspect of the present invention, the composition of a first and a second mannanase comprises a first mannanase having at least 59% sequence identity to SEQ ID NO: 23; and the second mannanase is a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 16, optionally the second mannanase is a variant of SEQ ID NO: 16.

Ratio Between First and Second Mannanases

It will be apparent that the ratio between the first mannanase and the second mannanase in a composition of the invention may vary depending on the particular choice of first and second mannanases and the intended use of the composition, and that the ratio for a given composition will be able to be determined by persons skilled in the art. In general, however, the weight ratio between the first mannanase and the second mannanase will typically be from about 2:98 to about 95:5, e.g. from about 10:90 to about 90:10, from about 20:80 to about 80:20, from about 30:70 to about 70:30, or from about 40:60 to about 60:40.

In some cases, it may be desired to have a higher content of the first mannanase relative to the second mannanase. In this case, the weight ratio between the first mannanase and the second mannanase may be from about 98:2 to about 50:50, e.g. from about 90:10 to about 60:40, or from about 80:20 to about 70:30.

Conversely, in other cases it may be desired to have a higher content of the second mannanase relative to the first mannanase. In this case, the weight ratio between the first mannanase and the second mannanase may be from about 2:98 to about 50:50, e.g. from about 10:90 to about 40:60, or from about 20:80 to about 30:70.

In some embodiments, the weight ratio between the first and the second mannanases is 25:75, 50:50, or 75:25.

Cleaning Compositions and/or Detergent Compositions

The present invention relates to compositions comprising a first mannanase and a second mannanase of the invention, which is cleaning compositions and/or detergent compositions.

In one embodiment, the present invention relates to cleaning compositions and/or detergent compositions comprising a first mannanase and a second mannanase and a suitable surfactant. In one embodiment, the detergent composition may be adapted for specific uses such as laundry, in particular household laundry, dish washing or hard surface cleaning.

Thus, in one embodiment, the detergent composition may be used for laundering, washing or cleaning a textile and/or a hard surface (such as dish wash). In an embodiment, the first and seconds mannanase have an enzyme detergency benefit (i.e. the enzymes improve the cleaning result compared to the same composition without the enzymes).

The detergent compositions may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations. The detergent compositions may find use in hard surface cleaning, automatic dishwashing applications, as well as cosmetic applications such as dentures, teeth, hair and skin.

The detergent composition may be in any convenient form, e.g., a bar, a tablet, a powder, a granule, a paste or a liquid. A liquid detergent may be aqueous, typically containing up to 70% water and 0-30% organic solvent, or non-aqueous.

Unless otherwise noted, all component or composition levels provided herein are made in reference to the active level of that component or composition, and are exclusive of impurities, for example, residual solvents or by-products, which may be present in commercially available sources.

The first mannanase and second mannanases of the invention are normally incorporated in the detergent composition (pods/caps, liquid detergent or powder detergent) at a total level of from 0.001% to 10% of enzyme protein by weight of the composition, such as 0.001% to 0.1%, 0.01% to 1.0% or 0.1% to 10% of enzyme protein by weight of the composition.

The first and second mannanases of the invention are normally incorporated in the washing composition in such amounts that their total concentration in the wash water is at a level of from 0.0001 to 1 ppm enzyme protein, such as 0.0001 to 0.01 ppm, such as 0.001 to 0.1 ppm or such as 0.01 to 1 ppm enzyme protein in wash water.

The detergent compositions provided herein are typically formulated such that, during use in aqueous cleaning operations, the wash water has a pH of from about 5.0 to about 11.5, or in alternative embodiments, from about 6.0 to about 10.5, such as from about 5 to about 11, from about 5 to about 10, from about 5 to about 9, from about 5 to about 8, from about 5 to about 7, from about 6 to about 11, from about 6 to about 10, from about 6 to about 9, from about 6 to about 8, from about 6 to about 7, from about 7 to about 11, from about 7 to about 10, from about 7 to about 9, or from about 7 to about 8. In some embodiments, granular or liquid laundry products are formulated such that the wash water has a pH from about 5.5 to about 8. Techniques for controlling pH at recommended usage levels include the use of buffers, alkalis, acids, etc., and are well known to those skilled in the art.

Enzyme component weights are based on total protein. All percentages and ratios are calculated by weight unless otherwise indicated. All percentages and ratios are calculated based on the total composition unless otherwise indicated. In the exemplified detergent composition, the enzyme levels are expressed by pure enzyme by weight of the total composition and unless otherwise specified, the detergent ingredients are expressed by weight of the total composition.

The mannanases of the present invention also find use in detergent additive products. A detergent additive product comprising a first and second mannanase of the invention is ideally suited for inclusion in a wash process when, e.g., temperature is low, such as at temperatures about 40° C. or below, the pH is between 6 and 8 and the washing time short, e.g., below 30 min.

The detergent additive product may comprise a first and second mannanase of the invention and preferably an additional enzyme. In one embodiment, the additive is packaged in dosage form for addition to a cleaning process. The single dosage may comprise a pill, tablet, gelcap or other single dosage unit including powders and/or liquids. In some embodiments, filler and/or carrier material(s) are included, suitable filler or carrier materials include, but are not limited to, various salts of sulphate, carbonate and silicate as well as talc, clay and the like. In some embodiments filler and/or carrier materials for liquid compositions include water and/or low molecular weight primary and secondary alcohols including polyols and diols. Examples of such alcohols include, but are not limited to, methanol, ethanol, propanol and isopropanol.

In one preferred embodiment, the first and second mannanase of the invention are employed in a granular composition or liquid, where the mannanases may be in form of an encapsulated particle. In one embodiment, the encapsulating material is selected from the group consisting of carbohydrates, natural or synthetic gums, chitin and chitosan, cellulose and cellulose derivatives, silicates, phosphates, borates, polyvinyl alcohol, polyethylene glycol, paraffin waxes and combinations thereof.

The compositions of the invention typically comprise one or more detergent ingredients. The term "detergent compositions" includes articles and cleaning and treatment compositions. The term "cleaning composition" includes, unless otherwise indicated, tablet, granular or powder-form all-purpose or "heavy-duty" washing agents, especially laundry detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use. The composition can also be in unit dose packages, for example a pod/cap or a pouch, including those known in the art and those that are water soluble, water insoluble and/or water permeable.

In embodiments in which cleaning and/or detergent components may not be compatible with the first or second mannanase of the present invention, suitable methods may be used for keeping the cleaning and/or detergent components and the mannanases separated (i.e., not in contact with each other) until combination of the components is appropriate. Such separation methods include any suitable method known in the art (e.g., gelcaps, encapsulation, tablets, and physical separation e.g., by use of a water dissolvable pouch having one or more compartments).

In some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), tin (II), cobalt (II), copper (II), nickel (II), and oxovanadium (IV)). The enzymes of the detergent compositions of the invention may also be stabilized using conventional stabilizing agents such as polyol, e.g., propylene glycol or glycerol, a sugar or sugar alcohol, lactic acid, and the composition may be formulated as described in, e.g., WO 92/19709 and WO 92/19708. The enzymes of the invention may also be stabilized by adding reversible enzyme inhibitors, e.g., of the protein type (as described in EP 544 777) or the boronic acid type. Other enzyme stabilizers are well known in the art, such as peptide aldehydes and protein hydrolysate, e.g. the mannanases according to the invention may be stabilized using peptide aldehydes or ketones such as described in WO2005/105826 and WO2009/118375.

Protected enzymes for inclusion in a detergent composition of the invention may be prepared, as mentioned above, according to the method disclosed in EP 238216.

The composition may be augmented with one or more agents for preventing or removing the formation of a biofilm. These agents may include, but are not limited to, dispersants, surfactants, detergents, other enzymes, antimicrobials, and biocides.

The compositions of the invention may be applied in dosing elements to be used in an auto-dosing device. The dosing elements comprising the composition of the present invention can be placed into a delivery cartridge as that described in WO 2007/052004 and WO 2007/0833141.

The dosing elements can have an elongated shape and set into an array forming a delivery cartridge which is the refill for an auto-dosing dispensing device as described in case WO 2007/051989. The delivery cartridge is to be placed in an auto-dosing delivery device, such as that described in WO 2008/053191.

Suitable disclosure of auto-dosing devices can be found in WO 2007/083139, WO 2007/051989, WO 2007/083141, WO 2007/083142 and EP2361964, Formulation of Mannanases in Granules In one aspect, the mannanase composition of the invention may be produced in the form of granules. A composition comprising non-dusting granulates comprising the first and second mannanases of the invention may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238216.

The mannanases may be formulated as a granule, for example as a co-granule that combines one or more enzymes. Each enzyme will then be present in more granules securing a more uniform distribution of enzymes in the detergent. This also reduces the physical segregation of different enzymes due to different particle sizes. Methods for producing multi-enzyme co-granulate for the detergent industry is disclosed in the www.ip.com disclosure IPCOM000200739D.

Another example of formulation of enzymes by the use of co-granulates is disclosed in WO 2013/188331, which relates to a detergent composition comprising (a) a multi-enzyme co-granule; (b) less than 10% w/w zeolite (anhydrous basis); and (c) less than 10% w/w phosphate salt (anhydrous basis), wherein said enzyme co-granule comprises from 10 to 98% w/w moisture sink component and the composition additionally comprises from 20 to 80% w/w detergent moisture sink component.

An embodiment of the invention relates to an enzyme granule/particle comprising the first and second mannanases. The granule is composed of a core, and optionally one or more coatings (outer layers) surrounding the core.

Typically the granule/particle size, measured as equivalent spherical diameter (volume based average particle size), of the granule is 20-2000 µm, particularly 50-1500 µm, 100-1500 µm or 250-1200 µm.

The core may include additional materials such as fillers, fibre materials (cellulose or synthetic fibres), stabilizing agents, solubilizing agents, suspension agents, viscosity regulating agents, light spheres, plasticizers, salts, lubricants and fragrances.

The core may include binders, such as synthetic polymer, wax, fat, or carbohydrate.

The core may comprise a salt of a multivalent cation, a reducing agent, an antioxidant, a peroxide decomposing catalyst and/or an acidic buffer component, typically as a homogenous blend.

The core may consist of an inert particle with the enzyme absorbed into it, or applied onto the surface, e.g., by fluid bed coating.

The core may have a diameter of 20-2000 µm, particularly 50-1500 µm, 100-1500 µm or 250-1200 µm.

The core can be prepared by granulating a blend of the ingredients, e.g., by a method comprising granulation techniques such as crystallization, precipitation, pan-coating, fluid bed coating, fluid bed agglomeration, rotary atomization, extrusion, prilling, spheronization, size reduction methods, drum granulation, and/or high shear granulation.

Methods for preparing the core can be found in Handbook of Powder Technology; Particle size enlargement by C. E. Capes; Volume 1; 1980; Elsevier. Preparation methods include known feed and granule formulation technologies, e.g.:

a) Spray dried products, wherein a liquid enzyme-containing solution is atomized in a spray drying tower to form small droplets which during their way down the drying tower dry to form an enzyme-containing particulate material. Very small particles can be produced this way (Michael S. Showell (editor); Powdered detergents; Surfactant Science Series; 1998; vol. 71; page 140-142; Marcel Dekker).

b) Layered products, wherein the enzyme is coated as a layer around a pre-formed inert core particle, wherein an enzyme-containing solution is atomized, typically in a fluid bed apparatus wherein the pre-formed core particles are fluidized, and the enzyme-containing solution adheres to the core particles and dries up to leave a layer of dry enzyme on the surface of the core particle. Particles of a desired size can be obtained this way if a useful core particle of the desired size can be found. This type of product is described in, e.g., WO 97/23606 c) Absorbed core particles, wherein rather than coating the enzyme as a layer around the core, the enzyme is absorbed onto and/or into the surface of the core. Such a process is described in WO 97/39116.

d) Extrusion or pelletized products, wherein an enzyme-containing paste is pressed to pellets or under pressure is extruded through a small opening and cut into particles which are subsequently dried. Such particles usually have a considerable size because of the material in which the extrusion opening is made (usually a plate with bore holes) sets a limit on the allowable pressure drop over the extrusion opening. Also, very high extrusion pressures when using a small opening increase heat generation in the enzyme paste, which is harmful to the enzyme (see also Michael S. Showell (editor); Powdered detergents; Surfactant Science Series; 1998; vol. 71; page 140-142; Marcel Dekker).

e) Prilled products, wherein an enzyme-containing powder is suspended in molten wax and the suspension is sprayed, e.g., through a rotating disk atomiser, into a cooling chamber where the droplets quickly solidify (Michael S. Showell (editor); Powdered detergents; Surfactant Science Series; 1998; vol. 71; page 140-142; Marcel Dekker). The product obtained is one wherein the enzyme is uniformly distributed throughout an inert material instead of being concentrated on its surface. Also U.S. Pat. Nos. 4,016,040 and 4,713,245 are documents relating to this technique f) Mixer granulation products, wherein a liquid is added to a dry powder composition of, e.g., conventional granulating components, the enzyme being introduced either via the liquid or the powder or both. The liquid and the powder are mixed and as the moisture of the liquid is absorbed in the dry powder, the components of the dry powder will start to adhere and agglomerate and particles will build up, forming granulates comprising the enzyme. Such a process is described in U.S. Pat. No. 4,106,991 and related documents EP 170360, EP 304332, EP 304331, WO 90/09440 and WO 90/09428. In a particular product of this process wherein various high-shear mixers can be used as granulators, granulates consisting of enzyme as enzyme, fillers and binders etc. are mixed with cellulose fibres to reinforce the particles to give the so-called T-granulate. Reinforced particles, being more robust, release less enzymatic dust.

g) Size reduction, wherein the cores are produced by milling or crushing of larger particles, pellets, tablets, briquettes etc. containing the enzyme. The wanted core particle fraction is obtained by sieving the milled or crushed product. Over and undersized particles can be recycled. Size reduction is described in (Martin Rhodes (editor); Principles of Powder Technology; 1990; Chapter 10; John Wiley & Sons).

h) Fluid bed granulation. Fluid bed granulation involves suspending particulates in an air stream and spraying a liquid onto the fluidized particles via nozzles. Particles hit by spray droplets get wetted and become tacky. The tacky particles collide with other particles and adhere to them and form a granule.

i) The cores may be subjected to drying, such as in a fluid bed drier. Other known methods for drying granules in the feed or detergent industry can be used by the skilled person. The drying preferably takes place at a product temperature of from 25 to 90° C. For some enzymes it is important the cores comprising the enzyme contain a low amount of water before coating. If water sensitive enzymes are coated before excessive water is removed, it will be trapped within the core and it may affect the activity of the enzyme negatively. After drying, the cores preferably contain 0.1-10% w/w water.

The core of the enzyme granule/particle may be surrounded by at least one coating, e.g., to improve the storage stability, to reduce dust formation during handling, or for coloring the granule. The optional coating(s) may include a salt coating, or other suitable coating materials, such as polyethylene glycol (PEG), methyl hydroxy-propyl cellulose (MHPC) and polyvinyl alcohol (PVA). Examples of enzyme granules with multiple coatings are shown in WO 93/07263 and WO 97/23606.

The coating may be applied in an amount of at least 0.1% by weight of the core, e.g., at least 0.5%, 1% or 5%. The amount may be at most 100%, 70%, 50%, 40% or 30%.

The coating is preferably at least 0.1 µm thick, particularly at least 0.5 µm, at least 1 µm or at least 5 µm. In a particular embodiment the thickness of the coating is below 100 µm. In a more particular embodiment the thickness of the coating is below 60 µm. In an even more particular embodiment the total thickness of the coating is below 40 µm.

The coating should encapsulate the core unit by forming a substantially continuous layer. A substantially continuous layer is to be understood as a coating having few or no holes, so that the core unit it is encapsulating/enclosing has few or none uncoated areas. The layer or coating should in particular be homogeneous in thickness.

The coating can further contain other materials as known in the art, e.g., fillers, antisticking agents, pigments, dyes, plasticizers and/or binders, such as titanium dioxide, kaolin, calcium carbonate or talc.

A salt coating may comprise at least 60% by weight w/w of a salt, e.g., at least 65%, at least 70%, at least 75%, at least 80%, at least 85%, at least 90%, at least 95% or at least 99% by weight w/w.

The salt may be added from a salt solution where the salt is completely dissolved or from a salt suspension wherein the fine particles is less than 50 µm, such as less than 10 µm or less than 5 µm.

The salt coating may comprise a single salt or a mixture of two or more salts. The salt may be water soluble, in particular having a solubility at least 0.1 grams in 100 g of water at 20° C., preferably at least 0.5 g per 100 g water, e.g., at least 1 g per 100 g water, e.g., at least 5 g per 100 g water.

The salt may be an inorganic salt, e.g., salts of sulphate, sulphite, phosphate, phosphonate, nitrate, chloride or carbonate or salts of simple organic acids (less than 10 carbon atoms, e.g., 6 or less carbon atoms) such as citrate, malonate or acetate. Examples of cations in these salts are alkali or earth alkali metal ions, the ammonium ion or metal ions of the first transition series, such as sodium, potassium, magnesium, calcium, zinc or aluminium. Examples of anions include chloride, bromide, iodide, sulphate, sulphite, bisulphite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, lactate, formate, acetate, butyrate, propionate, benzoate, tartrate, ascorbate or gluconate. In particular alkali- or earth alkali metal salts of sulphate, sulphite, phosphate, phosphonate, nitrate, chloride or carbonate or salts of simple organic acids such as citrate, malonate or acetate may be used.

The salt in the coating may have a constant humidity at 20° C. above 60%, particularly above 70%, above 80% or above 85%, or it may be another hydrate form of such a salt (e.g., anhydrate). The salt coating may be as described in WO 00/01793 or WO 2006/034710.

Specific examples of suitable salts are NaCl ($CH_{20°\ C.}$=76%), $Na_2CO_3$($CH_{20°\ C.}$=92%), $NaNO_3$ ($CH_{20°\ C.}$=73%), $Na_2HPO_4$($CH_{20°\ C.}$=95%), $Na_3PO_4$ ($CH_{25°\ C.}$=92%), $NH_4Cl$ ($CH_{20°\ C.}$=79.5%), $(NH_4)_2HPO_4$ ($CH_{20°\ C.}$=93.0%), $NH_4H_2PO_4$($CH_{20°\ C.}$=93.1%), $(NH_4)_2SO_4$ ($CH_{20°\ C.}$=81.1%), KCl ($CH_{20°\ C.}$=85%), $K_2HPO_4$($CH_{20°\ C.}$=92%), $KH_2PO_4$($CH_{20°\ C.}$=96.5%), $KNO_3$ ($CH_{20°\ C.}$=93.5%), $Na_2SO_4$ ($CH_{20°\ C.}$=93%), $K_2SO_4$ ($CH_{20°\ C.}$=98%), $KHSO_4$ ($CH_{20°\ C.}$=86%), $MgSO_4$ ($CH_{20°\ C.}$=90%), $ZnSO_4$ ($CH_{20°\ C.}$=90%) and sodium citrate ($CH_{25°\ C.}$=86%). Other examples include $NaH_2PO_4$, $(NH_4)H_2PO_4$, $CuSO_4$, $Mg(NO_3)_2$ and magnesium acetate.

The salt may be in anhydrous form, or it may be a hydrated salt, i.e. a crystalline salt hydrate with bound water(s) of crystallization, such as described in WO 99/32595. Specific examples include anhydrous sodium sulphate ($Na_2SO_4$), anhydrous magnesium sulphate ($MgSO_4$), magnesium sulphate heptahydrate ($MgSO_4 \cdot 7H_2O$), zinc sulphate heptahydrate ($ZnSO_4 \cdot 7H_2O$), sodium phosphate dibasic heptahydrate ($Na_2HPO_4 \cdot 7H_2O$), magnesium nitrate hexahydrate ($Mg(NO_3)_2(6H_2O)$), sodium citrate dihydrate and magnesium acetate tetrahydrate. Preferably the salt is applied as a solution of the salt, e.g., using a fluid bed.

Thus, in a further aspect, the present invention provides a granule, which comprises:

(a) a core comprising a mannanase according to the invention, and (b) optionally a coating consisting of one or more layer(s) surrounding the core.

Liquid Formulations

In one aspect, the mannanase composition of the invention may be produced as a liquid formulation comprising the first and second mannanases. Liquid enzyme formulations may be stabilized using a polyol, for example a polyol selected from the group consisting of glycerol, sorbitol, propylene glycol (monoproplylene glycol, MPG), ethylene glycol, diethylene glycol, triethylene glycol, 1,2-propylene glycol or 1,3-propylene glycol, dipropylene glycol, polyethylene glycol (PEG) having an average molecular weight below about 600 and polypropylene glycol (PPG) having an average molecular weight below about 600. Preferred polyols include glycerol, sorbitol and propylene glycol (MPG) or any combination thereof. A liquid formulation may e.g.

comprise 5%-80% polyol (by weight of the liquid formulation, w/w), such as 15%-75% polyol, 25%-70% polyol, 35%-65% polyol or 40%-60% polyol.

The formulation may further comprise a preservative, typically in an amount of 0.001% to 2.0% w/w. In one embodiment, the preservative is selected from the group consisting of phenoxy ethanol, 1,2-benzisothiazolin-3(2H)-one, sodium sorbate, potassium sorbate, sodium benzoate, potassium benzoate, methylisothiazolinone, chloro methylisothiazolinone, methyl parabene, ethyl parabene, propyl parabene, butyl parabene, quarterary ammonium salts (such as BAC/ADBAC; alkylbenzyl quarternary ammonium chloride, dioctyldimethylammonium chloride, didecyldimethylammonium chloride, cetrimonium chloride), essential oils and organic acids or any combination thereof.

In one embodiment, the mannanase content (total of the first and second mannanases) is between 0.0001% and 10% polypeptide (w/w) of the liquid formulation, such as 0.001% to 1% w/w polypeptide or 0.01% to 1% w/w polypeptide.

In one embodiment, the liquid formulation comprises one or more formulating agents, for example a formulating agent selected from the group consisting of glycerol, ethylene glycol, 1,2-propylene glycol or 1,3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, PVA, acetate and phosphate. Preferred formulating agents include 1,2-propylene glycol, 1,3-propylene glycol, sodium sulfate, dextrin, cellulose, sodium thiosulfate, kaolin and calcium carbonate.

In one embodiment, the liquid formulation may further comprise one or more additional enzyme such as those described below.

Other Enzymes

In one embodiment, a first and second mannanase of the invention, e.g. in the form of a granulate or liquid composition, is combined with one or more other enzymes, such as at least two enzymes, e.g. at least three, four or five other enzymes. Preferably, the enzymes have different substrate specificity, e.g., proteolytic activity, amylolytic activity, lipolytic activity, hemicellulytic activity or pectolytic activity.

The detergent additive as well as the detergent composition may comprise one or more enzymes such as a protease, lipase, cutinase, an amylase, carbohydrase, cellulase, pectinase, arabinase, galactanase, xylanase, oxidase, e.g., a laccase and/or peroxidase.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases:

Suitable cellulases include those of animal, vegetable or microbial origin.

Particularly suitable cellulases include those of bacterial or fungal origin. Chemically modified or protein engineered variants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO 1999/001544.

Commercially available cellulases include Celluzyme™, and Carezyme™ (Novozymes A/S), Clazinase™, and Puradax HA™ (Genencor International Inc.), and KAC-500 (B)™ (Kao Corporation).

Proteases:

Suitable proteases include those of bacterial, fungal, plant, viral or animal origin e.g. microbial or vegetable origin. Microbial origin is preferred. Chemically modified or protein engineered variants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those derived from *Bacillus* such as *Bacillus lentus, B. alkalophilus, B. subtilis, B. amyloliquefaciens, Bacillus pumilus* and *Bacillus gibsonii* described in; U.S. Pat. No. 7,262,042 and WO09/021867, and subtilisin *lentus*, subtilisin Novo, subtilisin Carlsberg, *Bacillus licheniformis*, subtilisin BPN', subtilisin 309, subtilisin 147 and subtilisin 168 described in WO89/06279 and protease PD138 described in (WO93/18140). Other useful proteases may be those described in WO92/175177, WO01/016285, WO02/026024 and WO02/016547. Examples of trypsin-like proteases are trypsin (e.g. of porcine or bovine origin) and the *Fusarium* protease described in WO89/06270, WO94/25583 and WO05/040372, and the chymotrypsin proteases derived from *Cellulomonas* described in WO05/052161 and WO05/052146.

A further preferred protease is the alkaline protease from *Bacillus lentus* DSM 5483, as described for example in WO95/23221, and variants thereof which are described in WO92/21760, WO95/23221, EP1921147 and EP1921148.

Examples of metalloproteases are the neutral metalloprotease as described in WO07/044993 (Genencor Int.) such as those derived from *Bacillus amyloliquefaciens*.

Examples of useful proteases are the variants described in: WO92/19729, WO96/034946, WO98/20115, WO98/20116, WO99/011768, WO01/44452, WO03/006602, WO04/03186, WO04/041979, WO07/006305, WO11/036263, WO11/036264, especially the variants with substitutions in one or more of the following positions: 3, 4, 9, 15, 27, 36, 57, 68, 76, 87, 95, 96, 97, 98, 99, 100, 101, 102, 103, 104, 106, 118, 120, 123, 128, 129, 130, 160, 167, 170, 194, 195, 199, 205, 206, 217, 218, 222, 224, 232, 235, 236, 245, 248, 252 and 274 using the BPN' numbering. More preferred the protease variants may comprise the mutations: S3T, V41, S9R, A15T, K27R, *36D, V68A, N76D, N87S,R, *97E, A98S, S99G,D,A, S99AD, S101G,M,R S103A, V104I,Y,N, S106A, G118V,R, H120D,N, N123S, S128L, P129Q, S130A, G160D, Y167A, R170S, A194P, G195E, V199M, V205I, L217D, N218D, M222S, A232V, K235L, Q236H, Q245R, N252K, T274A (using BPN' numbering).

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Neutrase®, Everlase® and Esperase® (Novozymes A/S), those sold under the tradename Maxatase®, Maxacal®, Maxapem®, Purafect®, Purafect Prime®, Preferenz™, Purafect MA®, Purafect Ox®, Purafect OxP®, Puramax®, Properase®, Effectenz™, FN2®, FN3®, FN4®, Excellase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

Lipases:

Suitable lipases include those of animal, vegetable or microbial origin. Particularly suitable lipases include those of bacterial or fungal origin. Chemically modified or protein engineered variants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens*, *Pseudomonas* sp. strain SD 705 (WO 95/06720 and WO 96/27002), *P. wisconsinensis* (WO 96/12012), a *Bacillus* lipase, e.g., from *B. subtilis* (Dartois et al., 1993, *Biochemica et Biophysica Acta*, 1131: 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™, Lipolase Ultra™, and Lipex™ (Novozymes A/S).

Amylases:

Suitable amylases which can be used together with mannanase of the invention may be an alpha-amylase or a glucoamylase and may be of bacterial or fungal origin. Chemically modified or protein engineered variants are included. Amylases include, for example, alpha-amylases obtained from *Bacillus*, e.g., a special strain of *Bacillus licheniformis*, described in more detail in GB 1,296,839. Suitable amylases include amylases having SEQ ID NO: 3 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444. Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193. Other amylases which are suitable are hybrid alpha-amylase comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase derived from *B. amyloliquefaciens* shown in SEQ ID NO: 6 of WO 2006/066594 and residues 36-483 of SEQ ID NO: 4 are those having the substitutions:

M197T;

H156Y+A181T+N190F+A209V+Q264S; or

G48A+T491+G107A+H156Y+A181T+N190F+I201F+A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184. Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476. More preferred variants are those having a deletion in positions 181 and 182 or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476. Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264. Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;

N128C+K178L+T182G+F202Y+Y305R+D319T+G475K;

S125A+N128C+K178L+T182G+Y305R+G475K; or

S125A+N128C+T131I+T165I+K178L+T182G+Y305R+G475K wherein the variants are C-terminally truncated and optionally further comprises a substitution at position 243 and/or a deletion at position 180 and/or position 181. Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions. Other examples are amylase variants such as those described in WO2011/098531, WO2013/001078 and WO2013/001087. Commercially available amylases are Duramyl™, Termamyl™, Fungamyl™, Stainzyme™, Stainzyme Plus™, Natalase™, Liquozyme X and BAN™ (from Novozymes A/S), and Rapidase™, Purastar™/Effectenz™, Powerase and Preferenz S100 (from Genencor International Inc./DuPont).

Peroxidases/Oxidases:

Suitable peroxidases/oxidases include those of plant, bacterial or fungal origin. Chemically modified or protein engineered variants are included. Examples of useful peroxidases include peroxidases from *Coprinus*, e.g., from *C. cinereus*, and variants thereof as those described in WO 93/24618, WO 95/10602, and WO 98/15257.

Lechinases/Beta-Glucanases:

Suitable Lechinases include those of bacterial or fungal origin. They may be chemically modified or protein engineered. Examples of useful beta-glucanases include those described in WO 2015/144824 (Novozymes A/S) and WO 99/06516 (Henkel KGAA).

Commercially available peroxidases include Guardzyme™ (Novozymes A/S).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates as described above, liquids, in particular stabilized liquids, or slurries.

In a preferred aspect of the present invention the first and second mannanase may be combined with at least two other enzymes. These additional enzymes are described in details in the section "other enzymes", for example at least three, four or five other enzymes. Preferably, the enzymes have different substrate specificity, e.g., carbolytic activity, proteolytic activity, amylolytic activity, lipolytic activity, hemicellulytic activity or pectolytic activity. The enzyme combination may for example be a first and second mannanase of the invention with another stain removing enzyme, e.g., a first and second mannanase of the invention and a protease, a first and second mannanase of the invention and a serine protease, a first and second mannanase of the invention and an amylase, a first and second mannanase of the invention and a cellulase, a first and second mannanase of the invention and a lipase, a first and second mannanase of the invention and a cutinase, a first and second mannanase of the invention and a pectinase or a first and mannanase of the invention and an anti-redeposition enzyme. More preferably, the first and second mannanase of the invention is combined with at least two other stain removing enzymes, e.g., a first and second mannanase of the invention, a lipase and an amylase; or a first and second mannanase of the invention, a protease and an amylase; or a first and second mannanase of the invention, a protease and a lipase; or a first and second mannanase of the invention, a protease and a pectinase; or a first and second mannanase of the invention, a protease and a cellulase; or a first and second mannanase of the invention, a protease and a hemicellulase; or a first and second mannanase of the invention, a protease and a cutinase; or a first and second mannanase of the invention, an amylase and a pectinase; or a first and second mannanase of the invention, an amylase and a cutinase; or a first and second mannanase of the invention, an amylase and a cellulase; or a first and second mannanase of the invention, an amylase and a hemicellulase; or a first and second mannanase of the invention, a lipase and a pectinase; or a first and second mannanase of the invention, a lipase and a cutinase; or a first and second mannanase of the invention, a lipase and a cellulase; or a first and second mannanase of the invention, a lipase and a hemicellulase. Even more preferably, a first and second mannanase of the invention may be combined with at least three other stain removing enzymes, e.g., a first and second mannanase of the invention, a protease, a lipase and an amylase; or a first and second mannanase of the invention, a protease, an amylase and a pectinase; or a first and second mannanase of the invention, a protease, an amylase and a cutinase; or a first and second mannanase of the invention, a protease, an amylase and a cellulase; or a first and second mannanase of the invention, a protease, an amylase and a hemicellulase; or a first and second mannanase of the invention, an amylase, a lipase and a pectinase; or a first and second mannanase of the invention, an amylase, a lipase and a cutinase; or a first and second mannanase of the invention, an amylase, a lipase and a cellulase; or a first and second mannanase of the invention, an amylase, a lipase and a hemicellulase; or a first and second mannanase of the invention, a protease, a lipase and a pectinase; or a first and second mannanase of the invention, a protease, a lipase and a cutinase; or a first and second mannanase of the invention, a protease, a lipase and a cellulase; or a first and second mannanase of the invention, a protease, a lipase and a hemicellulase. A first and second mannanase according to the present invention may be combined with any of the enzymes selected from the non-exhaustive list comprising: carbohydrases, such as an amylase, a hemicellulase, a pectinase, a cellulase, a xanthanase or a pullulanase, a peptidase, a protease or a lipase.

In a preferred embodiment, a first and second mannanase of the invention is combined with a serine protease, e.g., an S8 family protease such as Savinase®.

In another embodiment of the present invention, a first and second mannanase of the invention may be combined with one or more metalloproteases, such as an M4 metalloprotease, including Neutrase® or Thermolysin. Such combinations may further comprise combinations of the other detergent enzymes as outlined above.

Surfactants

Typically, the detergent composition comprises (by weight of the composition) one or more surfactants in the range of 0% to 50%, preferably from 2% to 40%, more preferably from 5% to 35%, more preferably from 7% to 30%, most preferably from 10% to 25%, even most preferably from 15% to 20%. In a preferred embodiment the detergent is a liquid or powder detergent comprising less than 40%, preferably less than 30%, more preferably less than 25%, even more preferably less than 20% by weight of surfactant. The composition may comprise from 1% to 15%, preferably from 2% to 12%, 3% to 10%, most preferably from 4% to 8%, even most preferably from 4% to 6% of one or more surfactants. Preferred surfactants are anionic surfactants, non-ionic surfactants, cationic surfactants, zwitterionic surfactants, amphoteric surfactants, and mixtures thereof. Preferably, the major part of the surfactant is anionic. Suitable anionic surfactants are well known in the art and may comprise fatty acid carboxylates (soap), branched-chain, linear-chain and random chain alkyl sulfates or fatty alcohol sulfates or primary alcohol sulfates or alkyl benzenesulfonates such as LAS and LAB or phenyl-alknesulfonates or alkenyl sulfonates or alkenyl benzenesulfonates or alkyl ethoxysulfates or fatty alcohol ether sulfates or alpha-olefin sulfonate or dodecenyl/tetradecnylsuccinic acid. The anionic surfactants may be alkoxylated. The detergent composition may also comprise from 1 wt % to 10 wt % of non-ionic surfactant, preferably from 2 wt % to 8 wt %, more preferably from 3 wt % to 7 wt %, even more preferably less than 5 wt % of non-ionic surfactant. Suitable non-ionic surfactants are well known in the art and may comprise alcohol ethoxylates, and/or alkyl ethoxylates, and/or alkylphenol ethoxylates, and/or glucamides such as fatty acid N-glucosyl N-methyl amides, and/or alkyl polyglucosides and/or mono- or diethanolamides or fatty acid amides. The detergent composition may also comprise from 0 wt % to 10 wt % of cationic surfactant, preferably from 0.1 wt % to 8 wt %, more preferably from 0.5 wt % to 7 wt %, even more preferably less than 5 wt % of cationic surfactant. Suitable cationic surfactants are well known in the art and may comprise alkyl quaternary ammonium compounds, and/or alkyl pyridinium compounds and/or alkyl quaternary phosphonium compounds and/or alkyl ternary sulphonium compounds. The composition preferably comprises surfactant in an amount to provide from 100 ppm to 5,000 ppm surfactant in the wash liquor during the laundering process. The composition upon contact with water typically forms a wash liquor comprising from 0.5 g/l to 10 g/l detergent composition. Many suitable surface active compounds are available and fully described in the literature, for example, in "Surface-Active Agents and Detergents", Volumes I and 11, by Schwartz, Perry and Berch.

Builders

The main role of builder is to sequester divalent metal ions (such as calcium and magnesium ions) from the wash solution that would otherwise interact negatively with the surfactant system. Builders are also effective at removing metal ions and inorganic soils from the fabric surface, leading to improved removal of particulate and beverage stains. Builders are also a source of alkalinity and buffer the pH of the wash water to a level of 9.5 to 11. The buffering capacity is also termed reserve alkalinity, and should preferably be greater than 4.

The detergent compositions of the present invention may comprise one or more detergent builders or builder systems. Many suitable builder systems are described in the literature, for example in Powdered Detergents, Surfactant science series volume 71, Marcel Dekker, Inc. Builder may comprise from 0% to 60%, preferably from 5% to 45%, more preferably from 10% to 40%, most preferably from 15% to 35%, even more preferably from 20% to 30% builder by weight of the subject composition. The composition may comprise from 0% to 15%, preferably from 1% to 12%, 2% to 10%, most preferably from 3% to 8%, even most preferably from 4% to 6% of builder by weight of the subject composition.

Builders include, but are not limited to, the alkali metal, ammonium and alkanolammonium salts of polyphosphates (e.g., tripolyphosphate STPP), alkali metal silicates, alkaline earth and alkali metal carbonates, aluminosilicate builders (e.g., zeolite) and polycarboxylate compounds, ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof. Ethanole amines (MEA, DEA, and TEA) may also contribute to the buffering capacity in liquid detergents.

Bleaches

The detergent compositions of the present invention may comprise one or more bleaching agents. In particular powdered detergents may comprise one or more bleaching agents. Suitable bleaching agents include other photobleaches, pre-formed peracids, sources of hydrogen peroxide, bleach activators, hydrogen peroxide, bleach catalysts and mixtures thereof. In general, when a bleaching agent is used, the compositions of the present invention may comprise from about 0.1% to about 50% or even from about 0.1% to about 25% bleaching agent by weight of the subject cleaning composition. Examples of suitable bleaching agents include:

(1) other photobleaches for example Vitamin K3;

(2) preformed peracids: Suitable preformed peracids include, but are not limited to, compounds selected from the group consisting of percarboxylic acids and salts, percarbonic acids and salts, perimidic acids and salts, peroxymonosulfuric acids and salts, for example, Oxone, and mixtures thereof. Suitable percarboxylic acids include hydrophobic and hydrophilic peracids having the formula R—(C═O)O—O-M wherein R is an alkyl group, optionally branched, having, when the peracid is hydrophobic, from 6 to 14 carbon atoms, or from 8 to 12 carbon atoms and, when the peracid is hydrophilic, less than 6 carbon atoms or even less than 4 carbon atoms; and M is a counterion, for example, sodium, potassium or hydrogen;

(3) sources of hydrogen peroxide, for example, inorganic perhydrate salts, including alkali metal salts such as sodium salts of perborate (usually mono- or tetra-hydrate), percarbonate, persulphate, perphosphate, persilicate salts and mixtures thereof. In one aspect of the invention the inorganic perhydrate salts are selected from the group consisting of sodium salts of perborate, percarbonate and mixtures thereof. When employed, inorganic perhydrate salts are typically present in amounts of from 0.05 to 40 wt %, or 1 to 30 wt % of the overall composition and are typically incorporated into such compositions as a crystalline solid that may be coated. Suitable coatings include inorganic salts such as alkali metal silicate, carbonate or borate salts or mixtures thereof, or organic materials such as water-soluble or dispersible polymers, waxes, oils or fatty soaps. Useful bleaching compositions are described in U.S. Pat. Nos. 5,576,282, and 6,306,812;

(4) bleach activators having R—(C═O)-L wherein R is an alkyl group, optionally branched, having, when the bleach activator is hydrophobic, from 6 to 14 carbon atoms, or from 8 to 12 carbon atoms and, when the bleach activator is hydrophilic, less than 6 carbon atoms or even less than 4 carbon atoms; and L is leaving group. Examples of suitable leaving groups are benzoic acid and derivatives thereof—especially benzene sulphonate. Suitable bleach activators include dodecanoyl oxybenzene sulphonate, decanoyl oxybenzene sulphonate, decanoyl oxybenzoic acid or salts thereof, 3,5,5-trimethyl hexanoyloxybenzene sulphonate, tetraacetyl ethylene diamine (TAED) and nonanoyloxybenzene sulphonate (NOBS). Suitable bleach activators are also disclosed in WO 98/17767. While any suitable bleach activator may be employed, in one aspect of the invention the subject cleaning composition may comprise NOBS, TAED or mixtures thereof; and (5) bleach catalysts that are capable of accepting an oxygen atom from peroxyacid and transferring the oxygen atom to an oxidizable substrate are described in WO 2008/007319. Suitable bleach catalysts include, but are not limited to: iminium cations and polyions; iminium zwitterions; modified amines; modified amine oxides; N-sulphonyl imines; N-phosphonyl imines; N-acyl imines; thiadiazole dioxides; perfluoroimines; cyclic sugar ketones and mixtures thereof. The bleach catalyst will typically be comprised in the detergent composition at a level of from 0.0005% to 0.2%, from 0.001% to 0.1%, or even from 0.005% to 0.05% by weight.

When present, the peracid and/or bleach activator is generally present in the composition in an amount of from about 0.1 to about 60 wt %, from about 0.5 to about 40 wt % or even from about 0.6 to about 10 wt % based on the composition. One or more hydrophobic peracids or precursors thereof may be used in combination with one or more hydrophilic peracid or precursor thereof.

The amounts of hydrogen peroxide source and peracid or bleach activator may be selected such that the molar ratio of available oxygen (from the peroxide source) to peracid is from 1:1 to 35:1, or even 2:1 to 10:1.

Adjunct Materials

Dispersants—The detergent compositions of the present invention can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms.

Dye Transfer Inhibiting Agents—The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent whitening agent—The detergent compositions of the present invention will preferably also contain additional components that may tint articles being cleaned, such as fluorescent whitening agent or optical brighteners. Any fluorescent whitening agent suitable for use in a laundry detergent composition may be used in the composition of the present invention.

The most commonly used fluorescent whitening agents are those belonging to the classes of diaminostilbene-sulphonic acid derivatives, diarylpyrazoline derivatives and bisphenyl-distyryl derivatives.

Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4 anilino-s-triazin-6-ylamino) stilbene disulphonate. Tinopal CBS is the disodium salt of 2,2'-bis-(phenyl-styryl) disulphonate.

Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins. Suitable fluorescent brightener levels include lower levels of from about 0.01, from 0.05, from about 0.1 or even from about 0.2 wt % to upper levels of 0.5 or even 0.75 wt %.

Fabric hueing agents—The detergent compositions of the present invention may also include fabric hueing agents such as dyes or pigments which when formulated in detergent compositions can deposit onto a fabric when said fabric is contacted with a wash liquor comprising said detergent compositions thus altering the tint of said fabric through absorption of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO 2005/03274, WO 2005/03275, WO 2005/03276 and EP 1 876 226. The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch.

Soil release polymers—The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series, volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523. Furthermore random graft co-polymers are suitable soil release polymers Suitable graft co-polymers are described in more detail in WO 2007/138054, WO 2006/108856 and WO 2006/113314. Other soil release polymers are substituted polysaccharide structures especially substituted cellulosic structures such as modified cellulose deriviatives such as those described in EP 1 867 808 or WO 2003/040279. Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-redeposition agents—The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, structurants for liquid detergents and/or structure elasticizing agents.

In one aspect the detergent is a compact fluid laundry detergent composition comprising: a) at least about 10%, preferably from 20 to 80% by weight of the composition, of surfactant selected from anionic surfactants, non-ionic surfactants, soap and mixtures thereof; b) from about 1% to about 30%, preferably from 5 to 30%, by weight of the composition, of water; c) from about 1% to about 15%, preferably from 3 to 10% by weight of the composition, of non-aminofunctional solvent; and d) from about 5% to about 20%, by weight of the composition, of a performance additive selected from chelants, soil release polymers, enzymes and mixtures thereof; wherein the compact fluid laundry detergent composition comprises at least one of: (i) the surfactant has a weight ratio of the anionic surfactant to the nonionic surfactant from about 1.5:1 to about 5:1, the surfactant comprises from about 15% to about 40%, by weight of the composition, of anionic surfactant and comprises from about 5% to about 40%, by weight of the composition, of the soap; (ii) from about 0.1% to about 10%, by weight of the composition, of a suds boosting agent selected from suds boosting polymers, cationic surfactants, zwitterionic surfactants, amine oxide surfactants, amphoteric surfactants, and mixtures thereof; and (ii) both (i) and (ii). All the ingredients are described in WO 2007/130562. Further polymers useful in detergent formulations are described in WO 2007/149806.

In another aspect the detergent is a compact granular (powdered) detergent comprising a) at least about 10%, preferably from 15 to 60% by weight of the composition, of surfactant selected from anionic surfactants, non-ionic surfactants, soap and mixtures thereof; b) from about 10 to 80% by weight of the composition, of a builder, preferably from 20% to 60% where the builder may be a mixture of builders selected from i) phosphate builder, preferably less than 20%, more preferably less than 10% even more preferably less than 5% of the total builder is a phosphate builder; ii) a zeolite builder, preferably less than 20%, more preferably less than 10% even more preferably less than 5% of the total builder is a zeolite builder; iii) citrate, preferably 0 to 5% of the total builder is a citrate builder; iv) polycarboxylate, preferably 0 to 5% of the total builder is a polycarboxylate builder v) carbonate, preferably 0 to 30% of the total builder is a carbonate builder and vi) sodium silicates, preferably 0 to 20% of the total builder is a sodium silicate builder; c) from about 0% to 25% by weight of the composition, of fillers such as sulphate salts, preferably from 1% to 15%, more preferably from 2% to 10%, more preferably from 3% to 5% by weight of the composition, of fillers; and d) from about 0.1% to 20% by weight of the composition, of enzymes, preferably from 1% to 15%, more preferably from 2% to 10% by weight of the composition, of enzymes.

The soils and stains that are important for detergent formulators are composed of many different substances, and a range of different enzymes, all with different substrate specificities have been developed for use in detergents both in relation to laundry and hard surface cleaning, such as dishwashing. These enzymes are considered to provide an enzyme detergency benefit, since they specifically improve stain removal in the cleaning process they are applied in as compared to the same process without enzymes. Stain removing enzymes that are known in the art include enzymes such as carbohydrases, amylases, proteases, lipases, cellulases, hemicellulases, xylanases, cutinases, and pectinase.

The cleaning process or the textile care process may for example be a laundry process, a dishwashing process or cleaning of hard surfaces such as bathroom tiles, floors, table tops, drains, sinks and washbasins. Laundry processes can for example be household laundering, but it may also be industrial laundering. Furthermore, the invention relates to a process for laundering of fabrics and/or garments where the process comprises treating fabrics with a washing solution containing a detergent composition, and at least one mannanase of the invention. The cleaning process or a textile care process can for example be carried out in a machine washing process or in a manual washing process. The washing solution can for example be an aqueous washing solution containing a detergent composition.

The fabrics and/or garments subjected to a washing, cleaning or textile care process of the present invention may be conventional washable laundry, for example household laundry. Preferably, the major part of the laundry is garments and fabrics, including knits, woven, denims, non-woven, felts, yarns, and towelling. The fabrics may be cellulose based such as natural cellulosics, including cotton, flax, linen, jute, ramie, sisal or coir or manmade cellulosics (e.g., originating from wood pulp) including viscose/rayon, ramie, cellulose acetate fibers (tricell), lyocell or blends thereof. The fabrics may also be non-cellulose based such as natural polyamides including wool, camel, cashmere, mohair, rabit and silk or synthetic polymer such as nylon, aramid, polyester, acrylic, polypropylen and spandex/elastane, or blends thereof as well as blend of cellulose based and non-cellulose based fibers. Examples of blends are blends of cotton and/or rayon/viscose with one or more companion material such as wool, synthetic fibers (e.g., polyamide fibers, acrylic fibers, polyester fibers, polyvinyl alcohol fibers, polyvinyl chloride fibers, polyurethane fibers, polyurea fibers, aramid fibers), and cellulose-containing fibers (e.g., rayon/viscose, ramie, flax, linen, jute, cellulose acetate fibers, lyocell).

The last few years there has been an increasing interest in replacing components in detergents, which are derived from petrochemicals with renewable biological components such as enzymes and polypeptides without compromising the wash performance. When the components of detergent compositions change new enzyme activities or new enzymes having alternative and/or improved properties compared to the common used detergent enzymes such as proteases, lipases and amylases is needed to achieve a similar or improved wash performance when compared to the traditional detergent compositions.

Typical detergent compositions include various components in addition to the enzymes, these components have different effects, some components like the surfactants lower the surface tension in the detergent, which allows the stain being cleaned to be lifted and dispersed and then washed away, other components like bleach systems removes discolor often by oxidation and many bleaches also have strong bactericidal properties, and are used for disinfecting and sterilizing. Yet other components like builder and chelator softens, e.g., the wash water by removing the metal ions from the liquid.

In a particular embodiment, the invention concerns the use of a composition comprising a first and second mannanase of the invention, wherein said enzyme composition further comprises at least one or more of the following a surfactant, a builder, a chelator or chelating agent, bleach system or bleach component in laundry or dish wash.

In a preferred embodiment of the invention the amount of a surfactant, a builder, a chelator or chelating agent, bleach system and/or bleach component are reduced compared to amount of surfactant, builder, chelator or chelating agent, bleach system and/or bleach component used without the added mannanase of the invention. Preferably the at least one component which is a surfactant, a builder, a chelator or chelating agent, bleach system and/or bleach component is present in an amount that is 1% less, such as 2% less, such as 3% less, such as 4% less, such as 5% less, such as 6% less, such as 7% less, such as 8% less, such as 9% less, such as 10% less, such as 15% less, such as 20% less, such as 25% less, such as 30% less, such as 35% less, such as 40% less, such as 45% less, such as 50% less than the amount of the component in the system without the addition of mannanase of the invention, such as a conventional amount of such component. In one aspect, the first and second mannanase of the invention are used in detergent compositions wherein said composition is free of at least one component which is a surfactant, a builder, a chelator or chelating agent, bleach system or bleach component and/or polymer.

Washing Method

The detergent compositions of the present invention are ideally suited for use in laundry applications. Accordingly, the present invention includes a method for laundering a fabric. The method comprises the steps of contacting a fabric to be laundered with a cleaning laundry solution comprising the detergent composition according to the invention. The fabric may comprise any fabric capable of being laundered in normal consumer use conditions. The solution preferably has a pH of from about 5.5 to about 8. The compositions may be employed at concentrations of from about 100 ppm, preferably 500 ppm to about 15,000 ppm in solution. The water temperatures typically range from about 5° C. to about 90° C., including about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C. and about 90° C. The water to fabric ratio is typically from about 1:1 to about 30:1.

In particular embodiments, the washing method is conducted at a pH of from about 5.0 to about 11.5, or in alternative embodiments, even from about 6 to about 10.5, such as about 5 to about 11, about 5 to about 10, about 5 to about 9, about 5 to about 8, about 5 to about 7, about 5.5 to about 11, about 5.5 to about 10, about 5.5 to about 9, about 5.5 to about 8, about 5.5. to about 7, about 6 to about 11, about 6 to about 10, about 6 to about 9, about 6 to about 8, about 6 to about 7, about 6.5 to about 11, about 6.5 to about 10, about 6.5 to about 9, about 6.5 to about 8, about 6.5 to about 7, about 7 to about 11, about 7 to about 10, about 7 to about 9, or about 7 to about 8, preferably about 5.5 to about 9, and more preferably about 6 to about 8.

In particular embodiments, the washing method is conducted at a degree of hardness of from about 0° dH to about 30° dH, such as about 1° dH, about 2° dH, about 3° dH, about 4° dH, about 5° dH, about 6° dH, about 7° dH, about 8° dH, about 9°dH, about 10° dH, about 11° dH, about 12° dH, about 13° dH, about 14° dH, about 15° dH, about 16° dH, about 17° dH, about 18° dH, about 19° dH, about 20° dH, about 21 dH, about 22° dH, about 23° dH, about 24° dH, about 25° dH, about 26° dH, about 27° dH, about 28° dH, about 29° dH, about 30° dH. Under typical European wash conditions, the degree of hardness is about 15° dH, under typical US wash conditions about 6° dH, and under typical Asian wash conditions, about 3° dH.

The present invention relates to a method of cleaning a fabric, a dishware or hard surface with a detergent composition of the invention comprising a first and second mannanase.

A preferred embodiment concerns a method of cleaning, said method comprising the steps of: contacting an object with a cleaning composition of the invention comprising a first and second mannanase under conditions suitable for cleaning said object. In a preferred embodiment the cleaning composition is a detergent composition and the process is a laundry or a dish wash process.

Still another embodiment relates to a method for removing stains from fabric which comprises contacting said a fabric with a composition of the invention comprising a first and second mannanase under conditions suitable for cleaning said object.

Low Temperature Uses

One embodiment of the invention concerns a method of doing laundry, dish wash or industrial cleaning comprising contacting a surface to be cleaned with a composition of the invention comprising a first and second mannanase, and wherein said laundry, dish wash, industrial or institutional cleaning is performed at a temperature of about 40° C. or below. One embodiment of the invention relates to the use of a composition comprising a first and second mannanase in laundry, dish wash or a cleaning process wherein the temperature in laundry, dish wash, industrial cleaning is about 40° C. or below In another embodiment, the invention concerns the use of a composition comprising a first and second mannanase according to the invention in a protein removing process, wherein the temperature in the protein removing process is about 40° C. or below.

In each of the above-identified methods and uses, the wash temperature is about 40° C. or below, such as about 39° C. or below, such as about 38° C. or below, such as about 37° C. or below, such as about 36° C. or below, such as about 35° C. or below, such as about 34° C. or below, such as about 33° C. or below, such as about 32° C. or below, such as about 31° C. or below, such as about 30° C. or below, such as about 29° C. or below, such as about 28° C. or below, such as about 27° C. or below, such as about 26° C. or below, such as about 25° C. or below, such as about 24° C. or below, such as about 23° C. or below, such as about 22° C. or below, such as about 21° C. or below, such as about 20° C. or below, such as about 19° C. or below, such as about 18° C. or below, such as about 17° C. or below, such as about 16° C. or below, such as about 15° C. or below, such as about 14° C. or below, such as about 13° C. or below, such as about 12° C. or below, such as about 11° C. or below, such as about 10° C. or below, such as about 9° C. or below, such as about 8° C. or below, such as about 7°

C. or below, such as about 6° C. or below, such as about 5° C. or below, such as about 4° C. or below, such as about 3° C. or below, such as about 2° C. or below, such as about 1° C. or below.

In another preferred embodiment, the wash temperature is in the range of about 5-40° C., such as about 5-30° C., about 5-20° C., about 5-10° C., about 10-40° C., about 10-30° C., about 10-20° C., about 15-40° C., about 15-30° C., about 15-20° C., about 20-40° C., about 20-30° C., about 25-40° C., about 25-30° C., or about 30-40° C. In particular preferred embodiments the wash temperature is about 20° C., about 30° C., or about 40° C.

Animal Feed and Animal Feed Additives

The present invention also relates to animal feed and animal feed additives comprising the first and second mannanase of the invention.

In one aspect, the animal feed or animal feed additive comprises the first and second mannanase and one or more components selected from the list consisting of vitamins, minerals and amino acids.

In one aspect, the animal feed or animal feed additive comprises a granule comprising a first and second mannanase and one or more components selected from the list consisting of vitamins, minerals and amino acids.

In one aspect, the animal feed or animal feed additive comprises a liquid formulation comprising a first and second mannanase and one or more components selected from the list consisting of vitamins, minerals and amino acids.

In an embodiment, the animal feed or animal feed additive further comprises one or more additional enzymes selected from the group consisting of acetylxylan esterase, acylglycerol lipase, amylase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lysophospholipase, lysozyme, alpha-mannosidase, phytase, phospholipase A1, phospholipase A2, phospholipase D, protease, pullulanase, pectinesterase, triacylglycerol lipase, xylanase, beta-xylosidase or any combination thereof.

In an embodiment, the animal feed or animal feed additive comprises one or more microbes selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp.*, Carnobacterium* sp.*, Clostridium butyricum, Clostridium* sp.*, Enterococcus faecium, Enterococcus* sp.*, Lactobacillus* sp.*, Lactobacillus acidophilus, Lactobacillus farciminus, Lactobacillus rhamnosus, Lactobacillus reuteri, Lactobacillus salivarius, Lactococcus lactis, Lactococcus* sp.*, Leuconostoc* sp.*, Megasphaera elsdenii, Megasphaera* sp.*, Pediococsus acidilactici, Pediococcus* sp.*, Propionibacterium thoenii, Propionibacterium* sp. and *Streptococcus* sp. or any combination thereof.

Uses

The compositions of the invention may be used in applications where mannan needs to be degraded. Examples of where mannanases could be used are in the production of bioethanol from softwood and palm kernel press cake, for the improvement of animal feed and in the hydrolysis of coffee. Furthermore, guar gum is used in many food products and in the oil and gas industry, so composition comprising the first and second mannanases of the invention could be used in detergents to remove mannan containing stains, for hydraulic fracturing to create subterranean fractures that extend from the borehole into rock formation in order to increase the rate at which fluids can be produced by the formation or for cleaning borehole filtercake. The mannan may thus be used in fracturing of a subterranean formation perpetrated by a well bore or the mannan may be used as a component in borehole filtercake.

In one aspect, a detergent composition or liquid formulation as described above may be used for degrading mannan, such as linear mannan, galactomannan, glucomannan and galactoglucomannan. In one aspect, a detergent composition, granule or liquid formulation as described above may be used in a process for degrading mannan, such as linear mannan, galactomannan, glucomannan and galactoglucomannan.

In one aspect, the detergent composition, granule or liquid formulation may be used for controlling the viscosity of drilling fluids. In one aspect, the detergent composition, granule or liquid formulation may be used in fracturing of a subterranean formation perpetrated by a well bore.

Compositions comprising the first and second mannanases of the invention may be used for preventing, reducing or removing malodor from an item. Thus in one embodiment, the detergent composition or granule described above may be used for preventing, reducing or removing malodor from an item.

Use of Compositions of the Invention in Preventing, Reducing or Removing a Biofilm Biofilm can develop on textiles when microorganisms are present on an item and stick together on the item. Some microorganisms tend to adhere to the surface of items such as textiles forming a biofilm on the surface. The biofilm may be sticky and the adhered microorganisms and/or the biofilm may be difficult to remove. Furthermore, the biofilm adheres soil due to the sticky nature of the biofilm. The commercially available laundry detergent compositions do not remove such adhered microorganisms or biofilm.

The present invention includes the use of a detergent composition, granule or liquid formulation as described above for preventing, reducing or removing a biofilm from a textile item. In one embodiment, the detergent composition, granule or liquid formulation is used for preventing, reducing or removing the stickiness of an item.

Use of Compositions of the Invention in Food Processing and Animal Feed

Several anti-nutritional factors can limit the use of specific plant material in the preparation of animal feed and food for humans. For example, plant material containing oligomannans such as mannan, galactomannan, glucomannan and galactoglucomannan can reduce the digestibility and absorption of nutritional compounds such as minerals, vitamins, sugars and fats by the animals. The negative effects are in particular due to the high viscosity of the mannan-containing polymers and to the ability of the mannan-containing polymers to adsorb nutritional compounds. These effects are reduced using mannan-containing polymers degrading enzymes, namely endo-beta-mannanase enzymes such as the mannanases described herein, which permit a higher proportion of mannan-containing polymers containing cheap plant material to be included in the feed resulting in a reduction of feed costs. Additionally, through the activity of the compositions of the invention, mannan-containing polymers are broken down to simpler sugars, which can be more readily assimilated to provide additional energy. Accordingly, the invention further relates to using the compositions of the invention for processing and/or manufacturing of food or animal feed.

Accordingly, the present invention relates to an animal feed composition and/or animal feed additive composition and/or pet food comprising a mannanase composition of the invention.

The present invention further relates to a method for preparing such animal feed composition and/or animal feed additive composition and/or pet food comprising mixing the composition of the invention with one or more animal feed ingredients and/or animal feed additive ingredients and/or pet food ingredients.

Furthermore, the present invention relates to the use of the composition of the invention in the preparation of an animal feed composition and/or animal feed additive composition and/or pet food.

Use of Compositions of the Invention for Degrading a Cellulosic Material and/or Producing a Fermentation Product The mannanase composition may be used for degrading a cellulosic material, for producing a fermentation product and for fermenting a cellulosic material e.g., in a process for producing a fermentation product, comprising: (a) saccharifying a cellulosic material with an enzyme composition comprising the first and second mannanase; (b) fermenting the saccharified cellulosic material with one or more fermenting microorganisms to produce the fermentation product; and (c) recovering the fermentation product from the fermentation. The cellulosic material may be pretreated before saccharification. In one embodiment, the enzyme composition comprises one or more enzymes selected from the group consisting of cellulase, AA9 polypeptide (Auxiliary Activity 9), hemicellulase, esterase, expansin, ligninolytic enzyme, oxidoreductase, pectinase, protease, and swollenin.

In another embodiment, the invention relates to a process of fermenting a cellulosic material, comprising: fermenting the cellulosic material with one or more fermenting microorganisms, wherein the cellulosic material is saccharified with an enzyme composition of the invention. The cellulosic material may be pretreated before saccharification. In one embodiment, the enzyme composition comprises one or more enzymes selected from the group consisting of cellulase, AA9 polypeptide, hemicellulase, esterase, expansin, ligninolytic enzyme, oxidoreductase, pectinase, protease, and swollenin.

Use of Compositions of the Invention for Fermented Beverages

In one aspect, the invention relates to a method of preparing a fermented beverage, such as beer or wine, comprising mixing the mannanase composition of the invention with malt and/or adjunct.

Another aspect concerns a method of providing a fermented beverage comprising the step of contacting a mash and/or a wort with the mannanase composition of the invention, e.g. in the form of a granule or a liquid formulation.

In the context of the present invention, the term "fermented beverage" is meant to comprise any beverage such as wine or beer produced by a method comprising a fermentation process, such as a microbial, bacterial and/or yeast fermentation.

In an aspect of the invention the fermented beverage is beer. The term "beer" is meant to comprise any fermented wort produced by fermentation/brewing of a starch-containing plant material. Often, beer is produced from malt or adjunct, or any combination of malt and adjunct as the starch-containing plant material. As used herein the term "malt" is understood as any malted cereal grain, such as malted barley or wheat.

As used herein the term "adjunct" refers to any starch and/or sugar containing plant material which is not malt, such as barley or wheat malt. As examples of adjuncts, mention can be made of materials such as common corn grits, refined corn grits, brewer's milled yeast, rice, sorghum, refined corn starch, barley, barley starch, dehusked barley, wheat, wheat starch, torrified cereal, cereal flakes, rye, oats, potato, tapioca, cassava and syrups, such as corn syrup, sugar cane syrup, inverted sugar syrup, barley and/or wheat syrups, and the like may be used as a source of starch As used herein, the term "mash" refers to an aqueous slurry of any starch and/or sugar containing plant material such as grist, e.g. comprising crushed barley malt, crushed barley, and/or other adjunct or a combination hereof, mixed with water later to be separated into wort and spent grains.

As used herein, the term "wort" refers to the unfermented liquor run-off following extracting the grist during mashing.

Use of Compositions of the Invention for Treating Coffee Extracts

The mannanase composition of the invention may also be used for hydrolyzing galactomannans present in liquid coffee extracts. In certain preferred embodiments, the mannanase composition of the invention is used to inhibit gel formation during freeze drying of liquid coffee extracts. The decreased viscosity of the extract reduces the energy consumption during drying. In certain other preferred embodiments, the mannanase composition of the invention is applied in an immobilized form in order to reduce enzyme consumption and avoid contamination of the coffee extract. This use is further disclosed in EP 676 145.

In general terms the coffee extract is incubated in the presence of a mannanase composition of the invention under conditions suitable for hydrolyzing galactomannans present in liquid coffee extract.

Thus in one embodiment, then invention relates to a process for producing a coffee extract, comprising the steps:
(a) providing roast and ground coffee beans;
(b) adding to said coffee beans water and the mannanase composition of the invention;
(c) incubating to make an aqueous coffee extract; and
(d) separating the coffee extract from the extracted coffee beans.

Use of Compositions of the Invention in Bakery Food Products

In another aspect, the invention relates to a method of preparing baked products comprising adding the mannanase composition of the invention to a dough, followed by baking the dough.

Examples of baked products are well known to those skilled in the art and include breads, rolls, puff pastries, sweet fermented doughs, buns, cakes, crackers, cookies, biscuits, waffles, wafers, tortillas, breakfast cereals, extruded products, and the like.

The mannanase composition of the invention may be added to dough as part of a bread improver composition. Bread improvers are compositions containing a variety of ingredients, which improve dough properties and the quality of bakery products, e.g. bread and cakes. Bread improvers are often added in industrial bakery processes because of their beneficial effects e.g. the dough stability and the bread texture and volume. Bread improvers usually contain fats and oils as well as additives like emulsifiers, enzymes, antioxidants, oxidants, stabilizers and reducing agents. In addition to the mannanase composition of the invention, other enzymes which may also be present in the bread improver including amylases, hemicellulases, amylolytic complexes, lipases, proteases, xylanases, pectinases, pullulanases, non-starch polysaccharide degrading enzymes and redox enzymes like glucose oxidase, lipoxygenase or ascorbic acid oxidase.

In one aspect, the mannanase composition of the invention may be added to dough as part of a bread improver composition which also comprises a glucomannan and/or galactomannan source such as konjac gum, guar gum, locust bean gum (*Ceratonia siliqua*), copra meal, ivory nut mannan (*Phyteleohas macrocarpa*), seaweed mannan extract, coconut meal, and the cell wall of brewers yeast (may be dried, or used in the form of brewers yeast extract).

A further aspect of the invention relates to the use of the mannanase composition in dough to improve dough tolerance, flexibility and stickiness. Preferably the dough to which the mannanase of the invention may be added is not a pure wheat flour dough, but comprises bran or oat, rice, millet, maize, or legume flour in addition to or instead of pure wheat flour.

A yet further aspect of the invention relates to the use of the mannanase composition of the invention in dough to improve the crumb structure and retard staling in the final baked product, such as bread.

Use of Compositions of the Invention in Dairy Food Products

In one aspect, the mannanase composition of the invention may be added to milk or any other dairy product to which has also been added a glucomannan and/or galactomannan. Typical glucomannan and/or galactomannan sources are listed above in the bakery aspects, and include guar or konjac gum. The combination of the mannanase of the invention with a glucomannan and/or galactomannan releases mannanase hydrolysates (mannooligosaccharides) which act as soluble prebiotics by promoting the selective growth and proliferation of probiotic bacteria (especially Bifidobacteria and *Lactobacillus* lactic acid bacteria) commonly associated with good health when found at favourable population densities in the large intestine or colon.

In one aspect, the invention relates to a method of preparing milk or dairy products comprising adding to the milk or dairy product (a) glucomannan, galactomannan and/or galactoglucomannan and (b) a mannanase composition of the invention.

In one aspect the mannanase composition of the invention is used in combination with any glucomannan or galactomannan prior to or following addition to a dairy based foodstuff to produce a dairy based foodstuff comprising prebiotic mannan hydrolysates. In a further aspect of the invention the thus produced mannooligosacharide-containing dairy product is capable of increasing the population of beneficial human intestinal microflora, and in a yet further aspect the dairy based foodstuff may comprise the mannanase composition of the invention together with any source of glucomannan and/or galactomannan and/or galactoglucomannan, and a dose sufficient for inoculation of at least one strain of bacteria (such as Bifidobacteria or *Lactobacillus*) known to be of benefit in the human large intestine. Preferably said dairy-based foodstuff is a yoghurt or milk drink.

Use of Compositions of the Invention for Paper Pulp Bleaching

The mannanase composition of the invention may further be used in the enzyme aided bleaching of paper pulps such as chemical pulps, semi-chemical pulps, kraft pulps, mechanical pulps or pulps prepared by the sulfite method. Thus, the invention relates to a method of bleaching paper pulps comprising incubating the paper pulp with a mannanase composition of the invention.

In some embodiments, the pulps are chlorine free pulps bleached with oxygen, ozone, peroxide or peroxyacids. In some embodiments, the mannanase composition of the invention is used in enzyme aided bleaching of pulps produced by modified or continuous pulping methods that exhibit low lignin contents. In some other embodiments, the mannanase composition is applied alone or preferably in combination with xylanase and/or endoglucanase and/or alpha-galactosidase and/or cellobiohydrolase enzymes.

The invention is further defined in the following paragraphs:

Paragraph 1. A composition comprising at least a first and a second mannanase, wherein:
  (A) said first mannanase is a glycoside hydrolase family 5 mannanase or a variant or fragment thereof having mannanase activity; and
  (B) said second mannanase is a glycoside hydrolase family 26 mannanase or a variant or fragment thereof having mannanase activity.

Paragraph 2. The composition of paragraph 1, wherein said first mannanase is a variant of a parent mannanase comprising at least one modification at a position corresponding to a position selected from positions 1,2, 3, 4, 5, 6, 8, 9, 10, 11, 13, 14, 15, 16, 17, 18, 19, 21, 23, 30, 32, 33, 34, 35, 37, 38, 39, 41, 44, 45, 47, 57, 59, 60, 62, 63, 65, 66, 67, 68, 70, 71, 74, 77, 78, 79, 80, 81, 82, 83, 93, 95, 96, 97, 98, 100, 104, 107, 108, 110, 111, 114, 115, 116, 118, 119, 131, 132, 133, 135, 136, 139, 142, 143, 146, 147, 150, 152, 154, 164, 167, 169, 172, 173, 174, 175, 176, 177, 180, 181, 183, 184, 185, 196, 199, 200, 201, 202, 203, 205, 206, 210, 212, 213, 214, 215, 226, 228, 229, 230, 234, 235, 241, 242, 243, 244, 245, 250, 254, 257, 258, 259, 260, 261, 262, 266, 267, 268, 270, 271, 272, 273, 276, 279, 280, 283, 285, 286, 288, 289, 290, 292, 293, 294, 295, 296, 298, 299, 300 and 301, wherein:
  numbering is according to SEQ ID NO: 2,
  each modification is independently a substitution or a deletion,
  the variant has mannanase activity, and
  the variant has at least 59%, e.g. at least 60%, at least 61%, at least 62%, at least 63%, at least 65%, at least 70%, at least 75%, at least 80%, at least 85%, at least 90%, at least 95%, at least 96%, at least 97%, at least 98%, or at least 99%, but less than 100% sequence identity to the mature polypeptide of SEQ ID NO: 2.

Paragraph 3. The composition of paragraph 1 or 2, wherein said second mannanase is selected from the group consisting of:
  (a) a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, or SEQ ID NO: 16;
  (b) a variant of the polypeptide in (a), wherein the variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28 or 29 positions compared to SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, or SEQ ID NO: 16;

(c) a polypeptide comprising the polypeptide of (a) or (b) and an N-terminal and/or C-terminal His-tag and/or HQ-tag;

(d) a polypeptide comprising the polypeptide of (a) or (b) and an N-terminal and/or C-terminal extension of up to 10 amino acids, e.g. 1, 2, 3, 4, 5, 6, 7, 8, 9 or 10 amino acids; and (e) a fragment of the polypeptide of (a) or (b) having mannanase activity and having at least 90% of the length of the mature polypeptide of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, or SEQ ID NO: 16.

Paragraph 4. The composition of any of the preceding paragraphs, wherein said first mannanase comprises a substitution in at least one of positions 3, 37, 47, 77, 82, 83, 93, 98, 116, 135, 136, 241, 257, 258, 260, 288, 294 and 295 wherein numbering is according to SEQ ID NO: 2.

Paragraph 5. The composition of paragraph 4, wherein said first mannanase comprises at least two substitutions compared to said parent mannanase and is selected from the group consisting of:
(a) a variant comprising a first substitution in at least one amino acid position selected from positions 260, 288, 294 and 295, and a second substitution in at least one other position in said variant; and
(b) a variant comprising substitutions in any two or more positions selected from positions 3, 37, 47, 77, 82, 83, 93, 98, 116, 135, 136, 241, 257 and 258.

Paragraph 6. The composition of paragraph 5, wherein said first mannanase is a variant (a) comprising a second substitution in at least one position selected from positions 1, 2, 3, 4, 5, 6, 8, 11, 13, 14, 18, 30, 32, 33, 34, 35, 37, 41, 45, 47, 57, 59, 60, 63, 65, 70, 71, 74, 77, 78, 80, 82, 83, 93, 95, 97, 98, 100, 104, 108, 111, 114, 116, 118, 119, 131, 133, 135, 136, 139, 142, 143, 150, 169, 172, 174, 176, 177, 180, 183, 184, 185, 196, 200, 202, 203, 205, 210, 213, 228, 229, 234, 235, 241, 243, 244, 250, 254, 257, 262, 266, 268, 270, 272, 273, 276, 279, 280, 283, 286, 290, 296, and 298, wherein numbering is according to SEQ ID NO: 2.

Paragraph 7. The composition of paragraph 6, wherein said first mannanase is a variant (a) comprising a second substitution in at least one position selected from positions 14, 37, 47, 77, 81, 82, 83, 93, 98, 116, 135, 136, 241, 242, 257 and 258 of the polypeptide of SEQ ID NO: 2.

Paragraph 8. The composition according to any of paragraphs 5-7, wherein said first mannanase is a variant (a) comprising at least two substitutions in positions selected from the group of positions: 14+260, 14+288, 14+294, 14+295, 37+260, 37+288, 37+294, 37+295, 47+260, 47+288, 47+294, 47+295, 77+260, 77+288, 77+294, 77+295, 81+260, 81+288, 81+294, 81+295, 82+260, 82+288, 82+294, 82+295, 83+260, 83+288, 83+294, 83+295, 93+260, 93+288, 93+294, 93+295, 98+260, 98+288, 98+294, 98+295, 116+260, 116+288, 116+294, 116+295, 135+260, 135+288, 135+294, 135+295, 136+260, 136+288, 136+294, 136+295, 241+260, 241+288, 241+294, 241+295, 242+260, 242+288, 242+294, 242+295, 257+260, 257+288, 257+294, 257+295, 258+260, 258+288, 258+294, 258+295 and 260+288, wherein numbering is according to SEQ ID NO: 2.

Paragraph 9. The composition according to any one of paragraphs 5-8, wherein said first mannanase is a variant (a) comprising a second and optionally a third substitution in one or both of positions 93 and 136 of the polypeptide of SEQ ID NO: 2.

Paragraph 10. The composition according to any one of the preceding paragraphs, wherein said first mannanase comprises at least two substitutions selected from A1G, A1V, N2E, S3P, G4D, F5H, Y6H, Y6M, Y6F, Y6W, Y6H, S8T, S8P, S8R, T11K, T11R, Y13F, D14S, D14K, N18V, N18R, A30T, Y32F, Y32W, K33Q, D34G, Q35L, T37P, E41V, E41N, N45G, G47S, G47A, D57N, G59Q, Q60R, K63R, K63Q, D65E, R70K, N71S, S74K, E77T, E77N, D78G, H80K, V82R, V82I, V82S, A83P, A83S, Y93Q, Y93A, S95D, A97R, S98P, S98D, N100Y, D104A, D104G, E108S, S111A, S111K, S111R, I114Q, I114M, I114W, K116R, D118K, T119R, S131T, E133R, E133Q, D135P, A136P, D139A, D139R, K142M, K142V, K142S, K142R, Q143R, N150T, N150R, N150S, Q169A, Q169R, Q169K, H172R, Y174R, Y174L, Y174W, Y174F, R176Q, E177S, E177Y, N180R, P183T, P183G, Q184E, Q184K, R185G, Y196W, Y196F, N200T, S202R, Q203T, R205K, R210L, R210G, R210M, N213V, N213D, T228S, N229D, E234F, E234Y, A235K, A235R, S241C, Q243K, Q243E, R244K, R244V, A250G, K254Y, G257W, G257E, G257A, G257G, W260F, Y262F, S266A, D268N, A270D, N272M, N272T, N273E, N273D, A276E, A276W, A276D, N279D, N279E, T280L, N283W, N283H, Y286W, Y286F, L288I, E290A, L294P, L294K, L294I, L294R, L294V, L294H, S295K, S295V, S295P, S295L, S295R, S295A, S295N, S295M, S295I, T296S and F298Y.

Paragraph 11. The composition of paragraph 5, wherein said first mannanase is a variant (b) comprising at least two substitutions selected from the group consisting of: S3P, T37P, G47A, G47S, E77T, V82I, V82R, A83P, Y93Q, Y93C, Y93A, Y93F, Y93I, Y93R, S98P, K116R, D135P, A136P, S241C, G257W, G257E, G257L, G257A, G257S, G257Y, G257F and P258Q.

Paragraph 12. The composition of any one of the preceding paragraphs, wherein said first mannanase is a variant comprising the substitutions Y93Q and A136P, and two or more substitutions selected from the group consisting of W260F, L288I, L294P and S295V.

Paragraph 13. The composition according to any one of the preceding paragraphs, wherein said parent mannanase of said first mannanase is a mannanase having at least 59%, e.g. at least 60%, at least 61%, at least 62%, at least 63%, at least 65%, at least 70%, at least 75%, at least 80%, at least 85%, at least 90%, at least 95%, at least 96%, at least 97%, at least 98%, at least 99%, or 100% sequence identity to the polypeptide of SEQ ID NO: 1 or SEQ ID NO: 2.

Paragraph 14. The composition of paragraph 13, wherein said parent mannanase comprises or consists of the polypeptide of SEQ ID NO: 1 or SEQ ID NO: 2.

Paragraph 15. The composition of paragraph 1, wherein said first mannanase comprises or consists of a mannanase having at least 59%, e.g. at least 60%, at least 61%, at least 62%, at least 63%, at least 65%, at least 70%, at least 75%, at least 80%, at least 85%, at least 90%, at least 95%, at least 96%, at least 97%, at least 98%, at least 99%, or 100% sequence identity to the polypeptide of SEQ ID NO: 17, SEQ ID NO: 18, SEQ ID NO: 19, SEQ ID NO: 20, SEQ ID NO: 21, SEQ ID NO: 22, or SEQ ID NO: 23.

Paragraph 16. The composition of paragraph 1, wherein said first mannanase comprises or consists of a mannanase having at least 59%, e.g. at least 60%, at least 61%, at least 62%, at least 63%, at least 65%, at least 70%, at least 75%, at least 80%, at least 85%, at least 90%, at least 95%, at least 96%, at least 97%, at least 98%, at least 99%, or 100% sequence identity to the polypeptide of SEQ ID NO: 17.

Paragraph 17. The composition of paragraph 1, wherein said first mannanase comprises or consists of a mannanase having at least 59%, e.g. at least 60%, at least 61%, at least 62%, at least 63%, at least 65%, at least 70%, at least 75%, at least 80%, at least 85%, at least 90%, at least 95%, at least 96%, at least 97%, at least 98%, at least 99%, or 100% sequence identity to the polypeptide of SEQ ID NO: 18.

Paragraph 18. The composition of paragraph 1, wherein said first mannanase comprises or consists of a mannanase having at least 59%, e.g. at least 60%, at least 61%, at least 62%, at least 63%, at least 65%, at least 70%, at least 75%, at least 80%, at least 85%, at least 90%, at least 95%, at least 96%, at least 97%, at least 98%, at least 99%, or 100% sequence identity to the polypeptide of SEQ ID NO: 19.

Paragraph 19. The composition of paragraph 1, wherein said first mannanase comprises or consists of a mannanase having at least 59%, e.g. at least 60%, at least 61%, at least 62%, at least 63%, at least 65%, at least 70%, at least 75%, at least 80%, at least 85%, at least 90%, at least 95%, at least 96%, at least 97%, at least 98%, at least 99%, or 100% sequence identity to the polypeptide of SEQ ID NO: 20.

Paragraph 20. The composition of paragraph 1, wherein said first mannanase comprises or consists of a mannanase having at least 59%, e.g. at least 60%, at least 61%, at least 62%, at least 63%, at least 65%, at least 70%, at least 75%, at least 80%, at least 85%, at least 90%, at least 95%, at least 96%, at least 97%, at least 98%, at least 99%, or 100% sequence identity to the polypeptide of SEQ ID NO: 21.

Paragraph 21. The composition of paragraph 1, wherein said first mannanase comprises or consists of a mannanase having at least 59%, e.g. at least 60%, at least 61%, at least 62%, at least 63%, at least 65%, at least 70%, at least 75%, at least 80%, at least 85%, at least 90%, at least 95%, at least 96%, at least 97%, at least 98%, at least 99%, or 100% sequence identity to the polypeptide of SEQ ID NO: 22.

Paragraph 22. The composition of paragraph 1, wherein said first mannanase comprises or consists of a mannanase having at least 59%, e.g. at least 60%, at least 61%, at least 62%, at least 63%, at least 65%, at least 70%, at least 75%, at least 80%, at least 85%, at least 90%, at least 95%, at least 96%, at least 97%, at least 98%, at least 99%, or 100% sequence identity to the polypeptide of SEQ ID NO: 23.

Paragraph 23. The composition of any one of paragraphs 1-22, wherein said second mannanase is selected from the group consisting of
(a) a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 3;
(b) a variant of the polypeptide in (a), wherein said variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28 or 29 positions compared to SEQ ID NO: 3;
(c) a polypeptide comprising the polypeptide of (a) or (b) and an N-terminal and/or C-terminal His-tag and/or HQ-tag;
(d) a polypeptide comprising the polypeptide of (a) or (b) and an N-terminal and/or C-terminal extension of up to 10 amino acids, e.g. 1, 2, 3, 4, 5, 6, 7, 8, 9 or 10 amino acids; and
(e) a fragment of the polypeptide of (a) or (b) having mannanase activity and having at least 90% of the length of the mature polypeptide of SEQ ID NO: 3.

Paragraph 24. The composition of any one of paragraphs 1-22, wherein said second mannanase is selected from the group consisting of
(a) a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 4;
(b) a variant of the polypeptide in (a), wherein said variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28 or 29 positions compared to SEQ ID NO: 4;
(c) a polypeptide comprising the polypeptide of (a) or (b) and an N-terminal and/or C-terminal His-tag and/or HQ-tag;
(d) a polypeptide comprising the polypeptide of (a) or (b) and an N-terminal and/or C-terminal extension of up to 10 amino acids, e.g. 1, 2, 3, 4, 5, 6, 7, 8, 9 or 10 amino acids; and
(e) a fragment of the polypeptide of (a) or (b) having mannanase activity and having at least 90% of the length of the mature polypeptide of SEQ ID NO: 4.

Paragraph 25. The composition of any one of paragraphs 1-22, wherein said second mannanase is selected from the group consisting of:
(a) a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 5;
(b) a variant of the polypeptide in (a), wherein said variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28 or 29 positions compared to SEQ ID NO: 5;
(c) a polypeptide comprising the polypeptide of (a) or (b) and an N-terminal and/or C-terminal His-tag and/or HQ-tag;
(d) a polypeptide comprising the polypeptide of (a) or (b) and an N-terminal and/or C-terminal extension of up to 10 amino acids, e.g. 1, 2, 3, 4, 5, 6, 7, 8, 9 or 10 amino acids; and
(e) a fragment of the polypeptide of (a) or (b) having mannanase activity and having at least 90% of the length of the mature polypeptide of SEQ ID NO: 5.

Paragraph 26. The composition of any one of paragraphs 1-22, wherein said second mannanase is selected from the group consisting of:
(a) a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 6;
(b) a variant of the polypeptide in (a), wherein said variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28 or 29 positions compared to SEQ ID NO: 6;
(c) a polypeptide comprising the polypeptide of (a) or (b) and an N-terminal and/or C-terminal His-tag and/or HQ-tag;
(d) a polypeptide comprising the polypeptide of (a) or (b) and an N-terminal and/or C-terminal extension of up to 10 amino acids, e.g. 1, 2, 3, 4, 5, 6, 7, 8, 9 or 10 amino acids; and
(e) a fragment of the polypeptide of (a) or (b) having mannanase activity and having at least 90% of the length of the mature polypeptide of SEQ ID NO: 6.

Paragraph 27. The composition of any one of paragraphs 1-22, wherein said second mannanase is selected from the group consisting of:
(a) a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 7;
(b) a variant of the polypeptide in (a), wherein said variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28 or 29 positions compared to SEQ ID NO: 7;
(c) a polypeptide comprising the polypeptide of (a) or (b) and an N-terminal and/or C-terminal His-tag and/or HQ-tag;
(d) a polypeptide comprising the polypeptide of (a) or (b) and an N-terminal and/or C-terminal extension of up to 10 amino acids, e.g. 1, 2, 3, 4, 5, 6, 7, 8, 9 or 10 amino acids; and
(e) a fragment of the polypeptide of (a) or (b) having mannanase activity and having at least 90% of the length of the mature polypeptide of SEQ ID NO: 7.

Paragraph 28. The composition of any one of paragraphs 1-22, wherein said second mannanase is selected from the group consisting of:
(a) a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 8;
(b) a variant of the polypeptide in (a), wherein said variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28 or 29 positions compared to SEQ ID NO: 8;
(c) a polypeptide comprising the polypeptide of (a) or (b) and an N-terminal and/or C-terminal His-tag and/or HQ-tag;
(d) a polypeptide comprising the polypeptide of (a) or (b) and an N-terminal and/or C-terminal extension of up to 10 amino acids, e.g. 1, 2, 3, 4, 5, 6, 7, 8, 9 or 10 amino acids; and
(e) a fragment of the polypeptide of (a) or (b) having mannanase activity and having at least 90% of the length of the mature polypeptide of SEQ ID NO: 8.

Paragraph 29. The composition of any one of paragraphs 1-22, wherein said second mannanase is selected from the group consisting of:
(a) a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 9;
(b) a variant of the polypeptide in (a), wherein said variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28 or 29 positions compared to SEQ ID NO: 9;
(c) a polypeptide comprising the polypeptide of (a) or (b) and an N-terminal and/or C-terminal His-tag and/or HQ-tag;
(d) a polypeptide comprising the polypeptide of (a) or (b) and an N-terminal and/or C-terminal extension of up to 10 amino acids, e.g. 1, 2, 3, 4, 5, 6, 7, 8, 9 or 10 amino acids; and
(e) a fragment of the polypeptide of (a) or (b) having mannanase activity and having at least 90% of the length of the mature polypeptide of SEQ ID NO: 9.

Paragraph 30. The composition of any one of paragraphs 1-22, wherein said second mannanase is selected from the group consisting of:
(a) a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 10;
(b) a variant of the polypeptide in (a), wherein said variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28 or 29 positions compared to SEQ ID NO: 10;
(c) a polypeptide comprising the polypeptide of (a) or (b) and an N-terminal and/or C-terminal His-tag and/or HQ-tag;
(d) a polypeptide comprising the polypeptide of (a) or (b) and an N-terminal and/or C-terminal extension of up to 10 amino acids, e.g. 1, 2, 3, 4, 5, 6, 7, 8, 9 or 10 amino acids; and
(e) a fragment of the polypeptide of (a) or (b) having mannanase activity and having at least 90% of the length of the mature polypeptide of SEQ ID NO: 10.

Paragraph 31. The composition of any one of paragraphs 1-22, wherein said second mannanase is selected from the group consisting of:
(a) a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 11;
(b) a variant of the polypeptide in (a), wherein said variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28 or 29 positions compared to SEQ ID NO: 11;
(c) a polypeptide comprising the polypeptide of (a) or (b) and an N-terminal and/or C-terminal His-tag and/or HQ-tag;
(d) a polypeptide comprising the polypeptide of (a) or (b) and an N-terminal and/or C-terminal extension of up to 10 amino acids, e.g. 1, 2, 3, 4, 5, 6, 7, 8, 9 or 10 amino acids; and
(e) a fragment of the polypeptide of (a) or (b) having mannanase activity and having at least 90% of the length of the mature polypeptide of SEQ ID NO: 11.

Paragraph 32. The composition of any one of paragraphs 1-22, wherein said second mannanase is selected from the group consisting of:
(a) a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 12;
(b) a variant of the polypeptide in (a), wherein said variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28 or 29 positions compared to SEQ ID NO: 12;
(c) a polypeptide comprising the polypeptide of (a) or (b) and an N-terminal and/or C-terminal His-tag and/or HQ-tag;
(d) a polypeptide comprising the polypeptide of (a) or (b) and an N-terminal and/or C-terminal extension of up to 10 amino acids, e.g. 1, 2, 3, 4, 5, 6, 7, 8, 9 or 10 amino acids; and
(e) a fragment of the polypeptide of (a) or (b) having mannanase activity and having at least 90% of the length of the mature polypeptide of SEQ ID NO: 12.

Paragraph 33. The composition of any one of paragraphs 1-22, wherein said second mannanase is selected from the group consisting of:
(a) a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 13;
(b) a variant of the polypeptide in (a), wherein said variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28 or 29 positions compared to SEQ ID NO: 13;
(c) a polypeptide comprising the polypeptide of (a) or (b) and an N-terminal and/or C-terminal His-tag and/or HQ-tag;
(d) a polypeptide comprising the polypeptide of (a) or (b) and an N-terminal and/or C-terminal extension of up to 10 amino acids, e.g. 1, 2, 3, 4, 5, 6, 7, 8, 9 or 10 amino acids; and
(e) a fragment of the polypeptide of (a) or (b) having mannanase activity and having at least 90% of the length of the mature polypeptide of SEQ ID NO: 13.

Paragraph 34. The composition of any one of paragraphs 1-22, wherein said second mannanase is selected from the group consisting of:
(a) a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 14;
(b) a variant of the polypeptide in (a), wherein said variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28 or 29 positions compared to SEQ ID NO: 14;
(c) a polypeptide comprising the polypeptide of (a) or (b) and an N-terminal and/or C-terminal His-tag and/or HQ-tag;
(d) a polypeptide comprising the polypeptide of (a) or (b) and an N-terminal and/or C-terminal extension of up to 10 amino acids, e.g. 1, 2, 3, 4, 5, 6, 7, 8, 9 or 10 amino acids; and
(e) a fragment of the polypeptide of (a) or (b) having mannanase activity and having at least 90% of the length of the mature polypeptide of SEQ ID NO: 14.

Paragraph 35. The composition of any one of paragraphs 1-22, wherein said second mannanase is selected from the group consisting of:
(a) a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 15;
(b) a variant of the polypeptide in (a), wherein said variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28 or 29 positions compared to SEQ ID NO: 15;
(c) a polypeptide comprising the polypeptide of (a) or (b) and an N-terminal and/or C-terminal His-tag and/or HQ-tag;
(d) a polypeptide comprising the polypeptide of (a) or (b) and an N-terminal and/or C-terminal extension of up to 10 amino acids, e.g. 1, 2, 3, 4, 5, 6, 7, 8, 9 or 10 amino acids; and
(e) a fragment of the polypeptide of (a) or (b) having mannanase activity and having at least 90% of the length of the mature polypeptide of SEQ ID NO: 15.

Paragraph 36. The composition of any one of paragraphs 1-22, wherein said second mannanase is selected from the group consisting of:
(a) a polypeptide having mannanase activity and at least 80%, e.g. at least 85%, at least 90%, at least 91%, at least 92%, at least 93%, at least 94%, at least 95%, at least 96%, at least 97%, at least 98%, at least 99% or 100% sequence identity to SEQ ID NO: 16;
(b) a variant of the polypeptide in (a), wherein said variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28 or 29 positions compared to SEQ ID NO: 16;

(c) a polypeptide comprising the polypeptide of (a) or (b) and an N-terminal and/or C-terminal His-tag and/or HQ-tag;

(d) a polypeptide comprising the polypeptide of (a) or (b) and an N-terminal and/or C-terminal extension of up to 10 amino acids, e.g. 1, 2, 3, 4, 5, 6, 7, 8, 9 or 10 amino acids; and (e) a fragment of the polypeptide of (a) or (b) having mannanase activity and having at least 90% of the length of the mature polypeptide of SEQ ID NO: 16.

Paragraph 37. The composition of any one of the preceding paragraphs, wherein said composition has a weight ratio between said first mannanase and said second mannanase is from about 2:98 to about 98:2, e.g. from about 10:90 to about 90:10, from about 20:80 to about 80:20, from about 30:70 to about 70:30, or from about 40:60 to about 60:40.

Paragraph 38. The composition of paragraph 37, wherein said weight ratio between said first mannanase and said second mannanase is from about 5:95 to about 50:50, e.g. from about 10:90 to about 40:60, or from about 20:80 to about 30:70.

Paragraph 39. The composition of paragraph 37, wherein said weight ratio between said first mannanase and said second mannanase is from about 95:5 to about 50:50, e.g. from about 90:10 to about 60:40, or from about 80:20 to about 70:30.

Paragraph 40. A detergent composition, comprising a first mannanase and a second mannanase as defined in any of claims 1-39 and at least one detergent component.

Paragraph 41. The detergent composition of paragraph 40, comprising at least one detergent component selected from the group consisting of surfactants, bleaching systems, chelating agents, stabilizing agents, hydrotophes, builders, co-builders, bleach activators, polymers and fabric-hueing agents.

Paragraph 42. The detergent composition of paragraph 41, comprising at least one surfactant selected from the group consisting of anionic surfactants, cationic surfactants, nonionic surfactants, and amphoteric surfactants.

Paragraph 43. The detergent composition of any one of paragraphs 40-42, comprising at least one additional enzyme, such as a protease, amylase or lipase.

Paragraph 44. The detergent composition of any one of paragraphs 40-43, wherein the composition is a laundry detergent composition or a hard surface cleaning composition such as a dish wash detergent composition, e.g. in the form of a liquid, gel, powder, granulate, paste or unit dose package.

Paragraph 45. Use of a detergent composition according to any one of paragraphs 40-44 for cleaning laundry or a hard surface such as dish wash.

Paragraph 46. A method of cleaning a textile or a hard surface, comprising contacting the textile or hard surface with a detergent composition according to any one of paragraphs 40-44.

Paragraph 47. Use of a composition comprising a first and second mannanase according to any one of paragraphs 1-39 or a detergent composition according to any one of paragraphs 40-44 for preventing, reducing or removing a biofilm from a surface.

Paragraph 48. A method for preventing, reducing or removing a biofilm from a surface, comprising contacting the surface with a composition comprising a first and second mannanase according to any one of paragraphs 1-39 or a detergent composition according to any one of paragraphs 40-44.

Paragraph 49. An animal feed composition, animal feed additive composition or pet food, comprising a first mannanase and a second mannanase as defined in any one of paragraphs 1-39 and one or more animal feed ingredients, animal feed additive ingredients and/or pet food ingredients.

Paragraph 50. Use of a composition comprising a first mannanase and a second mannanase according to any one of paragraphs 1-39 for degrading a cellulosic material and/or producing a fermentation product.

Paragraph 51. A method for degrading a cellulosic material and/or producing a fermentation product, comprising (a) saccharifying a cellulosic material with a composition comprising a first and second mannanase as defined in any one of paragraphs 1-39; (b) fermenting the saccharified cellulosic material with one or more fermenting microorganisms to produce the fermentation product; and (c) recovering the fermentation product from the fermentation product.

Paragraph 52. Use of a composition comprising a first mannanase and a second mannanase according to any one of paragraphs 1-51 for preparing a fermented beverage.

Paragraph 53. A method of preparing a fermented beverage, comprising mixing a composition comprising a first mannanase and a second mannanase according to any one of paragraphs 1-39 with a malt, a mash, a wort and/or an adjunct.

Paragraph 54. Use of a composition comprising a first mannanase and a second mannanase according to any one of paragraphs 1-39 for treating a coffee extract.

Paragraph 55. A process for producing a coffee extract, comprising:
(a) providing roast and ground coffee beans;
(b) adding to said coffee beans water and a composition comprising a first mannanase and a second mannanase according to any one of paragraphs 1-39;
(c) incubating to make an aqueous coffee extract; and
(d) separating the coffee extract from the extracted coffee beans.

Paragraph 54. Use of a composition comprising a first mannanase and a second mannanase according to any one of paragraphs 1-39 in a dough for preparing a baked product.

Paragraph 55. A method of preparing a baked product, comprising adding a composition comprising a first mannanase and a second mannanase according to any one of paragraphs 1-39 to a dough, and baking the dough.

Paragraph 56. Use of a composition comprising a first mannanase and a second mannanase according to any one of paragraphs 1-39 for preparing a dairy product.

Paragraph 57. A method of preparing a dairy product, comprising adding to milk or a dairy product (a) glucomannan, galactomannan and/or galactoglucomannan and (b) a composition comprising a first mannanase and a second mannanase according to any one of paragraphs 1-39.

Paragraph 58. Use of a composition comprising a first mannanase and a second mannanase according to any one of paragraphs 1-39 for paper pulp bleaching.

Paragraph 59. A method of paper pulp bleaching, comprising incubating paper pulp with a composition comprising a first mannanase and a second mannanase according to any one of paragraphs 1-39.

Paragraph 60. A method of hydraulic fracturing or fracking, comprising incubating an oil composition with a composition comprising a first mannanase and a second mannanase according to any one of paragraphs 1-39, and recovering oil and gas fractions.

The present invention is further described by the following examples that should not be construed as limiting the scope of the invention.

EXAMPLES

Materials

Chemicals used as buffers and substrates were commercial products of at least reagent grade.

Example 1: Reducing End Assay

For estimating the mannose yield after substrate hydrolysis, a reducing end assay developed by Lever (1972), Anal. Biochem. 47: 273-279, was used. The assay is based on 4-hydroxybenzoic acid hydrazide, which under alkaline conditions reacts with the reducing ends of saccharides. The product is a strong yellow anion, which absorbs at 410 nm.
Method
4-Hydroxybenzhydrazide (PAHBAH) (Sigma, H9882) was diluted in PAHBAH buffer to a concentration of 15 mg/ml. PAHBAH buffer contained: 50 g/L K—Na-tartrate (Merck, 1.08087) and 20 g/L sodium hydroxide (Sigma, S8045). This PAHBAH mix was made just before usage.

70 µl PAHBAH mix and MiliQ water were mixed in a 96 well PCR plate (Thermo Scientific). Samples from hydrolysis experiment were added. Samples and MiliQ always reached the total volume of 150 µl, but the dilution of the sample differed. The plate was sealed with Adhesive PCR Sealing Foil Sheets (Thermo Scientific). Plates were incubated at 95° C. for 10 min, cooled down and kept at 10° C. for 1 min in PTC-200 Thermal Cycler (MJ Research). 100 µl sample was transferred to a 96 well microtiter plate, flat bottomed (NuncTM) and color development measured at 405 nm on a SpectraMax 190 Absorbance Microplate Reader (Molecular Devices). Results were compared to mannose standards, that had undergone the same treatment and dilution as the samples to which they were compared.

Example 2: Automatic Mechanical Stress Assay (AMSA) for Laundry

The wash performance in laundry washing was assessed using the Automatic Mechanical Stress Assay (AMSA). With the AMSA, the wash performance of a large quantity of small volume enzyme-detergent solutions can be examined. The AMSA plate has a number of slots for test solutions and a lid firmly squeezing the laundry sample, the textile to be washed against all the slot openings. During the washing time, the plate, test solutions, textile and lid were vigorously shaken to bring the test solution in contact with the textile and apply mechanical stress in a regular, periodic oscillating manner.

The wash performance was measured as the brightness of the color of the textile washed. Brightness can also be expressed as the intensity of the light reflected from the sample when illuminated with white light. When the sample is stained the intensity of the reflected light is lower, than that of a clean sample. Therefore, the intensity of the reflected light can be used to measure wash performance.

Color measurements were made with a professional flat-bed scanner (Kodak iQsmart, Kodak, Midtager 29, DK-2605 Brondby, Denmark), which was used to capture an image of the washed textile.

To extract a value for the light intensity from the scanned images, 24-bit pixel values from the image were converted into values for red, green and blue (RGB). The intensity value (Int) was calculated by adding the RGB values together as vectors and then taking the length of the resulting vector:

$$Int = \sqrt{r^2 + g^2 + b^2}$$

Example 3: Cloning and Expression of GH26 Beta-1,4-Mannanases from *Paenibacillus woosongensis*

The gene encoding the GH26 mannanase from *Paenibacillus woosongensis* (SEQ ID NO: 3) was expressed as a full-length version including the GH26 domain and a CBM35 domain. It was expressed as an intracellular enzyme with a 6×His tag added directly on the C-terminal of the protein. The construct was made as linear integration construct where the gene was fused by PCR between two *Bacillus subtilis* homologous chromosomal regions along with a strong promoter and a chloramphenicol resistance marker. The fusion was made by SOE PCR (Horton, R. M., Hunt, H. D., Ho, S. N., Pullen, J. K. and Pease, L. R. (1989) Engineering hybrid genes without the use of restriction enzymes, gene splicing by overlap extension Gene 77: 61-68). The SOE PCR method is also described in patent application WO 2003095658. The genes were expressed under the control of a triple promoter system (as described in WO 99/43835), consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence. The linear PCR constructs where transformed into *Bacillus subtilis*. Transformants were selected on LB plates supplemented with 6 µg of chloramphenicol per ml. A recombinant *Bacillus subtilis* clone from each construct containing the integrated expression construct was cultivated in 3 L flasks containing 500 ml yeast extract-based medium at 30° C. for 3 days with shaking at 250 rpm. Each of the culture broths were centrifuged at 20,000×g for 20 minutes and the supernatants were carefully decanted from the pelleted material. Each supernatant was filtered using a filtration unit equipped with a 0.2 µm filter (Nalgene) to remove any cellular debris. The enzymes were purified from the filtered supernatant as described in Example 6.

Example 4: Cloning and Expression of GH26 Beta-1,4-Mannanases from *Paenibacillus illinoisensis*

The gene encoding the GH26 mannanase from *Paenibacillus illinoisensis* (SEQ ID NO: 4) was expressed in 2 versions. First as the full-length gene including the GH26 domain and a CBM35 domain and secondly as a truncated version only containing the GH26 domain. Both constructs expressed the enzyme as a secreted enzyme. In the full-length construct the genes native secretion signal was replaced with a *Bacillus clausii* secretion signal (with the following amino acid sequence: MKKPLGKIVASTAL-LISVAFSSSIASA) and a 6×His tag was added directly on the C-terminal of the protein. In the truncated construct the genes native secretion signal was replaced with a *Bacillus*

*licheniformis* secretion signal (with the following amino acid sequence: MKQQKRLYARLLTLLFALIFLL-PHSAAAA) and a 6×His tag was added directly on the C-terminal of the protein.

The genes were expressed under the control of a triple promoter system (as described in WO 1999/43835), consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence. The linear PCR constructs where transformed into *Bacillus subtilis*. Transformants were selected on LB plates supplemented with 6 μg of chloramphenicol per ml. A recombinant *Bacillus subtilis* clone from each construct containing the integrated expression construct was cultivated in 3 L flasks containing 500 ml yeast extract-based medium at 30° C. for 3 days with shaking at 250 rpm. Each of the culture broths were centrifuged at 20,000×g for 20 minutes and the supernatants were carefully decanted from the pelleted material. Each supernatant was filtered using a filtration unit equipped with a 0.2 μm filter (Nalgene) to remove any cellular debris. The enzymes were purified from the filtered supernatant as described in Example 6.

Example 5: Site-Directed Mutagenesis of First Mannanase

The gene of Mannanase (SEQ ID NO: 2) was cloned into the *Bacillus subtilis* expression cassette and transformed in the expression host, *Bacillus subtilis*. A Mega PCR-based site-directed mutagenesis (SDM) was carried out to generate variants of the Mannanase gene by introducing mutations at specific sites. SDM was carried out using a single mutagenic primer of 20-30 base pairs with the desired amino acid change (substitution/deletion/insertion) lying in the middle of the oligonucleotide with sufficient flanking residues (9-15 base pairs). Two PCR reactions were involved 1) generation of C-terminal fragment with the flanking C-terminal reverse primer and the forward mutagenic primer 2) generation of Mega PCR product using the C-terminal fragment as the reverse mega-primer and the flanking N-terminal forward primer to give the full-length cassette. The Mega PCR product was then transformed in to the *Bacillus* host, where site-specific homologous recombination in the *Bacillus* chromosome takes place.

After 18-20 hours of growth in LB agar media with appropriate antibiotic, the transformed colonies were picked and inoculated in to the aqueous expression media and given for screening assays. The hits from the screening assays were subjected to culture PCR and sent for sequence confirmation. The polymerase used for the PCR reaction was Phusion DNA polymerase (obtained from ThermoScientific, Cat. No.: F530L).

Example 6: Purification of GH26 Mannanase

The construct of the GH26 mannanases was purified in the following way: The pH of the supernatant was adjusted to pH 8 with 3 M Tris, left for 1 hour, and then filtered using a filtration unit equipped with a 0.2 μm filter (Nalgene). The filtered supernatant was applied to a 5 ml HisTrap™ Excel column (GE Healthcare Life Sciences) pre-equilibrated with 5 column volumes (CV) of 50 mM Tris/HCl pH 8. Unbound protein was eluted by washing the column with 8 CV of 50 mM Tris/HCl pH 8. The mannanase was eluted with 50 mM HEPES pH 7-10 mM imidazole and elution was monitored by absorbance at 280 nm. The eluted mannanase was desalted on a HiPrep™ 26/10 desalting column (GE Healthcare Life Sciences) pre-equilibrated with 3 CV of 50 mM HEPES pH 7-100 mM NaCl. The mannanase was eluted from the column using the same buffer at a flow rate of 10 ml/minute. Relevant fractions were selected and pooled based on the chromatogram and SDS-PAGE analysis using 4-12% Bis-Tris gels (Invitrogen) and 2-(N-morpholino) ethanesulfonic acid (MES) SDS-PAGE running buffer (Invitrogen). The gel was stained with InstantBlue (Novexin) and destained using miliQ water. The concentration of the purified enzyme was determined by absorbance at 280 nm

Example 7: Wash Performance of Compositions Comprising a GH5 Mannanase and a GH26 Mannanase Experiments were conducted as described in Example 2 using a one cycle wash procedure and the experimental conditions specified in Table 1. The mannanase enzymes used herein were as follows:

GH5 mannanase from *Bacillus bogoriensis* (SEQ ID NO: 2)

GH26 mannanase from *Paenibacillus woosongensis* (SEQ ID NO: 3)

GH26 mannanase from *Paenibacillus illinoisensis* (SEQ ID NO: 4)

GH26 mannanase from *Yunnania penicillata* (SEQ ID NO: 7)

TABLE 1

| Conditions for AMSA Washing Trial 1: Model detergent at 20° C. | |
| --- | --- |
| Test Solution | Model B detergent 3.3 g/L |
| | Model T detergent 5.3 g/L |
| Test solution volume | 160 μL |
| Enzyme dose | 0.250 mg/L, this includes mixtures by weight (w/w) of GH5 mannanase and GH26 mannanases |
| pH | Model B, pH unadjusted (measured to be 7.8) |
| | Model T, pH unadjusted (measured to be 9.7) |
| Wash time | 20 minutes |
| Temperature | 20° C. |
| Water hardness | 15° dH |
| $Ca^{2+}:Mg^{2+}:CO_3^{2-}$ ratio | 4:1:7.5 |

Water hardness was adjusted by addition of $CaCl_2$, $MgCl_2$, and $NaHCO_3$ to the test system. After washing, the textiles were flushed in tap water and air-dried. Two types of commercial test material swatches were used, C-S-43, Guar gum with carbon black on cotton and C-S-73, Locust bean gum with pigment on cotton, available from Center for Testmaterials BV, Stoomloggerweg 11, 3133 KT Vlaardingen, the Netherlands.

TABLE 2

| Model detergent B composition | | |
| --- | --- | --- |
| Ingredient (abbreviation) | Explanation | Wt % |
| LAS | (C10-C13)alkylbenzene-sulfonic acid | 7.20 |
| SLES | sodium lauryl ether sulfate | 10.58 |
| Soy soap | | 2.75 |
| Coco soap | | 2.75 |
| AEO | alcohol ethoxylate | 6.60 |
| NaOH | Sodium hydroxide | 1.05 |
| Ethanol | | 2.70 |
| Isopropanol | | 0.30 |

TABLE 2-continued

Model detergent B composition

| Ingredient (abbreviation) | Explanation | Wt % |
|---|---|---|
| MPG | monopropylene glycol | 6.00 |
| Glycerol | | 1.71 |
| TEA | triethanolamine | 3.33 |
| Sodium formate | | 1.00 |
| Sodium citrate | | 2.00 |
| DTMPA | diethylenetriaminepentakis(methylene)pentakis(phosphonic acid), heptasodium salt | 0.48 |
| PCA | polycarboxylic acid type polymer, sodium salt | 0.46 |
| Phenoxyethanol | | 0.50 |
| Ion exchanged water | | 50.59 |

TABLE 3

Model detergent T composition

| Ingredient (abbreviation) | Explanation | Wt % |
|---|---|---|
| LAS | alkylbenzene-sulfonic acid, sodium salt | 11.72 |
| AS | sodium alkyl sulfafe, sodium salt | 1.97 |
| Soap | | 2.15 |
| AEO | alcohol ethoxylate | 3.33 |
| Sodium carbonate | | 14.97 |
| Sodium (di)silicate | | 3.12 |
| Zeolite 4A + PCA | zeolite 4A + copoly(acrylic acid/maleic acid), sodium salt | 20.38 |
| HEDP | 1-hydroxyethane-1,1-diylbis(phosphonic acid), tetrasodium salt; tetrasodium etidronate | 0.15 |
| Sodium citrate | | 2.00 |
| CPP | copolymer polyether/polyester | 0.51 |
| Sodium sulfate | | 38.70 |
| Silicone | | 1.00 |

Tables 4 and 5 below show the results of the AMSA assay in the two model detergent compositions for each of the three individual enzymes as well as for combinations of GH5 with each of the two GH26 enzymes in three different ratios (by weight) for each combination. The results are expressed as the delta intensity (ΔInt), which is calculated by subtracting the detergent blank. Each measurement is the average of minimum 10 separate wells in the AMSA setup. Based on the values obtained for the pure mannanases, an expected effect of the mixtures is calculated, allowing the synergy of each mixture to be determined as the difference between the actual wash performance and the expected performance.

TABLE 4

AMSA wash results in model detergent B (Table 2)

| | SEQ ID NO: 2 | SEQ ID NO: 3 | SEQ ID NO: 4 | SEQ ID NO: 7 | Expected effect | Actual effect | Synergy |
|---|---|---|---|---|---|---|---|
| Guar gum swatch C-S-43 | | | | | | | |
| Pure Mannanase | 16 | 24 | 22 | 24 | | | |
| SEQ ID NO: 2-SEQ ID NO: 3, 25:75 | | | | | 22 | 30 | 8 |
| SEQ ID NO: 2-SEQ ID NO: 3, 50:50 | | | | | 20 | 32 | 12 |
| SEQ ID NO: 2-SEQ ID NO: 3, 75:25 | | | | | 18 | 29 | 11 |
| SEQ ID NO: 2-SEQ ID NO: 4, 25:75 | | | | | 21 | 28 | 7 |
| SEQ ID NO: 2-SEQ ID NO: 4, 50:50 | | | | | 19 | 28 | 9 |
| SEQ ID NO: 2-SEQ ID NO: 4, 75:25 | | | | | 18 | 30 | 12 |
| SEQ ID NO: 2-SEQ ID NO: 7, 50:50 | | | | | 20 | 24 | 4 |
| Locust bean gum swatch C-S-73 | | | | | | | |
| Pure Mannanase | 19 | 18 | 18 | 21 | | | |
| SEQ ID NO: 2-SEQ ID NO: 3, 25:75 | | | | | 18 | 25 | 7 |
| SEQ ID NO: 2-SEQ ID NO: 3, 50:50 | | | | | 19 | 25 | 6 |
| SEQ ID NO: 2-SEQ ID NO: 3, 75:25 | | | | | 19 | 28 | 9 |
| SEQ ID NO: 2-SEQ ID NO: 4, 25:75 | | | | | 18 | 24 | 6 |
| SEQ ID NO: 2-SEQ ID NO: 4, 50:50 | | | | | 19 | 23 | 4 |
| SEQ ID NO: 2-SEQ ID NO: 4, 75:25 | | | | | 19 | 24 | 5 |
| SEQ ID NO: 2-SEQ ID NO: 7, 50:50 | | | | | 20 | 27 | 7 |

TABLE 5

AMSA wash results in model detergent T (Table 3)

| | SEQ ID NO: 2 | SEQ ID NO: 3 | SEQ ID NO: 4 | SEQ ID NO: 7 | Expected effect | Actual effect | Synergy |
|---|---|---|---|---|---|---|---|
| Guar gum swatch C-S-43 | | | | | | | |
| Pure Mannanase | 11 | 21 | 14 | 16 | | | |
| SEQ ID NO: 2-SEQ ID NO: 3, 25:75 | | | | | 19 | 30 | 11 |
| SEQ ID NO: 2-SEQ ID NO: 3, 50:50 | | | | | 16 | 29 | 13 |
| SEQ ID NO: 2-SEQ ID NO: 3, 75:25 | | | | | 14 | 28 | 14 |

TABLE 5-continued

AMSA wash results in model detergent T (Table 3)

| | SEQ ID NO: 2 | SEQ ID NO: 3 | SEQ ID NO: 4 | SEQ ID NO: 7 | Expected effect | Actual effect | Synergy |
|---|---|---|---|---|---|---|---|
| SEQ ID NO: 2-SEQ ID NO: 4, 25:75 | | | | | 13 | 24 | 11 |
| SEQ ID NO: 2-SEQ ID NO: 4, 50:50 | | | | | 13 | 28 | 15 |
| SEQ ID NO: 2-SEQ ID NO: 4, 75:25 | | | | | 12 | 26 | 14 |
| SEQ ID NO: 2-SEQ ID NO: 7, 50:50 | | | | | 14 | 20 | 6 |
| Locust bean gum swatch C-S-73 | | | | | | | |
| Pure Mannanase | 17 | 12 | 8 | 12 | | | |
| SEQ ID NO: 2-SEQ ID NO: 3, 25:75 | | | | | 13 | 26 | 13 |
| SEQ ID NO: 2-SEQ ID NO: 3, 50:50 | | | | | 15 | 27 | 12 |
| SEQ ID NO: 2-SEQ ID NO: 3, 75:25 | | | | | 16 | 26 | 10 |
| SEQ ID NO: 2-SEQ ID NO: 4, 25:75 | | | | | 10 | 26 | 16 |
| SEQ ID NO: 2-SEQ ID NO: 4, 50:50 | | | | | 13 | 29 | 16 |
| SEQ ID NO: 2-SEQ ID NO: 4, 75:25 | | | | | 15 | 34 | 19 |
| SEQ ID NO: 2-SEQ ID NO: 7, 50:50 | | | | | 15 | 29 | 14 |

The results show that the combinations of GH5 and GH26 mannanases were exhibiting an actual wash performance that was clearly superior to the expected wash performance based on the individual enzymes. This synergy was observed in both model detergent compositions.

Example 8: Wash Performance of Compositions Comprising a GH5 Mannanase and a GH26 Mannanase The mannanase enzymes used herein were as follows:
GH5 mannanase from *Bacillus bogoriensis* (SEQ ID NO: 2)
GH5 mannanase (SEQ ID NO: 18)
GH5 mannanase from *Bacillus lentus* (SEQ ID NO: 19)
GH5 mannanase (SEQ ID NO: 22)
GH26 mannanase from *Paenibacillus illinoisensis* (SEQ ID NO: 4)
GH26 mannanase from *Salipaludibacillus agaradhaerens* (SEQ ID NO: 14)

The experiments were conducted as described in the Automatic Mechanical Stress Assay (AMSA) for laundry method of Example 2 using a one cycle wash procedure and the experimental conditions specified in Table 6.

TABLE 6

Conditions for AMSA Washing Trial 1: Model detergent at 20° C.

| | |
|---|---|
| Test Solution | Model B detergent 3.3 g/L |
| Test solution volume | 160 μL |
| Enzyme dose | 0.05 and 0.250 mg/L e.p. in respectively, Table 8 and Table 9, this includes mixtures by weight (w/w) of GH5 mannanase and GH26 mannanases |
| pH | Model B unadjusted |
| Wash time | 20 minutes |
| Temperature | 20° C. |
| Water hardness | 15° dH |
| $Ca^{2+}:Mg^{2+}:CO_3^{2-}$ ratio | 4:1:7.5 |

Water hardness was adjusted by addition of $CaCl_2$, $MgCl_2$, and $NaHCO_3$ to the test system. After washing the textiles were flushed in tap water and air-dried. one types of swatch was used; this is a commercial test material, C-S-43, Guar gum with carbon black on cotton, available from Center for Testmaterials BV, Stoomloggerweg 11, 3133 KT Vlaardingen, the Netherlands.

TABLE 7

Model B detergent composition

| Ingredient (abbreviation) | Explanation | Purity | Wt % |
|---|---|---|---|
| LAS | linear alkylbenzenesulfonate | 91 | 7.2 |
| AEOS | alkyl ethoxysulfate | 70.5 | 4.2 |
| Soy soap | | 100 | 2.75 |
| Coco soap | | 100 | 2.75 |
| AEO | alcohol ethoxylate | 100 | 6.6 |
| NaOH | Sodium hydroxide | 100 | 1.2 |
| Ethanol | | 100 | 3 |
| MPG | monopropylene glycol | 100 | 6 |
| glycerol | | 85 | 2 |
| TEA | triethanolamine | 100 | 3 |
| Sodium formiate | | 100 | 1 |
| Sodium citrate | | 100 | 2 |
| DTMPA | Diethylenetriaminepenta (methylenephosphonic acid) | 100 | 0.2 |
| PCA | polycarboxylic acid type polymer | 100 | 0.2 |
| Ion exchanged water | | 100 | 57.9 |

Results are presented for one dose of each enzyme or enzyme mixture. Each number is the delta intensity (ΔInt) calculated by subtracting the detergent blank. Each measurement is the average of minimum 10 separate wells in the AMSA set up.

TABLE 8

| 0.05 ppm total enzyme dose (50:50) | GH5 alone | GH26 alone | Expected effect 50:50 blend | Observed effect 50:50 blend | Synergy |
|---|---|---|---|---|---|
| SEQ ID NO: 2: SEQ ID NO: 14 | 16 | 19 | 17.5 | 22 | 4.5 |
| SEQ ID NO: 2: SEQ ID NO: 4 | 16 | 13 | 14.5 | 22 | 7.5 |
| SEQ ID NO: 18: SEQ ID NO: 14 | 15 | 19 | 17.0 | 18 | 1.0 |
| SEQ ID NO: 18: SEQ ID NO: 4 | 15 | 13 | 14.0 | 21 | 7.0 |
| SEQ ID NO: 19: SEQ ID NO: 14 | 16 | 19 | 17.5 | 22 | 4.5 |
| SEQ ID NO: 19: SEQ ID NO: 4 | 16 | 13 | 14.5 | 22 | 7.5 |
| SEQ ID NO: 22: SEQ ID NO: 14 | 11 | 19 | 15.0 | 17 | 2.0 |
| SEQ ID NO: 22: SEQ ID NO: 4 | 11 | 13 | 12.0 | 17 | 5.0 |

TABLE 9

| 0.25 ppm total enzyme dose | GH5 alone | GH26 alone | Expected effect 50:50 blend | Observed effect 50:50 blend | Synergy |
|---|---|---|---|---|---|
| SEQ ID NO: 2:SEQ ID NO: 14 | 22 | 33 | 27.5 | 32 | 4.5 |
| SEQ ID NO: 2: SEQ ID NO: 4 | 22 | 27 | 24.5 | 35 | 10.5 |
| SEQ ID NO: 18: SEQ ID NO: 14 | 19 | 33 | 26 | 33 | 7.0 |
| SEQ ID NO: 18: SEQ ID NO: 4 | 19 | 27 | 23 | 32 | 9.0 |
| SEQ ID NO: 19: SEQ ID NO: 14 | 25 | 33 | 29 | 36 | 7.0 |

TABLE 9-continued

| 0.25 ppm total enzyme dose | GH5 alone | GH26 alone | Expected effect 50:50 blend | Observed effect 50:50 blend | Synergy |
|---|---|---|---|---|---|
| SEQ ID NO: 19: SEQ ID NO: 4 | 25 | 27 | 26 | 32 | 6.0 |
| SEQ ID NO: 22: SEQ ID NO: 14 | 18 | 33 | 25.5 | 33 | 7.5 |
| SEQ ID NO: 22: SEQ ID NO: 4 | 18 | 27 | 22.5 | 31 | 8.5 |

The mixtures of GH5 mannanase and GH26 mannanase are superior to the expected effect, exhibiting a clear synergy.

The invention claimed is:

1. A detergent composition comprising at least a first and a second mannanase, wherein:
   (A) said first mannanase is a glycoside hydrolase family 5 mannanase of SEQ ID NO: 2 or a variant or fragment thereof having mannanase activity and wherein the variant has at least 80% but less than 100% sequence identity to the mature polypeptide of SEQ ID NO: 2; and
   (B) said second mannanase is a glycoside hydrolase family 26 mannanase of SEQ ID NO: 4 or a variant or fragment thereof having mannanase activity and wherein the variant has at least 80% but less than 100% sequence identity to the mature polypeptide of SEQ ID NO: 4;
   and comprising at least one detergent component selected from the group consisting of surfactants, bleaching systems, chelating agents, stabilizing agents, hydrotropes, builders, co-builders, bleach activators, polymers and fabric-hueing agents.

2. The composition of claim 1, wherein said first mannanase is a variant of a parent mannanase comprising at least one modification at a position corresponding to a position selected from positions 1, 2, 3, 4, 5, 6, 8, 9, 10, 11, 13, 14, 15, 16, 17, 18, 19, 21, 23, 30, 32, 33, 34, 35, 37, 38, 39, 41, 44, 45, 47, 57, 59, 60, 62, 63, 65, 66, 67, 68, 70, 71, 74, 77, 78, 79, 80, 81, 82, 83, 93, 95, 96, 97, 98, 100, 104, 107, 108, 110, 111, 114, 115, 116, 118, 119, 131, 132, 133, 135, 136, 139, 142, 143, 146, 147, 150, 152, 154, 164, 167, 169, 172, 173, 174, 175, 176, 177, 180, 181, 183, 184, 185, 196, 199, 200, 201, 202, 203, 205, 206, 210, 212, 213, 214, 215, 226, 228, 229, 230, 234, 235, 241, 242, 243, 244, 245, 250, 254, 257, 258, 259, 260, 261, 262, 266, 267, 268, 270, 271, 272, 273, 276, 279, 280, 283, 285, 286, 288, 289, 290, 292, 293, 294, 295, 296, 298, 299, 300 and 301, wherein:
   numbering is according to SEQ ID NO: 2,
   each modification is independently a substitution or a deletion,
   the variant has mannanase activity, and
   the variant has at least 80% but less than 100% sequence identity to the mature polypeptide of SEQ ID NO: 2.

3. The composition of claim 1, wherein said second mannanase is selected from the group consisting of:
   (a) a variant of SEQ ID NO: 4, wherein the variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28 or 29 positions compared to SEQ ID NO: 4;
   (b) a polypeptide comprising the variant of (a) and an N-terminal and/or C-terminal His-tag and/or HQ-tag;
   (c) a polypeptide comprising the variant of (a) and an N-terminal and/or C-terminal extension of up to 10 amino acids, e.g. 1, 2, 3, 4, 5, 6, 7, 8, 9 or 10 amino acids; and
   (d) a fragment of the variant of (a) having mannanase activity and having at least 90% of the length of the mature polypeptide of SEQ ID NO: 4.

4. The composition of claim 2, wherein said first mannanase comprises a substitution in at least one of positions 3, 37, 47, 77, 82, 83, 93, 98, 116, 135, 136, 241, 257, 258, 260, 288, 294 and 295 wherein numbering is according to SEQ ID NO: 2.

5. The composition of claim 4, wherein said first mannanase comprises at least two substitutions compared to said parent mannanase and is selected from the group consisting of:
   (a) a variant comprising a first substitution in at least one amino acid position selected from positions 260, 288, 294 and 295, and a second substitution in at least one other position in said variant; and
   (b) a variant comprising substitutions in any two or more positions selected from positions 3, 37, 47, 77, 82, 83, 93, 98, 116, 135, 136, 241, 257 and 258.

6. The composition of claim 5, wherein said first mannanase is a variant (a) comprising a second substitution in at least one position selected from positions 1, 2, 3, 4, 5, 6, 8, 11, 13, 14, 18, 30, 32, 33, 34, 35, 37, 41, 45, 47, 57, 59, 60, 63, 65, 70, 71, 74, 77, 78, 80, 82, 83, 93, 95, 97, 98, 100, 104, 108, 111, 114, 116, 118, 119, 131, 133, 135, 136, 139, 142, 143, 150, 169, 172, 174, 176, 177, 180, 183, 184, 185, 196, 200, 202, 203, 205, 210, 213, 228, 229, 234, 235, 241, 243, 244, 250, 254, 257, 262, 266, 268, 270, 272, 273, 276, 279, 280, 283, 286, 290, 296, and 298, wherein numbering is according to SEQ ID NO: 2.

7. The composition of claim 6, wherein said first mannanase is a variant (a) comprising a second substitution in at least one position selected from positions 14, 37, 47, 77, 81, 82, 83, 93, 98, 116, 135, 136, 241, 242, 257 and 258 of the polypeptide of SEQ ID NO: 2.

8. The composition according to claim 1, wherein said first mannanase is a variant (a) comprising at least two substitutions in positions selected from the group of positions: 14+260, 14+288, 14+294, 14+295, 37+260, 37+288, 37+294, 37+295, 47+260, 47+288, 47+294, 47+295, 77+260, 77+288, 77+294, 77+295, 81+260, 81+288, 81+294, 81+295, 82+260, 82+288, 82+294, 82+295, 83+260, 83+288, 83+294, 83+295, 93+260, 93+288, 93+294, 93+295, 98+260, 98+288, 98+294, 98+295, 116+260, 116+288, 116+294, 116+295, 135+260, 135+288, 135+294, 135+295, 136+260, 136+288, 136+294, 136+295, 241+260, 241+288, 241+294, 241+295, 242+260, 242+288, 242+294, 242+295, 257+260, 257+288, 257+294, 257+295, 258+260, 258+288, 258+294, 258+295 and 260+288, wherein numbering is according to SEQ ID NO: 2.

9. The composition according to claim 5, wherein said first mannanase is a variant (a) comprising a second and optionally a third substitution in one or both of positions 93 and 136 of the polypeptide of SEQ ID NO: 2.

10. The composition according to claim 1, wherein said first mannanase comprises at least two substitutions selected from A1G, A1V, N2E, S3P, G4D, F5H, Y6H, Y6M, Y6F, Y6W, Y6H, S8T, S8P, S8R, T11K, T11R, Y13F, D14S, D14K, N18V, N18R, A30T, Y32F, Y32W, K33Q, D34G, Q35L, T37P, E41V, E41N, N45G, G47S, G47A, D57N, G59Q, Q60R, K63R, K63Q, D65E, R70K, N71S, S74K, E77T, E77N, D78G, H80K, V82R, V82I, V82S, A83P, A83S, Y93Q, Y93A, S95D, A97R, S98P, S98D, N100Y, D104A, D104G, E108S, S111A, S111K, S111R, I114Q, I114M, I114W, K116R, D118K, T119R, S131T, E133R, E133Q, D135P, A136P, D139A, D139R, K142M, K142V, K142S, K142R, Q143R, N150T, N150R, N150S, Q169A, Q169R, Q169K, H172R, Y174R, Y174L, Y174W, Y174F, R176Q, E177S, E177Y, N180R, P183T, P183G, Q184E, Q184K, R185G, Y196W, Y196F, N200T, S202R, Q203T, R205K, R210L, R210G, R210M, N213V, N213D, T228S, N229D, E234F, E234Y, A235K, A235R, S241C, Q243K, Q243E, R244K, R244V, A250G, K254Y, G257W, G257E, G257A, G257G, W260F, Y262F, S266A, D268N, A270D, N272M, N272T, N273E, N273D, A276E, A276W, A276D, N279D, N279E, T280L, N283W, N283H, Y286W, Y286F, L288I, E290A, L294P, L294K, L294I, L294R, L294V, L294H, S295K, S295V, S295P, S295L, S295R, S295A, S295N, S295M, S295I, T296S and F298Y wherein numbering is according to SEQ ID NO: 2.

11. The composition of claim 2, wherein said parent mannanase comprises or consists of the polypeptide of SEQ ID NO: 1 or SEQ ID NO: 2.

12. The composition of claim 1, wherein said composition has a weight ratio between said first mannanase and said second mannanase is from about 2:98 to about 98:2, e.g. from about 10:90 to about 90:10, from about 20:80 to about 80:20, from about 30:70 to about 70:30, or from about 40:60 to about 60:40.

13. The composition of claim 12, wherein said weight ratio between said first mannanase and said second mannanase is from about 5:95 to about 50:50, e.g. from about 10:90 to about 40:60, or from about 20:80 to about 30:70.

14. The composition of claim 12, wherein said weight ratio between said first mannanase and said second mannanase is from about 95:5 to about 50:50, e.g. from about 90:10 to about 60:40, or from about 80:20 to about 70:30.

15. The detergent composition of claim 1, comprising at least one surfactant selected from the group consisting of anionic surfactants, cationic surfactants, nonionic surfactants, and amphoteric surfactants.

16. The detergent composition of claim 1, comprising at least one additional enzyme, such as a protease, amylase or lipase.

17. The detergent composition of claim 1, wherein the composition is a laundry detergent composition or a hard surface cleaning composition in the form of a liquid, gel, powder, granulate, paste or unit dose package.

18. A method of cleaning a textile or a hard surface, comprising contacting the textile or hard surface with a detergent composition according to claim 1.

19. A method for preventing, reducing or removing a biofilm from a surface, comprising contacting the surface with a detergent composition according to claim 1.

* * * * *

UNITED STATES PATENT AND TRADEMARK OFFICE
CERTIFICATE OF CORRECTION

PATENT NO. : 11,866,748 B2
APPLICATION NO. : 16/754698
DATED : January 9, 2024
INVENTOR(S) : Klinger et al.

It is certified that error appears in the above-identified patent and that said Letters Patent is hereby corrected as shown below:

In the Claims

Please amend Claim 10 (Column 224, Line 62) as follows:
10. The composition according to claim 1, wherein said first mannanase comprises at least two substitutions selected from A1G, A1V, N2E, S3P, G4D, F5H, Y6H, Y6M, Y6F, Y6W, Y6H, S8T, S8P, S8R, T11K, T11R, Y13F, D14S, D14K, N18V, N18R, A30T, Y32F, Y32W, K33Q, D34G, Q35L, T37P, E41V, E41N, N45G, G47S, G47A, D57N, G59Q, Q60R, K63R, K63Q, D65E, R70K, N71S, S74K, E77T, E77N, D78G, H80K, V82R, V82I, V82S, A83P, A83S, Y93Q, Y93A, S95D, A97R, S98P, S98D, N100Y, D104A, D104G, E108S, S111A, S111K, S111R, I114Q, I114M, I114W, K116R, D118K, T119R, S131T, E133R, E133Q, D135P, A136P, D139A, D139R, K142M, K142V, K142S, K142R, Q143R, N150T, N150R, N150S, Q169A, Q169R, Q169K, H172R, Y174R, Y174L, Y174W, Y174F, R176Q, E177S, E177Y, N180R, P183T, P183G, Q184E, Q184K, R185G, Y196W, Y196F, N200T, S202R, Q203T, R205K, R210L, R210G, R210M, N213V, N213D, T228S, N229D, E234F, E234Y, A235K, A235R, S241C, Q243K, Q243E, R244K, R244V, A250G, K254Y, G257W, G257E, G257A, G257G, W260F, Y262F, S266A, D268N, A270D, N272M, N272T, N273E, N273D, A276E, A276W, A276D, N279D, N279E, T280L, N283W, N283H, Y286W, Y286F, L288I, E290A, L294P, L294K, L294I, L294R, L294V, L294H, S295K, S295V, S295P, S295L, S295R, S295A, S295N, S295M, S295I, T296S and F298Y wherein numbering is according to SEQ ID NO: 2.

Signed and Sealed this
Twenty-fifth Day of June, 2024

Katherine Kelly Vidal
*Director of the United States Patent and Trademark Office*

SEQUENCE LISTING

```
<160> NUMBER OF SEQ ID NOS: 23

<210> SEQ ID NO 1
<211> LENGTH: 326
<212> TYPE: PRT
<213> ORGANISM: Bacillus bogoriensis
<220> FEATURE:
<221> NAME/KEY: SIGNAL
<222> LOCATION: (1)..(28)
<220> FEATURE:
<221> NAME/KEY: mat_peptide
<222> LOCATION: (29)..(326)

<400> SEQUENCE: 1

Met Lys Gln Gln Lys Arg Leu Tyr Ala Arg Leu Leu Thr Leu Leu Phe
            -25                 -20                 -15

Ala Leu Ile Phe Leu Leu Pro His Ser Ala Ala Ala Asn Ser Gly
        -10                  -5                  -1   1

Phe Tyr Val Ser Gly Thr Thr Leu Tyr Asp Ala Asn Gly Asn Pro Phe
  5                  10                  15                  20

Val Met Arg Gly Ile Asn His Gly His Ala Trp Tyr Lys Asp Gln Ala
                 25                  30                  35

Thr Thr Ala Ile Glu Gly Ile Ala Asn Thr Gly Ala Asn Thr Val Arg
             40                  45                  50

Ile Val Leu Ser Asp Gly Gly Gln Trp Thr Lys Asp Asp Ile His Thr
         55                  60                  65

Val Arg Asn Leu Ile Ser Leu Ala Glu Asp Asn His Leu Val Ala Val
     70                  75                  80

Leu Glu Val His Asp Ala Thr Gly Tyr Asp Ser Ile Ala Ser Leu Asn
 85                  90                  95                 100

Arg Ala Val Asp Tyr Trp Ile Glu Met Arg Ser Ala Leu Ile Gly Lys
                105                 110                 115

Glu Asp Thr Val Ile Ile Asn Ile Ala Asn Glu Trp Phe Gly Ser Trp
                120                 125                 130

Glu Gly Asp Ala Trp Ala Asp Gly Tyr Lys Gln Ala Ile Pro Arg Leu
            135                 140                 145

Arg Asn Ala Gly Leu Asn His Thr Leu Met Val Asp Ala Ala Gly Trp
        150                 155                 160

Gly Gln Phe Pro Gln Ser Ile His Asp Tyr Gly Arg Glu Val Phe Asn
165                 170                 175                 180

Ala Asp Pro Gln Arg Asn Thr Met Phe Ser Ile His Met Tyr Glu Tyr
                185                 190                 195

Ala Gly Gly Asn Ala Ser Gln Val Arg Thr Asn Ile Asp Arg Val Leu
                200                 205                 210
```

```
Asn Gln Asp Leu Ala Leu Val Ile Gly Glu Phe Gly His Arg His Thr
            215                 220                 225

Asn Gly Asp Val Asp Glu Ala Thr Ile Met Ser Tyr Ser Glu Gln Arg
        230                 235                 240

Gly Val Gly Trp Leu Ala Trp Ser Trp Lys Gly Asn Gly Pro Glu Trp
245                 250                 255                 260

Glu Tyr Leu Asp Leu Ser Asn Asp Trp Ala Gly Asn Asn Leu Thr Ala
                265                 270                 275

Trp Gly Asn Thr Ile Val Asn Gly Pro Tyr Gly Leu Arg Glu Thr Ser
            280                 285                 290

Arg Leu Ser Thr Val Phe
            295

<210> SEQ ID NO 2
<211> LENGTH: 298
<212> TYPE: PRT
<213> ORGANISM: Bacillus bogoriensis

<400> SEQUENCE: 2

Ala Asn Ser Gly Phe Tyr Val Ser Gly Thr Thr Leu Tyr Asp Ala Asn
1               5                   10                  15

Gly Asn Pro Phe Val Met Arg Gly Ile Asn His Gly His Ala Trp Tyr
                20                  25                  30

Lys Asp Gln Ala Thr Thr Ala Ile Glu Gly Ile Ala Asn Thr Gly Ala
            35                  40                  45

Asn Thr Val Arg Ile Val Leu Ser Asp Gly Gly Gln Trp Thr Lys Asp
50                  55                  60

Asp Ile His Thr Val Arg Asn Leu Ile Ser Leu Ala Glu Asp Asn His
65                  70                  75                  80

Leu Val Ala Val Leu Glu Val His Asp Ala Thr Gly Tyr Asp Ser Ile
                85                  90                  95

Ala Ser Leu Asn Arg Ala Val Asp Tyr Trp Ile Glu Met Arg Ser Ala
                100                 105                 110

Leu Ile Gly Lys Glu Asp Thr Val Ile Ile Asn Ile Ala Asn Glu Trp
            115                 120                 125

Phe Gly Ser Trp Glu Gly Asp Ala Trp Ala Asp Gly Tyr Lys Gln Ala
130                 135                 140

Ile Pro Arg Leu Arg Asn Ala Gly Leu Asn His Thr Leu Met Val Asp
145                 150                 155                 160

Ala Ala Gly Trp Gly Gln Phe Pro Gln Ser Ile His Asp Tyr Gly Arg
                165                 170                 175

Glu Val Phe Asn Ala Asp Pro Gln Arg Asn Thr Met Phe Ser Ile His
                180                 185                 190

Met Tyr Glu Tyr Ala Gly Gly Asn Ala Ser Gln Val Arg Thr Asn Ile
            195                 200                 205

Asp Arg Val Leu Asn Gln Asp Leu Ala Leu Val Ile Gly Glu Phe Gly
210                 215                 220

His Arg His Thr Asn Gly Asp Val Asp Glu Ala Thr Ile Met Ser Tyr
225                 230                 235                 240

Ser Glu Gln Arg Gly Val Gly Trp Leu Ala Trp Ser Trp Lys Gly Asn
                245                 250                 255

Gly Pro Glu Trp Glu Tyr Leu Asp Leu Ser Asn Asp Trp Ala Gly Asn
                260                 265                 270

Asn Leu Thr Ala Trp Gly Asn Thr Ile Val Asn Gly Pro Tyr Gly Leu
```

```
                      275                 280                 285

Arg Glu Thr Ser Arg Leu Ser Thr Val Phe
    290                 295

<210> SEQ ID NO 3
<211> LENGTH: 330
<212> TYPE: PRT
<213> ORGANISM: Paenibacillus woosongensis

<400> SEQUENCE: 3

Ile Arg Thr Gly Thr Leu Asn Pro Glu Ala Thr Ala Glu Ala Arg
1               5                   10                  15

Ala Leu Met Asn Tyr Leu Leu Ser Gln Tyr Gly Gln Lys Ile Ile Ser
                20                  25                  30

Gly Gln Gln Thr Leu Glu Asp Val Glu Trp Ile Lys Gln Gln Thr Gly
            35                  40                  45

Lys Tyr Pro Ala Ile Phe Ser Thr Asp Leu Met Asp Tyr Ser Pro Ser
    50                  55                  60

Arg Val Asp His Gly Ala Ser Ser Thr Glu Val Glu Lys Met Ile Glu
65                  70                  75                  80

Trp Tyr Lys Arg Gly Gly Ile Val Ser Leu Cys Trp His Trp Asn Ala
                85                  90                  95

Pro Lys Gly Ile Gly Gly Asn Glu Pro Gly Asn Glu Trp Trp Arg Gly
            100                 105                 110

Phe Tyr Thr Glu Phe Thr Thr Phe Asp Val Glu Tyr Ala Leu Asn His
    115                 120                 125

Pro Asp Ser Glu Asp Tyr Gln Leu Leu Ile Arg Asp Ile Asp Ala Ile
130                 135                 140

Ala Val Gln Leu Lys Arg Leu Gln Glu Ala Asn Val Pro Val Leu Trp
145                 150                 155                 160

Arg Pro Leu His Glu Ala Glu Gly Thr Trp Phe Trp Trp Gly Ala Lys
                165                 170                 175

Gly Pro Glu Pro Ala Lys Gln Leu Tyr Arg Leu Met Tyr Asp Arg Leu
            180                 185                 190

Thr Asn Asp His Lys Leu Asn Asn Leu Ile Trp Val Trp Asn Ser Glu
    195                 200                 205

Lys Lys Asp Trp Tyr Pro Gly Asp Asp Val Val Asp Met Val Ser Val
210                 215                 220

Asp Ile Tyr Asn Pro Ala Gly Asp Tyr Asn Pro Ser Ile Ala Lys Tyr
225                 230                 235                 240

Glu Ala Leu Val Ser Leu Ala Asp Asn Lys Lys Met Ala Ala Leu Ala
                245                 250                 255

Glu Asn Gly Pro Ile Pro Asp Pro Asp Ala Leu Gln Glu Tyr Gly Ala
            260                 265                 270

Asp Trp Ser Phe Phe Ser Thr Trp Thr Gly Asp Tyr Ile Arg Asp Gly
    275                 280                 285

Lys Thr Asn Thr Ile Glu His Leu Lys Lys Val Tyr Gln His Asp Tyr
290                 295                 300

Val Ile Thr Leu Asp Glu Leu Pro Ala Asp Cys Thr Pro Ile Leu Met
305                 310                 315                 320

Ile Arg Gln Arg Met Val Asn Gln Gln Gly
                325                 330

<210> SEQ ID NO 4
<211> LENGTH: 312
```

```
<212> TYPE: PRT
<213> ORGANISM: Paenibacillus illinoisensis

<400> SEQUENCE: 4

Ala Ser Pro Gln Ala Lys Ala Leu Met Lys Phe Met Thr Asn Gln Tyr
1               5                   10                  15

Gly Lys Lys Ile Ile Ser Gly Gln Gln Thr Leu Glu Asp Ala Ala Trp
            20                  25                  30

Ile Tyr Gln Gln Thr Gly Lys Tyr Pro Ala Leu Val Ser Ser Asp Leu
        35                  40                  45

Met Asp Tyr Ser Pro Ser Arg Val Glu Asn Gly Ser Thr Ser Asn Glu
    50                  55                  60

Val Glu Lys Met Met Glu Trp Tyr Lys Arg Gly Ile Val Ser Leu
65                  70                  75                  80

Ser Trp His Trp Asn Ala Pro Lys Gly Ile Gly Ser Asn Glu Pro Gly
                85                  90                  95

His Glu Trp Trp Arg Gly Phe Asn Thr Glu Phe Thr Thr Phe Asp Val
                100                 105                 110

Glu Tyr Ala Leu Asn His Pro Glu Ser Glu Asp Tyr Lys Leu Leu Ile
            115                 120                 125

Arg Asp Ile Asp Ala Ile Ala Thr Gln Leu Lys Arg Leu Gln Glu His
130                 135                 140

His Ile Pro Val Leu Trp Arg Pro Leu His Glu Ala Glu Gly Gly Trp
145                 150                 155                 160

Phe Trp Trp Gly Ala Lys Gly Pro Glu Pro Ala Lys Lys Leu Tyr Arg
                165                 170                 175

Leu Met Tyr Glu Arg Leu Thr Glu Lys His Gly Leu Asn Asn Leu Ile
            180                 185                 190

Trp Val Trp Asn Ser Val Lys Glu Glu Trp Tyr Pro Gly Asp Asp Val
        195                 200                 205

Val Asp Met Val Ser Val Asp Ile Tyr Asn Pro Pro Gly Asp Tyr Ser
210                 215                 220

Pro Asn Ile Ala Lys Tyr Asp Glu Leu Leu Phe Leu Ser Lys His Lys
225                 230                 235                 240

Lys Leu Val Ala Leu Ala Glu Asn Gly Pro Ile Pro Asp Pro Asp Leu
                245                 250                 255

Leu Gln Thr Tyr Gly Ala His Trp Ser Tyr Phe Asn Thr Trp Thr Gly
            260                 265                 270

Asp Val Leu Arg Asp Gly Lys Thr Asn Thr Lys Glu His Leu Lys Lys
        275                 280                 285

Val Tyr Asn His Asp Asn Val Ile Thr Leu Asp Glu Leu Pro Lys Gly
    290                 295                 300

Leu Tyr Asp Ser Pro Arg Trp Lys
305                 310

<210> SEQ ID NO 5
<211> LENGTH: 699
<212> TYPE: PRT
<213> ORGANISM: Neobulgaria sp.

<400> SEQUENCE: 5

Thr Val Phe Glu Ala Glu Lys Gly Thr Leu Ala Gly Gly Leu Thr Ile
1               5                   10                  15

Ala Thr Asp Val Thr Gly Tyr Thr Gly Thr Gly Tyr Val Thr Asn Phe
            20                  25                  30
```

-continued

```
Ala Asp Ala Ala Ala Leu Leu Thr Phe Thr Val Asn Gly Leu Thr Ala
         35                  40                  45

Gly Ser Tyr Asp Leu Thr Leu Thr Tyr Ser Ala Gln Tyr Gly Asp Lys
 50                  55                  60

Phe Thr Thr Val Ser Val Asn Gly Ala Ser Gly Ile Glu Val Ala Ile
 65                  70                  75                  80

Thr Asn Val Thr Thr Ala Thr Trp Thr Ala Thr Ile Gly Thr Phe
                 85                  90                  95

Thr Leu Thr Ala Gly Asp Asn Thr Val Ser Cys Ala Asp Asp Trp Gly
                100                 105                 110

Trp Tyr Leu Ile Asp Ser Leu Thr Val Ile Pro Thr Pro Ala Lys Pro
            115                 120                 125

Ile Thr Ile Val Asp Val Ser Asn Gly Ala Thr Ala Gln Ala Glu Asp
130                 135                 140

Gly Ile Leu Thr Gly Thr Thr Val Gly Thr Thr Thr Ala Gly Tyr Thr
145                 150                 155                 160

Gly Thr Gly Tyr Val Thr Gly Phe Thr Ala Thr Gly Thr Gln Val Thr
                165                 170                 175

Ile Asn Leu Ser Ser Thr Lys Gln Ala Leu Tyr Asp Val Val Arg
            180                 185                 190

Tyr Ala Ala Ile Tyr Gly Gln Lys Tyr Thr Thr Met Gln Leu Asn Gly
            195                 200                 205

Val Gly Gly Ser Glu Ile Leu Leu Leu Asp Thr Thr Thr Ala Thr Ser
            210                 215                 220

Pro Trp Ala Asn Ala Thr Ala Gly Gln Val Leu Leu Ala Ser Gly Asn
225                 230                 235                 240

Asn Thr Leu Thr Phe Met Asn Asp Trp Gly Trp Tyr Phe Ile Asp Ala
                245                 250                 255

Val Tyr Val Thr Pro Ser Pro Ala Pro Ala Pro His Lys Val Thr Asn
            260                 265                 270

Ala Leu Val Asp Ala Lys Ala Leu Ala Ser Thr His Ala Leu Phe Asn
            275                 280                 285

Thr Leu Leu Ala Lys Tyr Gly Ser Gly Asp Ile Phe Ser Gly Gln Ala
            290                 295                 300

Asp Pro Thr Gly Val Thr Trp Ile Glu Ser Asn Leu Gly Thr Thr Lys
305                 310                 315                 320

Thr Pro Ala Ile Ile Gly Leu Asp Met Ile Glu Tyr Ser Pro Thr Arg
                325                 330                 335

Val Leu Tyr Gly Ser Thr Ser Thr Ala Val Glu Asp Ala Ile Ala Phe
            340                 345                 350

Asp Lys Arg Gly Gly Met Val Ala Phe Gln Trp His Trp Asn Ala Pro
            355                 360                 365

Ala Asp Leu Ile Asn Asn Asp Thr Val Pro Trp Trp Lys Gly Phe Tyr
            370                 375                 380

Ser Tyr Gly Thr Thr Phe Asn Leu Thr Ala Ala Leu Ala Asn Pro Ser
385                 390                 395                 400

Gly Ser Asp Tyr Ala Leu Leu Ile Ser Asp Met Asp Ala Ile Ala Val
                405                 410                 415

Gln Leu Leu Arg Leu Gln Ala Ala Gly Val Pro Val Leu Trp Arg Pro
            420                 425                 430

Leu His Glu Ala Asp Gly Thr Trp Phe Trp Trp Gly Asn Phe Gly Ala
            435                 440                 445

Ala Ser Cys Val Ser Leu Tyr Arg Ile Met Tyr Asp Arg Tyr Thr Asn
```

```
                450            455            460
Tyr His Gly Leu His Asn Leu Ile Trp Val Trp Asn Ser Val Thr Pro
465                 470                 475                 480

Ser Trp Tyr Pro Gly Ala Asp Val Val Asp Ile Leu Gly Tyr Asp Ser
                    485                 490                 495

Tyr Pro Ala Val Gly Asp His Gly Pro Val Ser Ser Gln Tyr Asn Ala
                500                 505                 510

Leu Ile Thr Leu Gly Gly Asp Thr Lys Leu Val Thr Leu Pro Glu Val
            515                 520                 525

Gly Asn Ile Pro Asp Pro Ala Ile Leu Lys Leu Tyr His Ala Asp Trp
        530                 535                 540

Ser Tyr Phe Val Thr Trp Asn Gln Asp Tyr Ile Leu Thr Asp Thr Tyr
545                 550                 555                 560

Asn Pro Leu Ala Phe Lys Gln Gln Val Tyr Asn Asp Pro Thr Val Leu
                    565                 570                 575

Lys Leu Thr Asp Leu Gly Asn Trp Lys Gly Ala Ala Thr Ser Thr Ile
                580                 585                 590

Val Ser Ser Thr Ser Lys Val Ser Thr Thr Ser Ser Leu Ile Thr
            595                 600                 605

Ser Thr Thr Lys Lys Thr Ser Ser Thr Val Val Ser Thr Thr Ser
        610                 615                 620

Ser Thr Val Lys Thr Thr Ser Thr Ser Lys Val Ser Ser Ser Thr
625                 630                 635                 640

Thr Lys Val Ser Ser Thr Thr Lys Val Thr Thr Thr Ser Thr Thr
                    645                 650                 655

Ser Ala Val Ala Thr Ala Thr Ala Gly His Trp Gly Gln Cys Gly Gly
                660                 665                 670

Thr Gly Trp Thr Gly Pro Thr Val Cys Ala Ser Gly Phe Thr Cys
            675                 680                 685

Ala Val Ser Pro Pro Tyr Tyr Tyr Gln Cys Leu
        690                 695
```

<210> SEQ ID NO 6
<211> LENGTH: 452
<212> TYPE: PRT
<213> ORGANISM: Preussia aemulans

<400> SEQUENCE: 6

```
Gln Thr Val Ile Tyr Gln Ala Glu Gln Ala Lys Leu Ser Gly Val Thr
1               5                   10                  15

Val Glu Phe Ser Ile Ile Lys Gln Val Val Gly Thr Gly Tyr Val Glu
                20                  25                  30

Gly Phe Asp Glu Ser Thr Asp Ser Ile Thr Phe Thr Val Glu Ser Thr
            35                  40                  45

Thr Ala Ala Leu Tyr Asp Leu Ala Leu Thr Tyr Asn Gly Pro Tyr Gly
        50                  55                  60

Asp Lys Tyr Thr Asn Val Val Leu Asn Asn Ala Ala Gly Ser Gln Val
65                  70                  75                  80

Ser Leu Pro Ala Thr Thr Ala Trp Thr Thr Val Pro Ala Gly Gln Val
                85                  90                  95

Leu Leu Asn Ala Gly Ala Asn Thr Ile Gln Ile Gln Asn Asn Trp Gly
            100                 105                 110

Trp Tyr Leu Val Asp Ser Ile Ser Leu Lys Pro Ala Ala Thr Arg Gly
        115                 120                 125
```

Ala His Gln Ile Thr Thr Lys Pro Val Asn Lys Asn Ala Asn Ser Asp
    130                 135                 140

Ala Lys Ala Leu Leu Lys Tyr Leu Gly Ser Ile Tyr Gly Lys Lys Ile
145                 150                 155                 160

Leu Ser Gly Gln Gln Asp Leu Ser Ser Leu Asp Trp Val Thr Lys Asn
                165                 170                 175

Val Gly Lys Thr Pro Ala Val Leu Gly Leu Asp Thr Met Asp Tyr Ser
            180                 185                 190

Glu Ser Arg Lys Ser Arg Gly Ala Val Ser Thr Asp Val Asp Lys Ala
                195                 200                 205

Ile Ala Phe Ala Lys Lys Gly Ile Val Thr Phe Cys Trp His Trp
    210                 215                 220

Gly Ala Pro Thr Gly Leu Phe Asp Ser Ala Ala Gln Pro Trp Tyr Arg
225                 230                 235                 240

Gly Phe Tyr Thr Asp Ala Thr Asp Phe Asn Ile Glu Thr Ala Leu Lys
                245                 250                 255

Asp Thr Thr Asn Ala Asn Tyr Thr Leu Leu Met Lys Asp Ile Asp Thr
                260                 265                 270

Ile Ala Val Gln Leu Lys Lys Leu Gln Asp Ala Gly Val Pro Val Ile
    275                 280                 285

Trp Arg Pro Leu His Glu Ala Glu Gly Gly Trp Phe Trp Trp Gly Ala
    290                 295                 300

Lys Gly Pro Glu Pro Ala Lys Lys Leu Trp Lys Ile Met Tyr Asp Arg
305                 310                 315                 320

Leu Thr Asn Gln His Gly Leu Asn Asn Leu Val Trp Thr Trp Asn Ser
                325                 330                 335

Val Ala Pro Asn Trp Tyr Pro Gly Asp Asp Thr Val Asp Ile Val Ser
            340                 345                 350

Ala Asp Thr Tyr Ser Gln Gly Asp His Gly Pro Ile Ser Ala Thr Tyr
                355                 360                 365

Asn Asn Leu Leu Ala Leu Thr Asn Asp Thr Lys Ile Ile Ala Ala Ala
    370                 375                 380

Glu Ile Gly Ser Val Met Glu Pro Ala Gln Leu Gln Ala Tyr Gln Ala
385                 390                 395                 400

Asp Trp Val Tyr Phe Cys Val Trp Ser Gly Glu Phe Ile Asp Gly Gly
                405                 410                 415

Val Trp Asn Ser Leu Asp Phe Leu Lys Lys Val Tyr Asn Asp Pro Tyr
            420                 425                 430

Val Leu Thr Leu Asp Glu Ile Gln Gly Trp Lys Thr Ala Arg Gly Lys
        435                 440                 445

Pro Arg Val Ser
    450

<210> SEQ ID NO 7
<211> LENGTH: 312
<212> TYPE: PRT
<213> ORGANISM: Yunnania penicillata

<400> SEQUENCE: 7

Ala Pro Ser Thr Thr Pro Val Asn Glu Lys Ala Thr Asp Ala Ala Lys
1               5                   10                  15

Asn Leu Leu Ser Tyr Leu Val Glu Gln Ala Ala Asn Gly Val Thr Leu
            20                  25                  30

Ser Gly Gln Gln Asp Leu Glu Ser Ala Gln Trp Val Ser Asp Asn Val
        35                  40                  45

```
Gly Lys Trp Pro Ala Ile Leu Gly Ile Asp Phe Met Asp Tyr Ser Pro
         50                  55                  60

Ser Arg Val Glu Tyr Gly Ala Val Gly Ser Thr Val Pro Asp Ala Ile
 65                  70                  75                  80

Ser Tyr Asp Ser Asp Gly Gly Ile Val Thr Phe Cys Trp His Trp Gly
                 85                  90                  95

Ser Pro Ser Gly Thr Tyr Asn Thr Thr Asp Gln Pro Trp Trp Ser Asn
            100                 105                 110

Phe Tyr Thr Glu Ala Thr Ala Phe Asp Ile Ala Ala Ala Met Asp Asp
        115                 120                 125

Pro Asp Ser Ala Asp Tyr Asn Leu Leu Val Arg Asp Ile Asp Ala Ile
130                 135                 140

Ser Glu Leu Leu Leu Gln Leu Gln Asp Leu Asp Ile Pro Ile Leu Trp
145                 150                 155                 160

Arg Pro Leu His Glu Ala Glu Gly Gly Trp Phe Trp Trp Gly Ala Lys
                165                 170                 175

Gly Pro Glu Ala Cys Ile Ala Leu Tyr Arg Leu Met Phe Asp Arg Met
            180                 185                 190

Thr Asn His His Gly Leu Asn Asn Leu Leu Trp Val Trp Asn Ser Val
        195                 200                 205

Asp Pro Ser Trp Tyr Pro Gly Asn Asp Val Val Asp Ile Val Ser Ala
210                 215                 220

Asp Ile Tyr Ala Asp Ala Gly Asp His Ser Pro Gln Glu Glu Thr Phe
225                 230                 235                 240

Ala Ser Leu Gln Ser Leu Thr Gly Asp Thr Lys Leu Val Ala Leu Gly
                245                 250                 255

Glu Val Gly Asn Ile Pro Asp Pro Ala Ser Thr Gly Gly Val Ala Asp
            260                 265                 270

Trp Ala Tyr Trp Val Thr Trp Asn Gly Asp Phe Ile Lys Gly Glu Asp
        275                 280                 285

Tyr Asn Pro Leu Glu Tyr Lys Lys Glu Val Phe Ser Ala Glu Asn Ile
290                 295                 300

Ile Thr Arg Asp Glu Val Asp Val
305                 310

<210> SEQ ID NO 8
<211> LENGTH: 327
<212> TYPE: PRT
<213> ORGANISM: Myrothecium roridum

<400> SEQUENCE: 8

Gly Thr Ile Glu Asn Arg Gln Trp Leu Thr Tyr Asn Pro Val Asp Ser
1               5                  10                  15

Ala Ala Thr Thr Glu Ala Arg Ala Leu Leu Arg Tyr Ile Gln Ser Gln
                20                  25                  30

Tyr Gly Trp Arg Tyr Leu Ser Gly Gln Gln Arg Ala Glu Val Gln
            35                  40                  45

Trp Leu Lys Ser Asn Ile Gly Lys Thr Pro Ala Ile Gln Gly Ser Asp
        50                  55                  60

Leu Ile Asp Tyr Ser Pro Ser Arg Val Ser Tyr Gly Ala Thr Ser Thr
65                  70                  75                  80

Ala Val Glu Asp Ala Ile Ala Phe Asp Arg Gln Gly Gly Ile Val Thr
                85                  90                  95

Phe Thr Trp His Trp Asn Ala Pro Asn Cys Leu Tyr Asn Ser Ala Asp
```

-continued

```
                100              105             110
Gln Pro Trp Tyr Phe Gly Phe Tyr Thr Lys Ala Thr Cys Phe Asn Ile
            115                 120             125
Gln Ala Ala Leu Ala Gln Gly Ser Asn Gly Ala Asp Tyr Lys Leu Leu
            130                 135             140
Ile Arg Asp Ile Asp Ala Ile Ala Val Gln Leu Lys Arg Leu Arg Asp
145                 150                 155                 160
Ala Lys Val Pro Ile Leu Phe Arg Pro Leu His Glu Pro Asp Gly Ala
                165                 170             175
Trp Phe Trp Trp Gly Ala Lys Gly Ser Gly Pro Phe Lys Gln Leu Trp
            180                 185             190
Asp Ile Leu Tyr Asp Arg Leu Thr Lys Tyr His Gly Leu His Asn Met
            195                 200             205
Leu Trp Val Cys Asn Thr Glu Lys Ser Asp Trp Tyr Pro Gly Asn Asn
            210                 215             220
Lys Cys Asp Ile Ala Thr Thr Asp Val Tyr Val Asn Ala Gly Asp His
225                 230                 235                 240
Ser Val Gln Lys Ser His Trp Asp Ala Leu Tyr Gly Val Ser Gly Gly
                245                 250             255
Gln Arg Ile Leu Ala Leu Gly Glu Val Gly Val Ile Pro Asp Pro Glu
            260                 265             270
Arg Gln Ala Ser Glu Asn Val Pro Trp Ala Tyr Trp Met Thr Trp Asn
            275                 280             285
Gly Tyr Phe Ile Arg Asp Gly Asn Tyr Asn Ser Arg Asn Phe Leu Gln
            290                 295             300
Ser Thr Phe Ser Asn Ala Arg Val Val Thr Leu Asp Gly Thr Ser Pro
305                 310                 315                 320
Leu Gly Asn Trp Lys Ser Ser
                325

<210> SEQ ID NO 9
<211> LENGTH: 452
<212> TYPE: PRT
<213> ORGANISM: Chaetomium brasiliense

<400> SEQUENCE: 9

Val Pro Cys Gly Gly Ser Asn Ser Gly Pro Arg Thr Tyr Glu Ala
1               5                   10              15
Glu Asp Ala Asp Leu Thr Gly Thr Asn Ile Asp Thr Ala Gln Ser Gly
                20                  25              30
Phe Thr Gly Ser Gly Tyr Val Thr Gly Phe Asp Gln Ala Thr Asp Lys
            35                  40              45
Val Thr Phe Lys Val Asp Ser Pro Ser Leu Lys Leu Tyr Asp Leu Ser
            50                  55              60
Ile Arg Val Ala Ala Ile Tyr Gly Glu Lys Arg Thr Asn Val Val Leu
65                  70                  75                  80
Asn Asn Gly Ala Ser Ser Glu Val Tyr Phe Ala Ala Ser Glu Thr Phe
                85                  90              95
Thr Thr Val Ala Ala Gly Gln Val Leu Leu Asn Glu Gly Ala Asn Thr
                100             105             110
Ile Asp Leu Val Ser Asn Trp Gly Trp Tyr Leu Ile Asp Ser Ile Thr
            115                 120             125
Leu Thr Pro Ser Thr Gln Arg Pro Pro His Asn Ile Asn Pro Ser Pro
            130                 135             140
```

Val Asn Pro Ser Ala Asn Ala Asp Ala Lys Gly Leu Tyr Thr Tyr Leu
145                 150                 155                 160

Arg Ser Ile Tyr Gly Lys Lys Ile Leu Ser Gly Gln Gln Glu Leu Ser
            165                 170                 175

Trp Ser Asn Trp Ile Thr Thr Gln Thr Gly Lys Thr Pro Ala Leu Val
            180                 185                 190

Ser Val Asp Leu Met Asp Tyr Ser Pro Ser Arg Val Glu Arg Gly Thr
            195                 200                 205

Val Gly Thr Ala Val Glu Glu Ala Ile Thr His Ala Gln Arg Gly Gly
210                 215                 220

Ile Val Ser Val Leu Trp His Trp Asn Ala Pro Thr Gly Leu Tyr Asp
225                 230                 235                 240

Thr Glu Glu Asn Lys Trp Trp Ser Gly Phe Tyr Thr Arg Ala Thr Asp
            245                 250                 255

Phe Asp Val Ala Ala Ala Leu Ser Ser Thr Thr Asn Ala Asn Tyr Thr
            260                 265                 270

Leu Ile Leu Arg Asp Ile Asp Ala Ile Ala Val Gln Leu Lys Lys Leu
            275                 280                 285

Gln Asp Ala Gly Val Pro Val Leu Phe Arg Pro Leu His Glu Ala Glu
290                 295                 300

Gly Gly Trp Phe Trp Trp Gly Ala Lys Gly Ala Glu Pro Cys Lys Lys
305                 310                 315                 320

Leu Tyr Ala Leu Leu Tyr Asp Arg Leu Thr Asn Tyr His Lys Ile Asn
            325                 330                 335

Asn Leu Ile Trp Val Trp Asn Ser Ile Leu Glu Glu Trp Tyr Pro Gly
            340                 345                 350

Asp Ala Thr Val Asp Ile Leu Ser Ala Asp Val Tyr Ala Gln Gly Asn
            355                 360                 365

Gly Pro Ile Ser Thr Gln Tyr Asn Gln Leu Ile Glu Leu Gly Lys Asp
            370                 375                 380

Lys Lys Met Ile Ala Ala Ala Glu Val Gly Ala Ala Pro Leu Pro Asn
385                 390                 395                 400

Leu Leu Gln Ala Tyr Glu Ala His Trp Leu Trp Phe Thr Val Trp Gly
            405                 410                 415

Asp Thr Phe Ile Asn Asn Ala Glu Trp Asn Ser Val Asp Val Leu Lys
            420                 425                 430

Gln Val Tyr Thr Ser Asp Tyr Val Leu Thr Leu Asp Glu Ile Gln Gly
            435                 440                 445

Trp Arg Gly Ala
    450

<210> SEQ ID NO 10
<211> LENGTH: 541
<212> TYPE: PRT
<213> ORGANISM: Ascobolus stictoideus

<400> SEQUENCE: 10

Gln Thr Tyr Thr Leu Glu Ala Glu Ala Gly Thr Leu Thr Gly Val Thr
1               5                   10                  15

Val Met Asn Glu Ile Ala Gly Phe Ser Gly Thr Gly Tyr Val Gly Gly
            20                  25                  30

Trp Asp Glu Asp Ala Asp Thr Val Ser Leu Thr Phe Thr Ser Asp Ala
            35                  40                  45

Thr Lys Leu Tyr Asp Val Lys Ile Arg Tyr Ser Gly Pro Tyr Gly Ser
50                  55                  60

```
Lys Tyr Thr Arg Ile Ser Tyr Asn Gly Ala Thr Gly Asp Ile Ser
 65                  70                  75                  80

Leu Pro Glu Thr Thr Glu Trp Ala Thr Val Asn Ala Gly Gln Ala Leu
                 85                  90                  95

Leu Asn Ala Gly Ser Asn Thr Ile Lys Leu His Asn Asn Trp Gly Trp
            100                 105                 110

Tyr Leu Ile Asp Ala Val Ile Leu Thr Pro Ser Val Pro Arg Pro Pro
            115                 120                 125

His Gln Val Thr Asp Ala Leu Val Asn Thr Asn Ser Asn Ala Val Thr
            130                 135                 140

Lys Gln Leu Met Lys Phe Leu Val Ser Lys Tyr His Lys Ala Tyr Ile
145                 150                 155                 160

Thr Gly Gln Gln Glu Leu His Ala His Gln Trp Val Glu Lys Asn Val
                165                 170                 175

Gly Lys Ser Pro Ala Ile Leu Gly Leu Asp Phe Met Asp Tyr Ser Pro
                180                 185                 190

Ser Arg Val Glu Phe Gly Thr Thr Ser Gln Ala Val Glu Gln Ala Ile
            195                 200                 205

Asp Phe Asp Lys Arg Gly Gly Ile Val Thr Phe Ala Trp His Trp Asn
            210                 215                 220

Ala Pro Ser Gly Leu Ile Asn Thr Pro Gly Ser Glu Trp Trp Arg Gly
225                 230                 235                 240

Phe Tyr Thr Glu His Thr Thr Phe Asp Val Ala Ala Leu Gln Asn
                245                 250                 255

Thr Thr Asn Ala Asn Tyr Asn Leu Leu Ile Arg Asp Ile Asp Ala Ile
                260                 265                 270

Ala Val Gln Leu Lys Arg Leu Gln Thr Ala Gly Val Pro Val Leu Trp
            275                 280                 285

Arg Pro Leu His Glu Ala Glu Gly Gly Trp Phe Trp Trp Gly Ala Lys
            290                 295                 300

Gly Pro Glu Pro Ala Lys Lys Leu Tyr Lys Ile Leu Tyr Asp Arg Leu
305                 310                 315                 320

Thr Asn Tyr His Lys Leu Asn Asn Leu Ile Trp Val Trp Asn Ser Val
                325                 330                 335

Ala Lys Asp Trp Tyr Pro Gly Asp Glu Ile Val Asp Val Leu Ser Phe
            340                 345                 350

Asp Ser Tyr Pro Ala Gln Pro Gly Asp His Gly Pro Val Ser Ala Gln
            355                 360                 365

Tyr Asn Ala Leu Val Glu Leu Gly Lys Asp Lys Lys Leu Ile Ala Ala
            370                 375                 380

Thr Glu Val Gly Thr Ile Pro Asp Pro Asp Leu Met Gln Leu Tyr Glu
385                 390                 395                 400

Ser Tyr Trp Ser Phe Phe Val Thr Trp Glu Gly Glu Phe Ile Glu Asn
                405                 410                 415

Gly Val His Asn Ser Leu Glu Phe Leu Lys Lys Leu Tyr Asn Asn Ser
            420                 425                 430

Phe Val Leu Asn Leu Asp Thr Ile Gln Gly Trp Lys Asn Gly Ala Gly
            435                 440                 445

Ser Ser Thr Thr Thr Val Lys Ser Thr Thr Thr Pro Thr Thr Thr
            450                 455                 460

Ile Lys Ser Thr Thr Thr Thr Pro Val Thr Thr Pro Thr Thr Val Lys
465                 470                 475                 480
```

```
Thr Thr Thr Thr Pro Thr Thr Ala Thr Thr Val Lys Ser Thr Thr
                485                 490                 495

Thr Thr Ala Gly Pro Thr Pro Thr Ala Val Ala Gly Arg Trp Gln Gln
            500                 505                 510

Cys Gly Gly Ile Gly Phe Thr Gly Pro Thr Cys Glu Ala Gly Thr
            515                 520                 525

Thr Cys Asn Val Leu Asn Pro Tyr Tyr Ser Gln Cys Leu
            530                 535                 540

<210> SEQ ID NO 11
<211> LENGTH: 526
<212> TYPE: PRT
<213> ORGANISM: Chaetomium virescens

<400> SEQUENCE: 11

Pro Arg Asp Pro Gly Ala Thr Ala Arg Thr Phe Glu Ala Glu Asp Ala
1               5                   10                  15

Thr Leu Ala Gly Thr Asn Val Asp Thr Ala Leu Ser Gly Phe Thr Gly
                20                  25                  30

Thr Gly Tyr Val Thr Gly Phe Asp Gln Ala Ala Asp Lys Val Thr Phe
            35                  40                  45

Thr Val Asp Ser Ala Ser Thr Glu Leu Tyr Asp Leu Ser Ile Arg Val
    50                  55                  60

Ala Ala Ile Tyr Gly Asp Lys Arg Thr Ser Val Val Leu Asn Gly Gly
65                  70                  75                  80

Ala Ser Ser Glu Val Tyr Phe Pro Ala Gly Glu Thr Trp Thr Asn Val
                85                  90                  95

Ala Ala Gly Gln Leu Leu Asn Gln Gly Ser Asn Thr Ile Asp Ile
            100                 105                 110

Val Ser Asn Trp Gly Trp Tyr Leu Ile Asp Ser Ile Thr Leu Thr Pro
            115                 120                 125

Ser Thr Pro Arg Pro Ala His Gln Ile Asn Glu Ala Pro Val Asn Ala
    130                 135                 140

Ala Ala Asp Lys Asn Ala Lys Ala Leu Tyr Ser Tyr Leu Arg Ser Ile
145                 150                 155                 160

Tyr Gly Lys Lys Ile Leu Ser Gly Gln Gln Glu Leu Ser Leu Ser Asn
                165                 170                 175

Trp Ile Ala Gln Gln Thr Gly Lys Thr Pro Ala Leu Val Ser Val Asp
            180                 185                 190

Leu Met Asp Tyr Ser Pro Ser Arg Val Glu Arg Gly Thr Val Gly Thr
    195                 200                 205

Ala Val Glu Glu Ala Ile Gln His His Asn Arg Gly Gly Ile Val Ser
210                 215                 220

Val Leu Trp His Trp Asn Ala Pro Thr Gly Leu Tyr Asp Thr Glu Glu
225                 230                 235                 240

His Arg Trp Trp Ser Gly Phe Tyr Thr Ser Ala Thr Asp Phe Asp Val
                245                 250                 255

Ala Ala Ala Leu Ser Ser Thr Thr Asn Ala Asn Tyr Thr Leu Leu Ile
            260                 265                 270

Arg Asp Ile Asp Ala Ile Ala Val Gln Leu Lys Arg Leu Gln Ser Ala
    275                 280                 285

Gly Val Pro Val Leu Phe Arg Pro Leu His Glu Ala Glu Gly Gly Trp
290                 295                 300

Phe Trp Trp Gly Ala Lys Gly Pro Glu Pro Ala Lys Lys Leu Trp Gly
305                 310                 315                 320
```

-continued

Ile Leu Tyr Asp Arg Val Thr Asn His His Gln Ile Asn Asn Leu Leu
            325                 330                 335

Trp Val Trp Asn Ser Ile Leu Pro Glu Trp Tyr Pro Gly Asp Ala Thr
            340                 345                 350

Val Asp Ile Leu Ser Ala Asp Val Tyr Ala Gln Gly Asn Gly Pro Met
            355                 360                 365

Ser Thr Gln Tyr Asn Gln Leu Ile Glu Leu Gly Lys Asp Lys Lys Met
            370                 375                 380

Ile Ala Ala Ala Glu Val Gly Ala Ala Pro Leu Pro Asp Leu Leu Gln
385                 390                 395                 400

Ala Tyr Glu Ala His Trp Leu Trp Phe Thr Val Trp Gly Asp Ser Phe
            405                 410                 415

Ile Asn Asn Ala Asp Trp Asn Ser Leu Asp Thr Leu Lys Lys Val Tyr
            420                 425                 430

Thr Ser Asp Tyr Val Leu Thr Leu Asp Glu Ile Gln Gly Trp Gln Gly
            435                 440                 445

Ser Thr Pro Ser Ala Thr Thr Thr Ser Ser Thr Thr Thr Pro Ser Ala
            450                 455                 460

Thr Thr Thr Thr Thr Thr Pro Ser Thr Thr Ala Thr Thr Ala Thr Pro
465                 470                 475                 480

Ser Ala Thr Thr Thr Ala Ser Pro Val Thr Tyr Ala Glu His Trp Gly
            485                 490                 495

Gln Cys Ala Gly Lys Gly Trp Thr Gly Pro Thr Thr Cys Arg Pro Pro
            500                 505                 510

Tyr Thr Cys Lys Tyr Gln Asn Asp Trp Tyr Ser Gln Cys Leu
            515                 520                 525

<210> SEQ ID NO 12
<211> LENGTH: 527
<212> TYPE: PRT
<213> ORGANISM: Paenibacillus ihumii

<400> SEQUENCE: 12

Ser Ser Ala Leu Pro Asp Thr Val Val Lys Glu Ala Pro Ser Ala Ser
1               5                   10                  15

Pro Thr Asn Gly Ile Thr Val Thr Phe Ala Asp Ala Val Leu Thr Gly
            20                  25                  30

Tyr Gly Ile Glu Lys Arg Gly Ser Val Lys Glu Asn Glu Asp Thr Leu
            35                  40                  45

Tyr Asp Gly Lys Gly Tyr Ile Ser Tyr Phe Phe Asp Glu Asp Ala Asn
        50                  55                  60

Ala Ala Glu Pro Val Gly Ser Ala Thr Phe Thr Val Asp Val Ala Glu
65                  70                  75                  80

Ala Gly Leu Tyr Lys Leu Ser Leu Gly Tyr Tyr Leu Pro Glu Gly Tyr
            85                  90                  95

Gly Asp Lys Val Thr Ser Ile Glu Ile Asn Gly Ala Thr Gly Thr Glu
            100                 105                 110

Leu Thr Leu Asp Glu Pro Ala Ala Gly Thr Val Arg Ala Glu Lys Met
            115                 120                 125

Val Ser Lys Val Leu Leu Asn Ala Gly Ser Asn Thr Ile Lys Ile Met
            130                 135                 140

Arg Gly Trp Gly Tyr Tyr Gly Ile Glu His Ile Lys Leu Glu Pro Ala
145                 150                 155                 160

Gly Ala Ala Ser Ser Ser Asn Lys Leu Ala Ala Glu Asp Gly Pro Met

```
                165                 170                 175

Thr Gly Ala Leu Asn Asn Pro Glu Ala Thr Pro Glu Ala Arg Ala Leu
            180                 185                 190

Met Asp Tyr Leu Leu Ser Gln Tyr Gly Gln Lys Ile Ile Ser Gly Gln
        195                 200                 205

Gln Thr Ile Glu Asp Ile Glu Trp Ile Lys Gln Gln Thr Gly Lys Tyr
    210                 215                 220

Pro Ala Ile Phe Ser Thr Asp Leu Met Asp Tyr Ser Pro Ser Arg Ile
225                 230                 235                 240

Glu Asn Gly Ala Ser Ser Thr Glu Val Glu Lys Met Ile Glu Trp Tyr
                245                 250                 255

Lys Arg Gly Gly Ile Val Ser Leu Cys Trp His Trp Asn Ala Pro Lys
            260                 265                 270

Gly Ile Gly Gly Asn Glu Pro Gly His Glu Trp Trp Arg Gly Phe Tyr
        275                 280                 285

Thr Glu Phe Thr Thr Phe Asp Val Glu Phe Ala Leu Asn His Leu Asp
    290                 295                 300

Ser Glu Asp Tyr Gln Leu Leu Ile Arg Asp Ile Asp Ala Ile Ala Val
305                 310                 315                 320

Gln Leu Lys Arg Leu Gln Asp Ala Asn Val Pro Val Leu Trp Arg Pro
                325                 330                 335

Leu His Glu Ala Glu Gly Gly Trp Phe Trp Trp Gly Ala Lys Gly Pro
            340                 345                 350

Glu Pro Ala Lys Gln Leu Tyr Arg Leu Met Tyr Asp Arg Leu Thr His
        355                 360                 365

Asp His Asn Leu Asn Asn Leu Ile Trp Ile Trp Asn Ser Glu Lys Lys
    370                 375                 380

Asp Trp Tyr Pro Gly Asp Val Val Asp Ile Val Ser Val Asp Ile
385                 390                 395                 400

Tyr Asn Pro Ala Glu Asp Tyr Asn Pro Ser Ile Ala Lys Tyr Glu Gly
                405                 410                 415

Leu Val Ser Leu Val Asn Gly Lys Lys Met Ala Ala Leu Ala Glu Asn
            420                 425                 430

Gly Pro Ile Pro Asp Pro Asp Ala Leu Gln Ala Tyr Gly Ala Glu Trp
        435                 440                 445

Ser Phe Phe Ser Thr Trp Thr Gly Asp Tyr Ile Arg Asp Gly Lys Thr
    450                 455                 460

Asn Thr Met Glu His Leu Lys Lys Val Tyr His Asp Tyr Val Ile
465                 470                 475                 480

Thr Leu Asp Glu Leu Pro Ala Asp Leu Tyr Ala Asn Pro Glu Phe Glu
                485                 490                 495

Ala Glu Asn Gly Glu Ser Ala Gly Met Thr Arg Ala Asn Gly Gln Glu
            500                 505                 510

Ser His Ser Lys Gly Gly Tyr Thr Thr Gly Met Glu Pro Lys Asn
        515                 520                 525

<210> SEQ ID NO 13
<211> LENGTH: 491
<212> TYPE: PRT
<213> ORGANISM: Paenibacillus sp.

<400> SEQUENCE: 13

Ala Ile Thr Val Pro Gly Phe Val Val Glu Pro His Thr Ser Ser Asp
1               5                   10                  15
```

Gln Asn Gln Ala Ile Ile Ala Thr Tyr Asn Asp Ala Ser Ile Glu Gly
                20                  25                  30

Tyr Gly Ile Lys Lys Arg Asp Glu Thr Thr Ala Lys Ala Glu Asp Asp
            35                  40                  45

Leu Tyr Asp Gly Thr Gly Tyr Ile Ser Tyr Phe Phe Glu Glu Asp Glu
        50                  55                  60

Lys Ala Thr Ala Gln Lys Gly Ser Ala Thr Phe His Val Lys Ala Pro
65                  70                  75                  80

Glu Asn Gly Leu Tyr Glu Leu Ser Leu Gly Tyr Ile Pro Glu Gly
                85                  90                  95

Asn Gly Asp Lys Ala Thr Ser Ile Gln Val Asn Gly Ser Gly Ala Gly
            100                 105                 110

Glu Leu Met Leu Ser Ala Pro Lys Gln Gly Thr Val Arg Ala Glu Lys
        115                 120                 125

Lys Met Thr Lys Val Leu Leu Asn Ser Gly Asn Asn Ser Ile Gln Ile
130                 135                 140

Leu Arg Gly Trp Gly Tyr Tyr Gly Ile Glu Tyr Ile Lys Leu Glu Arg
145                 150                 155                 160

Val Glu Pro Arg Ile Thr Thr Gln Lys Thr Lys Met Asp Pro Leu Ser
            165                 170                 175

Asn Ser Lys Ala Ser Pro Gln Ala Lys Ala Leu Met Lys Phe Met Thr
        180                 185                 190

Asn Gln Tyr Gly Lys Lys Ile Ile Ser Gly Gln Gln Thr Leu Glu Asp
            195                 200                 205

Ala Thr Trp Ile Tyr Gln Gln Thr Gly Lys Tyr Pro Ala Leu Val Ser
210                 215                 220

Ser Asp Leu Met Asp Tyr Ser Pro Ser Arg Val Glu Asn Gly Ser Thr
225                 230                 235                 240

Ser Asn Glu Val Glu Lys Met Met Glu Trp Tyr Lys Arg Gly Gly Ile
            245                 250                 255

Val Ser Leu Ser Trp His Trp Asn Ala Pro Lys Gly Ile Gly Gly Asn
            260                 265                 270

Glu Pro Gly His Glu Trp Trp Arg Gly Phe Asn Thr Glu Phe Thr Thr
        275                 280                 285

Phe Asp Val Glu Tyr Ala Leu Asp His Pro Glu Ser Glu Asp Tyr Lys
    290                 295                 300

Leu Leu Ile Arg Asp Ile Asp Ala Ile Ala Ala Gln Leu Lys Arg Leu
305                 310                 315                 320

Gln Glu His His Ile Pro Val Leu Trp Arg Pro Leu His Glu Ala Glu
            325                 330                 335

Gly Gly Trp Phe Trp Trp Gly Ala Lys Gly Pro Glu Pro Ala Lys Lys
        340                 345                 350

Leu Tyr Arg Leu Met Tyr Glu Arg Leu Thr Glu Lys His Lys Leu Asn
    355                 360                 365

Asn Leu Ile Trp Val Trp Asn Ser Val Lys Glu Trp Tyr Pro Gly
        370                 375                 380

Asp Asp Val Val Asp Met Val Ser Val Asp Ile Tyr Asn Pro Pro Gly
385                 390                 395                 400

Asp His Ser Pro Ser Ile Ala Lys Tyr Asp Glu Leu Leu Phe Leu Ser
            405                 410                 415

Lys His Lys Lys Leu Val Ala Leu Ala Glu Asn Gly Pro Ile Pro Asp
        420                 425                 430

Pro Asp Leu Leu Gln Thr Tyr Gly Ala His Trp Ser Tyr Phe Asn Thr

```
                435                 440                 445
Trp Thr Gly Asp Val Leu Arg Asp Gly Lys Thr Asn Thr Lys Glu His
    450                 455                 460

Leu Lys Lys Val Tyr Asn His Asp Asn Val Ile Thr Leu Asp Glu Leu
465                 470                 475                 480

Pro Lys Gly Leu Tyr Gly Cys Pro Arg Trp Lys
                485                 490

<210> SEQ ID NO 14
<211> LENGTH: 458
<212> TYPE: PRT
<213> ORGANISM: Salipaludibacillus agaradhaerens

<400> SEQUENCE: 14

Asn Tyr Glu Ser Glu Val Arg Arg Phe Glu Ala Glu Asp Ala Thr Leu
1               5                   10                  15

Asn Gly Val Thr Val Lys Asn Ser Glu Pro Gly Phe Ser Gly Thr Gly
                20                  25                  30

Tyr Val Gly Asp Phe Glu Asp Ser Gln Ser Val Thr Phe His Val
            35                  40                  45

Asp Val Pro Glu Thr Asp Leu Tyr Thr Leu Thr Ile Gly Tyr Gly Ala
50                  55                  60

Ile Tyr Gly Ser Glu Lys Val Ala Asn Val Leu Val Asn Gly Glu Lys
65                  70                  75                  80

Leu Ser Ser Phe Thr Met Gly Ser Gly Phe Gly Lys Ala Ser Ala Gly
                85                  90                  95

Asn Ile Val Leu Asn Ser Gly Ser Asn Thr Ile Ser Ile Thr Pro Asp
                100                 105                 110

Trp Thr His Phe Ala Ile Asp Tyr Ile Glu Val Lys Leu Thr Pro Glu
                115                 120                 125

Pro Ile Lys His Asn Val Glu Lys Lys Leu Ile Asn Pro Asn Ala Thr
            130                 135                 140

Asp Glu Ala Lys Val Leu Met Ser Tyr Leu Val Asp Asn Phe Gly Glu
145                 150                 155                 160

Lys Ile Leu Ser Gly Gln His Asp Phe Pro Asn Thr Arg Pro Asp Asp
                165                 170                 175

Leu Glu Tyr Ile Tyr Glu Ile Thr Gly Lys Tyr Pro Ala Ile Leu Gly
                180                 185                 190

Leu Asp Phe Ile Asp Asn Ser Pro Ser Arg Val Glu Tyr Gly Ala Phe
            195                 200                 205

Ala Asp Glu Thr Pro Val Ala Ile Asn Trp Trp Asn Lys Gly Gly Ile
210                 215                 220

Val Thr Phe Thr Trp His Trp Asn Ala Pro Lys Asp Leu Leu Asp Glu
225                 230                 235                 240

Pro Gly Asn Glu Trp Trp Arg Gly Phe Tyr Thr Glu Ala Thr Thr Phe
                245                 250                 255

Asp Val Glu Tyr Ala Leu Asn His Pro Asp Ser Glu Asp Tyr Lys Leu
            260                 265                 270

Leu Ile Arg Asp Ile Asp Val Ile Ala Asp Glu Leu Lys Lys Leu Gln
            275                 280                 285

Lys Ala Asp Val Pro Val Leu Trp Arg Pro Leu His Glu Ala Glu Gly
        290                 295                 300

Lys Trp Phe Trp Trp Gly Lys Lys Gly Pro Glu Pro Ala Lys Glu Leu
305                 310                 315                 320
```

```
Trp Leu Leu Met Tyr Asp Arg Met Thr Asn Tyr His Asn Leu Asn Asn
                325                 330                 335

Leu Ile Trp Val Trp Asn Ser Ile Glu Glu Asp Trp Tyr Pro Gly Asp
            340                 345                 350

Glu Tyr Val Asp Ile Val Ser Phe Asp Ser Tyr Pro Gly Asp Tyr Asn
            355                 360                 365

Tyr Ser Pro Met Ser Gly Gln Tyr Glu Ala Leu Lys Glu Leu Ser Ser
        370                 375                 380

Asn Lys Lys Ile Ile Ala Ile Ala Glu Asn Gly Pro Ile Pro Asp Pro
385                 390                 395                 400

Asp Leu Leu Gln Arg Tyr His Ala His Tyr Ser Trp Phe Thr Thr Trp
                405                 410                 415

Asn Gly Asp Ile Leu Arg Glu Gln Asn Ser Glu Glu His Leu Lys Asn
            420                 425                 430

Val Tyr Asn His Asp Tyr Val Ile Thr Leu Asp Glu Leu Pro Asp Phe
            435                 440                 445

Glu Thr Tyr Lys Glu Asp Val Pro Leu Glu
        450                 455

<210> SEQ ID NO 15
<211> LENGTH: 370
<212> TYPE: PRT
<213> ORGANISM: Geobacillus tepidamans

<400> SEQUENCE: 15

Lys Lys Gln Lys Asn Pro Ser Lys Pro Asn Ser Lys Arg Val Glu Asn
1               5                   10                  15

Leu Val Asp Pro Leu Ala Thr Asp Asp Thr Lys Ser Leu Phe Ala Tyr
            20                  25                  30

Leu Lys Asp Val Arg Gly Lys Gln Val Leu Phe Gly His Gln His Ala
        35                  40                  45

Ile Asp Glu Gly Leu Thr Leu Ile Gly Ser Lys Glu Leu Glu Ser Glu
    50                  55                  60

Val Lys Asn Ser Val Gly Asp Phe Pro Ala Val Phe Gly Trp Asp Thr
65                  70                  75                  80

Leu Ser Leu Glu Gly Lys Glu Lys Pro Gly Val Pro Asn Asp Pro Lys
                85                  90                  95

Gln Ser Arg Ala Asn Leu Val Ala Ser Met Lys Lys Val His Lys Leu
            100                 105                 110

Gly Gly Ile Ile Ala Leu Ser Ala His Met Pro Asn Phe Val Thr Gly
        115                 120                 125

Gly Ser Phe Asn Asp Thr Thr Gly Asn Val Val Glu His Ile Leu Pro
    130                 135                 140

Gly Gly Asp Lys Asn Ala Glu Phe Asn Ser Phe Leu Asp Asn Ile Ala
145                 150                 155                 160

Gln Phe Ala Lys Glu Leu Lys Asp Asp Lys Gly Lys Gln Ile Pro Ile
                165                 170                 175

Leu Phe Arg Pro Phe His Glu Gln Asn Gly Ser Trp Phe Trp Trp Gly
            180                 185                 190

Ala Lys Thr Thr Thr Pro Ser Gln Tyr Ile Glu Ile Tyr Arg Tyr Thr
        195                 200                 205

Val Glu Tyr Leu Arg Asp Lys Lys Gly Val His Asn Phe Leu Tyr Val
    210                 215                 220

Tyr Ser Pro Asn Gly Thr Phe Gly Gly Ser Glu Ala Asn Tyr Leu Thr
225                 230                 235                 240
```

```
Thr Tyr Pro Gly Asp Asp Tyr Val Asp Ile Leu Gly Met Asp Gln Tyr
                245                 250                 255

Asp Asn Gln Ser Asn Pro Gly Thr Thr Gln Phe Leu Thr Asn Leu Val
            260                 265                 270

Lys Asp Leu Glu Met Ile Ser Lys Leu Ala Asp Thr Lys Gly Lys Ile
        275                 280                 285

Ala Ala Phe Ser Glu Phe Gly Tyr Ser Pro Gln Gly Met Lys Thr Thr
    290                 295                 300

Gly Asn Gly Asp Leu Lys Trp Phe Thr Lys Val Leu Asn Ala Ile Lys
305                 310                 315                 320

Ala Asp Arg Asn Ala Lys Arg Ile Ala Tyr Met Gln Thr Trp Ala Asn
                325                 330                 335

Phe Gly Leu Asn Gly Asn Leu Phe Val Pro Tyr Asn Asp Ala Pro Asn
            340                 345                 350

Gly Leu Gly Asp His Glu Leu Leu Pro Asp Phe Ile Asn Tyr Tyr Lys
        355                 360                 365

Asp Pro
    370

<210> SEQ ID NO 16
<211> LENGTH: 1062
<212> TYPE: PRT
<213> ORGANISM: Bacillus sp. SWT81

<400> SEQUENCE: 16

Ser Gln Glu Gly Arg Gln Leu Asn Met Ala Asp Glu Asp Ala Ser Lys
1               5                   10                  15

Tyr Thr Lys Glu Leu Phe Ala Phe Leu Gln Asp Val Ser Gly Ser Gln
            20                  25                  30

Val Leu Phe Gly Gln Gln His Ala Thr Asp Glu Gly Leu Thr Leu Thr
        35                  40                  45

Asn Pro Ala Pro Arg Thr Gly Ser Thr Gln Ser Glu Val Phe Asn Ala
    50                  55                  60

Val Gly Asp Tyr Pro Ala Val Phe Gly Trp Asp Thr Asn Ser Leu Asp
65                  70                  75                  80

Gly Arg Glu Lys Pro Gly Ile Ala Gly Asn Val Glu Gln Ser Ile Lys
                85                  90                  95

Asn Thr Ala Gln Ser Met Lys Val Ala His Asp Leu Gly Gly Ile Ile
            100                 105                 110

Thr Leu Ser Met His Pro Asp Asn Phe Val Thr Gly Gly Pro Tyr Gly
        115                 120                 125

Asp Thr Thr Gly Asn Val Val Lys Glu Ile Leu Pro Gly Gly Ser Lys
    130                 135                 140

His Ala Glu Phe Asn Ala Trp Leu Asp Asn Ile Ala Ala Leu Ala His
145                 150                 155                 160

Glu Leu Lys Asp Glu Asn Gly Glu Pro Ile Pro Met Ile Phe Arg Pro
                165                 170                 175

Phe His Glu Gln Thr Gly Ser Trp Phe Trp Trp Gly Ala Ser Thr Thr
            180                 185                 190

Ser Pro Glu Gln Tyr Lys Ala Ile Phe Arg Tyr Thr Val Glu Tyr Leu
        195                 200                 205

Arg Asp Val Lys Gly Val Asn Asn Ile Leu Tyr Gly Phe Ser Pro Gly
    210                 215                 220

Ala Gly Pro Ala Gly Asp Val Asn Arg Tyr Leu Glu Thr Tyr Pro Gly
```

-continued

```
        225                 230                 235                 240
Asp Asp Tyr Val Asp Ile Phe Gly Ile Asp Asn Tyr Asp Asn Lys Asp
                245                 250                 255
Asn Ala Gly Ser Glu Ala Trp Leu Ser Gly Met Val Lys Asp Leu Ala
            260                 265                 270
Met Ile Ser Arg Leu Ala Glu Gln Lys Glu Lys Val Ala Ala Phe Thr
        275                 280                 285
Glu Tyr Gly Tyr Ser Ala Thr Gly Ile Asn Arg Gln Gly Asn Thr Leu
    290                 295                 300
Asp Trp Tyr Thr Arg Val Leu Asp Ala Ile Ala Asp Glu Asp Ala
305                 310                 315                 320
Arg Lys Ile Ser Tyr Met Leu Thr Trp Ala Asn Phe Gly Trp Pro Asn
                325                 330                 335
Asn Met Tyr Val Pro Tyr Arg Asp Ile His Asn Glu Leu Gly Gly Asp
            340                 345                 350
His Glu Leu Leu Pro Asp Phe Glu Ala Phe His Ala Asp Asp Tyr Thr
        355                 360                 365
Ala Phe Arg Asp Glu Ile Lys Gly Lys Ile Tyr Asn Thr Gly Lys Glu
    370                 375                 380
Tyr Thr Val Ser Pro His Glu Pro Phe Met Tyr Val Ile Ser Pro Ile
385                 390                 395                 400
Thr Gly Ser Thr Val Thr Ser Glu Thr Val Thr Ile Gln Ala Lys Val
                405                 410                 415
Ala Asn Asp Glu His Ala Arg Val Thr Phe Arg Val Asp Gly Ser Ser
            420                 425                 430
Leu Glu Glu Glu Met Val Phe Asn Asp Asp Thr Leu Tyr Tyr Thr Gly
        435                 440                 445
Ser Phe Thr Pro Asp Ala Ala Val Asn Gly Gly Ala Val Asp Val Ile
    450                 455                 460
Val Ala Tyr Tyr Ser Ser Gly Glu Lys Val Gln Glu Glu Thr Ile Arg
465                 470                 475                 480
Leu Phe Val Lys Ile Pro Glu Met Ser Leu Leu Thr Leu Thr Phe Asp
                485                 490                 495
Asp Asp Ile Asn Gly Ile Lys Ser Asn Gly Thr Trp Pro Glu Asp Gly
            500                 505                 510
Val Thr Ser Glu Ile Asp His Ala Ile Val Asp Gly Asp Gly Lys Leu
        515                 520                 525
Met Phe Ser Val Gln Gly Met Ser Pro Thr Glu Thr Trp Gln Glu Leu
    530                 535                 540
Lys Leu Glu Leu Thr Glu Leu Ser Asp Val Asn Ile Asp Ala Val Lys
545                 550                 555                 560
Lys Met Lys Phe Asp Ala Leu Ile Pro Ala Gly Ser Glu Glu Gly Ser
                565                 570                 575
Val Gln Gly Ile Val Gln Leu Pro Pro Asp Trp Glu Thr Lys Tyr Gly
            580                 585                 590
Met Asn Glu Thr Thr Lys Ser Ile Lys Asp Leu Glu Thr Val Thr Val
        595                 600                 605
Asn Gly Ser Asp Tyr Lys Arg Leu Glu Val Thr Val Ser Ile Asp Asn
    610                 615                 620
Gln Gly Gly Ala Thr Gly Ile Ala Leu Ser Leu Val Gly Ser Gln Leu
625                 630                 635                 640
Asp Leu Leu Glu Pro Val Tyr Ile Asp Asn Ile Glu Leu Leu Asn Ser
                645                 650                 655
```

```
Phe Glu Ala Pro Pro Ala Asp Ser Phe Leu Val Asp Phe Glu Gly
            660             665             670

Tyr Phe Gly Asp Asp Thr Leu Leu His Arg Asn Tyr Ser Asn Gly
            675             680             685

Asp Pro Ile Thr Leu Ser Leu Thr Ser Glu Phe Lys Asn Asn Gly Glu
            690             695             700

Phe Gly Leu Lys Tyr Asp Tyr Ser Ile Gly Ser Met Gly Tyr Ala Gly
705             710             715             720

Arg Gln Thr Ser Leu Gly Pro Val Asp Trp Ser Gly Ala Asn Ala Phe
            725             730             735

Glu Phe Trp Met Lys His Gly Gln Leu Glu Gly Asn His Leu Thr Val
            740             745             750

Gln Ile Arg Ile Gly Asp Val Ser Phe Glu Lys Asn Leu Glu Leu Met
            755             760             765

Asp Ala His Glu Gly Val Val Thr Ile Pro Phe Ser Glu Phe Ala Pro
            770             775             780

Ala Ala Trp Glu Asn Lys Pro Gly Val Ile Ile Asp Glu Gln Lys Leu
785             790             795             800

Lys Arg Val Ser Gln Phe Ala Leu Tyr Thr Gly Gly Ala Arg Gln Ser
            805             810             815

Gly Thr Ile Tyr Phe Asp Asp Leu Arg Ala Val Tyr Asp Glu Ser Leu
            820             825             830

Pro Ser Val Pro Val Pro Lys Glu Glu Glu Glu Lys Glu Val Ala
            835             840             845

Pro Ile Ile Tyr His Phe Glu Ser Gly Ile Asp Asn Trp Glu Gly Gly
            850             855             860

Gln Ala Thr His Ser Asn Gly His Leu Lys Val Thr Arg Leu Gly
865             870             875             880

Glu Gly Gln Gln Thr Glu Val Lys Lys Thr Ser Asn Tyr Asn Leu Thr
            885             890             895

Gly Tyr Asn Tyr Ile Val Ala Asn Ile Lys His Asp Asp Thr Gly Met
            900             905             910

Phe Gly Ser Asp Pro Leu Gln Val Lys Ile Phe Thr Lys Ala Gly Gly
            915             920             925

Trp Val Trp Ala Asp Ser Gly Asn Gln Pro Ile Tyr Ser Asp Asp Tyr
930             935             940

Thr Gln Val Val Tyr Asp Ile Thr Thr Leu Ala Asn Lys Asn Ala Val
945             950             955             960

Gln Glu Ile Gly Phe Glu Phe Leu Ala Pro Ser Gly Ser Ser Gly Thr
            965             970             975

Thr Asn Pro Phe Ile Asp Ser Val Ala Ile Val Thr Ser Leu Asp Gln
            980             985             990

Leu Ser Glu Gln Pro Glu Gln Pro  Glu Gln Pro Gly Thr  Pro Asp Thr
            995             1000            1005

Asp Asp  Asn Lys Glu Asp  Lys  Asp Arg Arg Asn Val  Glu Val Asn
    1010            1015            1020

Glu Glu  Gly Gln Lys Leu Pro  Lys Thr Ala Thr Ser  Ile Phe Asn
    1025            1030            1035

Tyr Leu  Leu Ile Gly Phe Val  Phe Val Gly Ile Gly  Phe Ser Leu
    1040            1045            1050

Phe Ile  Tyr Lys Arg Arg Lys  Thr Val
    1055            1060
```

<210> SEQ ID NO 17
<211> LENGTH: 309
<212> TYPE: PRT
<213> ORGANISM: Bacillus bogoriensis

<400> SEQUENCE: 17

Ala Asn Ser Gly Phe Tyr Val Ser Gly Thr Thr Leu Tyr Asp Ala Asn
1               5                   10                  15

Gly Asn Pro Phe Val Met Arg Gly Ile Asn His Gly His Ala Trp Tyr
            20                  25                  30

Lys Asp Gln Ala Thr Thr Ala Ile Glu Gly Ile Ala Asn Thr Gly Ala
        35                  40                  45

Asn Thr Val Arg Ile Val Leu Ser Asp Gly Gly Gln Trp Thr Lys Asp
    50                  55                  60

Asp Ile His Thr Val Arg Asn Leu Ile Ser Leu Ala Glu Asp Asn His
65                  70                  75                  80

Leu Val Ala Val Pro Glu Val His Asp Ala Thr Gly Tyr Asp Ser Ile
                85                  90                  95

Ala Ser Leu Asn Arg Ala Val Asp Tyr Trp Ile Glu Met Arg Ser Ala
            100                 105                 110

Leu Ile Gly Lys Glu Asp Thr Val Ile Ile Asn Ile Ala Asn Glu Trp
        115                 120                 125

Phe Gly Ser Trp Glu Gly Asp Ala Trp Ala Asp Gly Tyr Lys Gln Ala
    130                 135                 140

Ile Pro Arg Leu Arg Asn Ala Gly Leu Asn His Thr Leu Met Val Asp
145                 150                 155                 160

Ala Ala Gly Trp Gly Gln Phe Pro Gln Ser Ile His Asp Tyr Gly Arg
                165                 170                 175

Glu Val Phe Asn Ala Asp Pro Gln Arg Asn Thr Met Phe Ser Ile His
            180                 185                 190

Met Tyr Glu Tyr Ala Gly Gly Asn Ala Ser Gln Val Arg Thr Asn Ile
        195                 200                 205

Asp Arg Val Leu Asn Gln Asp Leu Ala Leu Val Ile Gly Glu Phe Gly
    210                 215                 220

His Arg His Thr Asn Gly Asp Val Asp Glu Ala Thr Ile Met Ser Tyr
225                 230                 235                 240

Ser Glu Gln Arg Gly Val Gly Trp Leu Ala Trp Ser Trp Lys Gly Asn
                245                 250                 255

Gly Pro Glu Trp Glu Tyr Leu Asp Leu Ser Asn Asp Trp Ala Gly Asn
            260                 265                 270

Asn Leu Thr Ala Trp Gly Asn Thr Ile Val Asn Gly Pro Tyr Gly Leu
        275                 280                 285

Arg Glu Thr Ser Arg Leu Ser Thr Val Phe Thr Gly Gly Gly Ser Asp
    290                 295                 300

Gly Gly Thr Ser Pro
305

<210> SEQ ID NO 18
<211> LENGTH: 309
<212> TYPE: PRT
<213> ORGANISM: Artificial Sequence
<220> FEATURE:
<223> OTHER INFORMATION: Synthetic Construct

<400> SEQUENCE: 18

Ala Asn Ser Gly Phe Tyr Val Ser Gly Thr Thr Leu Tyr Asp Ala Asn

-continued

```
1               5                   10                  15

Gly Asn Pro Phe Val Met Arg Gly Ile Asn His Gly His Thr Trp Tyr
            20                  25                  30

Lys Asp Gln Ala Thr Thr Ala Ile Glu Gly Ile Ala Asn Thr Gly Ala
        35                  40                  45

Asn Thr Val Arg Ile Val Leu Ser Asp Gly Gly Gln Trp Thr Lys Asp
    50                  55                  60

Asp Ile His Thr Val Arg Asn Leu Ile Ser Leu Ala Glu Asp Asn His
65                  70                  75                  80

Leu Val Ala Val Leu Glu Val His Asp Ala Thr Gly Gln Asp Asp Ile
                85                  90                  95

Ala Ser Leu Asn Arg Ala Val Asp Tyr Trp Ile Glu Met Arg Ser Ala
            100                 105                 110

Leu Ile Gly Lys Glu Lys Thr Val Ile Ile Asn Ile Ala Asn Glu Trp
        115                 120                 125

Phe Gly Ser Trp Glu Gly Asp Pro Trp Ala Arg Gly Tyr Lys Gln Ala
    130                 135                 140

Ile Pro Arg Leu Arg Asn Ala Gly Leu Asn His Thr Leu Met Val Asp
145                 150                 155                 160

Ala Ala Gly Trp Gly Gln Phe Pro Gln Ser Ile His Asp Tyr Gly Arg
                165                 170                 175

Glu Val Phe Asn Ala Asp Pro Gln Arg Asn Thr Met Phe Ser Ile His
            180                 185                 190

Met Tyr Glu Tyr Ala Gly Gly Thr Ala Arg Gln Val Arg Thr Asn Ile
        195                 200                 205

Asp Gly Val Leu Asn Gln Asp Leu Ala Leu Val Ile Gly Glu Phe Gly
    210                 215                 220

His Arg His Thr Asn Gly Asp Val Asp Glu Ala Thr Ile Met Ser Tyr
225                 230                 235                 240

Ser Glu Gln Arg Gly Val Gly Trp Leu Ala Trp Ser Trp Lys Gly Asn
                245                 250                 255

Gly Pro Glu Phe Glu Tyr Leu Asp Leu Ser Asn Asp Trp Ala Gly Asn
            260                 265                 270

Asn Leu Thr Ala Trp Gly Asn Thr Ile Val His Gly Pro Tyr Gly Ile
        275                 280                 285

Arg Glu Thr Ser Arg Pro Val Thr Val Phe Thr Gly Gly Gly Ser Asp
    290                 295                 300

Gly Gly Thr Ser Pro
305

<210> SEQ ID NO 19
<211> LENGTH: 299
<212> TYPE: PRT
<213> ORGANISM: Bacillus lentus

<400> SEQUENCE: 19

Ala Ser Gly Phe Tyr Val Ser Gly Thr Ile Leu Cys Asp Ser Thr Gly
1               5                   10                  15

Asn Pro Phe Lys Ile Arg Gly Ile Asn His Ala His Ser Trp Phe Lys
            20                  25                  30

Asn Asp Ser Ala Thr Ala Met Glu Ala Ile Ala Ala Thr Gly Ala Asn
        35                  40                  45

Thr Val Arg Ile Val Leu Ser Asn Gly Gln Gln Tyr Ala Lys Asp Asp
    50                  55                  60
```

```
Ala Asn Thr Val Ser Asn Leu Leu Ser Leu Ala Asn Gln His Lys Leu
 65                  70                  75                  80

Ile Ala Ile Leu Glu Val His Asp Ala Thr Gly Ser Asp Ser Val Ser
                 85                  90                  95

Ala Leu Asp His Ala Val Asp Tyr Trp Ile Glu Met Lys Asn Val Leu
            100                 105                 110

Val Gly Lys Glu Asp Arg Val Leu Ile Asn Ile Ala Asn Glu Trp Tyr
        115                 120                 125

Gly Thr Trp Asp Ser Asn Gly Trp Ala Asp Gly Tyr Lys Ser Ala Ile
    130                 135                 140

Pro Lys Leu Arg Asn Ala Gly Ile Asn His Thr Leu Ile Val Asp Ala
145                 150                 155                 160

Ala Gly Trp Gly Gln Tyr Pro Gln Ser Ile Val Asp Lys Gly Asn Glu
                165                 170                 175

Val Phe Asn Ser Asp Pro Leu Arg Asn Thr Ile Phe Ser Ile His Met
            180                 185                 190

Tyr Glu Tyr Ala Gly Gly Asn Ala Asp Met Val Arg Ala Asn Ile Asp
        195                 200                 205

Gln Val Leu Asn Lys Gly Leu Ala Val Ile Gly Glu Phe Gly His
    210                 215                 220

Tyr His Thr Gly Gly Asp Val Asp Glu Thr Ala Ile Met Ser Tyr Thr
225                 230                 235                 240

Gln Gln Lys Gly Val Gly Trp Leu Ala Trp Ser Trp Lys Gly Asn Gly
                245                 250                 255

Ala Glu Trp Leu Tyr Leu Asp Leu Ser Tyr Asp Trp Ala Gly Asn His
            260                 265                 270

Leu Thr Glu Trp Gly Glu Thr Ile Val Asn Gly Ala Asn Gly Leu Lys
        275                 280                 285

Ala Thr Ser Thr Arg Ala Pro Ile Phe Gly Asn
    290                 295

<210> SEQ ID NO 20
<211> LENGTH: 297
<212> TYPE: PRT
<213> ORGANISM: Paenibacillus sp.A1

<400> SEQUENCE: 20

Met Ala Thr Gly Phe Tyr Val Ser Gly Asn Lys Leu Tyr Asp Ser Thr
 1               5                  10                  15

Gly Lys Pro Phe Val Met Arg Gly Val Asn His Gly His Ser Trp Phe
                20                  25                  30

Lys Asn Asp Leu Asn Thr Ala Ile Pro Ala Ile Ala Lys Thr Gly Ala
            35                  40                  45

Asn Thr Val Arg Ile Val Leu Ser Asn Gly Ser Leu Tyr Thr Lys Asp
        50                  55                  60

Asp Leu Asn Ala Val Lys Asn Ile Ile Asn Val Asn Gln Asn Lys
 65                  70                  75                  80

Met Ile Ala Val Leu Glu Val His Asp Ala Thr Gly Lys Asp Asp Tyr
                 85                  90                  95

Asn Ser Leu Asp Ala Ala Val Asn Tyr Trp Ile Ser Ile Lys Glu Ala
            100                 105                 110

Leu Ile Gly Lys Glu Asp Arg Val Ile Val Asn Ile Ala Asn Glu Trp
        115                 120                 125

Tyr Gly Thr Trp Asn Gly Ser Ala Trp Ala Asp Gly Tyr Lys Lys Ala
    130                 135                 140
```

```
Ile Pro Lys Leu Arg Asn Ala Gly Ile Lys Asn Thr Leu Ile Val Asp
145                 150                 155                 160

Ala Ala Gly Trp Gly Gln Phe Pro Gln Ser Ile Val Asp Tyr Gly Gln
                165                 170                 175

Ser Val Phe Ala Ala Asp Ser Gln Lys Asn Thr Val Phe Ser Ile His
            180                 185                 190

Met Tyr Glu Tyr Ala Gly Lys Asp Ala Ala Thr Val Lys Ala Asn Met
        195                 200                 205

Glu Asn Val Leu Asn Lys Gly Leu Ala Leu Ile Ile Gly Glu Phe Gly
    210                 215                 220

Gly Tyr His Thr Asn Gly Asp Val Asp Glu Tyr Ala Ile Met Arg Tyr
225                 230                 235                 240

Gly Gln Glu Lys Gly Val Gly Trp Leu Ala Trp Ser Trp Tyr Gly Asn
                245                 250                 255

Ser Ser Gly Leu Asn Tyr Leu Asp Met Ala Thr Gly Pro Asn Gly Ser
            260                 265                 270

Leu Thr Ser Phe Gly Asn Thr Val Val Asn Asp Thr Tyr Gly Ile Lys
        275                 280                 285

Asn Thr Ser Gln Lys Ala Gly Ile Phe
    290                 295

<210> SEQ ID NO 21
<211> LENGTH: 298
<212> TYPE: PRT
<213> ORGANISM: Artificial Sequence
<220> FEATURE:
<223> OTHER INFORMATION: Synthetic Construct

<400> SEQUENCE: 21

Met Ala Thr Gly Phe Tyr Val Ser Gly Asn Lys Leu Tyr Asp Ser Thr
1               5                   10                  15

Gly Lys Glu Phe Val Met Arg Gly Val Asn His Gly His Thr Trp Phe
            20                  25                  30

Lys Asn Asp Leu Asn Glu Ala Ile Pro Ala Ile Ala Lys Thr Gly Ala
        35                  40                  45

Asn Thr Val Arg Ile Val Leu Ser Asn Gly Val Gln Tyr Thr Arg Asp
    50                  55                  60

Asp Leu Asp Ala Val Lys Asn Ile Ile Asn Val Val Asn Gln Asn Lys
65                  70                  75                  80

Met Ile Ala Val Leu Glu Val His Asp Ala Thr Gly Lys Asp Asp Tyr
            85                  90                  95

Asp Ser Leu Asp Ala Ala Ile Asn Tyr Trp Ile Ser Ile Lys Glu Ala
        100                 105                 110

Leu Ile Gly Lys Glu Asp Arg Val Ile Val Asn Ile Ala Asn Glu Trp
    115                 120                 125

Met Gly Thr Trp Asn Gly Ser Ala Trp Ala Asp Gly Tyr Lys Lys Ala
130                 135                 140

Ile Pro Lys Leu Arg Asn Ala Gly Ile Lys Asn Thr Leu Ile Val Asp
145                 150                 155                 160

Ala Ala Gly Trp Gly Gln Tyr Pro Gln Ser Ile Val Asp Tyr Gly Gln
                165                 170                 175

Ser Val Phe Ala Ala Asp Ser Leu Lys Asn Thr Val Phe Ser Ile His
            180                 185                 190

Met Tyr Glu Tyr Ala Gly Lys Asp Ala Ala Thr Val Lys Ala Asn Met
        195                 200                 205
```

Glu Asn Val Leu Asn Lys Gly Leu Ala Leu Ile Ile Gly Glu Phe Gly
    210                 215                 220

Cys Tyr His Val Asn Gly Asp Val Asp Glu Leu Ala Ile Met Arg Tyr
225                 230                 235                 240

Gly Gln Glu Leu Gly Val Gly Trp Leu Ala Trp Ser Trp Tyr Gly Asn
                245                 250                 255

Ser Asp Gly Leu Arg Tyr Leu Asp Met Ala Thr Gly Pro Asn Gly Ser
            260                 265                 270

Leu Thr Ser Phe Gly Asn Thr Val Val Asn Asp Thr Tyr Gly Ile Lys
        275                 280                 285

Asn Thr Ser Gln Lys Ala Gly Ile Phe Gln
    290                 295

<210> SEQ ID NO 22
<211> LENGTH: 298
<212> TYPE: PRT
<213> ORGANISM: Artificial sequence
<220> FEATURE:
<223> OTHER INFORMATION: Synthetic Construct

<400> SEQUENCE: 22

Met Ala Thr Gly Phe Tyr Val Ser Gly Asn Lys Leu Tyr Asp Ser Thr
1               5                   10                  15

Gly Lys Glu Phe Val Met Arg Gly Val Asn His Gly His Thr Trp Phe
            20                  25                  30

Lys Asn Asp Leu Asn Glu Ala Ile Pro Ala Ile Ala Lys Thr Gly Ala
        35                  40                  45

Asn Thr Val Arg Ile Val Leu Ser Asn Gly Val Gln Tyr Thr Arg Asp
    50                  55                  60

Asp Leu Asn Ala Val Lys Asn Ile Ile Asn Val Val Asn Gln Asn Lys
65                  70                  75                  80

Met Ile Ala Val Leu Glu Val His Asp Ala Thr Gly Lys Asp Asp Tyr
                85                  90                  95

Asp Ser Leu Asp Ala Ala Val Asn Tyr Trp Ile Ser Ile Lys Glu Ala
            100                 105                 110

Leu Ile Gly Lys Glu Asp Arg Val Ile Val Asn Ile Ala Asn Glu Trp
        115                 120                 125

Met Gly Thr Trp Asn Gly Ser Ala Trp Ala Asp Gly Tyr Lys Lys Ala
    130                 135                 140

Ile Pro Lys Leu Arg Asn Ala Gly Ile Lys Asn Thr Leu Ile Val Asp
145                 150                 155                 160

Ala Ala Gly Trp Gly Gln Phe Ser Gln Ser Ile Val Asp Tyr Gly Gln
                165                 170                 175

Ser Val Phe Ala Ala Asp Ser Leu Lys Asn Thr Val Phe Ser Ile His
            180                 185                 190

Met Tyr Glu Tyr Ala Gly Lys Asp Ala Ala Thr Val Lys Ala Asn Met
        195                 200                 205

Glu Asn Val Leu Asn Lys Gly Leu Ala Leu Ile Ile Gly Glu Phe Gly
    210                 215                 220

Cys Tyr His Val Asn Gly Asp Val Asp Glu Leu Ala Ile Met Arg Tyr
225                 230                 235                 240

Gly Gln Glu Leu Gly Val Gly Trp Leu Ala Trp Ser Trp Tyr Gly Asn
                245                 250                 255

Ser Asp Gly Leu Arg Tyr Leu Asp Met Ala Thr Gly Pro Asn Gly Ser
            260                 265                 270

Leu Thr Ser Phe Gly Asn Thr Val Val Asn Asp Thr Tyr Gly Ile Lys
        275                 280                 285

Asn Thr Ser Gln Lys Ala Gly Ile Phe Gln
        290                 295

<210> SEQ ID NO 23
<211> LENGTH: 298
<212> TYPE: PRT
<213> ORGANISM: Artificial Sequence
<220> FEATURE:
<223> OTHER INFORMATION: Synthetic Construct

<400> SEQUENCE: 23

Met Ala Thr Gly Phe Tyr Val Ser Gly Thr Lys Leu Tyr Asp Ser Thr
1               5                   10                  15

Gly Lys Glu Phe Val Met Arg Gly Val Asn His Gly His Thr Trp Phe
            20                  25                  30

Lys Asn Asp Leu Asn Glu Ala Ile Pro Ala Ile Ala Lys Thr Gly Ala
        35                  40                  45

Asn Thr Val Arg Ile Val Leu Ser Asn Gly Val Gln Tyr Thr Arg Asp
    50                  55                  60

Asp Leu Asp Ala Val Lys Asn Ile Ile Asn Val Val Asn Gln Asn Lys
65                  70                  75                  80

Met Ile Ala Val Leu Glu Val His Asp Ala Thr Gly Lys Asp Asp Tyr
                85                  90                  95

Asp Ser Leu Asp Ala Ala Val Asn Tyr Trp Ile Ser Ile Lys Glu Ala
            100                 105                 110

Leu Ile Gly Lys Glu Asp Arg Val Ile Val Asn Ile Ala Asn Glu Trp
        115                 120                 125

Met Gly Thr Trp Asn Gly Ser Ala Trp Ala Asp Gly Tyr Lys Gln Ala
    130                 135                 140

Ile Pro Lys Leu Arg Asn Ala Gly Ile Lys Asn Thr Leu Ile Val Asp
145                 150                 155                 160

Ala Ala Gly Trp Gly Gln Phe Ser Gln Ser Ile Val Asp Tyr Gly Gln
                165                 170                 175

Ser Val Phe Ala Ala Asp Ser Leu Lys Asn Thr Val Phe Ser Ile His
            180                 185                 190

Met Tyr Glu Tyr Ala Gly Lys Asp Ala Ala Thr Val Lys Ala Asn Met
        195                 200                 205

Glu Asn Val Leu Asn Lys Gly Leu Ala Leu Ile Ile Gly Glu Phe Gly
    210                 215                 220

Pro Tyr His Val Asn Gly Asp Val Asp Glu Leu Ala Ile Met Arg Tyr
225                 230                 235                 240

Gly Gln Glu Leu Gly Val Gly Trp Leu Ala Trp Ser Trp Tyr Gly Asn
                245                 250                 255

Ser Asp Gly Leu Arg Tyr Leu Asp Met Ala Thr Gly Pro Asn Gly Ser
            260                 265                 270

Leu Thr Ser Phe Gly Asn Thr Val Val Asn Asp Thr Tyr Gly Ile Lys
        275                 280                 285

Asn Thr Ser Gln Lys Ala Gly Ile Phe Gln
        290                 295